(12) United States Patent
Sebti et al.

(10) Patent No.: US 9,597,329 B2
(45) Date of Patent: Mar. 21, 2017

(54) AURORA KINASE INHIBITORS AND METHODS OF MAKING AND USING THEREOF

(71) Applicants: Said M. Sebti, Tampa, FL (US); Ernst Schönbrunn, Tampa, FL (US); Nicholas J. Lawrence, Tampa, FL (US); Harshani R. Lawrence, Tampa, FL (US); Matthew P. Martin, Tampa, FL (US)

(72) Inventors: Said M. Sebti, Tampa, FL (US); Ernst Schönbrunn, Tampa, FL (US); Nicholas J. Lawrence, Tampa, FL (US); Harshani R. Lawrence, Tampa, FL (US); Matthew P. Martin, Tampa, FL (US)

(73) Assignee: H. Lee Moffitt Cancer Center and Research Institute, Inc, Tampa, FL (US)

( * ) Notice: Subject to any disclaimer, the term of this patent is extended or adjusted under 35 U.S.C. 154(b) by 0 days.

(21) Appl. No.: 15/012,428

(22) Filed: Feb. 1, 2016

(65) Prior Publication Data
US 2017/0000787 A1    Jan. 5, 2017

Related U.S. Application Data

(62) Division of application No. 14/008,586, filed as application No. PCT/US2012/031494 on Mar. 30, 2012, now Pat. No. 9,249,124.

(60) Provisional application No. 61/469,373, filed on Mar. 30, 2011, provisional application No. 61/585,091, filed on Jan. 10, 2012.

(51) Int. Cl.
| *A61K 31/506* | (2006.01) |
| *A61K 31/505* | (2006.01) |
| *A61K 31/5377* | (2006.01) |
| *A61K 31/635* | (2006.01) |

(52) U.S. Cl.
CPC .......... *A61K 31/505* (2013.01); *A61K 31/506* (2013.01); *A61K 31/5377* (2013.01); *A61K 31/635* (2013.01)

(58) Field of Classification Search
CPC  C07D 403/12; C07D 239/48; C07D 295/135; C07D 401/12; C07D 413/12; A61K 31/506; A61K 31/505
See application file for complete search history.

(56) References Cited

U.S. PATENT DOCUMENTS

| 7,442,705 B2 | 10/2008 | Guillemont et al. |
| 7,517,886 B2 | 4/2009 | Singh et al. |
| 7,671,063 B2 | 3/2010 | Baenteli et al. |
| 7,825,246 B2 | 11/2010 | Noronha et al. |
| 7,893,074 B2 | 2/2011 | Garcia-Echeverria et al. |
| 7,947,698 B2 | 5/2011 | Atuegbu et al. |
| 8,318,702 B2 | 11/2012 | Kondoh et al. |
| 8,450,335 B2 | 5/2013 | Singh et al. |
| 2003/0149266 A1 | 8/2003 | Pease et al. |
| 2010/0016318 A1 | 1/2010 | Axten et al. |
| 2010/0197918 A1 | 8/2010 | Singh et al. |
| 2013/0149266 A1 | 6/2013 | Homma et al. |

FOREIGN PATENT DOCUMENTS

| WO | 01/64654 | 9/2001 |
| WO | 03/055866 | 7/2003 |
| WO | 03/078404 | 9/2003 |
| WO | 2004/046118 | 6/2004 |
| WO | 2005/013996 | 2/2005 |
| WO | 2006/124874 | 11/2006 |

OTHER PUBLICATIONS

Angell et al., (2008) "Biphenyl Amide p38 Kinase Inhibitors 4: DFG-In and DFG-Out Binding Modes," *Bioorg Med Chem Lett*, 18:4433-4437.
Auffinger et al., (2004) "Halogen Bonds in Biological Molecules," *Proc Natl Acad Sci USA* 101:16789-16794.
Awale et al., (2008) "Molecular docking guided 3D-QSAR CoMFA analysis of N-4-Pyrimidinyl-1H-indazol-4-amine inhibitors of Leukocyte-specific protein tyrosine kinase", J. of Molec. Model. 14:937-947.
Bamborough et al., (2007) "N-4-Pyrimidinyl-1H-indazol-4-amine inhibitors of Lck: Indazoles as phenol isosteres with improved pharmacokinetics", Bioorg. & Med. Chem. Letters 17:4363-4368.
Becker et al., (2010) Centromere Localization of INCENP-Aurora B Is Sufficient to Support Spindle Checkpoint Function. *Cell Cycle* 9:1360-72.
Berndt et al., (2010) "The Akt Activation Inhibitor TCN-P Inhibits Akt Phosphorylation by Binding to the PH Domain of Akt and Blocking Its Recruitment to the Plasma Membrane," *Cell Death Differ*. 17(11):1795-804.
Betzi et al., (2011) "Discovery of a Potential Allosteric Ligand Binding Site in CDK2," *ACS Chem Biol* 6:492-501.
Breault et al., (2003) "Cyclin-Dependent Kinase 4Inhibitors as a Treatment for Cancer. Part 2: Identification and Optisation of Substituted 2,4-Bis Anilino Pyrimidines", Bioorg. & Med. Chem. Letters 13: 2961-2966.
Carmena et al., (2003) "The Cellular Geography of Aurora Kinases," *Nat Rev Mol Cell Biol* 4:842-54.
Choi et al.,(2009) "Discovery and Structural Analysis of Eph Receptor Tyrosine Kinase Inhibitors," *Bioorg Med Chem Lett* 19:4467-4470.
Comess et al., (2011) "Discovery and Characterization of Non-ATP site inhibitors of the Mitogen Activated Protein (MAP) Kinases," *ACS Chem Biol* 6:234-244.
Communication from CAS (May 19, 2015).
CAPLUS Abstract of T. Grahman et al., WO 2006124874 (Entered STN: Nov. 23, 2006).
CAS Index of Registry No. 1180658-63-2 (Entered STN: Sep. 4, 2009).
CAS Index of Registry Nos. 944795-28-2 & 944795-25-9 (Entered STN: Aug. 16, 2007).

(Continued)

*Primary Examiner* — Alexander R Pagano
(74) *Attorney, Agent, or Firm* — Meunier Carlin & Curfman LLC

(57) ABSTRACT

Described herein are inhibitors of Aurora kinase and their use in the treatment of cancer. Methods of screening for selective inhibitors of Aurora kinases are also disclosed.

12 Claims, 70 Drawing Sheets

(56) References Cited

OTHER PUBLICATIONS

CAPLUS Abstract of P. Bamborough et al., 17 Bioorganic & Medicinal Chemistry Letters 4363-4368 (2007) (Entered STN: Jul. 10, 2007).
Dar et al., (2011) "The Evolution of Protein Kinase Inhibitors From Antagonists to Agonists of Cellular Signaling," *Annu Rev Biochem* 80:769-95.
Dietrich et al., (2010) "The Design, Synthesis, and Evaluation of 8 Hybrid DFG-Out Allosteric Kinase Inhibitors: A Structural Analysis of the Binding Interactions of Gleevec, Nexavar, and BIRB-796," *Bioorg Med Chem* 18:5738-5748.
Dong et al., (2011) "Discovery of TAK-733, A potent and Selective MEK Allosteric Site Inhibitor for the Treatment of Cancer," *Bioorg Med Chem Lett* 21: 1315-1319.
Filomia et al., (2010) "Insights Into MAPK p38alpha DFG Flip Mechanism by Accelerated Molecular Dynamics," *Bioorg Med Chem* 18:6805-6812.
Fleming et al., (2010) "Nitrile-Containing Pharmaceuticals: Efficacious Roles of the Nitrile Pharmacophore," *J Med Chem* 53:7902-7917.
Gizatullin et al., (2006) "The Aurora Kinase Inhibitor VX-680 Induces Endoreduplication and Apoptosis Preferentially in Cells With Compromised p53-dependent Postmitotic Checkpoint Function," *Cancer Res.* 66(15):7668-77.
Gorgun et al., (2010) A Novel Aurora-A Kinase Inhibitor MLN8237 Induces Cytotoxicity and Cell-Cycle Arrest in Multiple Myeloma. *Blood* 115:5202-5213.
Green et al. (2011) "Update on Aurora Kinase Targeted Therapeutics in Oncology," *Expert Opin Drug Discov* 6:291-307.
Grigor et al, (1978) "Molecular—Biological Problems in the Search for, Production of, and Mechanism of Action of Drugs", Pharma. Chem. J. 12:421-427.
Gritsko et al., (2003) Activation and Overexpression of Centrosome Kinase BTAK/Aurora-A in Human Ovarian Cancer. *Clin Cancer Res* 9:1420-6.
Gunner et al., (2000) "Backbone Dipoles Generate Positive Potentials in All Proteins: Origins and Implications of the Effect," *Biophys J* 78:1126-1144.
Harrington et al., (2004) "VX-680, A Potent and Selective Small-Molecule Inhibitor of the Aurora Kinases, Suppresses Tumor Growth in Vivo," *Nat Med* 10:262-7.
Howard et al., (2009) "Fragment-Based Discovery of the Pyrazol-4-yl Urea (AT9283), A Multitargeted Kinase Inhibitor With Potent Aurora Kinase Activity," *J Med Chem* 52:379-88.
International Preliminary Report on Patentability issued in PCT Application No. PCT/US2009/52171 dated Oct. 1, 2013.
International Preliminary Report on Patentability issued in corresponding PCT Application No. PCT/US2012/031494 dated Oct. 10, 2013.
Jones et al., (2010) "Aromatic Chloride to Nitrile Transformation: Medicinal and Synthetic Chemistry," *Med Chem Comm* 1:309-318.
Karn et al., (1983) "Synthesis and Antiinflamatory Properties of o-Carboxyphenylamino Pyrimidines", Pharma. Chem. J. 17:777-779.
Keen et al., (2004) "Aurora-Kinase Inhibitors As Anticancer Agents," *Nat Rev Cancer* 4:927-36.
Kuglstatter et al., (2010) "X-Ray Crystal Structure of JNK2 Complexed with the p38alpha Inhibitor BIRB796: Insights Into the Rational Design of DFG-Out Binding MAP Kinase Inhibitors," *Bioorg Med Chem Lett* 20:5217-5220.
Liu et al., (2007) "Discovery of a New Class of 4-anilinopyrimidines as Potent c-Jun N-terminal Kinase Inhibitors: Synthesis and SAR Studies", Bioorg. & Med. Chem. Letters 17:668-672.
Lu et al., (2009) "H Contacts in Biomolecular Systems: How They Contribute to Protein-Ligand Binding Affinity," *J Phys Chem* 113:12615-12621.
Lu et al., (2009), Halogen Bonding-A Novel Interaction for Rational Drug Design?, J Med Chem 52: 2854-2862.
Martin et al.,(2012) "A Novel Mechanism by Which Small Molecule Inhibitor Induce the DFG Flip in Aurora A", ACS Chem. Biol. 7:698-706.
Marumoto, et al., (2005) "Aurora-A—A Guardian of Poles," Nat Rev Cancer 5:42-50.
Metrangolo et al., (2001) "Halogen Bonding: A Paradigm in Supramolecular Chemistry," *Chemistry* 7:2511-2519.
Metrangolo et al., (2008) Halogen Bonding in Supramolecular Chemistry, *Angew Chem Int Ed Engl* 47:6114-6127.
Muller et al., (2007) "Fluorine in Pharmaceuticals: Looking Beyond Intuition," Science 317:1881-1886.
Murray et al., (2009) Expansion of the Sigma-Hole Concept, *J Mol Model* 15:723-729.
Nagar et al., (2002) "Crystal Structures of the Kinase Domain of c-Abl in Complex With the Small Molecule Inhibitors PD173955 and imatinib (STI-571)," *Cancer Res* 62:4236-4243.
Nakamura (1996) "Roles of Electrostatic Interaction in Proteins," *Q Rev Biophys* 29:1-90.
Neves-Petersen et al., (2003) "Protein Electrostatics: A Review of the Equations and Methods Used to Model Electrostatic Equations in Biomolecules—Applications in Biotechnology," *Biotechnol Ann Rev* 9:315-395.
Parisini et al., (2011) "Halogen Bonding in Halocarbonprotein Complexes: A Structural Survey," *Chem Soc Rev* 40:2267-2278.
Pargellis et al., (2002) "Inhibition of p38 MAP Kinase by Utilizing a Novel Allosteric Binding Site," *Nat Struct Biol* 9:268-72.
Politzer et al., (2007) "An Overview of Halogen Bonding," *J Mol Model* 13:305-311.
Politzer et al., (2010) "Halogen Bonding: An Electrostatically-Driven Highly Directional Noncovalent Interaction," *Phys Chem Chem Physics: PCCP* 12:7748-7757.
Schindler et al., (2000) "Structural Mechanism for STI-571 Inhibition of Abelson Tyrosine Kinase," *Science* 289/5486:1938-1942.
Schneider et al., (2011) "The Structure of CDK8/CycC Implicates Specificity in the CDK/cyclin Family and Reveals Interaction with a Deep Pocket Binder," *J Mol Biol* 412:251-266.
Seeliger et al., (2009) "Equally Potent Inhibition of c-Src and Abl by Compounds That Recognize Inactive Kinase Conformations," *Cancer Res* 69:2384-2392.
Solanki et al., (2011) "Benzimidazole Inhibitors Induce a DFG-Out Conformation of Never in Mitosis Gene A-Related Kinase 2 (Nek2) Without Binding to the Back Pocket and Reveal a Nonlinear Structure-Activity Relationship," *J Med Chem* 54:1626-1639.
Stork et al., (2007) "Electrostatics of Proteins in Dielectric Solvent Continua. II. First Applications in Molecular Dynamics Simulations," *J Chem Phys* 126:165106.
Xu et al. (2011) "Two TPX2-Dependent Switches Control the activity of Aurora A," *PloS one* 6:16757.
Zhang et al., (2010)"Targeting Bcr-Abl by Combining Allosteric with ATP-Binding-Site Inhibitor," *Nature* 463:501-506.

Library 2

2a, $R^1 = R^2 = H$, $R^3 = o$-COOH (method $a$, 68%)

2b, $R^1 = R^2 = H$, $R^3 = o$-CONH (method $a$, 63%)

2c, $R^1 = R^2 = R^3 = H$ (method $a$, 26%)

2d, $R^1 = R^2 = H$, $R^3 = p$-COOH (method $a$, 78%)

2e, $R^1 = R^2 = H$, $R^3 = o$-COOH$_3$ (method $a$, 45%)

2f, $R^1 = H$, $R^2 = CH_3$, $R^3 = o$-COOH (method $a$, 41%)

2g, $R^1 = F$, $R^2 = H$, $R^3 = o$-COOH (method $a$, 55%)

2h, $R^1 = N_2H$, $R^2 = H$, $R^3 = o$-COOH (method $a$, 57%)

2i, $R^1 = H$, $R^2 = NH_2$, $R^3 = o$-COOH (method $a$, 43%)

2j, $R^1 = CH_3$, $R^2 = H$, $R^3 = o$-COOH (method $a$, 52%)

2k, $R^1 = F$, $R^2 = H$, $R^3 = o$-Cl (method $b$, 47%)

2l, $R^1 = R^2 = H$, $R^3 = o$-Cl (method $b$, 87%)

2m, $R^1 = Cl$, $R^2 = H$, $R^3 = o$-COOH (method $a$, 42%)

2n, $R^1 = R^2 = Cl$, $R^3 = o$-COOH (method $a$, 32%)

2o, $R^1 = Cl$, $R^2 = H$, $R^3 = o$-Cl (method $b$, 60%)

2p, $R^1 = F$, $R^2 = H$, $R^3 = o$-Cl, $o$-Cl (bis-chloro), method k in Fig. 5.

2q, $R^1 = F$, $R^2 = H$, $R^3 = o$-NO , method k in Fig. 5.

4a, $R^1 = NH_2$, $R^2 = H$, $R^3 = o$-COOH, $R^4 = p$-COOH (method $h$, 65%)

4b, $R^1 = H$, $R^2 = NH_2$, $R^3 = o$-COOH, $R^4 = p$-COOH (method $h$, 79%)

4c, $R^1 = Cl$, $R^2 = Cl$, $R^3 = o$-COOH, $R^4 = p$-COOH (method $h$, 32%)

4d, $R^1 = Cl$, $R^2 = H$, $R^3 = o$-COOH, $R^4 = p$-COOH, (method $h$, 72%)

FIG. 4B

Library 3

1, $R^1 = R^2 = H$, $R^3 = o\text{-COOH}$, $R^4 = p\text{-COOH}$ (method $h$, 85%)
3a, $R^1 = R^2 = H$, $R^3 = o\text{-COOH}$, $R^4 = o\text{-CONH}_2$ (method $d$, 53%)
3b, $R^1 = R^2 = H$, $R^3 = o\text{-CONH}$, $R^4 = H$ (method $d$, 54%)
3c, $R^1 = R^2 = H$, $R^3 = o\text{-COOH}$, $R^4 = $ 4-morpholino (method $e$, 32%)
3d, $R^1 = R^2 = H$, $R^3 = o\text{-COOH}$, $R^4 = o\text{-COOH}$ (method $d$, 60%)
3e, $R^1 = R^2 = H$, $R^3 = o\text{-COOCH}_3$, $R^4 = p\text{-COOCH}_3$ (method $d$, 32%)
3f, $R^1 = R^2 = R^3 = R^4 = H$ (method $d$, 49%)
3g, $R^1 = R^2 = H$, $R^3 = o\text{-CONH}_2$, $R^4 = p\text{-COHN}_2$ (method $d$, 48%)
3h, $R^1 = R^2 = R^3 = H$, $R^4 = p\text{-COOH}$ (method $d$, 71%)
3i, $R^1 = R^2 = N$, $R^3 = R^4 = p\text{-COOH}$ (method $d$, 99%)
3j, $R^1 = CH_3$, $R^2 = H$, $R^3 = o\text{-COOH}$, $R^4 = p\text{-COOH}$, (method $g$, 36%)
3k, $R^1 = H$, $R^2 = CH_3$, $R^3 = o\text{-COOH}$, $R^4 = p\text{-COOH}$ (method $d$, 53%)
3l, $R^1 = R^2 = H$, $R^3 = o\text{-Cl}$, $R^4 = p\text{-COOH}$, (method $e$, 43%,)
3m, $R^1 = F$, $R^2 = H$, $R^3 = o\text{-COOH}$, $R^4 = H$ (method $e$, 94%)
3n, $R^1 = F$, $R^2 = H$, $R^3 = o\text{-COOH}$, $R^4 = p\text{-COOH}$, (method $e$, 59%)
3o, $R^1 = F$, $R^2 = H$, $R^3 = o\text{-Cl}$, $R^4 = p\text{-COOH}$, (method $m$, Fig. 5, 52%)
3p, $R^1 = F$, $R^2 = H$, $R^3 = o\text{-Cl}$, $R^4 = H$, (method $m$, Fig. 5, 51%)
3q, $R^1 = H$, $R^2 = N$, $R^3 = o\text{-COOH}$, $R^4 = m\text{-COOH}$, (method $d$, 72%)
3r, $R^1 = F$, $R^2 H$, $R^3 = o\text{-COOH}$, $R^4 = m\text{-COOH}$, (method $m$, scheme 2, 66%)
3s, $R^1 = Cl$, $R^2 = H$, $R^3 = o\text{-COOH}$, $R^4 = p\text{-COOEt}$, (method $f$ (ii), 90%)
3t, $R^1 = R^2 = Cl$, $R^3 = o\text{-COOH}$, $R^4 = p\text{-COOEt}$, (method $f$(ii), 17%)
3u, $R^1 = NH_2$, $R^2 = H$, $R^3 = o\text{-COOH}$, $R^4 = p\text{-COOEt}$ (method $f(i)$, 72%)
3v, $R^1 = H$, $R^2 = NH_2$, $R^3 = o\text{-COOH}$, $R^4 = p\text{-COOEt}$ (method $e$, 33%)
3w, $R^1 = R^2 = NH_2$, $R^3 = o\text{-COOH}$, $R^4 = p\text{-COOMe}$ (method $m$, Fig. 5, 76%)
3x, $R^1 = Fl$, $R^2 = H$, $R^3 = o\text{-Cl}$, $o\text{-Cl}$ (bis-chloro), $R^4 = $ COOH, method $f(ii)$
3y, $R^1 = F$, $R^2 = H$, $R^3 = o\text{-NO}_2$, $R^4 = $ COOH, method $f(ii)$.

FIG. 4C

Library 5

5a, R = *ortho*-F, 59% (*method i*)

5b, R = *ortho*-Cl and 4-F, 46% (*method i*)

5c, R = *ortho*-OCF$_3$, 48% (*method i*)

5d, R = *ortho*-OMe, 60% (*method j*)

5e, R = *ortho*-CN, 22% (*method k*)

5f, R = *ortho*-CF$_3$, 38% (*method k*)

5g, R = *ortho*-Br 63% (*method b*)

5h, R = *ortho*-I, 79% (*method b*)

5i, R = *ortho*-Ph, 54% (*method i*)

Library 6

6a, R = ortho-F, R¹= para-COOH, 69% (method m)
6b, R = ortho-CF₃, R¹= H, 84% (method m)
6c, R = ortho-Cl and 4-F, R¹= para-COOH, 69% (method m)
6d, R = ortho-OCF₃, R¹= para-COOH, 58% (method m)
6e, R = ortho-OMe, R¹= para-COOH, 68% (method m)
6f, R = ortho-OMe, R¹= H, 76% (method m)
6g, R = ortho-CN, R¹= H, 24% (method m)
6h, R = ortho-CF₃, R¹= para-COOH, 82% (method m)
6i, R = ortho-Br, R¹= para-COOH, 47% (method m)
6j, R = ortho-Cl, R¹= para-CH₂-COOH, 70% (method l)
6k, R = rpcho-Cl, R¹= para-COOH and meta-OH, 62% from 6u(method o)
6l, R = ortho-F, R¹= H, 55% (method m)
6m, R = ortho-I, R¹= para-COOH, 32% (method m)
6n, R = ortho-CN, R¹= para-COOH, 15% (method m)
6o, R = ortho-Cl, R¹= meta-COOH, 67% (method m)
6p, R = ortho-Cl, R¹= para-COOH₂, 70% (method l)
6q, R = ortho-Ph, R¹= para-COOH 67% (method m)
6r, R¹ = para-COOH, R²= Me, 80% (method m)
6s, R¹ = para-COOH, R²= Et, 71% (method m)
6t, R¹ = meta-COOH, 57% (method m)
6u, R = ortho-Cl, R¹= para-COOMe and meta-OH, 57% (method n)

FIG. 5C

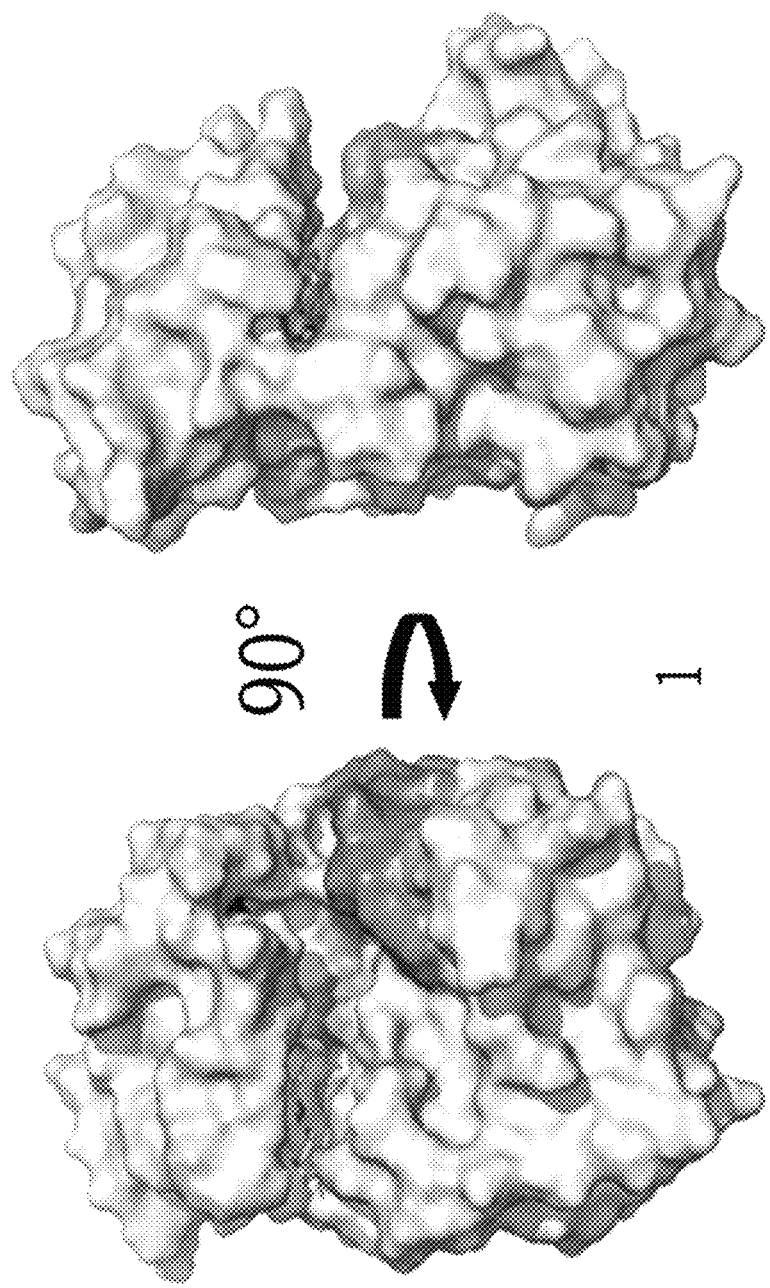

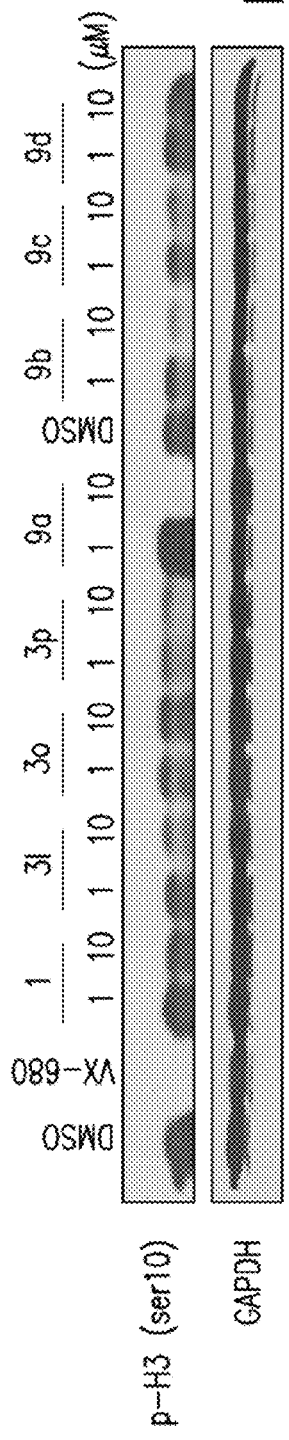
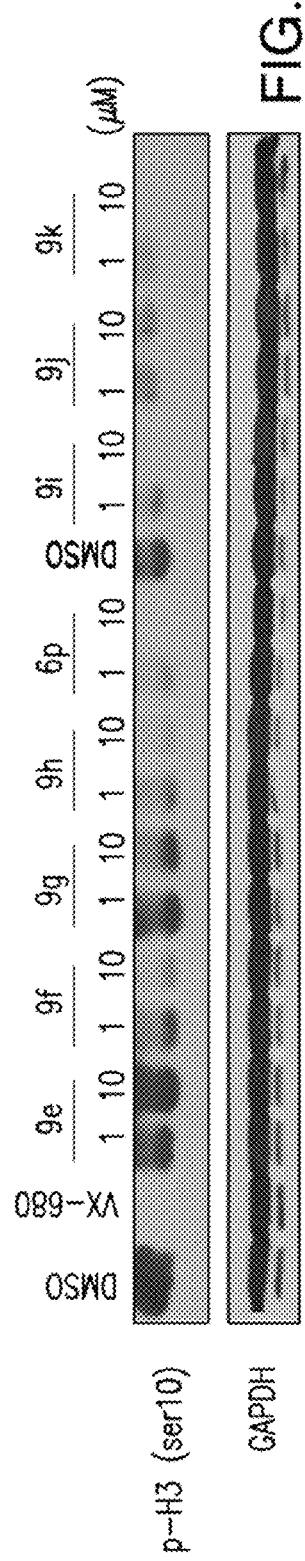
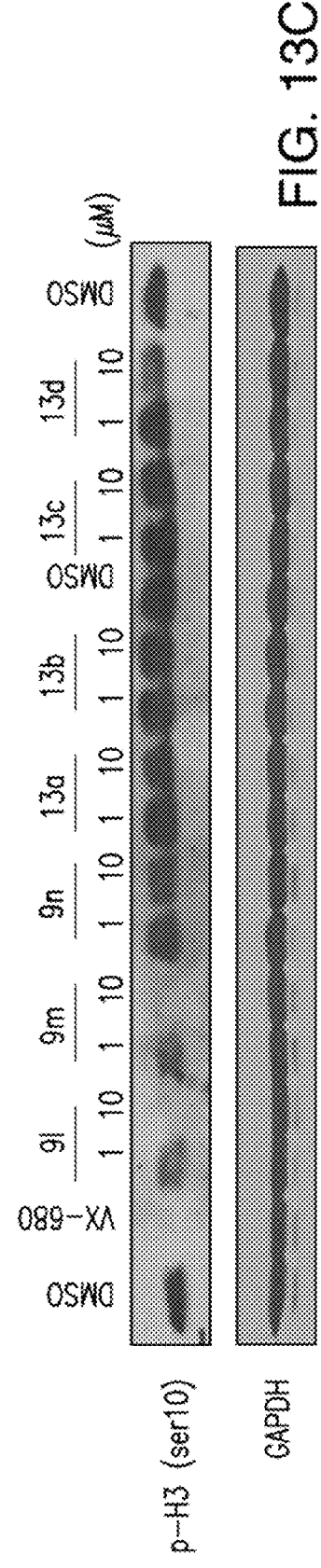
FIG. 13A
FIG. 13B
FIG. 13C

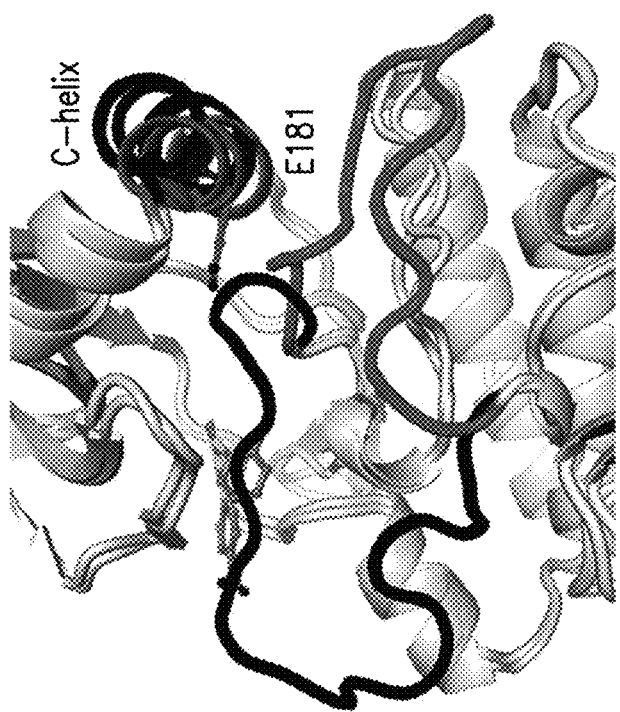
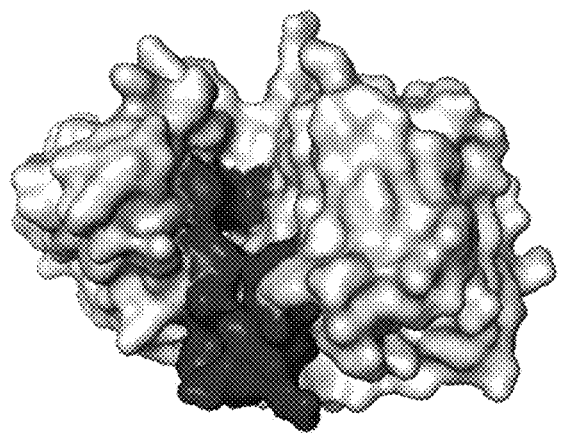
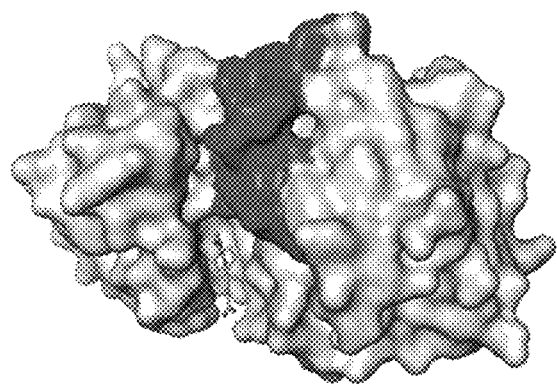
FIG. 15B
FIG. 15A 6 (-F)

AURORA KINASE INHIBITORS AND METHODS OF MAKING AND USING THEREOF

CROSS-REFERENCE TO PRIORITY APPLICATIONS

This application is a divisional of U.S. application Ser. No. 14/008,586, filed Nov. 12, 2013, which is a 371 National Phase of PCT/US2012/031494, filed Mar. 30, 2012, which claims the benefit of priority to U.S. Provisional Application No. 61/469,373, filed Mar. 30, 2011, and U.S. Provisional Application No. 61/585,091, filed Jan. 10, 2012, which are incorporated herein by reference in their entireties.

FIELD

The subject matter disclosed herein relates generally to cancer therapy and to anti-cancer compounds. More specifically, the subject matter disclosed herein relates to inhibitors of Aurora kinase and their use in the treatment of cancer. Methods of screening for selective inhibitors of Aurora kinases are also disclosed.

BACKGROUND

A majority of protein kinases share a common DFG (Asp-Phe-Gly) motif in the ATP site which transitions between two distinct conformations in response to phosphorylation of the contiguous activation loop: the active DFG-in and the inactive DFG-out states. Kinase inhibitors that bind only to the DFG-in state often suffer from a lack of target specificity, as the ATP site is wide open and able to accommodate diverse chemical scaffolds. By contrast, inhibitors able to induce and stabilize the DFG-out conformation are considered superior, as they render the active site architecture incompatible with substrate binding, resulting in enhanced potency and target selectivity. The clinical success of imatinib (Gleevec) as an inhibitor of Abl kinase (Nagar et al., (2002) Cancer Res 62:4236-4243) is attributed in large part to this distinct mode of action (Seeliger et al., (2009) Cancer Res 69:2384-2392) and has spurred the design of DFG-out inhibitors for other kinases, including MAP (Angell et al., (2008) Bioorg Med Chem Lett 18:4433-4437), JNK2 (Kuglstatter et al., (2010) Bioorg Med Chem Lett 20:5217-5220), Nek2 (Solanki et al., (2011) J Med Chem 54:1626-1639), and Eph receptor tyrosine kinase (Choi et al., (2009) Bioorg Med Chem Lett 19:4467-4470). However, all known Aurora kinase inhibitors, such as the aforementioned chemical probe VX680, are DFG-in inhibitors. Although the DFG motif is highly conserved among protein kinases, the mechanism by which small molecules induce the DFG flip is not well understood. Small molecules able to induce large conformational changes in the target enzyme have potential as superior lead compounds in drug discovery, as the altered structure of the dead-end complex is less suited for efficient interaction with substrate. This concept has led to the design of some of the most clinically successful kinases inhibitors to date. Imatinib and sorafenib stabilize the DFG-out conformation by establishing a bridging network of hydrogen bonds between the amide/urea inhibitor core and both a conserved glutamate side chain within the C-helix and the main chain amide of the DFG aspartate residue (Dietrich et al., (2010) Bioorg Med Chem 18:5738-5748). Molecular dynamics simulations were used to elucidate and propose a mechanism for the DFG-out conformation in MAPK p38a, in which the phenylalanine of the DFG motif is forced by the inhibitor from its hydrophobic pocket in the DFG-in (active state) to the solvent-exposed DFG-out (inactive state), triggering an overall rearrangement of the activation loop (Filomia et al., (2010) Bioorg Med Chem 18:6805-6812). However, the knowledge gained from these structures did not translate into an applicable method for the rational design of DFG-out inhibitors of other kinases.

DFG-out inhibitors of Aurora A utilizing a bisanilinopyrimidine scaffold are disclosed herein. A series of co-crystal structures established that electronegative and electron-withdrawing substituents, directed at the N-terminally flanking residue Ala273, yielded highly potent DFG-out inhibitors able to induce and stabilize a unique "DFG-out/loop-in" conformation. The data suggest an unprecedented mechanism of action, by which induced-dipole forces disrupt the charge distribution along the DFG peptide, causing the DFG to unwind. As the ADFG sequence is highly conserved among kinases, the strategy employed here to inhibit Aurora A may be applicable to other kinases as well.

SUMMARY

In accordance with the purposes of the disclosed materials and methods, as embodied and broadly described herein, the disclosed subject matter, in one aspect, relates to compounds, compositions and methods of making and using compounds and compositions. In specific aspects, the disclosed subject matter relates to cancer therapy and to anti-cancer compounds. More specifically, the subject matter disclosed herein relates to inhibitors of Aurora kinase and their use in the treatment of cancer. Further, disclosed herein are DFG-out inhibitors of Aurora kinase. Methods of screening for new Aurora kinase inhibitors are also disclosed.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

The patent or application file contains at least one drawing executed in color. Copies of this patent or patent application publication with color drawing(s) will be provided by the United States Patent and Trademark Office upon request and payment of the necessary fee.

FIG. 1A shows the structure of compound 1.

FIG. 2A shows the specific interactions of compound 1 with various residues of Aurora A (also shown in FIG. 1(b)).

The hinge region, DFG-in activation loop open conformation (compound 1).

FIG. 10A illustrates ATP bound to Aurora A. FIG. 10B illustrates compound 1 bound to Aurora A. FIG. 10C illustrates compound 31 bound to Aurora A.

FIG. 11A and FIG. 11B illustrate a comparison of surface structures for compounds 1 (FIG. 11A) and 31 (FIG. 11B) with Aurora A.

FIG. 12D shows compound 1 bound to Aurora A; $R^1$ hydrogen is shown near Leu194, Leu210 and Ala160, which are shown as spheres to show the narrow space $R^1$ is occupying in the binding region.

FIG. 13A through FIG. 13C illustrates the inhibition of phosphorylation of serine 10 on Histone H3 (substrate for Aurora a) in MDA-MB-468 cells by bisanilinopyrimidines with water solubilizing moieties. Inhibition at 2 concentrations (1 and 10 µM) for each compound is shown.

FIG. 15A through FIG. 15E show structural changes in Aurora A that are induced by DFG-out inhibitors. FIG. 15A is a surface representation of Aurora A in the DFG-in state (left, liganded with compound 3h) and DFG-out state (right, liganded with compound 3l); the activation loop is highlighted and the inhibitors are shown. FIG. 15B is a superposition that reveals global conformational changes upon binding of compound 7 particularly of the activation loop and the C-helix, which harbors the catalytic residue Glu181. In the DFG-in state, the loop is oriented away from the ATP site and the inhibitor is exposed to solvent. In the DFG-out state, the loop flips by about 180° and the N-terminal flank is positioned above the active site, shielding the inhibitor from solvent. FIG. 15C shows the conformation of the ADFGW segment in the DFG-in state liganded with compound 3h and the DFG-out state liganded with compound 7. The residue closest to the inhibitor is Ala273 (3.4 Å). The DFG-flip causes drastic conformational changes of the backbone, beginning with residue Asp274, forcing Trp277 and the entire activation loop to change direction. The binding interactions of Trp277 in the DFG-in and DFG-out states are shown in FIG. 26. The C-helix of FIG. 15B gives way to accommodate the new conformation of Phe275. FIG. 15D shows that, in the DFG-out conformation, the side chain of Asp274 interacts with residues Arg255 and Asp256, and the conformation of the activation loop is stabilized through hydrogen bonding interactions between the main chain atoms of His280 and Lys141. The loop is shaded according to temperature factors from light grey (low B-factor) to dark grey (high B-factor). Potential hydrogen bonding interactions are indicated as black dotted lines. FIG. 15E is a comparison of the molecular mode of action of VX680 (PDB 3E5A), compound 3h, and compound 3l (stereo presentation).

FIG. 16A shows compounds 3o and 13a are analogues of the DFG-out inhibitor compound 3l (substitutions are highlighted). Both inhibitors induced the DFG flip and displayed the same general interaction pattern as compound 3l. FIG. 16B shows that introduction of a fluorine to the pyrimidine ring (compound 3o) fosters van-der-Waals interactions with hydrophobic residues around the gatekeeper residue Leu210, resulting in increased inhibitory activity. FIG. 16C shows that substitution of tetrazole for carboxyl in para-position of the B-ring (compound 3a) preserves the electrostatic interaction with Arg137, and the inhibitory potency remains unchanged. Shown in blue mesh is the $2F_o$-$F_c$ electron density of the inhibitors, contoured at $1\sigma$. Potential hydrogen bonding and hydrophobic interactions are indicated as dotted lines.

FIG. 17A shows a model of the collision complex of the DFG-in state of Aurora A with the DFG-out inhibitor compound 3l, based on superimposition of the co-crystal structures of compounds 3l and 3h. Displayed are the closest distances (Å) between the chlorine substituent and the enzyme. The ~0.8 Å reduced distance in the dead-end complex indicates attraction of Ala273, a feature observed for the DFG-out inhibitors compounds 6a, 3l, 6i, and 6n and, to a lesser degree, for the DFG-in inhibitors compounds 6h and 6d (FIGS. 21 and 22). FIG. 17B is a schematic showing the electric dipoles along the C—R bonds (R=F, Cl, Br, C≡N) of the inhibitor can induce a dipole along the $C_\alpha$-$C_\beta$ bond of Ala273. The dipole-dipole interaction is stabilized by altering the charge distribution along the DFG backbone, allowing or forcing the compact DFG-in state to unwind. FIG. 17C shows a geometric arrangement of compounds 6h, 6d, 6a, 3l, 6i, and 6n and Ala273 in the experimentally determined dead-end complexes. Substituents able to induce the DFG flip (compounds 6a, 3l, 6i, and 6n) align linearly with the $C_\alpha$-$C_\beta$ bond of Ala273, whereas the C—F bonds of the DFG-in compounds 6h and 6d are positioned orthogonal.

FIG. 18A shows the ADFG-in states of Aurora A, ABL1, Rock1, and LCK are highly similar, indicating that exogenous dipoles directed at the alanine residue can induce similar structural changes in these kinases. FIG. 18B shows that CDK2, MAPK3, and MER adopt a different conformation in the C-terminal flank and therefore can respond to exogenous dipoles differently. The r.m.s.d. values for the ADFG-in state of various kinases with respect to Aurora A are shown in Table 2. FIG. 18C shows the conformation of compound 3l bound to the active site of Aurora A is incompatible for efficient binding with CDK2. The model was generated by superimposition of the complexes of Aurora—with compound 3l and CDK2 with compound 3l. FIG. 18D shows the co-crystal structure of CDK2 in complex with compound 3l and reveals that the bisanilinopyrimidine scaffold adopts an (s)-trans conformation (defined as the position of the groups colored red across the C—N bond), the A-ring pointing away from the DFG. FIG. 18E shows the (s)-cis and (s)-trans conformation of compound 3l found in Aurora A and CDK2, respectively. The $2F_o$-$F_c$ electron density around the inhibitor in Panel (d) is contoured at $1\sigma$. Potential hydrogen bonding, van-der-Waals interactions, and steric clashes are indicated as dotted lines. The structure of CDK2 with compound 3lh is shown in the FIG. 25.

(FIG. 21A) Aurora A—1, (FIG. 21B) Aurora A—6q, (FIG. 21C) Aurora A—6h, (FIG. 21D) Aurora A—6d.

(FIG. 22A) Aurora A—6a, (FIG. 22B) Aurora A—3l, (FIG. 22C) Aurora A—6i, (FIG. 22D) Aurora A—6n.

FIG. 23A through FIG. 23l show binding modes of bisanilinopyrimidine inhibitors with Aurora A. Crystal structures were determined for Aurora A liganded with different ortho-substituted bisanilinopyrimidine inhibitors. The hinge region (residues 211-213) is indicated in light grey, the DFG (residues 274-276) in darker grey, the activation loop (residues 277-293) in darkest grey. The dotted lines indicate the close distance of electronegative groups to the methyl group of Ala273. The $F_o$-$F_c$ electron density resulting from refinement omitting the inhibitor is shown as mesh, contoured at 2.5 G. The insets are surface representations of the overall structures. Compounds 3h, 1, 6q, 6h, and 6d are DFG-in inhibitors; compounds 6a, 3l, 6i, and 6n are DFG-out inhibitors.

FIG. 25A is the structure of 3h bound to CDK2. FIG. 25B is the structure of compound 3l bound to CDK2. Shown as mesh is the $F_o$-$F_c$ electron density map from refinements omitting the inhibitors, contoured at 2.5 G.

DETAILED DESCRIPTION

Figures 1A, 1B, 1C:
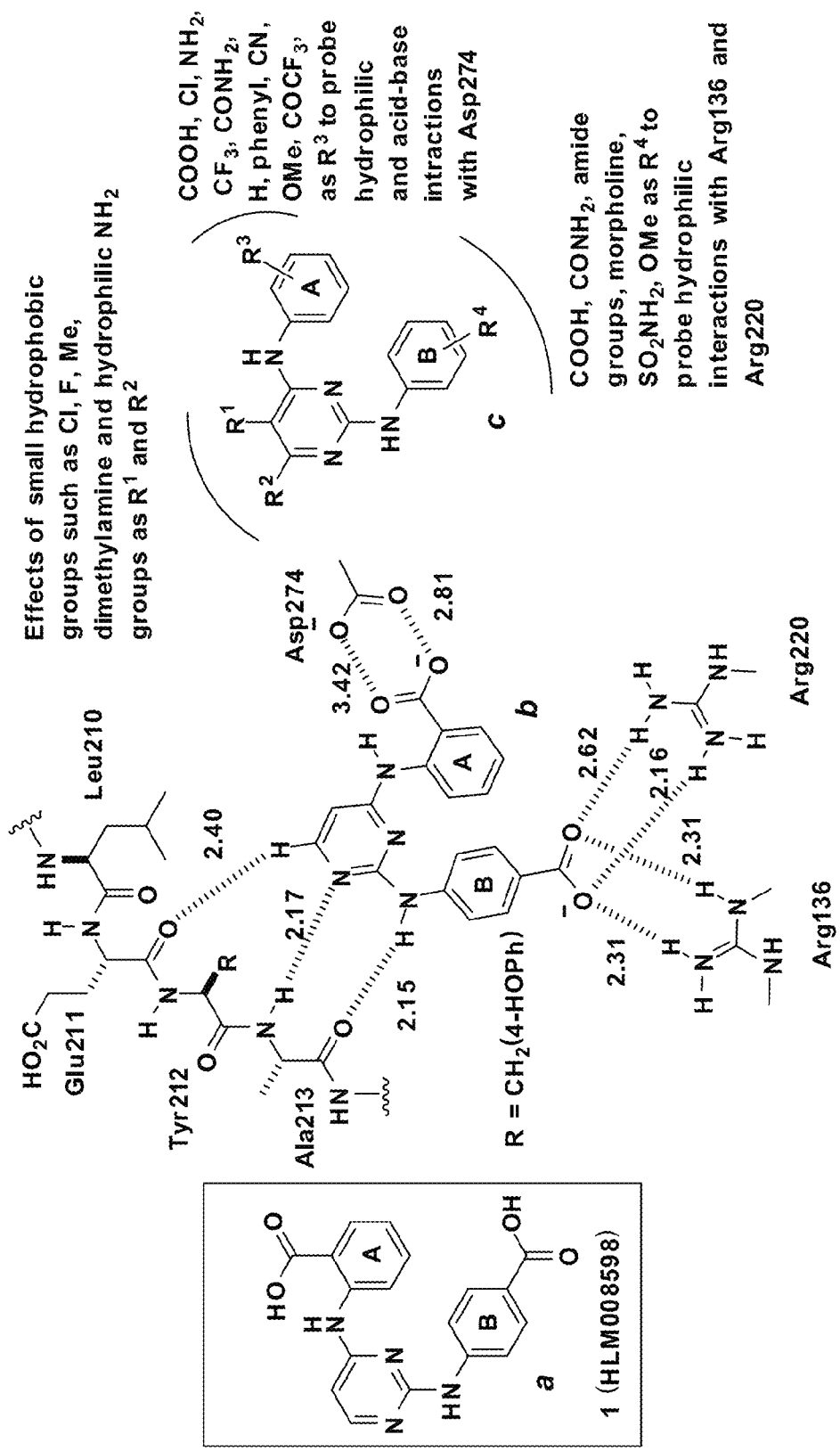
FIG. 1A shows compound 1, a potent and highly selective inhibitor for Aurora A over Aurora B, and its interactions with Aurora A. Synthetic alternatives to various functional groups on the molecule are also described. Specifically.
FIG. 1B shows the specific interactions of compound 1 with various residues of Aurora A.
FIG. 1C describes various synthetic modifications of compound 1.

The materials, compounds, compositions, and methods described herein may be understood more readily by reference to the following detailed description of specific aspects of the disclosed subject matter, the Figures, and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

GENERAL DEFINITIONS

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an inhibitor" includes mixtures of two or more such inhibitors, reference to "the kinase" includes mixtures of two or more such kinase, and the like.

"Optional" or "optionally" means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

By "reduce" or other forms of the word, such as "reducing" or "reduction," is meant lowering of an event or characteristic (e.g., tumor growth, metastasis). It is understood that this is typically in relation to some standard or expected value, in other words it is relative, but that it is not always necessary for the standard or relative value to be referred to. For example, "reduces tumor growth" means decreasing the amount of tumor cells relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, "treatment" refers to obtaining beneficial or desired clinical results. Beneficial or desired clinical results include, but are not limited to, any one or more of: alleviation of one or more symptoms (such as tumor growth or metastasis), diminishment of extent of cancer, stabilized (i.e., not worsening) state of cancer, preventing or delaying spread (e.g., metastasis) of the cancer, preventing or delaying occurrence or recurrence of cancer, delay or slowing of cancer progression, amelioration of the cancer state, and remission (whether partial or total).

The term "patient" preferably refers to a human in need of treatment with an anti-cancer agent or treatment for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others, that are in need of treatment with an anti-cancer agent or treatment.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

CHEMICAL DEFINITIONS

As used herein, the term "composition" is intended to encompass a product comprising the specified ingredients in the specified amounts, as well as any product which results, directly or indirectly, from combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The symbols $A^n$ is used herein as merely a generic substitutent in the definitions below.

The term "alkoxy" as used herein is an alkyl group bound through a single, terminal ether linkage; that is, an "alkoxy" group can be defined as $-OA^1$ where $A^1$ is alkyl as defined above.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl and heteroaryl group can be substituted or unsubstituted. The aryl and heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula $-C(O)H$. Throughout this specification "C(O)" is a short hand notation for C=O.

The terms "amine" or "amino" as used herein are represented by the formula $NA^1A^2A^3$, where $A^1$, $A^2$, and $A^3$ can be, independently, hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" as used herein is represented by the formula —C(O)O$^-$.

The term "ester" as used herein is represented by the formula —OC(O)A$^1$ or —C(O)OA$^1$, where A$^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula A$^1$OA$^2$, where A$^1$ and A$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula A$^1$C(O)A$^2$, where A$^1$ and A$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" as used herein refers to the halogens fluorine, chlorine, bromine, and iodine.

The term "hydroxyl" as used herein is represented by the formula —OH.

The term "nitro" as used herein is represented by the formula —NO$_2$.

The term "cyano" as used herein is represented by the formula —CN

The term "azido" as used herein is represented by the formula —N$_3$.

The term "sulfonyl" is used herein to refer to the sulfo-oxo group represented by the formula —S(O)$_2$A$^1$, where A$^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH$_2$.

The term "thiol" as used herein is represented by the formula —SH.

It is to be understood that the compounds provided herein may contain chiral centers. Such chiral centers may be of either the (R-) or (S-) configuration. The compounds provided herein may either be enantiomerically pure, or be diastereomeric or enantiomeric mixtures. It is to be understood that the chiral centers of the compounds provided herein may undergo epimerization in vivo. As such, one of skill in the art will recognize that administration of a compound in its (R-) form is equivalent, for compounds that undergo epimerization in vivo, to administration of the compound in its (S-) form.

As used herein, substantially pure means sufficiently homogeneous to appear free of readily detectable impurities as determined by standard methods of analysis, such as thin layer chromatography (TLC), nuclear magnetic resonance (NMR), gel electrophoresis, high performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modern methods for purification of the compounds to produce substantially chemically pure compounds are known to those of skill in the art. A substantially chemically pure compound may, however, be a mixture of stereoisomers.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

A "pharmaceutically acceptable" component is one that is suitable for use with humans and/or animals without undue adverse side effects (such as toxicity, irritation, and allergic response) commensurate with a reasonable benefit/risk ratio.

"Pharmaceutically acceptable salt" refers to a salt that is pharmaceutically acceptable and has the desired pharmacological properties. Such salts include those that may be formed where acidic protons present in the compounds are capable of reacting with inorganic or organic bases. Suitable inorganic salts include those formed with the alkali metals, e.g., sodium, potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). When two acidic groups are present, a pharmaceutically acceptable salt may be a mono-acid-mono-salt or a di-salt; similarly, where there are more than two acidic groups present, some or all of such groups can be converted into salts.

"Pharmaceutically acceptable excipient" refers to an excipient that is conventionally useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

A "pharmaceutically acceptable carrier" is a carrier, such as a solvent, suspending agent or vehicle, for delivering the disclosed compounds to the patient. The carrier can be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

Effective amounts of a compound or composition described herein for treating a mammalian subject can include about 0.1 to about 1000 mg/Kg of body weight of the subject/day, such as from about 1 to about 100 mg/Kg/day, especially from about 10 to about 100 mg/Kg/day. The doses can be acute or chronic. A broad range of disclosed composition dosages are believed to be both safe and effective.

Reference will now be made in detail to specific aspects of the disclosed materials, compounds, compositions, articles, and methods, examples of which are illustrated in the accompanying Examples and Figures.

Compounds

Disclosed are compounds that are Aurora kinase inhibitors, e.g., Aurora A, B, and/or C kinase inhibitors. These disclosed compounds can be used in various compositions as anti-cancer therapeutics.

In certain embodiments, the disclosed compounds have the chemical structure shown in Formula I.

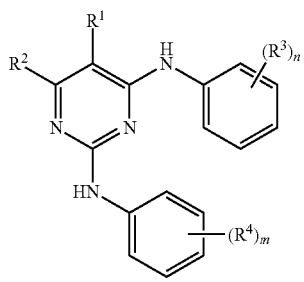

I

In Formula I, $R^1$ is selected from the group consisting of H, Cl, F, Br, I, $C_1$-$C_6$ alkyl, CN, $NO_2$, and $NH_2$.

Also in Formula I, $R^2$ is H, F, or Cl.

Additionally in Formula I, each $R^3$ is selected, independently, from the group consisting of Cl, Br, F, COOH, $CF_3$, CN, phenyl, $OCH_3$, $COR^5$, $CONH_2$, $CONR^5$, and $COONH_2$.

Further in Formula I, each $R^4$ is selected, independently, from the group consisting of H, COOH, $CONH_2$, $CONR^5$, $SO_2NH_2$, $CONSO_2R^5$, tetrazole, 4-morpholine, or $COR^5$. $R^5$ is $C_1$-$C_6$ alkyl, cycloalkyl, heteroaryl, or heteroalkyl.

Still further in Formula I, n is 1-5 (e.g., 1, 2, 3, 4, or 5) and m is 1-5 (e.g., 1, 2, 3, 4, or 5). Thus, in the disclosed compounds there can be from 1 to 5 different substituents $R^3$ and from 1 to 5 different substituents $R^4$. Pharmaceutically acceptable salts of these compounds are also disclosed.

In certain preferred aspects, the compound has formula I, wherein $R^3$ is 2-Cl, and n is 1. In other examples, the compound has formula I, wherein $R^4$ is 4-COOH, and m is 1. In still other examples, the compound has formula I, wherein $R^3$ is 2-Cl, n is 1, m is 1, and $R^4$ is COOH, $COR^5$, $CONH_2$, $CONR^5$, or $CONSO_2R^5$, wherein $R^5$ is $C_1$-$C_6$ alkyl, cycloalkyl, heteroaryl, or heteroalkyl.

Still further, the disclosed compounds can have the following formula II:

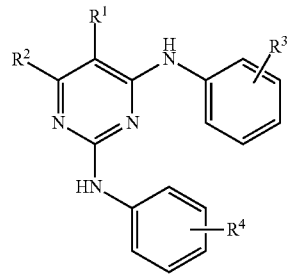

II

In Formula II, $R^1$ is selected from the group consisting of H, Cl, F, Br, I, $CH_3$ and $NH_2$; $R^2$ is H, F, or Cl.

Also in Formula II, $R^3$ is selected from the group consisting of 2-Cl, 2-Br, 2-F, 2-COOH, 2-$CF_3$, 2-CN, 2-phenyl, 2-$OCH_3$, 2-$COONH_2$, 4-COOH, 4-$OCH_3$.

Additionally in Formula II, $R^4$ is selected from the group consisting of H, COOH, 2-$CONH_2$, 4-$CONH_2$, $SO_2NH_2$, tetrazole, and 4-morpholine.

Still further, the disclosed compounds can have the following formula III:

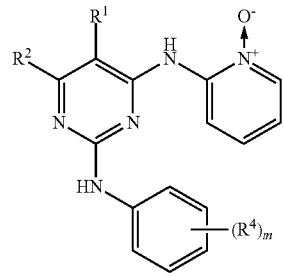

III

In Formula III, $R^1$, $R^2$, $R^4$, and m are as defined herein.

As disclosed herein, a series of compounds have been designed and prepared that, according to the data, have an unprecedented mechanism of action to induce the DFG flip in Aurora A, and other kinases as well, by induced-dipole forces. The vast majority of kinase inhibitors are so-called Type I inhibitors such as compounds 3h, 1, 6q, 6h, and 6d, which compete with ATP for binding to the open DFG-in state. The underlying mechanism by which small molecules induce the DFG flip is not understood, and experimental data are limited to a few well-studied cases such as Abl, p38-MAP and MEK1 (Schindler et al., (2000) *Science* 289:1938-1942; Pargellis et al., (2002) *Nat Struct Biol* 9:268-272). For these kinases, potent and selective Type II (partially allosteric) and Type III (fully allosteric) inhibitors have been designed, which act by occupying a pocket adjacent to the ATP site (Zhang et al., (2010) *Nature* 463:501-506; Comess et al., (2011) *ACS Chem Biol* 6:234-244; Dong et al., (2011) *Bioorg Med Chem Lett* 21:1315-1319). Although the here designed compounds 6a, 3l, 6i, 6n, 3o, and 13a are purely Type I, they induce and stabilize the DFG-out state with drastic consequences for the overall structure of the enzyme. These findings offer new opportunities in the rational design of DFG-out inhibitors of various kinases, by equipping suitable DFG-in inhibitor scaffolds with electric dipoles directed at the N-terminal flank.

Figure 3:
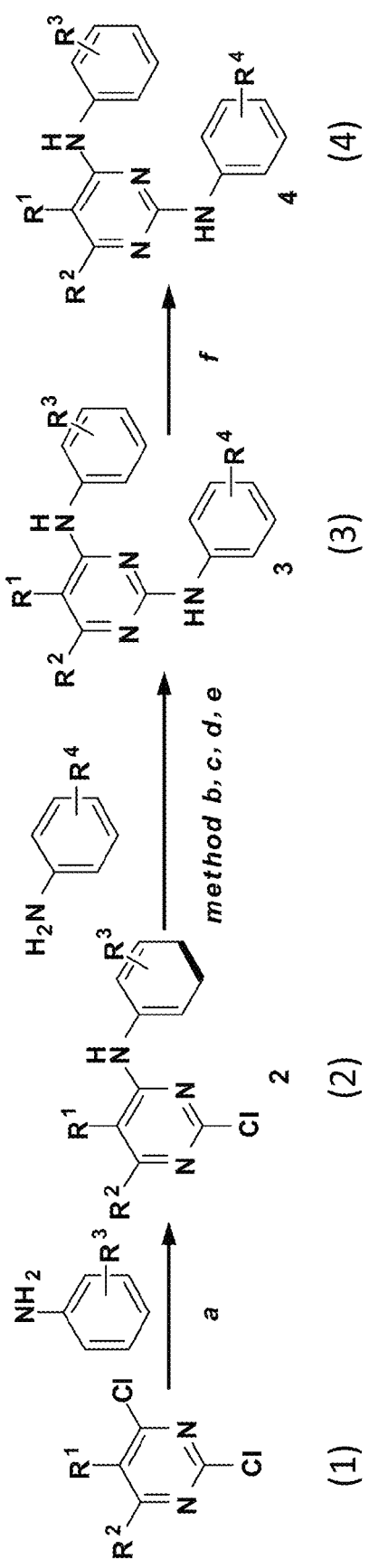
FIG. 3 is a general synthetic route to diphenylpyrimidine-2,4-diamine compounds. Reagents and conditions; method a: compound 1 is HLM008598 shown in FIG. 1, 0.1 M HCl in water (1-3 mL/mmol), microwave, 100° C., 30 min-24 h., 30-90% (when $R^3$=Cl, DIPEA, n-BuOH, seal tube, 150° C., reflux 4 days, 43%); method b: 0.1 M HCl in water (1.5 or 3 mL/mmol), microwave, 160° C., 15 min., 21-97%; method c: EtOH/1 M HCl water (1/1, 4 or 12 mL/mmol), microwave, 160° C., 15 min-1 h; method d: 4 M HCl in Dioxane (0.5 mL/mmol), 2-butanol (3 mL/mmol), seal tube, 120° C., overnight (24 h); method e: THF/1 M HCl water (1/2, 6 mL/mmol), microwave, 160° C., 15 min.); method THF/2 M NaOH water solution (1/2, 4 mL/mmol), seal tube, 100° C., 0.5, 69%.

FIG. 3 describes the general synthetic route used for preparation of dianilinipyrimidine (1) and diphenylpyrimidine-2,4-diamine-focused libraries (3) and (4) from readily available building blocks. The 2,4-dichloropyrimidine was initially reacted with the requisite commercially available anilines with the method predominantly using aqueous hydrochloric acid as the solvent, with microwave-assisted heating to obtain the required analogs (2). The library (2) was further functionalized to provide the libraries (3) and (4) bearing the B ring in good yields.

The common reported binding mode for kinases is 'DFG in', which is the ATP binding mode. See FIG. 14A through FIG. 16C. The compound 3h bound to Aurora A was observed in 'DFG in' mode, the same as ATP. Interestingly, the co-crystal structure of compound 3m with Aurora A showed the 'DFG out' conformation, which is rarely observed with Aurora A kinase. The ortho-Cl in A ring in compound 3m induces a large conformational change of the activation loop, where the ATP binding site is completely concealed by the closed activation loop.

The screening of compound 1 was identified as a potent and selective inhibitor for Aurora A (in vitro $IC_{50}$=0.073±0.002 μM) over Aurora B (in vitro $IC_{50}$=5.4±1.8 μM). Re-synthesis of (1) confirmed the structure and activity. The synthetic modifications around (1) are shown in the FIG. 1C.

Ortho-substitution on ring A impacts activity. Moving ortho-COOH to para-COOH reduced the activity (compound 3g, entry 8 of Table 1, $IC_{50}$=0.37 μM). Removing the substitution from ring A did not improve the activity (compound 3f, entry 7 of Table 1, $IC_{50}$=0.091 μM). Replacement of ortho-COOH in ring A with Cl improved the inhibitory activity by 2 fold (compound 3m, entry 15 of Table 1, $IC_{50}$=0.037 μM).

Para-substitution on ring B impacts activity. Moving para-COOH to ortho position decreased the activity (compound 3a, entry 2 of Table 1, $IC_{50}$=0.65 μM); replacement of para-COOH with ortho-$NH_2$ completely lost activity. Replacement of ortho-COOH with morpholine did not lead the improvement of activity (compound 3c, entry 4 of Table 1, $IC_{50}$=0.26 μM).

The removal of carboxylic acid from both ring A and ring B resulted in reduced inhibitory activity (compound 3d, entry 5 of Table 1, $IC_{50}$=1.9 μM). The methyl esters on both ring A and ring B showed no inhibitory activity. The substitution of the carboxylic acids on both ring A and ring B with primary amides retained the activity (compound 3e, entry 6 of Table 1, $IC_{50}$=0.086 μM).

The introduction of fluorine as $R^1$ on the pyrimidine ring showed 2-fold improvement of activity (compound 3h, entry 9 of Table 1, $IC_{50}$=0.039 μM). However, $CH_3$ and $NH_2$ groups as $R^1$ did not lead to an improvement in activity (compounds 3i and 4a, entries 10 and 11 of Table 1). This may indicate that larger hydrophobic groups or hydrophilic groups are not tolerated in the binding site.

The whole cell study of the pyrimdine library was carried out in MDA-MB-468 cell line. The original hit 1 and the most potent compounds 3m did not show inhibition in the cell assay, most probably due to poor solubility and cell permeability. The presence of carboxylic acid in both A and B rings showed poor cell activity. The compounds 3l, 3n, 3o and 3p (entries 14, 16, 17, 18 of Table 1) showed $IC_{50}$ less than 20 μM in whole cells.

In summary, Aurora A inhibitors with good activity have been identified. The X-ray crystallography studies assisted to understand the binding modes of the compounds under investigation. The conformational change observed with compound 3m (the activation loop closed) for Aurora A is an important observation in this study that has not been revealed with this class of compounds toward Aurora A.

Method

Further provided herein are methods of treating or preventing cancer in a subject, comprising administering to the subject an effective amount of a compound or composition as disclosed herein. The methods can further comprise administering a second compound or composition, such as, for example, anticancer agents or anti-inflammatory agents. Additionally, the method can further comprise administering an effective amount of ionizing radiation to the subject.

Methods of killing a tumor cell are also provided herein. The methods comprise contacting a tumor cell with an effective amount of a compound or composition as disclosed herein. The methods can further include administering a second compound or composition (e.g., an anticancer agent or an anti-inflammatory agent) or administering an effective amount of ionizing radiation to the subject.

Also provided herein are methods of radiotherapy of tumors, comprising contacting the tumor with an effective amount of a compound or composition as disclosed herein and irradiating the tumor with an effective amount of ionizing radiation.

Also disclosed are methods for treating oncological disorders in a patient. In one embodiment, an effective amount of one or more compounds or compositions disclosed herein is administered to a patient having an oncological disorder and who is in need of treatment thereof. The disclosed methods can optionally include identifying a patient who is or can be in need of treatment of an oncological disorder. The patient can be a human or other mammal, such as a primate (monkey, chimpanzee, ape, etc.), dog, cat, cow, pig, or horse, or other animals having an oncological disorder. Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Administration

The disclosed compounds can be administered either sequentially or simultaneously in separate or combined pharmaceutical formulations. When one or more of the disclosed compounds is used in combination with a second therapeutic agent, the dose of each compound can be either the same as or differ from that when the compound is used alone. Appropriate doses will be readily appreciated by those skilled in the art.

The term "administration" and variants thereof (e.g., "administering" a compound) in reference to a compound as described herein means introducing the compound or a prodrug of the compound into the system of the animal in need of treatment. When a compound as described herein or prodrug thereof is provided in combination with one or more other active agents (e.g., a cytotoxic agent, etc.), "administration" and its variants are each understood to include concurrent and sequential introduction of the compound or prodrug thereof and other agents.

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrastemal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 2003/0032594 and 2002/0120100 disclose amino acid sequences that can be coupled to another composition and that allows the composition to be translocated across biological membranes. U.S. Application Publication No. 2002/0035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively.

Many tumors and cancers have viral genome present in the tumor or cancer cells. For example, Epstein-Barr Virus (EBV) is associated with a number of mammalian malignancies. The compounds disclosed herein can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds disclosed herein can also be used in combination with viral based treatments of oncologic disease. For example, the compounds can be used with mutant herpes simplex virus in the treatment of non-small cell lung cancer (Toyoizumi, et al., "Combined therapy with chemotherapeutic agents and herpes simplex virus type IICP34.5 mutant (HSV-1716) in human non-small cell lung cancer," *Human Gene Therapy*, 1999, 10(18):17).

Therapeutic application of compounds and/or compositions containing them can be accomplished by any suitable therapeutic method and technique presently or prospectively known to those skilled in the art. Further, compounds and compositions disclosed herein have use as starting materials or intermediates for the preparation of other useful compounds and compositions.

Compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, hydrates, or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. No. 4,608,392; U.S. Pat. No. 4,992,478; U.S. Pat. No. 4,559,157; and U.S. Pat. No. 4,820,508.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art; for example, see U.S. Pat. No. 4,938,949.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

For the treatment of oncological disorders, compounds and agents and compositions disclosed herein can be administered to a patient in need of treatment prior to, subsequent to, or in combination with other antitumor or anticancer agents or substances (e.g., chemotherapeutic agents, immunotherapeutic agents, radiotherapeutic agents, cytotoxic agents, etc.) and/or with radiation therapy and/or with surgical treatment to remove a tumor. For example, compounds and agents and compositions disclosed herein can be used in methods of treating cancer wherein the patient is to be treated or is or has been treated with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation; East Hanover, N.J.) and HERCEPTIN (Genentech, Inc.; South San Francisco, Calif.), respectively. These other substances or radiation treatments can be given at the same as or at different times from the compounds disclosed herein. Examples of other suitable chemotherapeutic agents include, but are not limited to, altretamine, bleomycin, bortezomib (VELCADE), busulphan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib (IRESSA), gemcitabine, hydroxyurea, idarubicin, ifosfamide, imatinib (GLEEVEC), irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafur-uracil, temozolomide, thiotepa, tioguanine/thioguanine, topotecan, treosulfan, vinblastine, vincristine, vindesine, vinorelbine. In an exemplified embodiment, the chemotherapeutic agent is melphalan. Examples of suitable immunotherapeutic agents include, but are not limited to, alemtuzumab, cetuximab (ERBITUX), gemtuzumab, iodine 131 tositumomab, rituximab, trastuzamab (HERCEPTIN). Cytotoxic agents include, for example, radioactive isotopes (e.g., $I^{131}$, $I^{125}$, $Y^{90}$, $P^{32}$, etc), and toxins of bacterial, fungal, plant, or animal origin (e.g., ricin, botulinum toxin, anthrax toxin, aflatoxin, jellyfish venoms (e.g., box jellyfish, etc.) Also disclosed are methods for treating an oncological disorder comprising administering an effective amount of a compound and/or agent disclosed herein prior to, subsequent to, and/or in combination with administration of a chemotherapeutic agent, an immunotherapeutic agent, a radiotherapeutic agent, or radiotherapy.

Kits

Kits for practicing the methods described herein are further provided. By "kit" is intended any manufacture (e.g., a package or a container) comprising at least one reagent, e.g., anyone of the compounds described in Table 1. The kit can be promoted, distributed, or sold as a unit for performing the methods described herein. Additionally, the kits can contain a package insert describing the kit and methods for its use. Any or all of the kit reagents can be provided within containers that protect them from the external environment, such as in sealed containers or pouches.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Also disclosed are kits that comprise a composition comprising a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

Method of Screening

Also disclosed herein are methods of identifying a putative anti-cancer compound comprising contacting an Aurora kinase with a target compound and determining whether the compound binds the kinase in a DFG-out configuration, wherein a compound that binds the DFG-out configuration is identified as a putative anti-cancer compound.

EXAMPLES

The following examples are set forth below to illustrate the methods, compositions, and results according to the disclosed subject matter. These examples are not intended to be inclusive of all aspects of the subject matter disclosed herein, but rather to illustrate representative methods, compositions, and results. These examples are not intended to exclude equivalents and variations, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Certain materials, compounds, compositions, and components disclosed herein can be obtained commercially or readily synthesized using techniques generally known to those of skill in the art. For example, the starting materials and reagents used in preparing the disclosed compositions are either available from commercial suppliers such as Acros Organics (Morris Plains, N.J.), Fisher Scientific (Pittsburgh, Pa.), or Sigma Aldrich (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Standard techniques were used for molecular, genetic and biochemical methods. See, generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4th Ed, John Wiley & Sons, Inc.; as well as Guthrie et al., Guide to Yeast Genetics and Molecular Biology, Methods in Enzymology, Vol. 194, Academic Press, Inc., (1991), PCR Protocols: A Guide to Methods and Applications (Innis, et al. 1990. Academic Press, San Diego, Calif.), McPherson et al., PCR Volume 1, Oxford University Press, (1991), Culture of Animal Cells: A Manual of Basic Technique, 2nd Ed. (R. I. Freshney. 1987. Liss, Inc. New York, N.Y.), and Gene Transfer and Expression Protocols, pp. 109-128, ed. E. J. Murray, The Humana Press Inc., Clifton, N.J.).

Reagents and compounds for biochemical and crystallization experiments were purchased from Sigma-Aldrich and Hampton Research unless otherwise indicated. The peptide substrate for activity assays was synthesized in the Moffitt Cancer Center Proteomics Core, and the Aurora inhibitor VX680 was from LC laboratories. During protein purification, the protein concentration was determined using the Coomassie reagent from BioRad with bovine serum albumin as a standard. The concentration of crystallization grade proteins was determined by A280 molar absorbance using a nanodrop ND-1000 spectrophotometer (Nanodrop Technologies). Non-linear regression analysis was performed using SigmaPlot (Systat Software).

Cloning and Expression.

The gene coding for the human Aurora A kinase domain comprising residues 123-390 was synthesized by Geneart (Heidelberg, Germany) and subcloned into a modified pET28 plasmid to provide fusion with cleavable hexahistidine-tagged maltose binding protein (MBP). The protein was overexpressed in E. coli Tuner (DE3) cells at 16° C.

Protein Purification.

The enzyme was purified by FPLC using $Ni^{2+}$-affinity chromatography (GE Healthcare; Piscataway, N.J.) in 50 mM phosphate (pH 7.2) and 300 mM NaCl with a linear gradient of 10-250 mM imidazole, followed by overnight digestion with PreScission protease at 4° C. The protein was exchanged into 50 mM MES (pH 6.5) and 1 mM DTT by rapid gel filtration, and the cleaved Aurora A construct and His6-MBP proteins were separated using a SP Sepharose Fast Flow ion exchange column (GE Healthcare), eluted with a 0-500 mM NaCl linear gradient. The pooled eluate was then concentrated and loaded onto a HiLoad Prep Grade 26/60 Superdex 200 column (GE Healthcare) equilibrated with 50 mM HEPES (pH 7.4), 100 mM NaCl, and 1 mM DTT. The resulting eluate yielded crystallization-grade monomeric enzyme.

Isothermal Titration Calorimetry (ITC).

The binding of inhibitors to Aurora A kinase was analyzed with a MicroCal iTC200 titration calorimeter (GE Healthcare, Piscataway, N.J.). The protein was exchanged into 100 mM Na/K phosphate (pH 7.4) via PD-10 columns (GE Healthcare Lifesciences; Piscataway, N.J.). A total of 18 aliquots (2.2 µL each) of the protein solution (125 µM) were injected into 200 µL of the inhibitor solution (10 µM) at 25° C. The ITC cell mixture was constantly stirred at 1000 rpm and recorded for 120 seconds between injections. Heat generation due to dilution (blank) was determined in a separate experiment by diluting protein into buffer. The corrected heat values were fitted using a nonlinear least square curve-fitting algorithm (Microcal Origin 7.0) to obtain the stoichiometry (n), binding constant ($K_a$, $K_d$) and change in enthalpy of the enzyme-ligand interaction (ΔH). The ITC graphs are shown in the FIG. 20A through FIG. 20E.

Protein Crystallography.

Aurora A was exchanged into 50 mM phosphate buffer (pH 7.4) including 1 mM DTT via PD-10 columns and was concentrated to 20 mg $mL^{-1}$ using Amicon Ultra-4 10K centrifugal devices (Millipore; Billerica, Mass.). Aurora A crystals were grown using sitting drop vapor diffusion at 18° C. from a 1:1 volume ratio of Aurora A and reservoir solution (200 mM sodium tartrate/20% polyethylene glycol 3350 for the DFG-in inhibitors or 10% Tacsimate/20% polyethylene glycol 3350 for the DFG-out inhibitors) with a final inhibitor concentration of 1 mM. Crystals appeared after two days and were allowed to grow for another 2 days. For data collection, crystals were harvested in a cryoprotectant mixture consisting of the respective reservoir composition including 1 mM inhibitor, 50 mM phosphate pH (7.4) and 25% (v/v) ethylene glycol. Diffraction data were recorded at −180° C. in the Moffitt Cancer Center Chemical Biology Core using CuKα X-rays generated by a Rigaku Micro-Max 007-HF X-ray generator, focused by mirror optics and equipped with a Rigaku CCD Saturn 944 system on single crystals frozen in liquid $N_2$. Data were reduced with XDS (Kabsch, (1993) Automatic processing of rotation diffraction data from crystals of initially unknown symmetry and cell constants, *J Appl Crystallogr* 26:795-800). The 'DFG-in' crystals belonged to the $P6_1 22$ space group, containing one monomer in the asymmetric unit. The 'DFG-out' crystals belonged to space group $P3_2$ with two monomers in the asymmetric unit. The structures were determined by molecular replacement using MOLREP (CCP4) (1994) The CCP4 suite: programs for protein crystallography, *Acta Crystallogr D Biol Crystallogr* 50:760-763) and PDB entry 3FDN as the search model. PHENIX (Adams et al., (2010) PHENIX: a comprehensive Python-based system for macromolecular structure solution, *Acta Crystallogr D Biol Crystallogr* 66:213-221) was employed for refinement (minimization and simulated annealing), and model building was performed using Coot (Emsley et al., (2004) Coot: model-building tools for molecular graphics, *Acta Crystallogr D Biol Crystallogr* 60:2126-2132). Figures were drawn with PyMol (Schrödinger, LLC). CDK2 was co-crystallized with compounds 1 and 7 using previously established conditions (Betzi et al., (2011) Discovery of a potential allosteric ligand binding site in CDK2, *ACS Chem Biol* 6:492-501) and the structures were determined accordingly. Data and refinement statistics are shown in Table A, along with the Fo-Fc electron density maps from refinement cycles omitting the respective ligand (FIG. 23A through FIG. 25B).

TABLE A

Summary of data collection and structure refinement[a].

| Structure (PDB ID) | 1 (3UO5) | 3 (3UO4) | 4 (3UOD) | 5 (3UP2) |
|---|---|---|---|---|
| *Data Collection* | | | | |
| Space group | P6₁22 | P6₁22 | P6₁22 | P6₁22 |
| Unit cell dimensions (Å) | a = 81.79 b = 81.79 c = 173.77 | a = 83.08 b = 83.08 c = 172.76 | a = 81.98 b = 81.98 c = 173.81 | a = 82.44 b = 82.44 c = 173.14 |
| Resolution range | 20-2.70 (2.75-2.70) | 20-2.45 (2.50-2.45) | 20-2.50 (2.60-2.50) | 20-2.30 (2.40-2.30) |
| Unique reflections | 9540 (473) | 13594 (773) | 12584 (1353) | 16126 (1860) |
| Completeness (%) | 94.9 (96.7) | 99.6 (99.9) | 99.7 (99.9) | 99.7 (99.9) |
| I/σI | 36.9 (7.3) | 60.9 (9.1) | 51.8 (7.8) | 54.4 (10.7) |
| $R_{merge}^{b}$ (%) | 14.1 (31.6) | 3.4 (20.7) | 4.4 (22.9) | 3.1 (15.8) |
| *Structure refinement* | | | | |
| Protein atoms | 2195 | 2188 | 2188 | 2188 |
| Average B-factor (Å²) | 42 | 58 | 52 | 50 |
| Ligand atoms | 23 | 29 | 27 | 28 |
| Average B-factor (Å²) | 29 | 43 | 39 | 38 |
| Solvent molecules | 36 | 49 | 45 | 98 |
| Average B-factor (Å²) | 33 | 46 | 44 | 46 |
| r.m.s.d.[c] bonds (Å) | 0.014 | 0.004 | 0.009 | 0.010 |
| r.m.s.d. angles (°) | 1.2 | 1.0 | 1.2 | 1.2 |
| $R_{cryst}^{d}$ (%) | 21.5 | 22.0 | 20.6 | 20.8 |
| $R_{free}^{e}$ (%) | 27.4 | 25.7 | 26.2 | 24.9 |
| $R_{free}$ reflection set size | 393 (4.5%) | 612 (4.5%) | 567 (4.5%) | 775 (4.5%) |
| Coordinate error (Å) | 0.40 | 0.27 | 0.22 | 0.17 |
| Structure (PDB ID) | 6 (3UNZ) | 7 (3UO6) | 8 (3UOH) | 9 (3UOJ) |
| *Data Collection* | | | | |
| Space group | P3₂ | P3₂ | P3₂ | P3₂ |
| Unit cell dimensions (Å) | a = 85.78 b = 85.78 c = 76.56 | a = 85.71 b = 85.71 c = 76.66 | a = 85.75 b = 85.75 c = 76.94 | a = 85.71 b = 85.71 c = 77.08 |
| Resolution range | 20-2.80 (2.90-2.80) | 20-2.80 (2.90-2.80) | 20-2.80 (2.90-2.80) | 20-2.90 (3.00-2.90) |
| Unique reflections | 15425 (1514) | 15518 (1509) | 15512 (1541) | 13920 (1330) |
| Completeness (%) | 99.4 (99.4) | 99.0 (99.7) | 99.5 (99.9) | 99.1 (99.0) |
| I/σI | 27.6 (4.6) | 31.8 (4.7) | 30.9 (5.3) | 25.5 (4.5) |
| $R_{merge}^{b}$ (%) | 7.8 (39.7) | 6.8 (37.4) | 6.2 (32.2) | 6.5 (41.1) |
| *Structure refinement* | | | | |
| Protein atoms | 4318 | 4340 | 4340 | 4318 |
| Average B-factor (Å²) | 58 | 69 | 64 | 70 |
| Ligand atoms | 48 | 48 | 48 | 50 |
| Average B-factor (Å²) | 39 | 42 | 42 | 43 |
| Solvent molecules | 38 | 21 | 34 | 28 |
| Average B-factor (Å²) | 44 | 46 | 44 | 49 |
| r.m.s.d.[d] bonds (Å) | 0.007 | 0.013 | 0.009 | 0.013 |
| r.m.s.d. angles (°) | 1.3 | 1.5 | 1.2 | 1.9 |
| $R_{cryst}^{e}$ (%) | 23.1 | 22.9 | 23.0 | 22.7 |
| $R_{free}^{f}$ (%) | 27.7 | 27.6 | 28.8 | 27.4 |
| $R_{free}$ reflection set size | 695 (4.5%) | 614 (4.0%) | 699 (4.5%) | 557 (4.0 %) |
| Coordinate error (Å) | 0.42 | 0.41 | 0.42 | 0.48 |
| Structure (PDB ID) | 10 (3UOK) | 11 (3UOL) | CDK2-1 (3UNJ) | CDK2-7 (3UNK) |
| *Data Collection* | | | | |
| Space group | P3₂ | P3₂ | P2₁2₁2₁ | P2₁2₁2₁ |
| Unit cell dimensions (Å) | a = 85.74 b = 85.74 c = 76.69 | a = 85.75 b = 85.75 c = 76.72 | a = 53.22 b = 71.96 c = 72.65 | a = 52.95 b = 72.02 c = 72.37 |
| Resolution range | 20-2.95 (3.00-2.95) | 20-2.40 (2.50-2.40) | 20-1.90 (2.00-1.90) | 20-2.10 (2.20-2.10) |
| Unique reflections | 13174 (598) | 24248 (2768) | 22465 (3133) | 16682 (2127) |
| Completeness (%) | 99.5 (99.8) | 98.4 (98.0) | 99.4 (99.2) | 100 (99.8) |
| I/σI | 22.4 (3.8) | 30.2 (7.5) | 18.5 (7.5) | 20.7 (6.9) |
| $R_{merge}^{b}$ (%) | 7.7 (47.4) | 4.4 (23.9) | 5.9 (23.2) | 7.5 (23.8) |
| *Structure refinement* | | | | |
| Protein atoms | 4358 | 4320 | 2366 | 2371 |
| Average B-factor (Å²) | 57 | 58 | 27 | 28 |
| Ligand atoms | 50 | 52 | 23 | 24 |
| Average B-factor (Å²) | 36 | 43 | 21 | 25 |
| Solvent molecules | 17 | 124 | 214 | 153 |
| Average B-factor (Å²) | 37 | 50 | 31 | 27 |
| r.m.s.d.[d] bonds (Å) | 0.010 | 0.012 | 0.010 | 0.010 |
| r.m.s.d. angles (°) | 1.5 | 1.5 | 1.4 | 1.3 |
| $R_{cryst}^{e}$ (%) | 22.3 | 23.6 | 19.9 | 18.0 |
| $R_{free}^{f}$ (%) | 27.6 | 27.9 | 26.1 | 23.4 |
| $R_{free}$ reflection set size | 525 (4.0%) | 1067 (4.4%) | 1124 (5.0%) | 835 (5.0%) |
| Coordinate error (Å) | 0.44 | 0.40 | 0.25 | 0.21 |

[a]The structure with compound 2 has been deposited as PDB code 3UP7 (Lawrence et al, submitted).
[b]$R_{merge}$ = quality of amplitudes (F) in the scaled data set, Diederichs & Karplus (1997), Nature Struct. Biol. 4, 269-275.
[c]r.m.s.d. = root mean square deviation from ideal values.
[d]$R_{cryst}$ = 100 × Σ|$F_{obs}$-$F_{model}$|/$F_{obs}$ where $F_{obs}$ and $F_{model}$ are observed and calculated structure factor amplitudes, respectively.
[e]$R_{free}$ is $R_{cryst}$ calculated for randomly chosen unique reflections, which were excluded from the refinement.

Accession Codes.

The atomic coordinates and structure factors for Aurora A in complex with compounds 1 and 3-11, and CDK2 in complex with compounds 1 and 7, have been deposited under accession numbers 3UO5, 3UO4, 3UOD, 3UP2, 3UNZ, 3UO6, 3UOH, 3UOJ, 3UOK, 3UOL, 3UNJ and 3UNK, respectively. The crystal structure of Aurora A with compound 2 has been deposited under code 3UP7.

Example 1

SAR Studies

SAR studies were initiated while attempts were being made to co-crystallize compound 1 with Aurora A. Focused library synthesis based on 1 (FIG. 1A through FIG. 1C) was first undertaken varying 4 points of molecular diversity ($R^1$, $R^2$, $R^3$ and $R^4$, see FIG. 1C) by systematically replacing or introducing the functional groups in the A and B-rings. Replacement of the B ring para-carboxylic acid in 1 by hydrogen or a morpholino as in 3b or 3c resulted in 13- and 10-fold loss of inhibitory activity, respectively (Entries 3 and 4, Table 1). Replacing both carboxylic acid moieties in 1 with hydrogen as in 3f (Entry 7, Table 1) resulted in 70-fold loss of potency. In addition, replacement of both carboxylic acid moieties by corresponding methyl esters as shown in 3e (Entry 6, Table 1) resulted in over 4000-fold loss of potency. However, compound 3g (Entry 8, Table 1) with carboxyamide in ortho- and para-positions of the A and B rings respectively was only 6-fold less potent than the compound 1. The SAR data showed the positions of both carboxylic acid moieties in A and B rings are critical for activity. Moving the B ring para-carboxylic acid moiety to the ortho-position, as in 3d, demonstrated 5000-fold loss of potency (Entry 5, Table 1, $IC_{50}$=31,300 nM). The compound 3q (Entry 18, Table 1, $IC_{50}$=18.3 nM) with meta-carboxylic acid in the B ring had a 3-fold loss of in vitro potency. Furthermore, moving the A ring carboxylic acid moiety in compound 1 from ortho- to para-position, as in 13i (Entry 10, Table 1), resulted in 42 fold loss of potency. Replacement of the B ring para-carboxylic acid by ortho-amide (compound 3a) resulted in >than 1000-fold loss of Aurora A inhibitory activity (Entries 2, Table 1). These observations suggested that the ortho-position of the A ring and para-position of the B ring are associated with enzymatic activity and focused library synthesis.

Figure 2A:
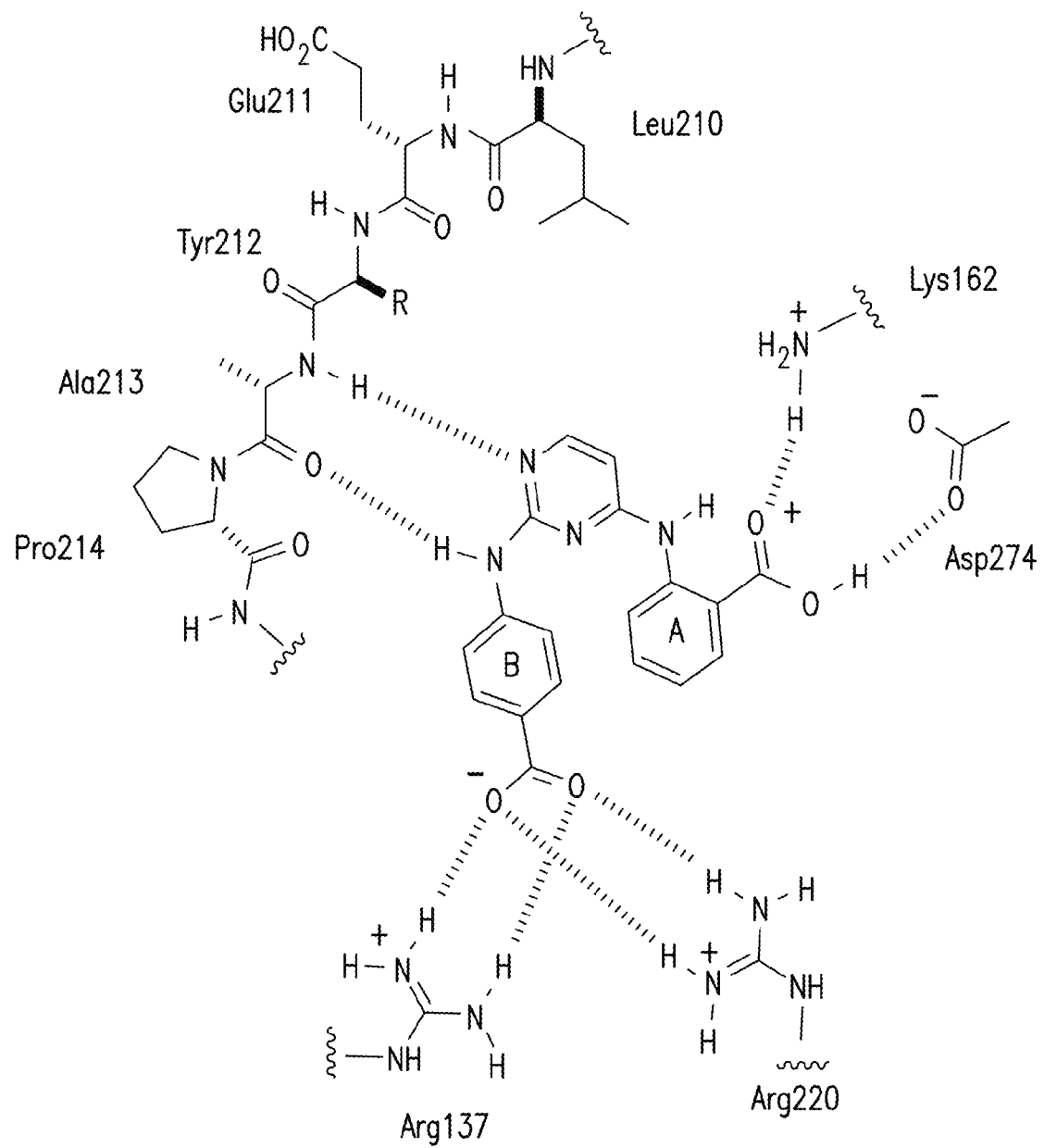
FIG. 2A is a drawing that shows compound 1's interactions with Aurora A.
Figure 2B:
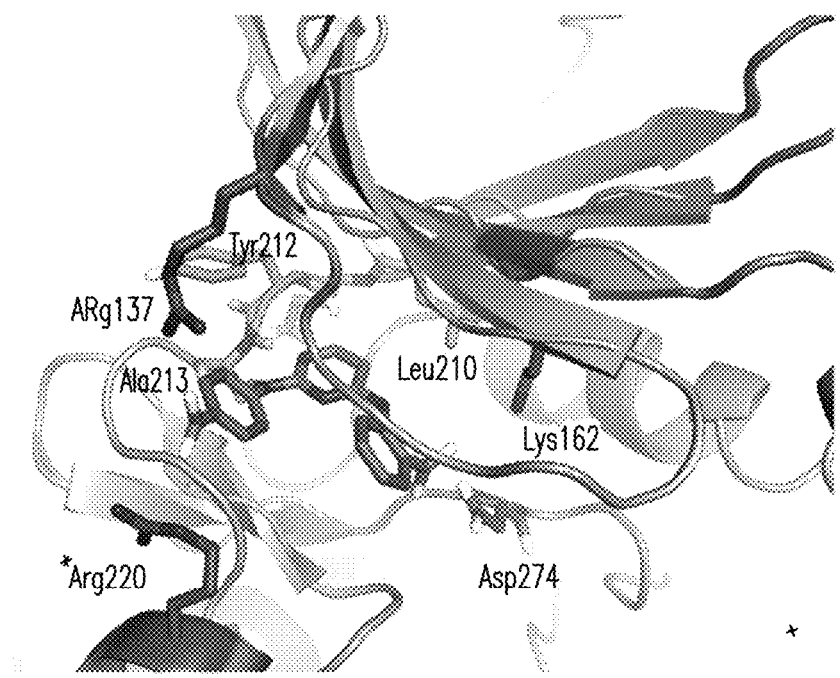
FIG. 2B shows the X-ray structure of compound 1 bound to Aurora A active site (compound 1).
Figure 2C:
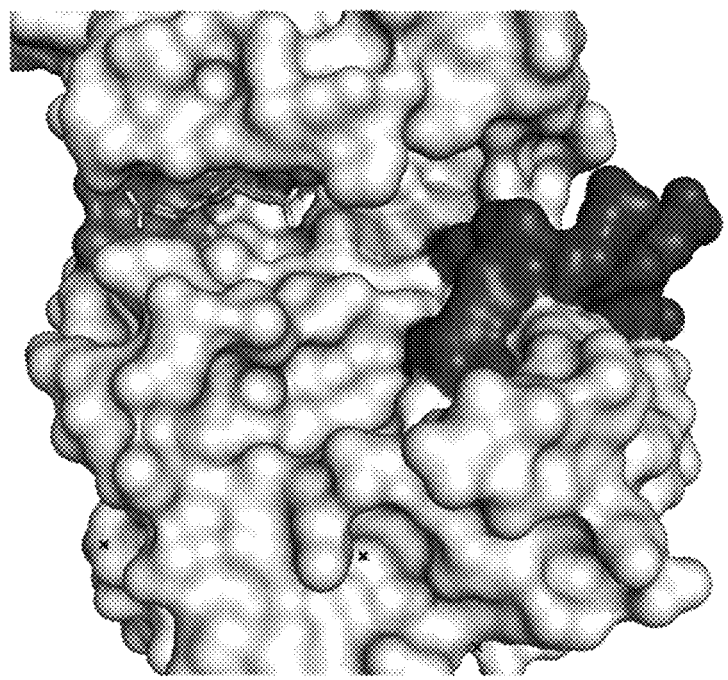
FIG. 2C shows compound 1 co-crystallized with Aurora A.
Figure 2D:
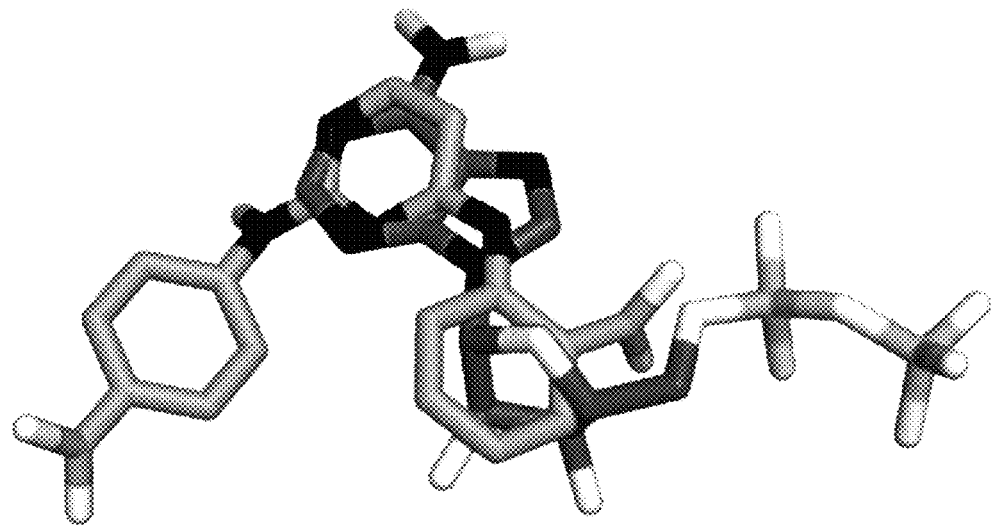
FIG. 2D is a structural overlay of ADP and compound 1.
Figure 22A:
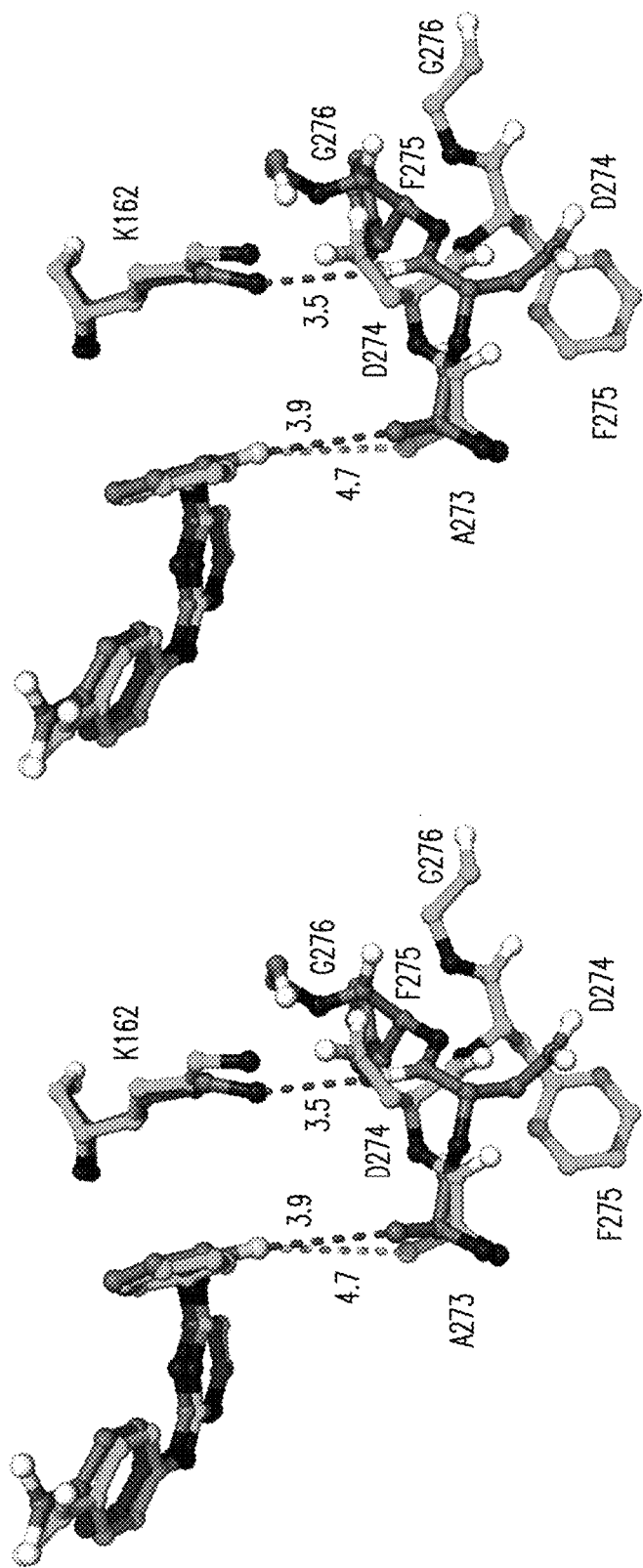
FIG. 22A through FIG. 22D show comparisons of the DFG-out dead-end complexes (stereo presentations). The structures of 1, 6q, and 6h were aligned with the structure of 3h. Shown are the inhibitors, the ADFG segment, Lys162 and distances in Å.
Figure 22B:
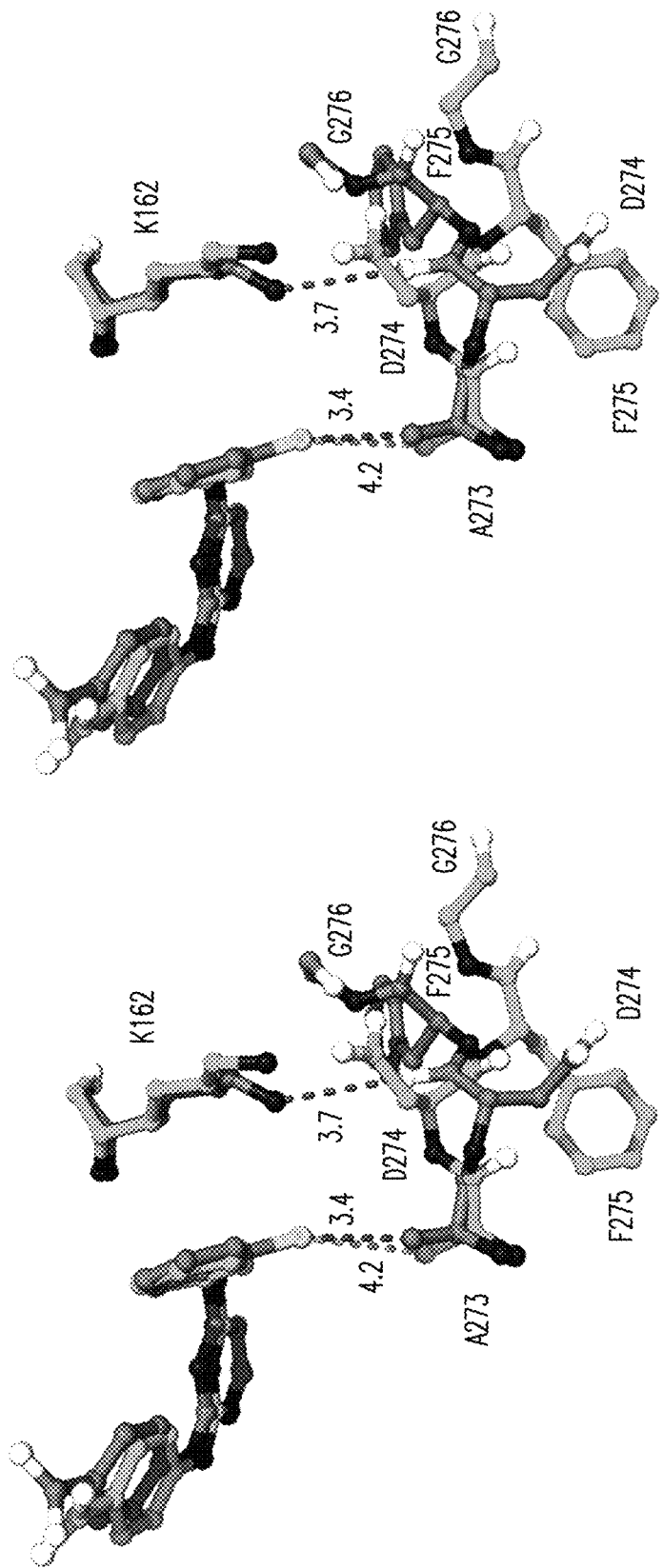
Figure 22C:
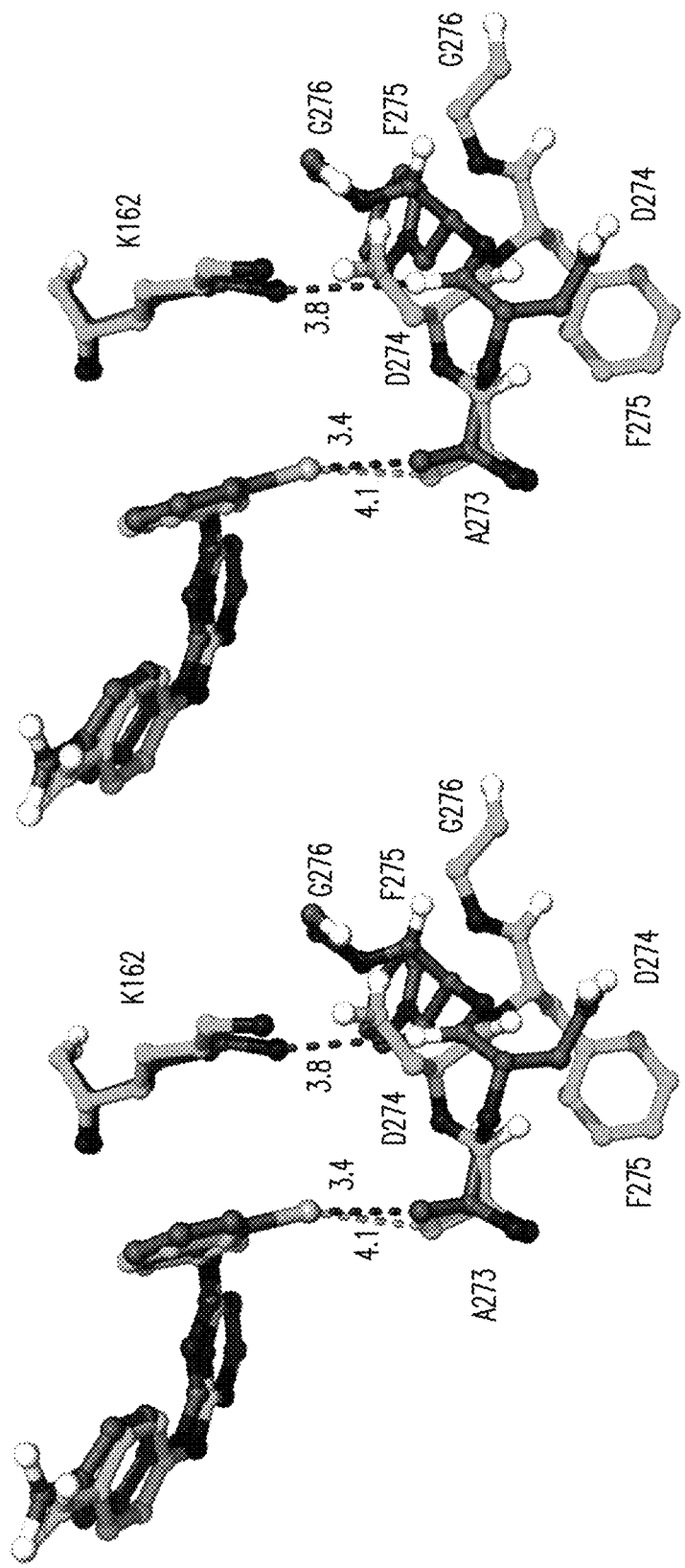
Figure 22D:
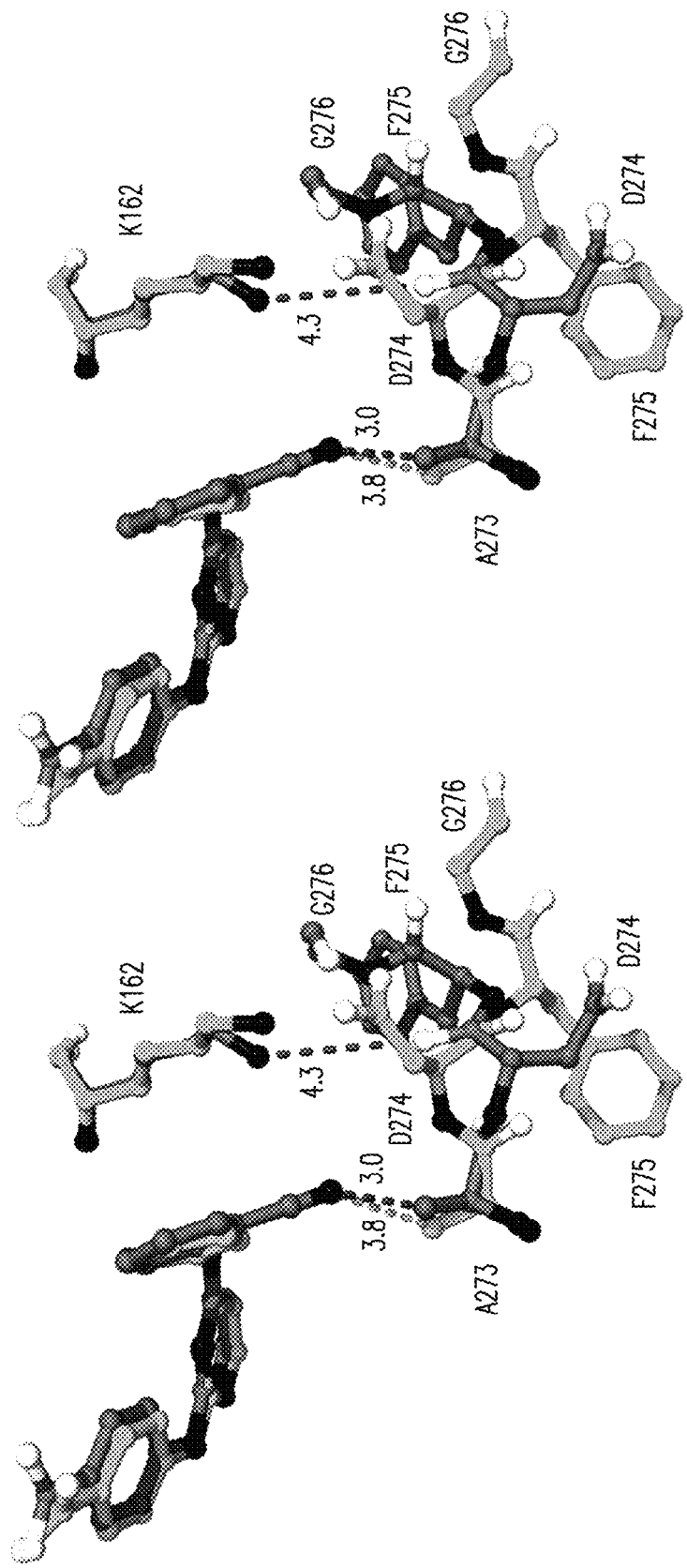
Figure 23A:
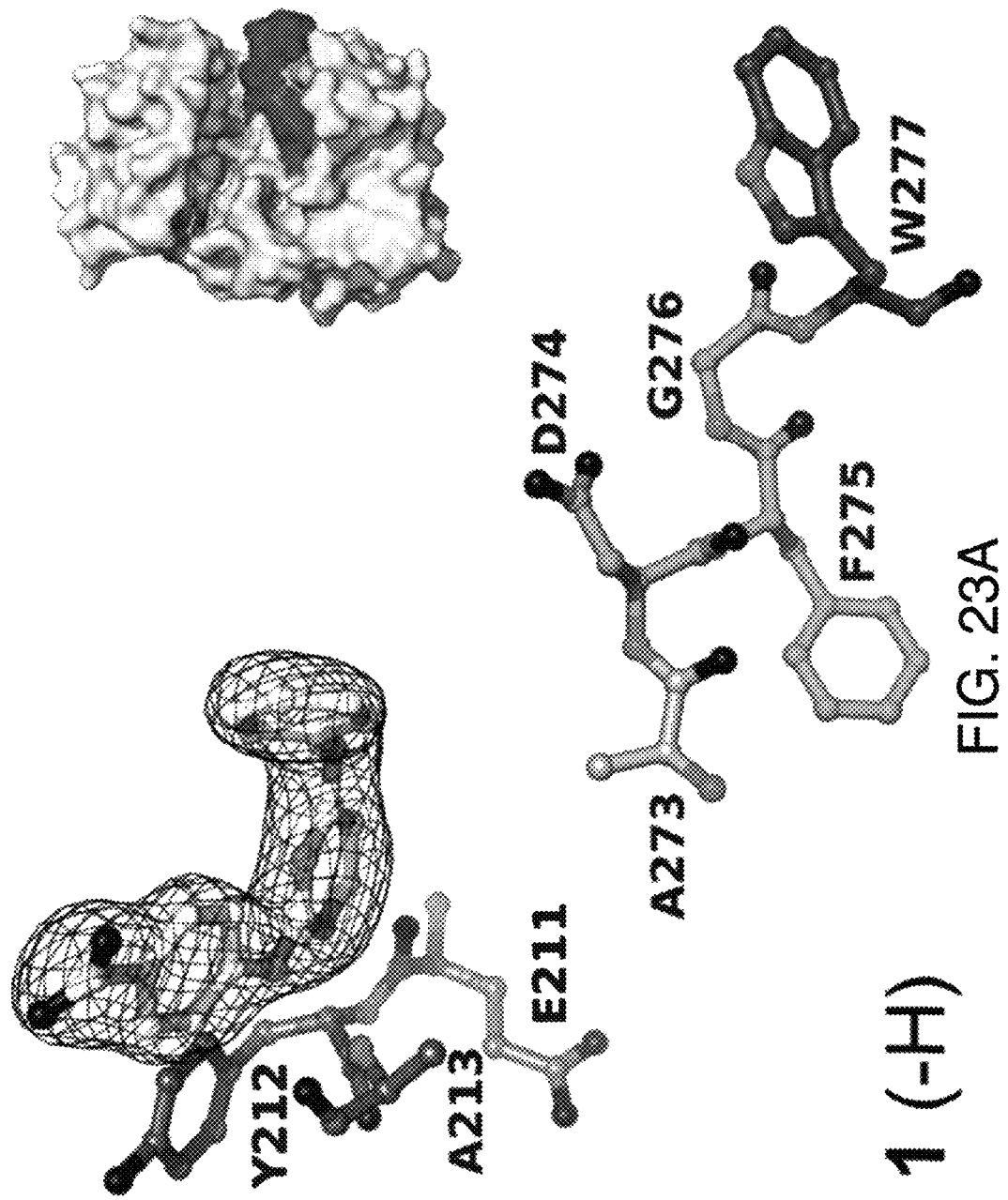
Figure 23B:
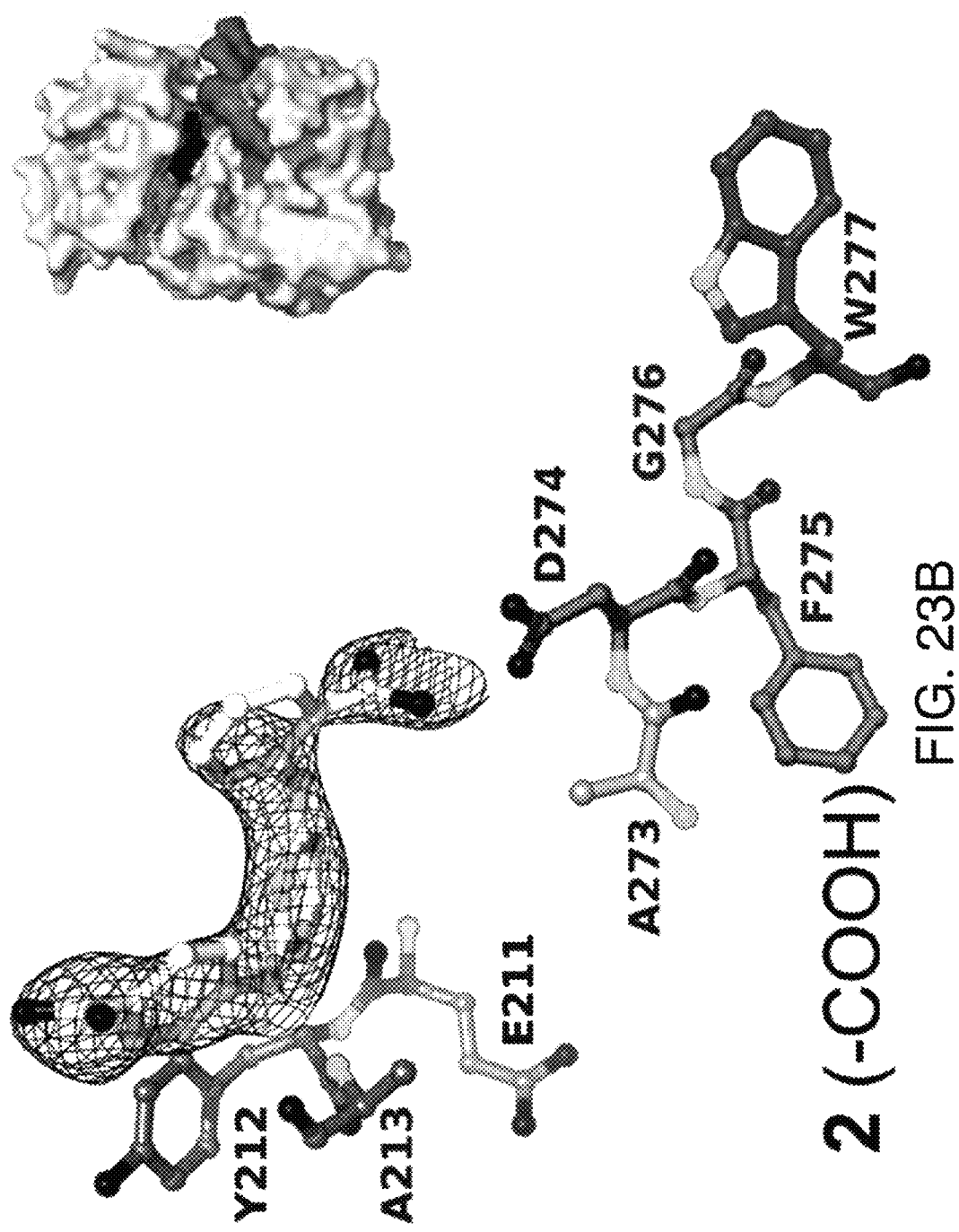
Figure 23C:
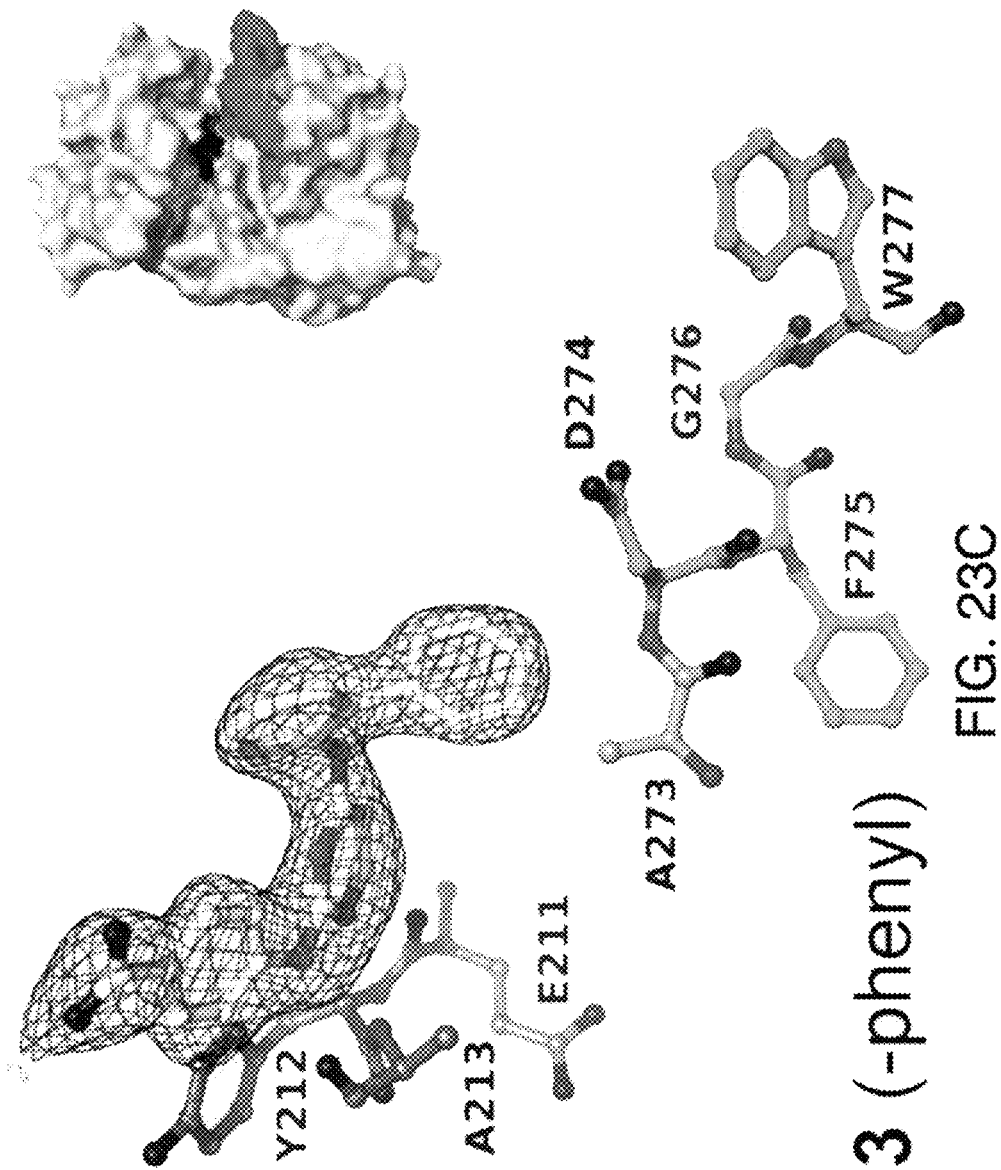
Figure 23D:
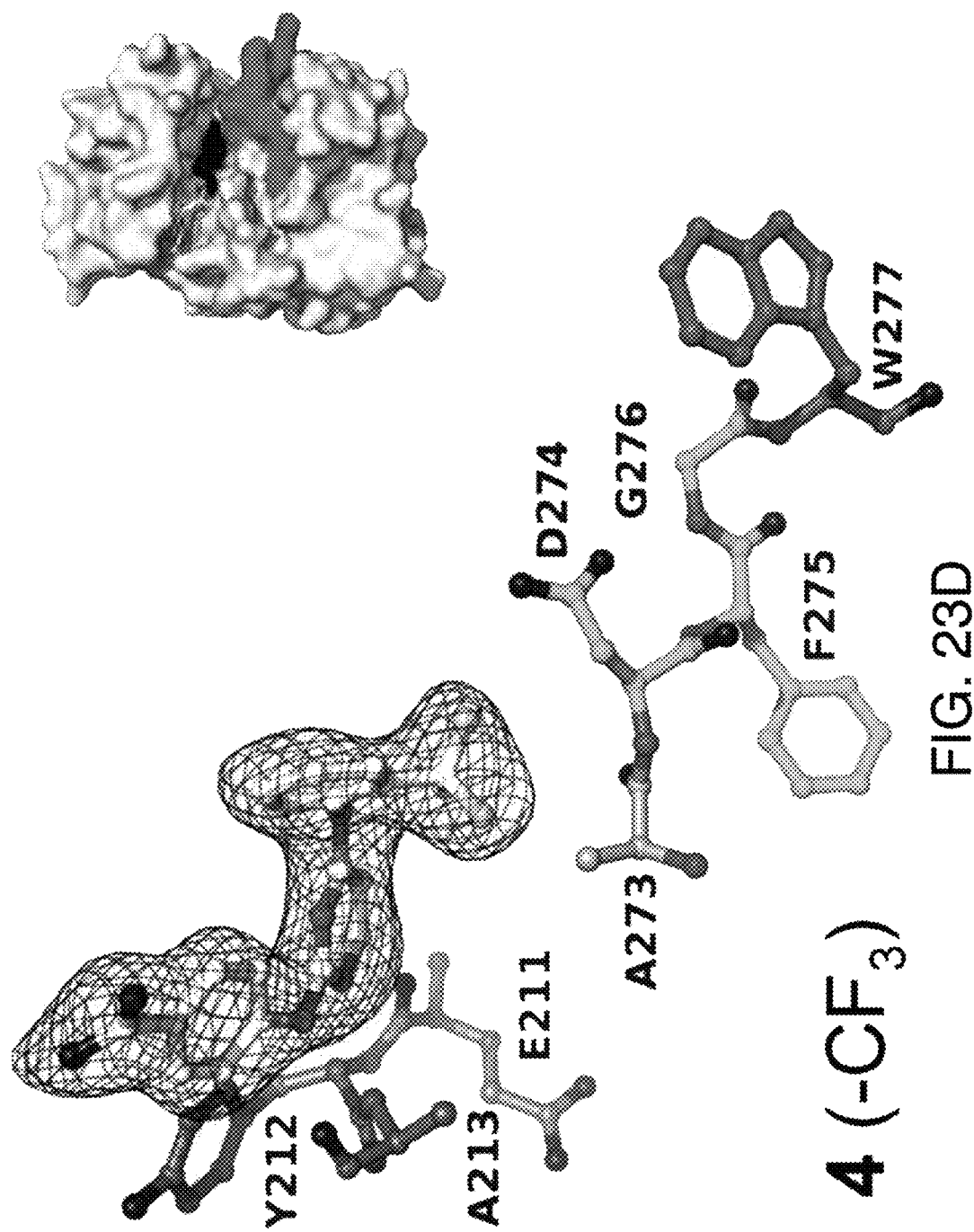
Figure 23E:
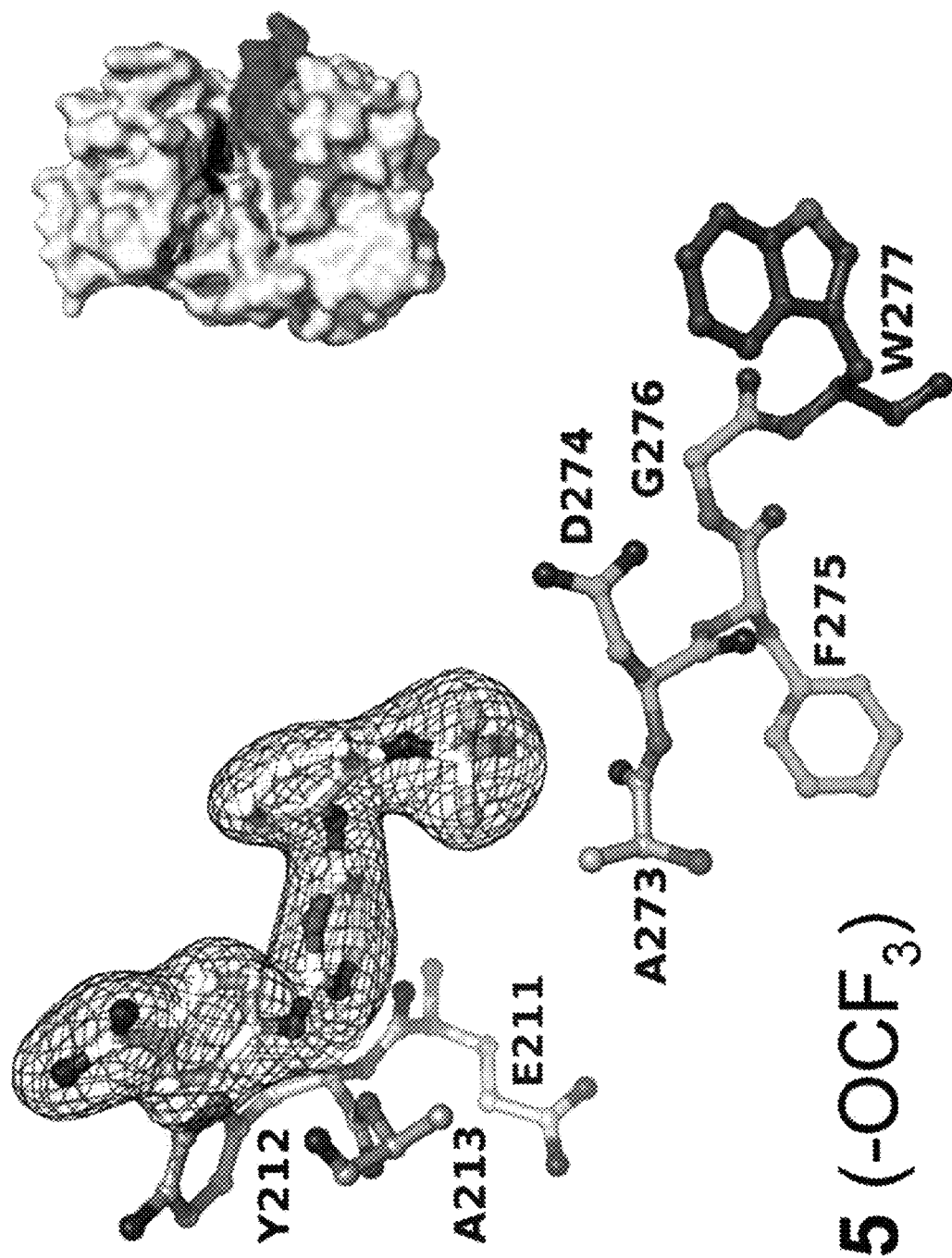
Figure 23F:
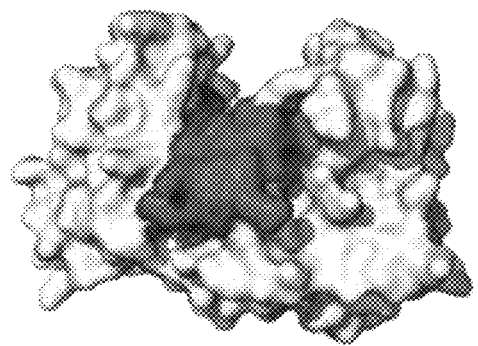
Figure 23F:
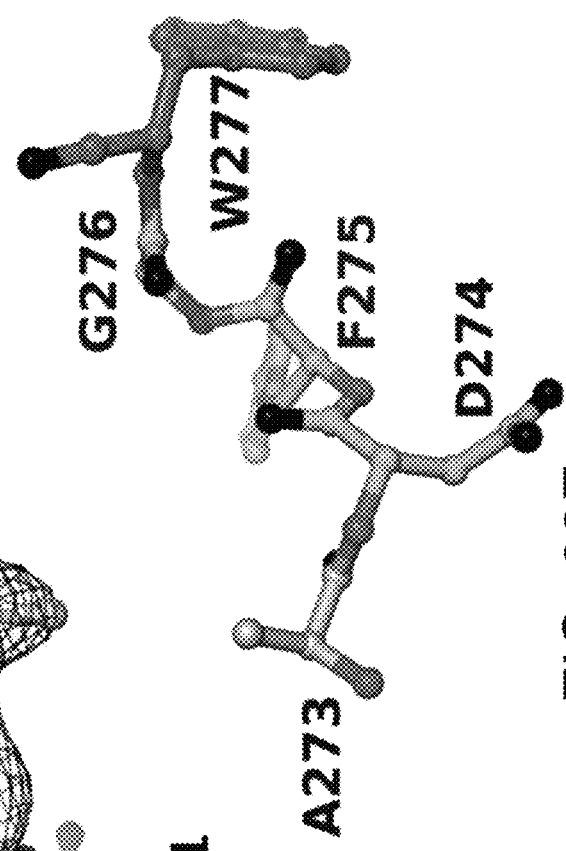
Figure 23F:
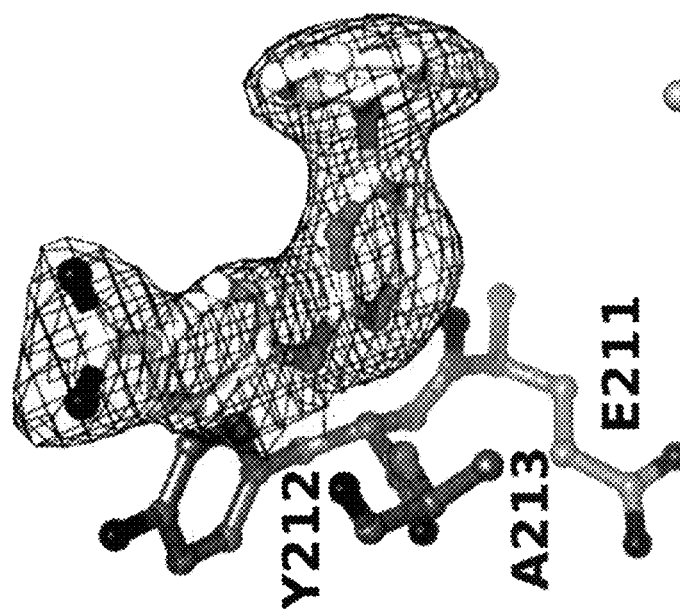
Figure 23G:
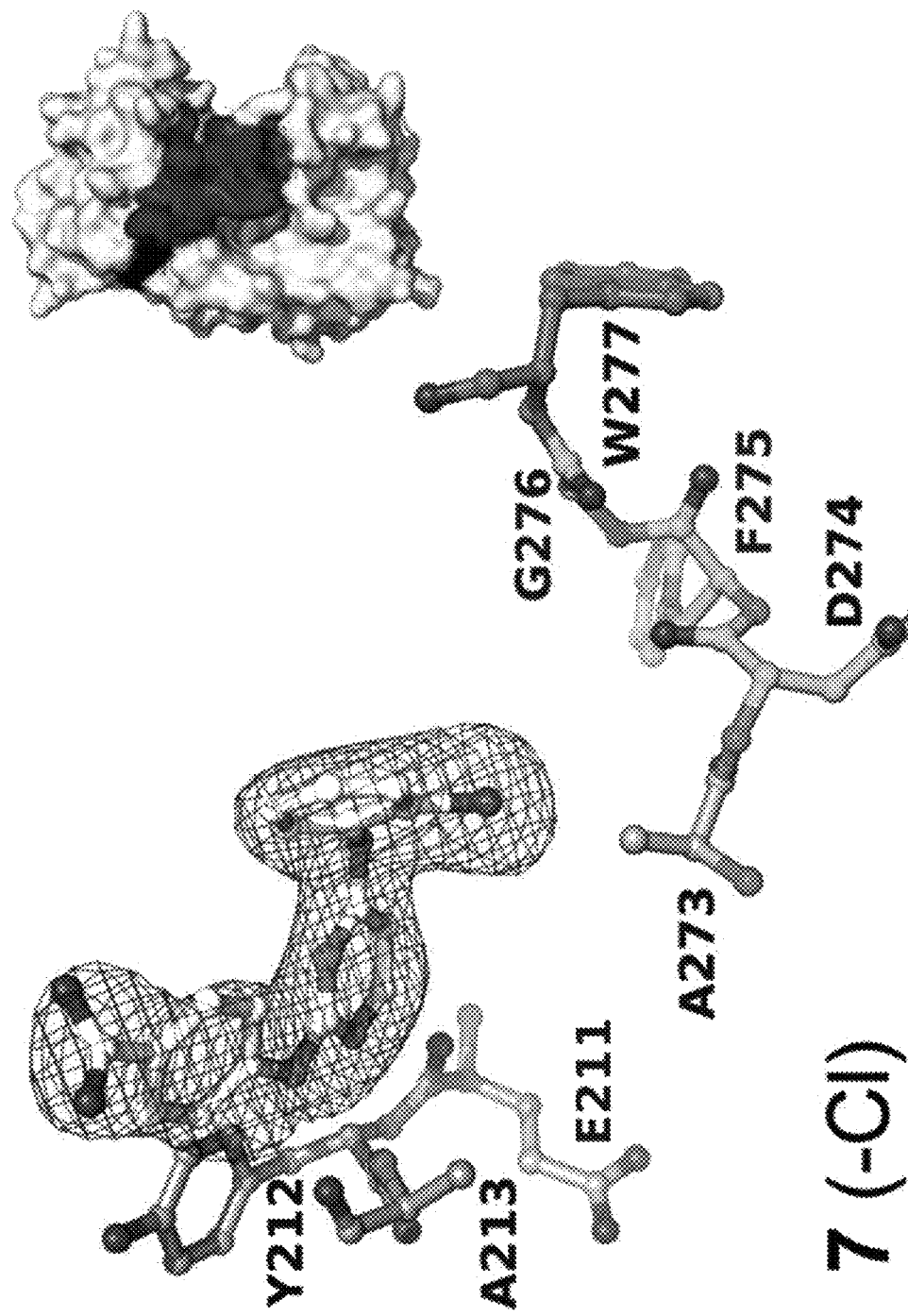
Figure 23H:
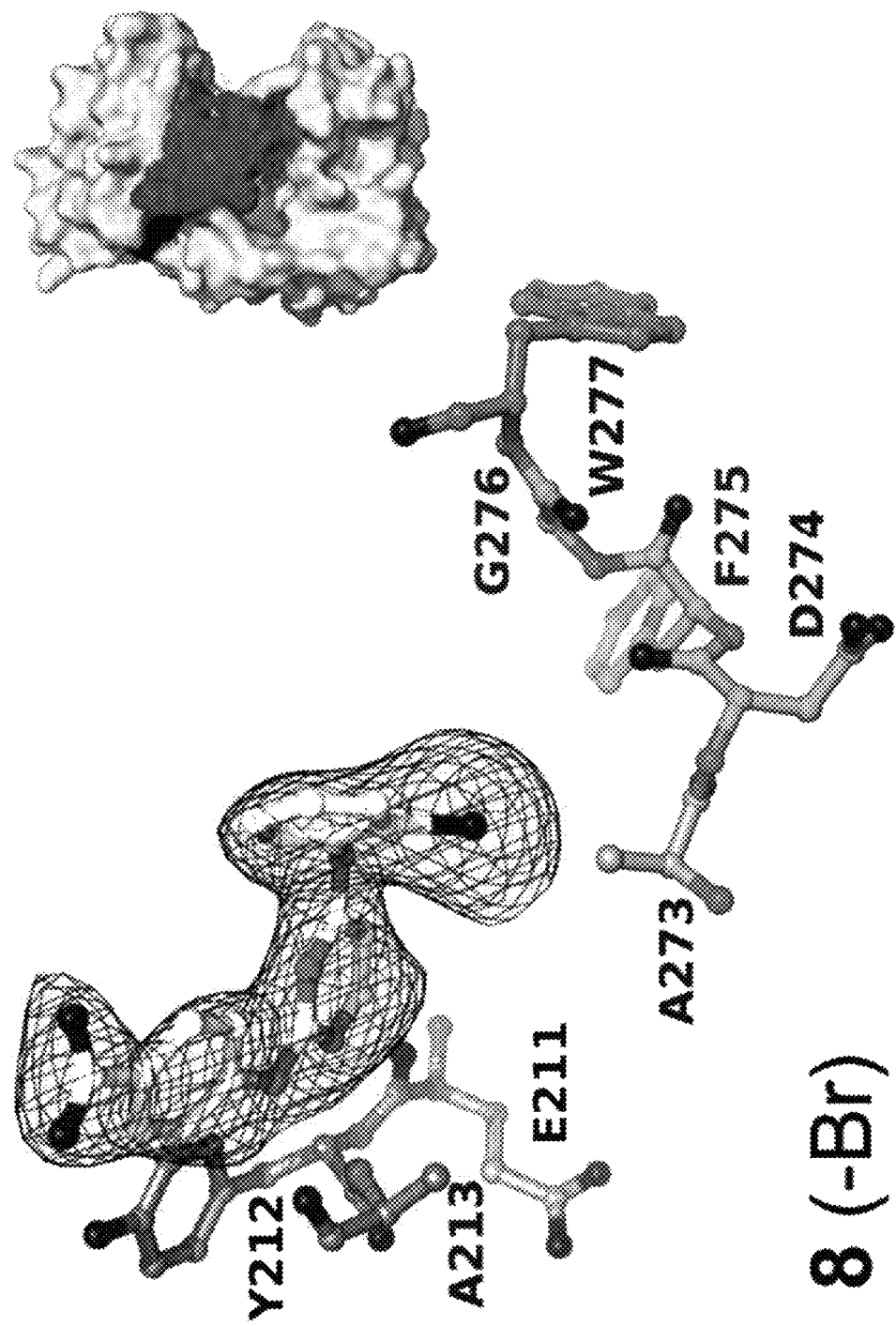
Figure 23I:
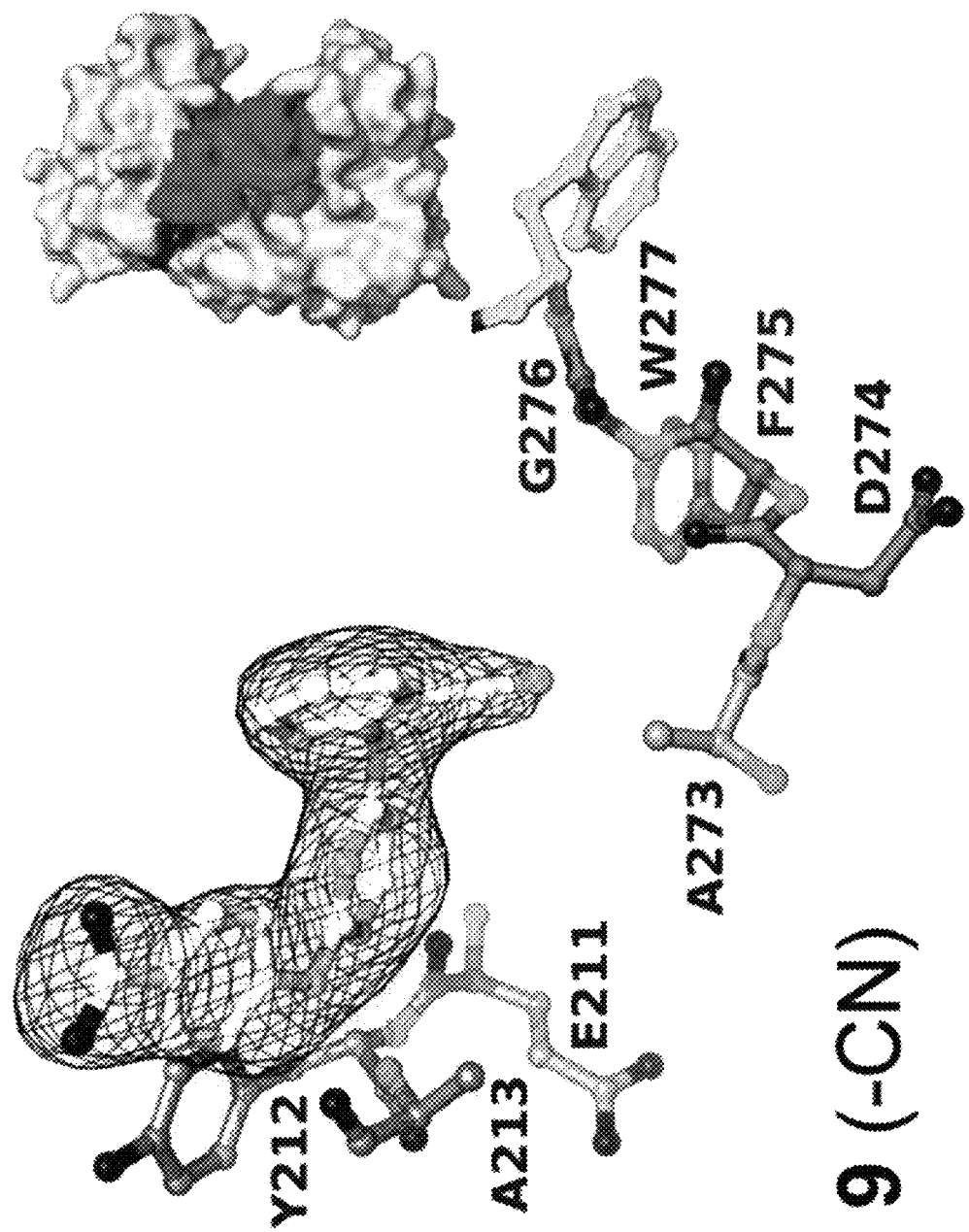
Figure 24A:
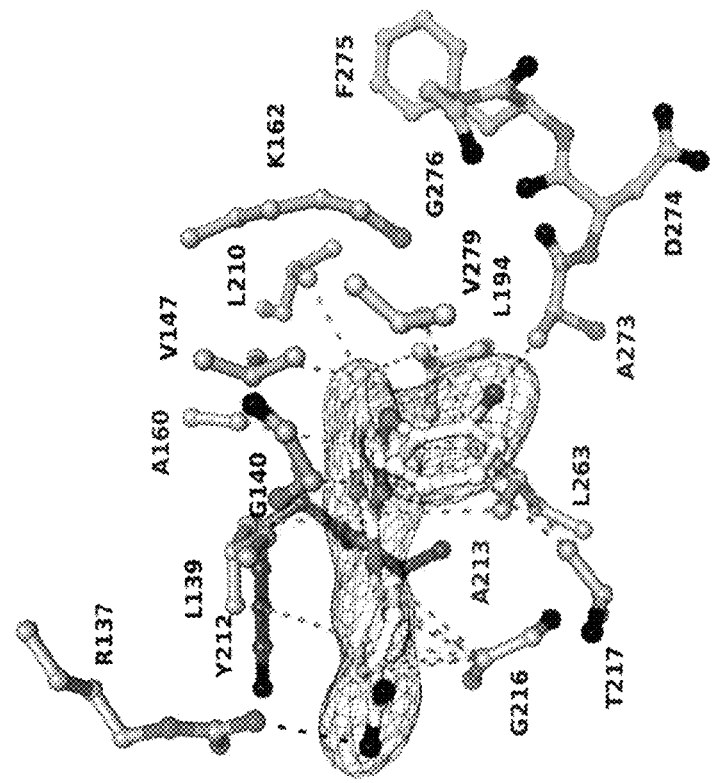
FIG. 24A and FIG. 24B show the crystal structures of 3o and 13a bound to Aurora A (Stereo presentations of the binding interactions between the DFG-out inhibitors 3o (FIG. 24A) and 13a (FIG. 24B) to Aurora A. The $F_o$-$F_c$ electron density map of the omitted inhibitor is contoured at 2.5 σ and shown in mesh. Potential hydrogen bonding and van der Waals interactions are indicated as dotted lines.
Figure 24A:
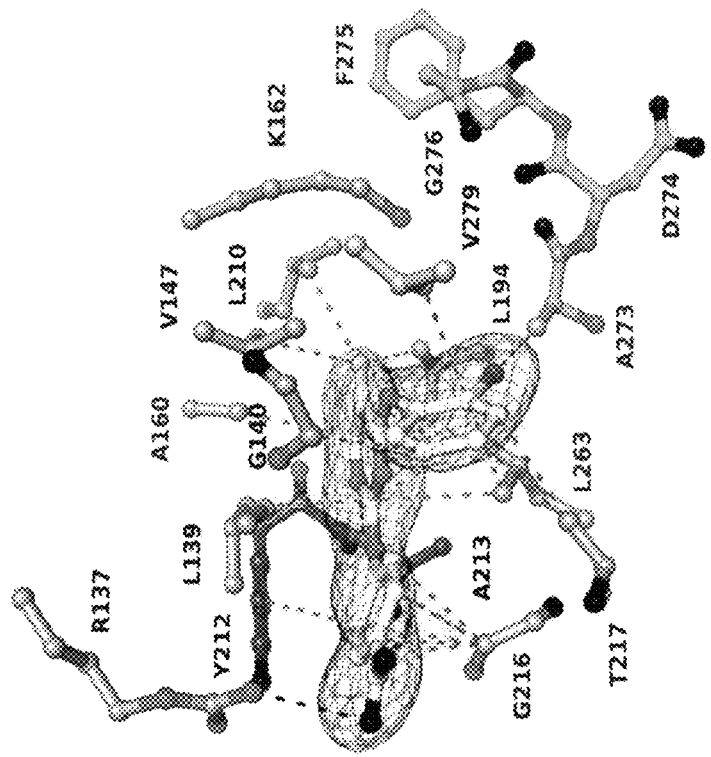
Figure 24B:
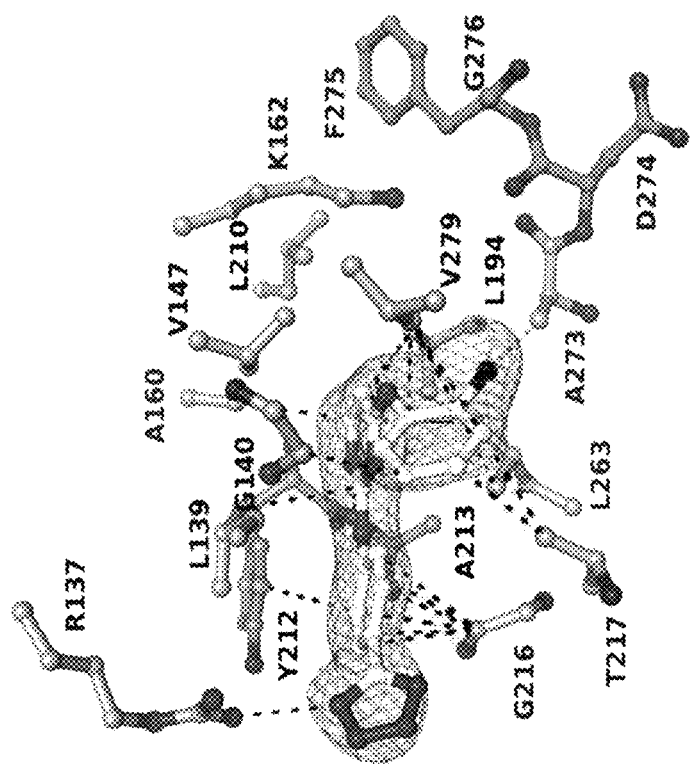
Figure 24B:
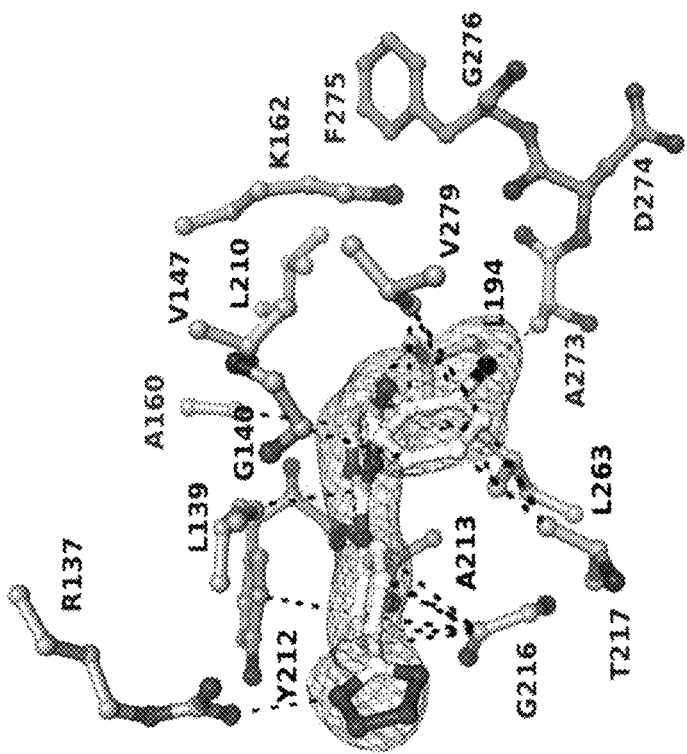
Figure 25A:
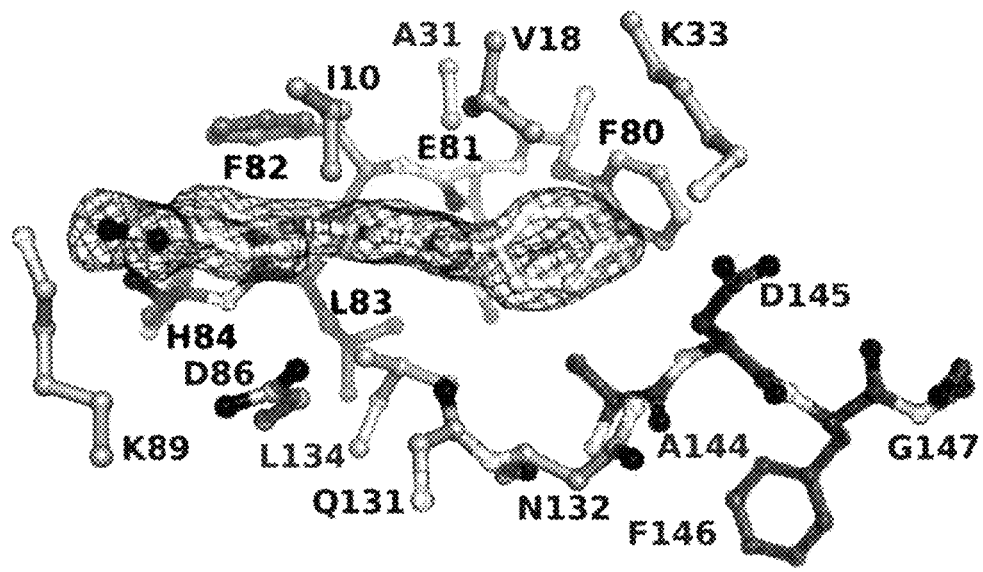
FIG. 25A and FIG. 25B show the co-crystal structures of Aurora A inhibitors with CDK2.
Figure 25B:
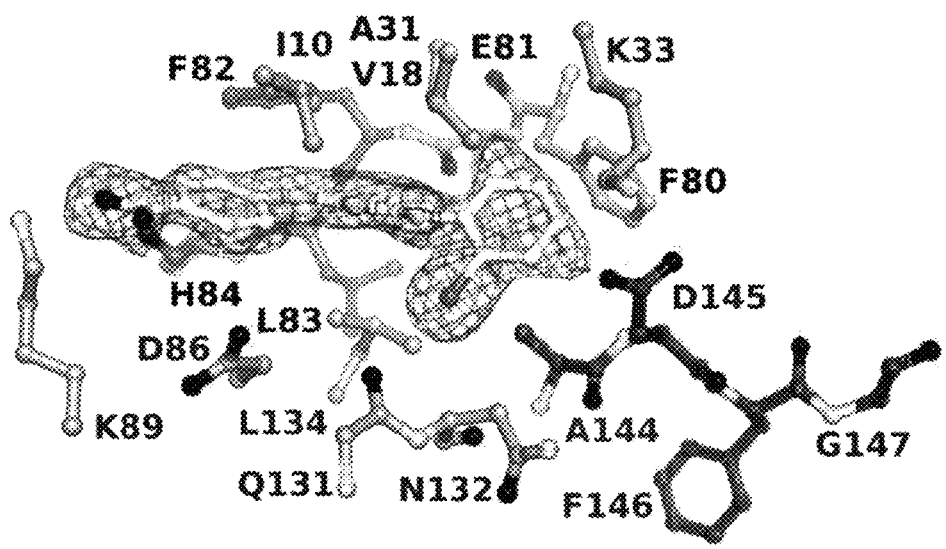
Figure 26A:
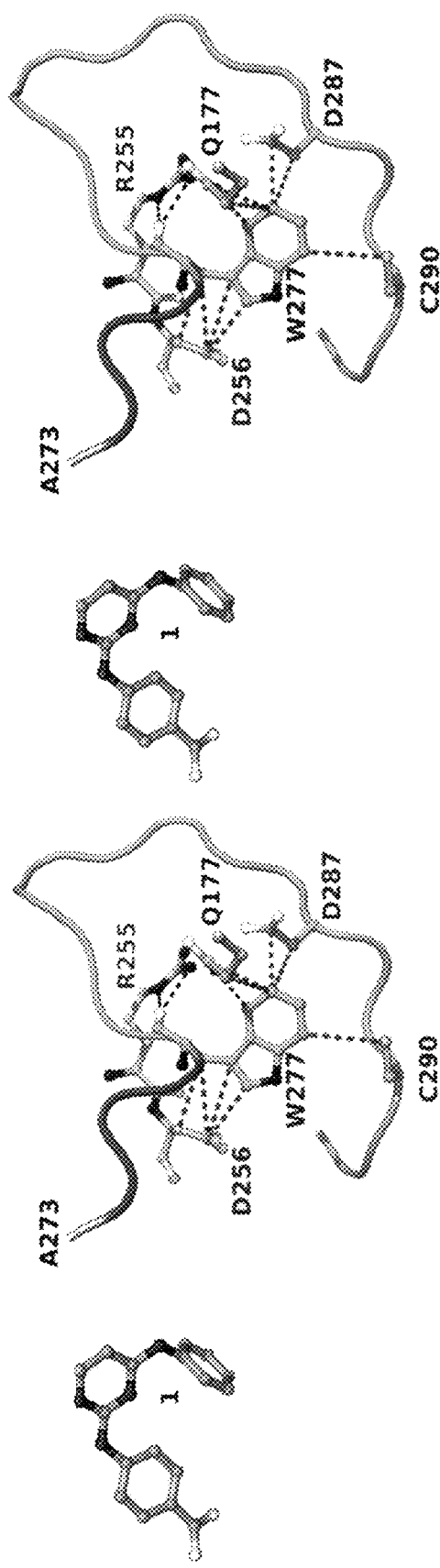
FIG. 26A shows that in the DFG-in state with compound 3h, the main chain carbonyl oxygen of Trp277 forms hydrogen bonding interactions with the guanidinium group of Arg255 (black dotted lines). The indole moiety is surrounded by mostly polar residues with weak potential for VDW interactions (dotted lines).
Figure 26B:
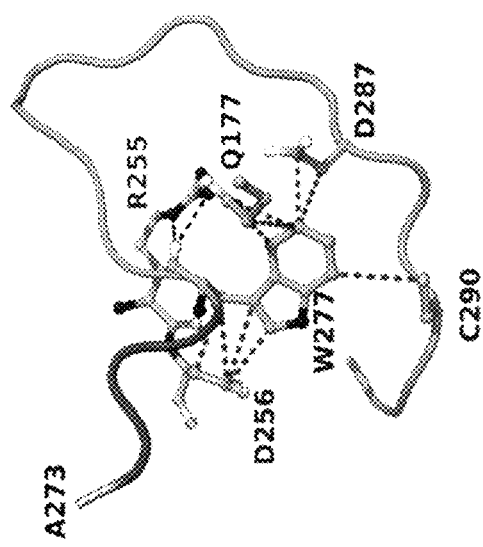
FIG. 26B shows that in the DFG-out state with compound 3l, the indole moiety is positioned in a strictly hydrophobic pocket with high VDW interaction potential; polar interactions between Trp277 and neighboring residues no longer exist.
Figure 26B:
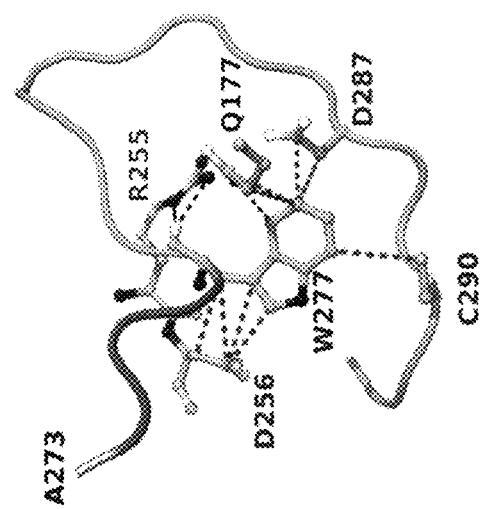
Figure 26B:
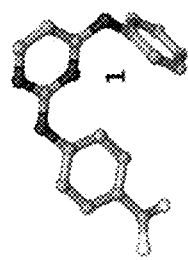

The X-ray co-crystal structure of 1 bound to Aurora A supports the above findings (FIG. 2A through FIG. 2E). Analysis of this structure shows the para-carboxylic acid group of the B ring forming key H-bond interactions with the solvent exposed residues Arg137 and Arg220 (FIG. 2A and FIG. 2B). Compound 1 is a type I kinase inhibitor that targets the ATP binding site (FIG. 2C). The pyrimidine scaffold and the amine moiety of the B-ring establish H-bonding with the hinge region (residues 211-213, FIG. 2A and FIG. 22B). Analysis of ADP/ATP bound to Aurora A indicated highly conserved residues Lys162, Asp274, and Glu181 undergoing electrostatic interactions with ADP phosphate moieties in the active site (FIG. 2D). Compound 1 bound to Aurora A shows these key residues in the active site are now in contact with the ortho-COOH moiety of the A-ring (FIG. 2B). The ortho-carboxylic acid of the A-ring in compound 1 is in the vicinity (3.5 Å) to form an electrostatic interaction with Lys162 (Figure FIG. 2B). The carboxylic acid moiety of the Asp-274 of the DFG motif (FIG. 2A and FIG. 2B) is also in close distance (3.2 Å) with Lys162 and the ortho-COOH moiety of compound 1 to form an H-bond. This key H-bonding network contributes to high in-vitro potency of the compound 1. This is consistent with the fact that compound 3f (Entry 7, Table 1), where both A and B-rings contain unsubstituted phenyl, was 70-fold less active than parent compound 1, and the dimethyl ester 3e lost the in-vitro inhibitory activity ($IC_{50}$ 24.6 µM, Entry 6, Table 1). These observations further confirm that the key interactions observed from the X-ray structure contribute to inhibitory activity (FIG. 2B). The loss of inhibitory activity observed with 3d (Entry 5, Table 1) in the SAR studies is consistent with the X-ray structure of compound 1 bound to Aurora A where ortho-substituted B ring causes steric clash with the main chain residues Ala213 and Pro214 (FIG. 2A and FIG. 2B). However, the activity of compound 3q is retained with carboxylic acid in the meta-position, and improved when fluorine is added as in 3r (Entries 18 and 19 table 1). The meta-COOH is able to interact with Arg220 and Arg137.

Figure 2E:
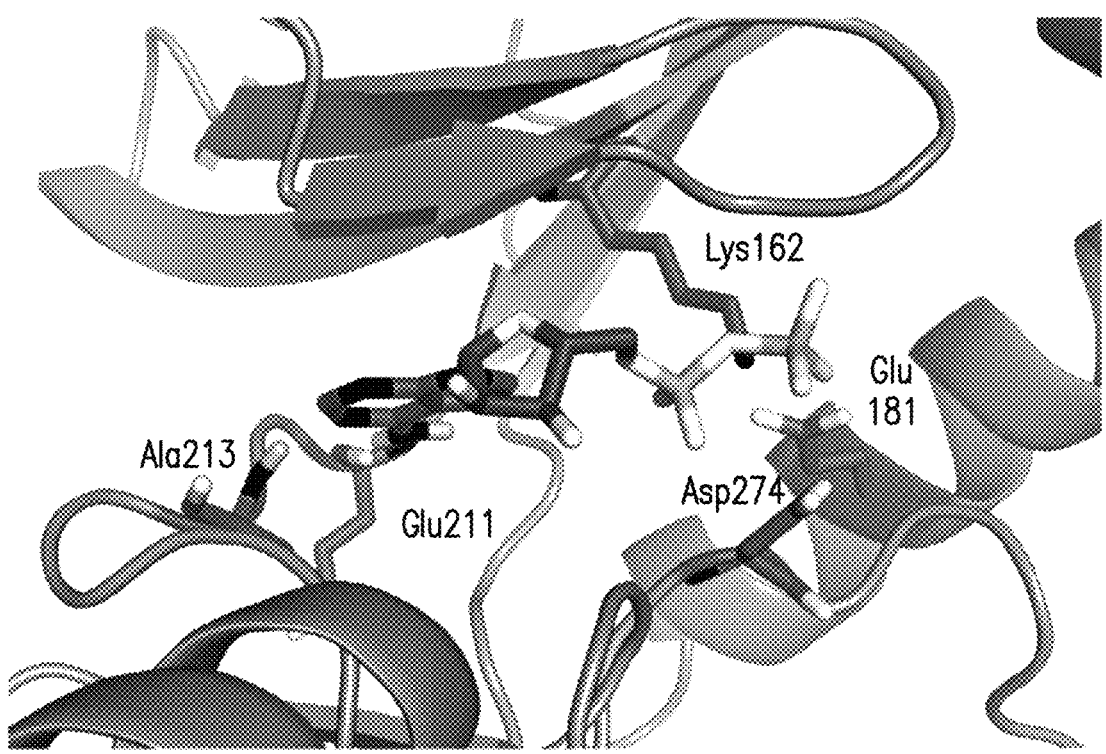
FIG. 2E shows ADP bound to Aurora A active site.

Several X-ray structures were obtained to detail the binding modes of this class of compounds with Aurora A (FIG. 12A through FIG. 12D). Substitution of both carboxylic acid groups in compound 1 by primary amides (FIG. 12B) reduced the inhibitory activity 6-fold (Entry 8, 3g, Table 1). The compound 3i (FIG. 12A), where the A-ring ortho-carboxylic acid is moved to the para-position, was 42-fold less potent than parent molecule (Table 1, Entry 10, $IC_{50}$=256 nM). Not to be bound by theory, this decrease in inhibitory activity may be due to lack of key binding interactions of the para-carboxyl or para-carboxamide groups in the A-ring with the Lys162 and Asp274 active site residues (FIG. 12A and FIG. 12B, compounds 3i and 3g bound to Aurora A). In contrast, removal of the ortho-carboxylic group, as in 3h (Entry 9, Table 1), retains activity. The co-crystal structure of compound 3i (FIG. 12A through FIG. 12D) does not explain the differences in activities of compounds 3h and 3i. Compound 14 (FIG. 12C), where A-ring has a $CF_3$ in the meta-position, is a weaker binder ($IC_{50}$=371 nM,) and has the trifluoromethyl group positioned in the region that binds the diposphate group of ADP (FIG. 2E). Thus, the presence of a hydrophobic group close to Asn261 and Glu260 does not contribute to binding affinity of Aurora A. Overall meta-substituents in the A-ring did not improve the activity.

The surprising observation that replacement of the ortho-carboxylic acid of the A ring in compound 1 with hydrogen as in 3h did not result in great loss of potency prompted the further SAR analysis at this position. Therefore, library 6 (FIG. 5C) was synthesized to detail the binding modes of Aurora A to bisanilinopyrimidines with different groups in the ortho-position of the A ring. To this end, analogs of compound 1 were synthesized by replacing the carboxylic acid in the ortho-position of the A ring by fluoro, chloro, bromo, iodo, trifluoromethyl, trifluoromethoxy, methoxy, cyano, and phenyl as ortho-substituents (6a-6q, FIG. 5C). Compounds with halogens (F, Cl, Br) at the ortho-position of the A ring and para-COOH moiety in the B ring (compounds 3l (Table 1) 6a and 6i (Table 2)) respectively improved potency by 1.5 to more than 3-fold, whereas compounds with bulky halogenated groups such as $OCF_3$ and $CF_3$ (Entries 27, 31 compounds 6d and 6h respectively in Table 2) were much less active at inhibiting Aurora A. Compound 6q (Entry 40, Table 2) with an ortho-phenyl group was 24 fold less potent than the compound 1, further indicating bulky groups are not tolerated in this region (Entry 40, Table 2). Compound 6n ($IC_{50}$=43 nM, Entry 37, Table 2), that possesses an ortho-CN group, is more than 17-fold less active than 3l. The in vitro activity of 3l ($IC_{50}$=2.5±0.3 nM, Entry 13, Table 1) with ortho-Cl and a para-COOH in B ring was further improved when $R^1$ is fluorine in compound 3o ($IC_{50}$=0.8±0.16 nM, Entry 16, Table 1). The para-COOH moiety in the B ring aided in maintaining the Aurora A inhibitory activity in library 6 (FIG. 5C). The removal of COOH moiety resulted in loss of in vitro potency as observed with 6b, 6f, 6g, and 6l (Entries 25, 29, 30 and 35, Table 2). The loss of in vitro inhibitory activity in compounds lacking a para-COOH moiety was a general trend observed with libraries 3 and 6 and highlights the importance of H-bond interactions associated with Arg137 and Arg220. Switching the position of B ring COOH moiety from para- to meta-position as in compound 6o (Entry 38, Table 2) reduced the inhibitory activity compared to 3o (Entry 16, Table 1). Modification of B ring para-COOH to para-$CONH_2$ in compound 6p reduced the in vitro activity by 5-fold (Entry 39, Table 2). Compounds 6r and 6s (Entries 41 and 42, Table 2) with N-alkylated moieties retained the activity; N-methyl derivative was highly potent ($IC_{50}$=8.5±1.2 nM) while the N-ethyl derivative was less active ($IC_{50}$=50.2±2.7 nM). Compound 6t (Entry 43, Table 2), with meta-COOH and fluorine as $R^1$, was 4-fold more potent as compared to compound 6o, where $R^1$ is hydrogen. Overall, the SAR indicated fluorine or chlorine as $R^1$ in this series is beneficial and improves in vitro and in vivo Aurora A activity (see Table 3).

Alignment of the Aurora A-ADP complex with compound 1 indicated $R^1$ and $R^2$ in compound 1 as potential sites for synthetic modifications (FIG. 2A, FIG. 2D, and FIG. 2E). The $R^1$ position (FIG. 1B) of the pyrimidine ring is in close proximity (~4 Å) to the gatekeeper residue Leu210 and $R^2$ is close to Glu211 (~3.5 Å) (FIG. 2A and FIG. 2B). To exploit this narrow space, small groups such as methyl (Entry 11, 3j, Table 1), amine (Entry 22, 4a, Table 1), chlorine (Entries 20 and 21 3s and 3t respectively, Table 1), and fluorine (Entries 15 and 17. 3n-3p) were first introduced as $R^1$. The methyl and $NH_2$ derivatives, compounds 3j and 4a respectively (Entries 11 and 22, Table 1), did not contribute to increased activity most probably due to the steric effect of these groups unable to establish desired interactions. In contrast, compounds with fluorine 3n, 3o (Entries 15-16, Table 1) and chlorine 3t (Entry 21, Table 1), were among the most potent inhibitors with $IC_{50}$ values between 0.8-4 nM (Entries 15, 16 and 21, Table 1). It is likely that fluorine and chlorine as $R^1$ (FIG. 2B) undergo van der Waals interactions with the side chains of the hydrophobic pocket of Ala160, Leu194 and Leu210 (FIG. 12D) as observed in the structures of fluoro-bisanilinopyrimidine inhibitors from Genentech. Substitution of the $R^2$ position (FIG. 1B) of the pyrimidine moiety with methyl, chloro, and amine, as shown in compounds 3k, 4c and 4b (Entries 12, 20 and 23 respectively, Table 1), decreased inhibitory activity, possibly due to steric clash with the backbone carbonyl of Glu211. By contrast, as mentioned above, synthetic modifications at $R^3$ (FIG. 2A and FIG. 2B) are largely tolerated since the region around the DFG is less confined than that opposite hinge region.

Aurora inhibitors that are cell permeable and able to inhibit Aurora A kinase in intact cells were next obtained. The potent compounds 3l, 3n, 3o, 3t, 6a, 6j, 6k and 6r that showed low nanomolar activities in the enzymatic assay however showed poor aqueous solubility and poor activity in intact cells. Introduction of water-solubilizing groups at the para-position of the B-ring was explored to improve both the solubility and cell permeability. Therefore, substitution of the para-carboxylic acid in the B-ring with groups that contain a variety of neutral polar moieties (FIG. 7A through FIG. 7B) were employed to exploit H-bond interactions with Arg137 and Arg220. Direct replacement of the para-COOH by the carboxylic acid isostere tetrazole moiety provided compounds 13a-13d that retained the in vitro potency similar to 3l (Entries 59, 60 and 61, Table 3 and FIG. 8) with good aqueous solubility (49 μg/ml in DMEM buffer at pH 7.4). An X-ray structure of compound 13a (FIG. 8) bound to Aurora A was obtained, and compound 13a adopted a binding conformation similar to compound 3l. The primary aim of the B-ring modifications described in FIG. 7A, FIG. 7B and FIG. 8 was to obtain a compound with chlorine at the ortho-position of the A-ring and a water-solubilizing moiety at the para-position of the B-ring.

TABLE 1

Synthetic Modifications, structure activity relationship studies and in-vitro activities of bisanilinipyrimidine libraries 3 and 4 against Aurora A.

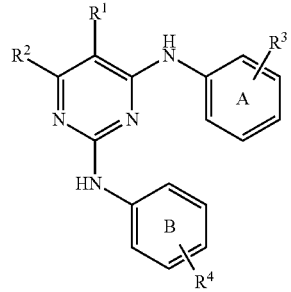

| Entry | Cmpd ID # | $R^1$ | $R^2$ | $R^3$ | $R^4$ | In Vitro activity ($IC_{50}$) (DiscoverX) |
|---|---|---|---|---|---|---|
| 1 | 1 | H | H | ortho-COOH | para-COOH | 6.1 ± 1.0 nM |
| 2 | 3a | H | H | ortho-COOH | ortho-$CONH_2$ | 9.0 ± 6.8 μM |
| 3 | 3b | H | H | ortho-COOH | H | 79.4 ± 18 nM |
| 4 | 3c | H | H | ortho-COOH | para-morpholine | 57.6 ± 5.4 nM |
| 5 | 3d | H | H | ortho-COOH | ortho-COOH | 31.3 ± 5.9 μM |
| 6 | 3e | H | H | ortho-COOMe | para-COOMe | 24.6 ± 6.0 μM |
| 7 | 3f | H | H | H | H | 423 ± 66 nM |
| 8 | 3g | H | H | ortho- | para-$CONH_2$ | 38.2 ± 8.8 nM |
| 9 | 3h | H | H | H | para-COOH | 10 ± 1.6 nM |
| 10 | 3i | H | H | para-COOH | para-COOH | 256 ± 38 nM |
| 11 | 3j | $CH_3$ | H | ortho-COOH | para-COOH | 281 ± 59 nM |
| 12 | 3k | H | $CH_3$ | ortho-COOH | para-COOH | >50 μM |
| 13 | 3l | H | H | ortho-Cl | para-COOH | 2.5 ± 0.3 nM |
| 14 | 3m | F | H | ortho-COOH | All H | 11.3 ± 1.7 nM |
| 15 | 3n | F | H | ortho-COOH | para-COOH | 3.9 ± 0.5 nM |
| 16 | 3o | F | H | ortho-Cl | para-COOH | 0.8 ± 0.16 nM |
| 17 | 3p | F | H | ortho-Cl | H | 19.9 ± 2.2 nM |
| 18 | 3q | H | H | ortho-COOH | meta-COOH | 18.3 ± 3.4 nM |
| 19 | 3r | F | H | ortho-COOH | meta-COOH | 5.1 ± 1.1 nM |
| 20 | 4c | Cl | Cl | ortho-COOH | para-COOH | 1.49 ± 0.196 μM |
| 21 | 4d | Cl | H | ortho-COOH | para-COOH | 3.17 ± 0.51 nM |
| 22 | 4a | $NH_2$ | H | ortho-COOH | para-COOH | 376 ± 64 nM |
| 23 | 4b | H | $NH_2$ | ortho-COOH | para-COOH | >50 μM |

TABLE 2

Structure activity relationship studies and in-vitro inhibitory activities of library 6 against Aurora A.

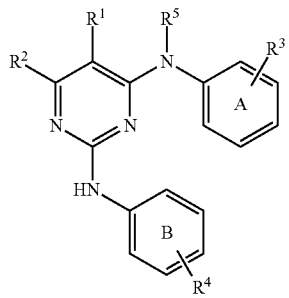

| Entry | Cmpd ID # | $R^1$ | $R^2$ | $R^3$ | $R^4$ | $R^5$ | IC$_{50}$ (nM) (DiscoverX) |
|---|---|---|---|---|---|---|---|
| 24 | 6a | H | H | ortho-F | para-COOH | H | 3.7 ± 0.7 nM |
| 25 | 6b | H | H | ortho-CF$_3$ | All H | H | 1773 ± 142 nM |
| 26 | 6c | H | H | 2-Cl-4-F | para-COOH | H | 2.0 ± 0.2 nM |
| 27 | 6d | H | H | ortho-OCF$_3$ | para-COOH | H | 28 ± 4.8 nM |
| 28 | 6e | H | H | ortho-OMe | para-COOH | H | 4.0 ± 0.2 nM |
| 29 | 6f | H | H | ortho-OMe | All H | H | 46.6 ± 8.4 nM |
| 30 | 6g | H | H | ortho-CN | All H | H | 560 ± 70.3 nM |
| 31 | 6h | H | H | ortho-CF$_3$ | para-COOH | H | 35 ± 4.1 nM |
| 31 | 6i | H | H | ortho-Br | para-COOH | H | 2.1 ± 0.4 nM |
| 33 | 6j | H | H | ortho-Cl | para-CH$_2$—COOH | H | 3.3 ± 1.5 nM |
| 34 | 6k | H | H | Ortho-Cl | para-COOH, meta-OH | H | 6.6 ± 0.6 nM |
| 35 | 6l | H | H | Ortho-F | All H | H | 284 ± 11.3 nM |
| 36 | 6m | H | H | Ortho-I | para-COOH | H | 35 ± 3.3 nM |
| 37 | 6n | H | H | Ortho-CN | para-COOH | H | 43 ± 58 nM |
| 38 | 6o | H | H | Ortho-Cl | meta-COOH | H | 18.7 ± 1.5 nM |
| 39 | 6p | H | H | ortho-Cl | para-CONH$_2$ | H | 30.2 ± 1.4 nM |
| 40 | 6q | H | H | ortho-phenyl | para-COOH | H | 149 ± 23 nM |
| 41 | 6r | H | H | ortho-Cl | para-COOH | CH$_3$ | 8.5 ± 1.2 nM |
| 42 | 6s | H | H | ortho-Cl | para-COOH | CH$_3$—CH$_2$ | 50.2 ± 2.7 nM |
| 43 | 6t | F | H | ortho-Cl | meta-COOH | H | 4.5 ± 1.1 nM |

TABLE 3

In-vivo and in vitro Aurora A activities of bisaniloinopyrimidines with water solubilizing moieties

| Entry | Compound ID | In-vitro IC$_{50}$ (nM) | In-vivo IC$_{50}$ (μM) [Aurora A inhibitory activity in MDA-MB-468 at 2 h] |
|---|---|---|---|
| 44 | 9a (RE1-043) | 216 ± 10.3 | 1-10 |

TABLE 3-continued
In-vivo and in vitro Aurora A activities of bisaniloinopyrimidines with water solubilizing moieties
| Entry | Compound ID | In-vitro IC$_{50}$ (nM) | In-vivo IC$_{50}$ (μM) [Aurora A inhibitory activity in MDA-MB-468 at 2 h] |
|---|---|---|---|
| 45 | 9b (Re1-032) 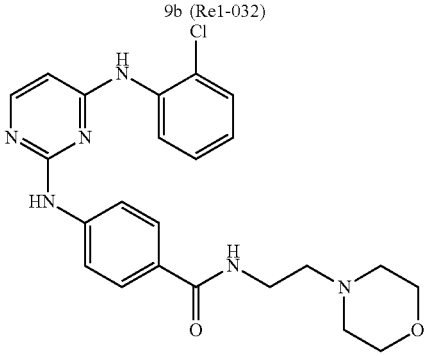 | 28.1 ± 5.5 | 1-10 |
| 46 | 9c (RE1-031) 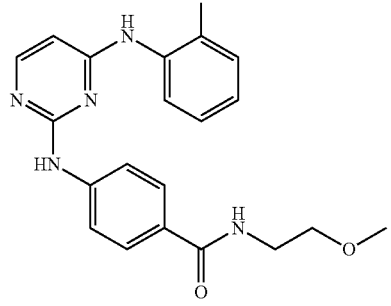 | 18 ± 2.8 | 1-10 |
| 47 | 9d (RE1-025) 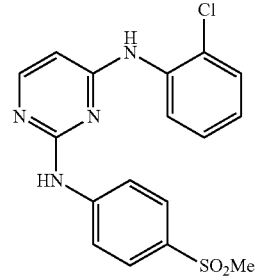 [SMILES: CS(=O)(=O)c1ccc(Nc2nccc(Nc3ccccc3Cl)n2)cc1] | 44.9 ± 4.7 | >10 |
| 48 | 9e (RE1-039) 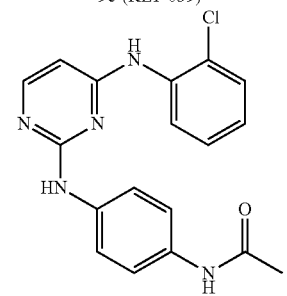 | 71.2 ± 9.0 | >10 |

TABLE 3-continued

In-vivo and in vitro Aurora A activities of bisaniloinopyrimidines with water solubilizing moieties

| Entry | Compound ID | In-vitro IC$_{50}$ (nM) | In-vivo IC$_{50}$ (μM) [Aurora A inhibitory activity in MDA-MB-468 at 2 h] |
|---|---|---|---|
| 49 | 9f (RE1-019) | 316 ± 44.2 | 1-10 |
| 50 | 9g (HM5-018-2) | 116.5 ± 10.6 | >10 |
| 51 | 9h (YL5-146-4) | 27 ± 7.6 | <1 |
| 52 | 6p (YL5-145) | 30.2 ± 1.4 | <1 |

TABLE 3-continued

In-vivo and in vitro Aurora A activities of bisaniloinopyrimidines with water solubilizing moieties

| Entry | Compound ID | In-vitro IC$_{50}$ (nM) | In-vivo IC$_{50}$ (μM) [Aurora A inhibitory activity in MDA-MB-468 at 2 h] |
|---|---|---|---|
| 53 | 9i (YL5-146-3) | 253 ± 41.6 | <1 |
| 54 | 9j (HM6-007-1) | 21.4 ± 2.5 | <1 |
| 55 | 9k (HM6-020-2) | 23.2 ± 1.6 | <1 |
| 56 | 9l (HM4-153-2) | 12.3 ± 1.1 | <1 |

TABLE 3-continued

In-vivo and in vitro Aurora A activities of bisaniloinopyrimidines with water solubilizing moieties

| Entry | Compound ID | In-vitro IC$_{50}$ (nM) | In-vivo IC$_{50}$ (μM) [Aurora A inhibitory activity in MDA-MB-468 at 2 h] |
|---|---|---|---|
| 57 | 9m (HM6-021-4) | 14.4 ± 1.7 | <1 |
| 58 | 9n (HM6-029-1) | 21.2 ± 2.2 | >10 |
| 59 | 13a (SO2-162) | 3.1 ± 0.16 | >10 |
| 60 | 13b (SO3-033) | 2.9 ± 0.30 | >10 |

TABLE 3-continued

In-vivo and in vitro Aurora A activities of bisaniloinopyrimidines with water solubilizing moieties

| Entry | Compound ID | In-vitro IC$_{50}$ (nM) | In-vivo IC$_{50}$ (μM) [Aurora A inhibitory activity in MDA-MB-468 at 2 h] |
|---|---|---|---|
| 61 | 13c (SO3-036) | 17.3 ± 2.3 | >10 |
| 62 | 13d (SO3-035) | 3.0 ± 0.53 | 1-10 |

TABLE 4

IC$_{50}$ data

| Compound ID | Cmpd # | R$^1$ | R$^2$ | R$^3$ | R$^4$ | IC$_{50}$ (μM) (in vitro) LDH/PK | IC$_{50}$ (nM) (DiscoverX) |
|---|---|---|---|---|---|---|---|
| RK2-014 | 14 | H | H | meta-CF$_3$ | para-COOH | 3.94 | 186.5 ± 26 |
| RK2-017-01 | 15 | H | H | meta-CF$_3$ | para-CONH$_2$ | 0.226 ± 0.046 | 371.5 ± 56 |
| RK2-037 | 16 | H | H | meta-CF$_3$ | meta-isobutyramide | 1.4 | 1.43 ± 0.3 μM |
| RK2-025 | 17 | H | H | meta-CF$_3$ | meta-CF$_3$ | 10 | 23.7 ± 7.4 μM |
| RK2-015-03 | 18 | H | H | meta-CF$_3$ | ortho-COOH | 64 | 25.7 ± 7.2 μM |
| RK2-017-02 | 19 | H | H | meta-CF$_3$ | meta-CONH$_2$ | 3.6 | 1.26 ± 0.2 μM |
| RK2-053 | 20 | H | H | meta-CF$_3$ | meta-acetamide | 0.91 | 3.6 ± 0.9 μM |
| RK2-015-02 | 21 | H | H | meta-CF$_3$ | meta-COOH | 9.32 | 16.2 ± 7.3 μM |
| RK2-056 | 22 | H | H | meta-CF$_3$ | meta-butyramide | >15 | — |
| RK2-046-02 | 23 | H | H | meta-CF$_3$ | meta-propionamide | ? | 15.4 ± 6.7 μM |
| RK2-013 | 24 | H | H | meta-CF$_3$ | meta-cyclopropane carboxamide | ? | >50 μM |
| RK2-015-01 | 25 | H | H | meta-CF$_3$ | All H | 14.1 | — |
| RK2-046-01 | 26 | H | H | meta-CF$_3$ | meta-$^t$butylcarboxyamide | 7.46 | 8.87 ± 2.9 μM |

TABLE 4-continued

IC$_{50}$ data

[Chemical structure: pyrimidine with R$^1$, R$^2$ substituents, NH-phenyl(R$^3$) and HN-phenyl(R$^4$) groups]

| Compound ID | Cmpd # | R$^1$ | R$^2$ | R$^3$ | R$^4$ | IC$_{50}$ (μM) (in vitro) LDH/PK | IC$_{50}$ (nM) (DiscoverX) |
|---|---|---|---|---|---|---|---|
| RK2-044 | 27 | H | H | meta-CF$_3$ | meta-cyclopentylcarboxamide | 6.25 | 23.0 ± 3.0 μM |
| RK2-052 | 28 | H | H | meta-CF$_3$ | meta-isobutylcarboxamide | >150 | 21.6 ± 1.0 μM |
| RK2-043 | 29 | H | H | meta-CF$_3$ | meta-(4-chlorobenzyl)carboxamide | 10.2 | >50 μM |
| RK2-049 | 30 | H | H | meta-CF$_3$ | meta-benzylcarboxamide | 8.5 | >50 μM |
| YL5-048 | 31 | H | Me$_2$N | H | All H | >15 | >50 μM |
| YL5-050 | 32 | H | Me$_2$N | ortho-COOH | All H | >15 | >50 μM |
| YL5-068 | 33 | NH$_2$ | H | ortho-COOH | para-COOC$_2$H$_5$ | 0.26 | 1.49 ± 0.49 μM |
| YL5-146-5 | 34 | H | H | ortho-Cl | para-OCH$_3$ | | |
| YL5-080 | 35 | Me | H | ortho-COOH | para-COOH | 0.145 | |

Example 2

Figure 19:
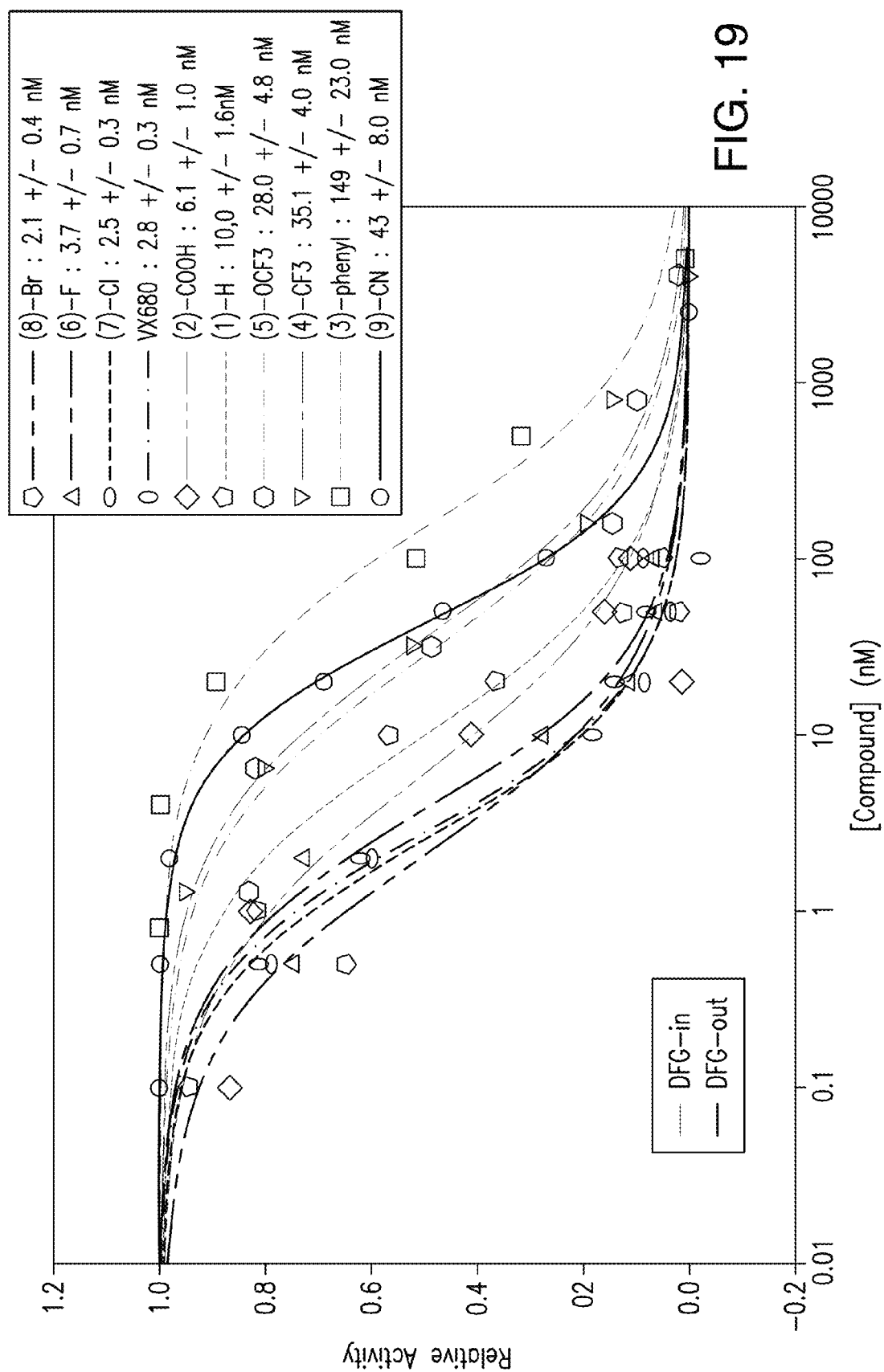
FIG. 19 is a graph showing $IC_{50}$ determination of bisanilinopyrimidine inhibitors with Aurora A.

Effects of Aurora A Inhibitors on the Phosphorylation of the Aurora A Substrate, Histone H3, in Breast Cancer Cells The synthetic peptide LRRASLG served as a substrate for Aurora A. Formation of ADP from ATP was quantified using a coupled enzyme assay (DiscoverX, Fremont, Calif.) in which a fluorescent resorufin dye is generated from the interaction of ADP with hydrogen peroxide and 10-acetyl-3,7-dihydroxy-phenoxazine (excitation and emission wavelengths of 540 and 590 nm, respectively). Reactions were carried out at room temperature in 15 mM HEPES buffer (pH 7.4) containing 20 mM NaCl, 1 mM EGTA, 0.02% Tween 20, 10 mM MgCl$_2$, 5% (v/v) DMSO, and 2.3 nM Aurora A. Inhibitor was added to the mixture, and the reaction was initiated by the addition of 75 μM ATP and 2 mM peptide substrate. All kinetic assays were performed in 384-well plates using a Wallac Envision 2102 plate reader (Perkin Elmer). IC$_{50}$ values for were obtained by fitting the data to equation (1), $$A = \frac{1}{1 + \left(\frac{[I]}{IC_{50}}\right)^n} \quad (1)$$

where A is the remaining activity, [I] is the concentration of the inhibitor, and n is the Hill slope coefficient. CDK2 IC$_{50}$ values were measured using the same assay as described (Betzi et al., (2011) Discovery of a potential allosteric ligand binding site in CDK2, *ACS Chem Biol* 6:492-501). The dose-response curves are shown in the supplemental material (FIG. 19).

The ability of the most potent Aurora A kinase inhibitors in vitro to block the phosphorylation of serine 10 on Histone H3 was investigated, a well established Aurora A substrate. To this end, MDA-MB-468 breast cancer cells were treated with the inhibitors at various concentrations for 2 hours and processed for immunoblotting.

Specifically, MDA-MB-468 cells (American Type Culture Collection) were maintained in Dulbecco's modified Eagle's medium (DMEM) plus 10% fetus bovine serum (FBS) (Invitrogen, US) at 37° C., 5% CO$_2$. The cells were plated in 6 cm dishes at a density of 2×10$^5$ cells/dish. Cells were then treated with the compounds (0-10 μM); DMSO was used as a negative control and 0.5 μM VX-680 (Tozasertib) (Selleck Chemical LLC) was used as a positive control. Cells were harvested after 2 h of treatment and processed for SDS-PAGE and western blotting as described previously (Gizatullin et al., "The Aurora kinase inhibitor VX-680 induces endoreduplication and apoptosis preferentially in cells with compromised p53-dependent postmitotic checkpoint function" *Cancer Res.* (2006) 66 (15):7668-77). After electro-transfer onto nitrocellulose membranes, the membranes were blocked at room temperature for 1 h with TBS containing 5% (w/v) milk and then washed with a mixture of TBS containing 0.2% Tween 20 (Sigma). The membranes were then gently shaken at 4° C. overnight with anti-phospho histone H3 (Ser 10) antibody (9701, Cell Signaling), and anti-GAPDH monoclonal antibody (E10086CF, Covance) diluted in TBS containing 5% BSA. The membranes were then incubated with HRP conjugated anti-rabbit or anti-mouse IgG antibody (Jackson ImmunoResearch Lab.) at room temperature for 1 h followed by washing with Tween 20-PBS. The membranes were washed again with PBS and developed with the ECL system (PerkinElmer) as described previously (Berndt et al., "The Akt activation inhibitor TCN-P inhibits Akt phosphorylation by binding to the PH domain of Akt and blocking its recruitment to the plasma membrane." Cell Death Differ. (2010) 17(11):1795-804).

FIG. 13A through FIG. 13C shows that compound 1, which contains a carboxylic acid moiety on each of the A-ring and the B-ring, as well as one of the most potent compounds 31 (in vitro IC$_{50}$=2.52±0.3 nM), where the A-ring carboxylate was replaced by a chlorine but still contains a carboxylate on the B-ring, had little effect on Histone H3 phosphorylation levels in MDA-MB-468 cells. Similarly, 3o (in vitro $IC_{50}$=0.8±0.16 nM), which in addition to a carboxylate on the B-ring and a chlorine on the A-ring also contains a fluorine on the pyrimidine ring, also had little effect on Histone H3 phosphorylation levels. In contrast, 3p (in vitro $IC_{50}$=19.9±2.2 nM), which lacks both carboxylates, showed improved ability to inhibit Histone H3 phosphorylation. The ability of these compounds to inhibit Aurora A activity in intact cells was determined by varying the substituents on the B-ring. FIG. 13A through FIG. 13C show that replacement of the B-ring carboxylate with tetrazole such as in 13a, 13b, 13c, and 13d did not improve activity. In contrast, in compounds with a chlorine on the A-ring, substituting the B-ring carboxylate with a carboxamide (6p, Table 3), sulfonamide (9i, Table 3) or morpholino (9h, Table 3) greatly improved their activity and resulted in suppression of Histone H3 phosphorylation with concentrations as low as 1 µM. Similarly, compounds with ortho-chlorine on the A-ring and fluorine as $R^1$ on the pyrimidine ring, substitutions of the carboxylic acid moiety with carboxamide (9m, Table 3), morpholino (9j, Table 3), methylene morpholino (9k, Table 3), and sulfonamide (9n, Table 3), also greatly improved the ability to suppress Histone H3 phosphorylation. Other modifications resulted in mediocre to good improvements, and these included analogues that occupied the para-position with $NHCOCH_3$ (9e, Table 3), $SO_2CH_3$ (9d, Table 3), $CONHC_2H_4OCH_3$ (9c, Table 1), $CONHC_2H_4OH$ (9m, Table 3), $CONHC_2H_4$-morpholino (9a, Table 3), para-COOH and meta-$OCH_3$ (9g, Table 3) and $CONHC_2H_4N(CH_3)_2$ (9b, Table 3). Taken together, these results demonstrate that in vitro Aurora A inhibitors that contain carboxylic groups are inactive in intact cells but that those where the B-ring carboxylic moiety was replaced by carboxamide, sulfonamide, or morpholino groups are highly potent at inhibiting in intact cells the phosphorylation of the Aurora A kinase substrate.

Example 3

Selection of a Chemical Scaffold Suitable to Probe the DFG Motif of Aurora A

Compound 2 is a potent inhibitor of Aurora A with an $IC_{50}$ value of 6.1 nM in vitro. The co-crystal structure confirmed that compound 2 is a typical Type I inhibitor which binds to the hinge region (Ala213) without perturbing the DFG-in state (Asp274-Phe275-Gly276) (FIG. 14A through FIG. 14I, Table 5). The unusually high potency of the hit compound, the feasibility of focused library synthesis of the bisanilinopyrimidine scaffold, and the availability of robust co-crystallization conditions allowed the DFG region of Aurora A to be targeted for the design of DFG-out inhibitors. The ortho-position of the A-ring, as it is appropriately positioned for the introduction of functional groups to target the DFG, was determined. Synthesized analogues were characterized by enzyme kinetics, isothermal titration calorimetry (ITC), and protein crystallography. Inhibitory activity (expressed as $IC_{50}$) and binding affinity (expressed as dissociation constant, $K_d$) followed the same trend among the substituents tested (FIG. 14A through FIG. 14I, Table 6). The consistently higher $K_d$ values obtained by ITC are likely due to differences in experimental conditions and detection limits of the activity and binding assays. Compounds 3l, 6i, and 3o were equal to or more potent than the well-studied Aurora inhibitor VX680, which displayed an $IC_{50}$ value of 2.8 nM. For comparison, the in vitro activity of VX680 against Aurora A was previously determined to $IC_{50}$=1.4 nM (10) and $K_i$=0.6 nM (8) using different assays.

TABLE 5

Inhibitory activity and binding affinity of bisanilinopyrimidine inhibitors towards Aurora A.

| Cmpd | PDB | $R_1$ | $R_2$ | $R_3$ | $IC_{50}$ $(nM)^a$ | $ITC^a$ $K_d$ (nM) |
|---|---|---|---|---|---|---|
| 3h | 3UO5 | —H | —H | —COOH | 10 ± 1.6 | 39 ± 5.9 |
| 1 | 3UP7 | —COOH | —H | —COOH | 6.1 ± 1.0 | 34 ± 5.9 |
| 6q | 3UO4 | -phenyl | —H | —COOH | 149 ± 23 | 299 ± 27 |
| 6h | 3UOD | —$CF_3$ | —H | —COOH | 35 ± 4.1 | 49 ± 5.2 |
| 6d | 3UP2 | —$OCF_3$ | —H | —COOH | 28 ± 4.8 | 40 ± 5.6 |
| 6a | 3UNZ | —F | —H | —COOH | 3.7 ± 0.7 | 16 ± 1.6 |
| 3l | 3UO6 | —Cl | —H | —COOH | 2.5 ± 0.3 | 15 ± 1.5 |
| 6i | 3UOH | —Br | —H | —COOH | 2.1 ± 0.4 | 13 ± 2.2 |
| 6n | 3U0J | —CN | —H | —COOH | 43 ± 8.0 | 51 ± 5.5 |
| 3o | 3UOK | —Cl | —F | —COOH | 0.8 ± 0.2 | n/a |
| 13a | 3U0L | —Cl | —H | -Tetrazole | 3.1 ± 0.4 | 18 ± 2.7 |
| VX680 | | | | | 2.8 ± 0.3 | 17 ± 3.7 |

Figure 20A:
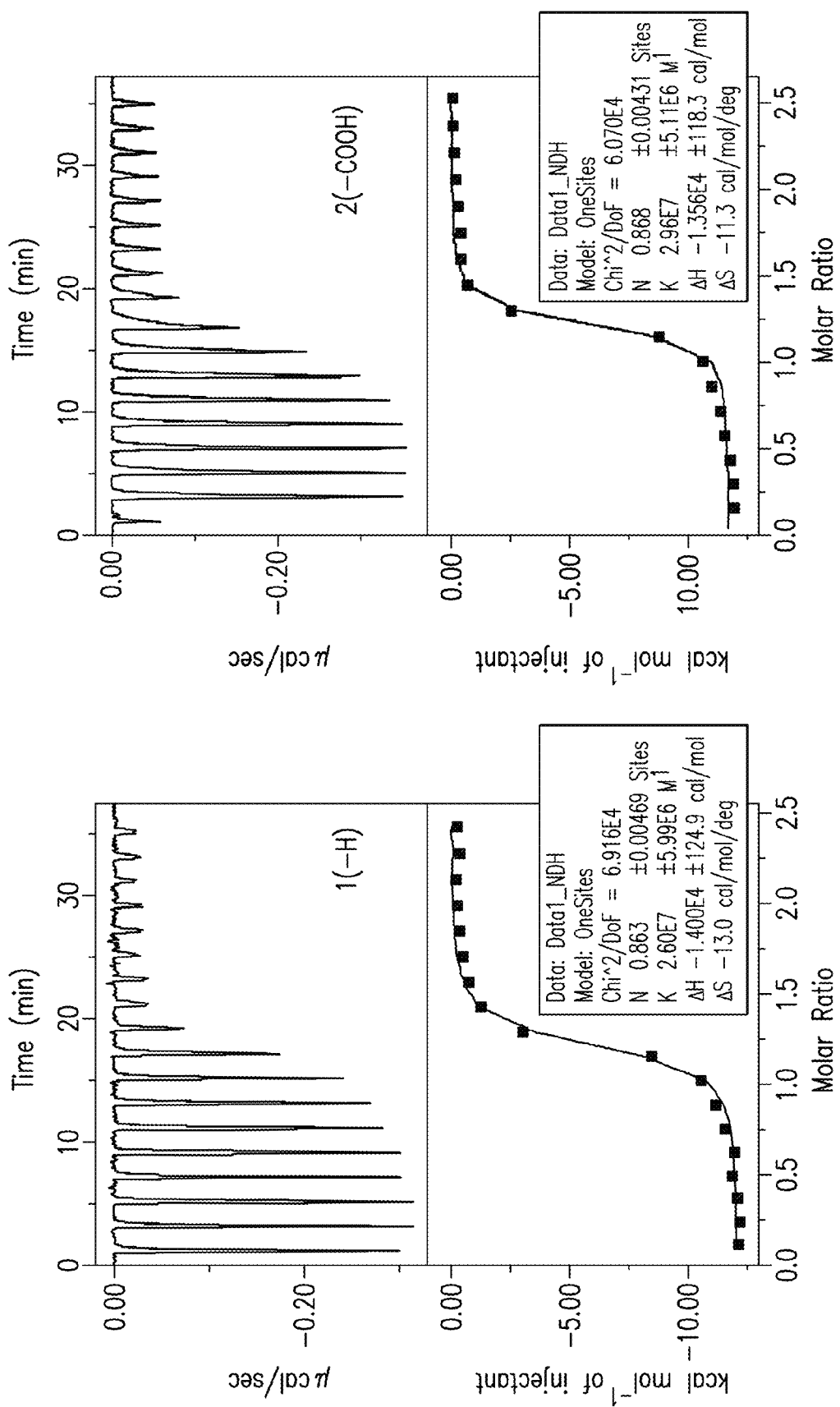
FIG. 20A through FIG. 20E show binding studies of bisanilinopyrimidine inhibitors with Aurora A by ITC.
Figure 20B:
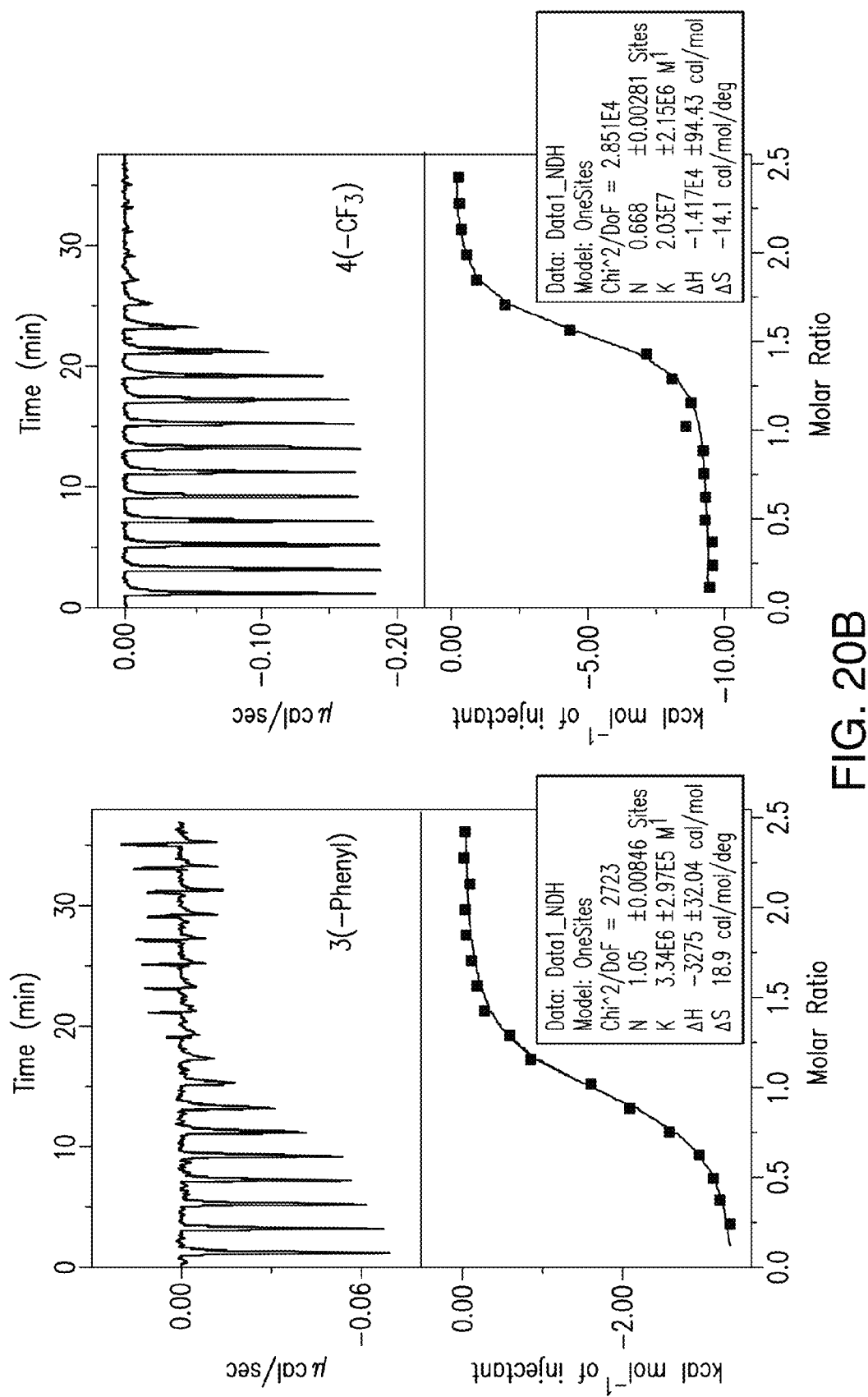
Figure 20C:
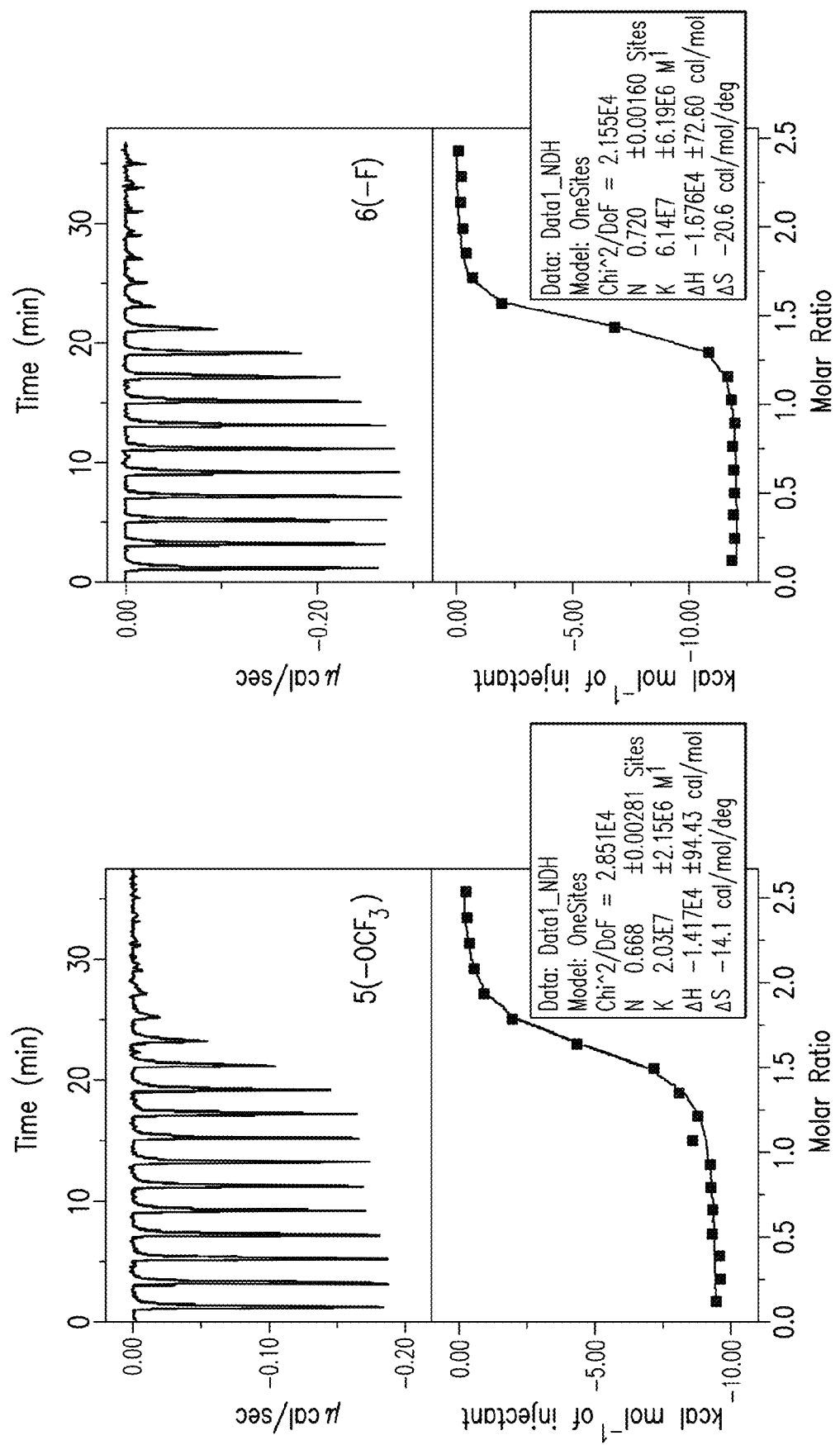
Figure 20D:
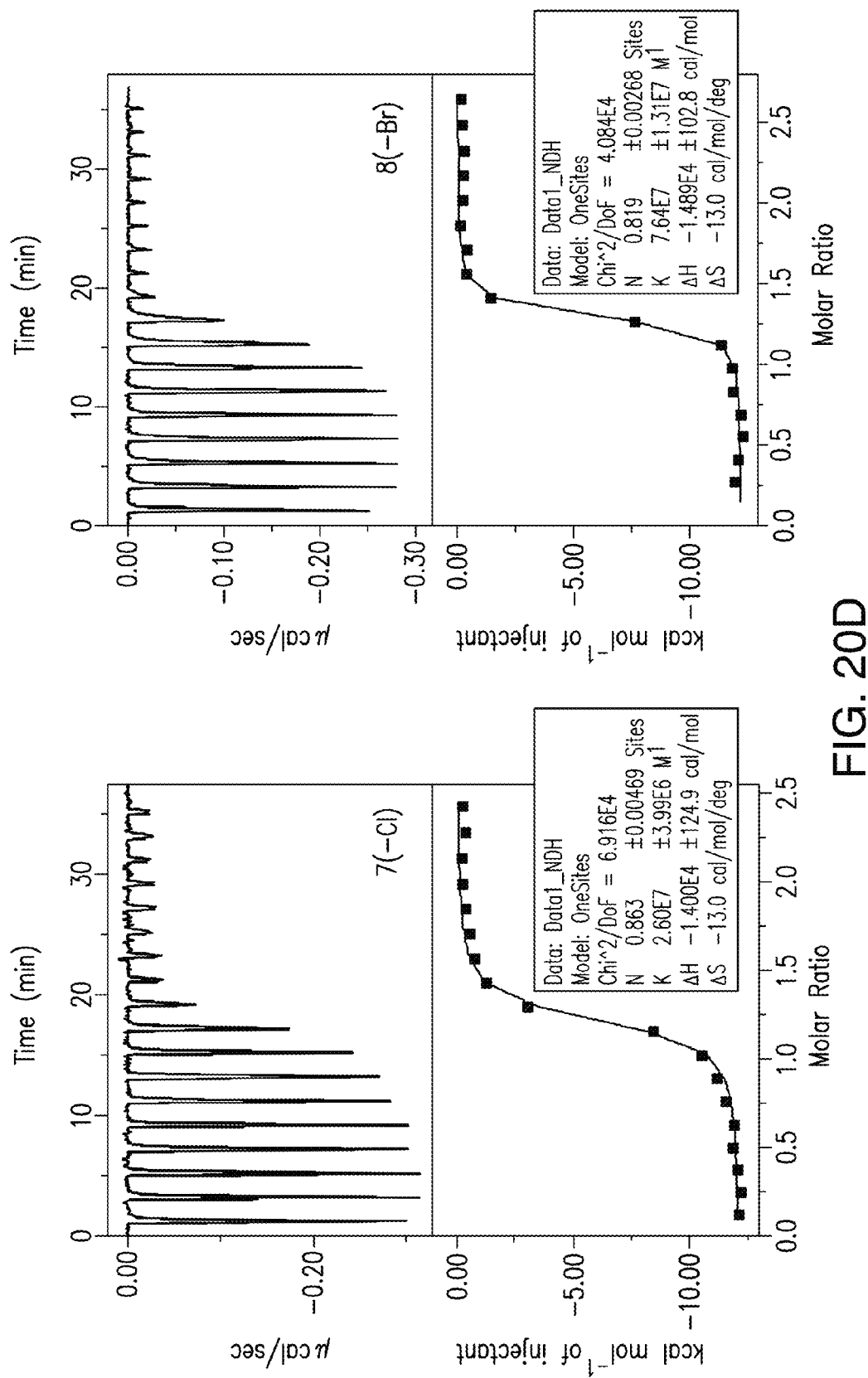
Figure 20E:
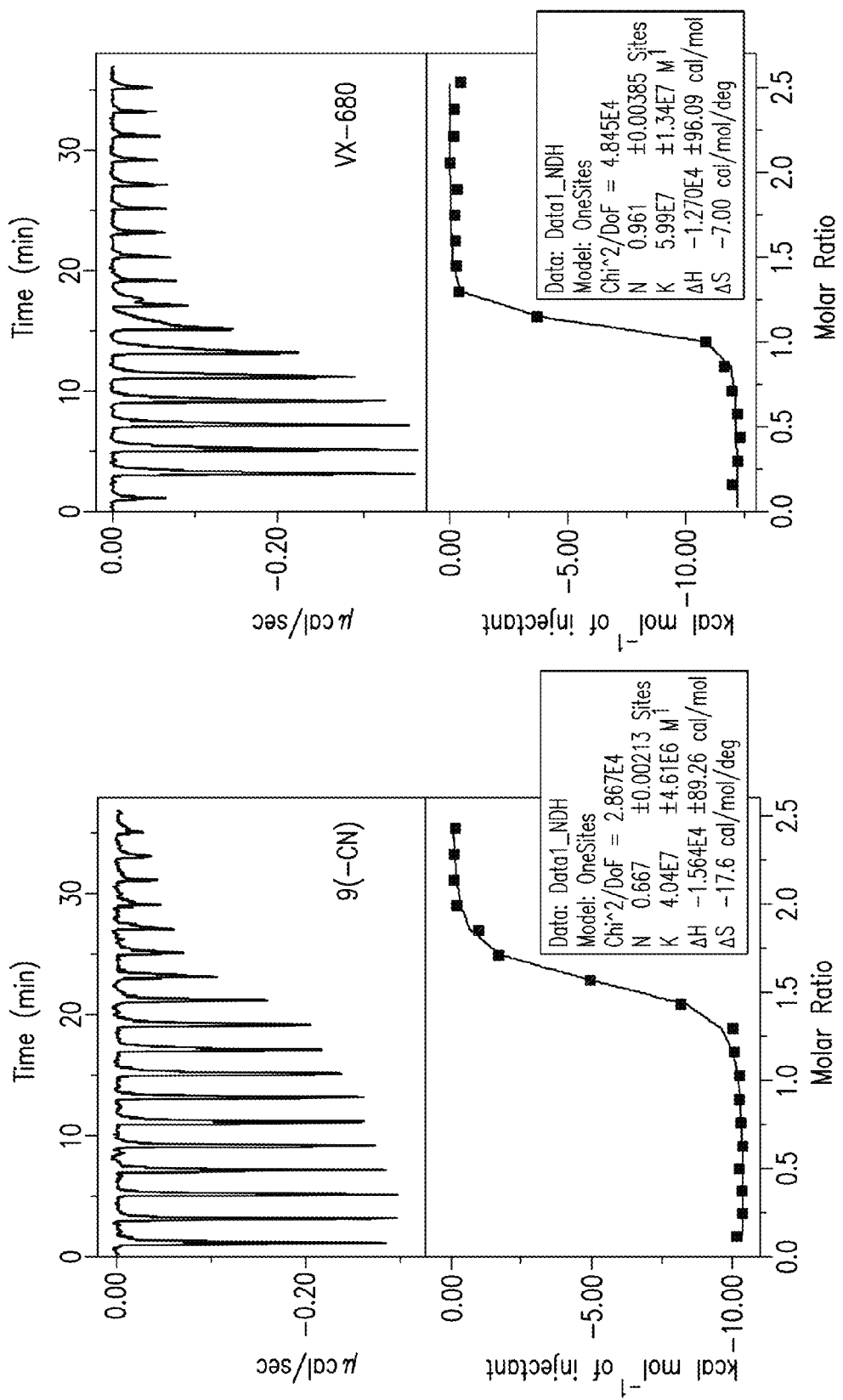
Figure 21A:
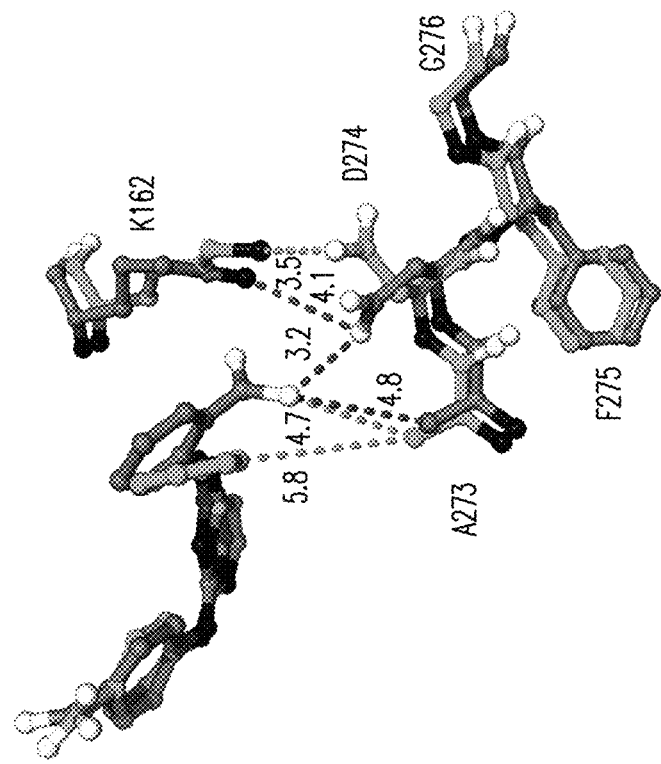
FIG. 21A through FIG. 21D show comparisons of the DFG-in dead-end complexes (stereo presentations). The structures of compounds 1, 6q, 6h, and 6d were aligned with the structure of 3h. Shown are the inhibitors, the ADFG segment, Lys162 and distances in Å.
Figure 21A:
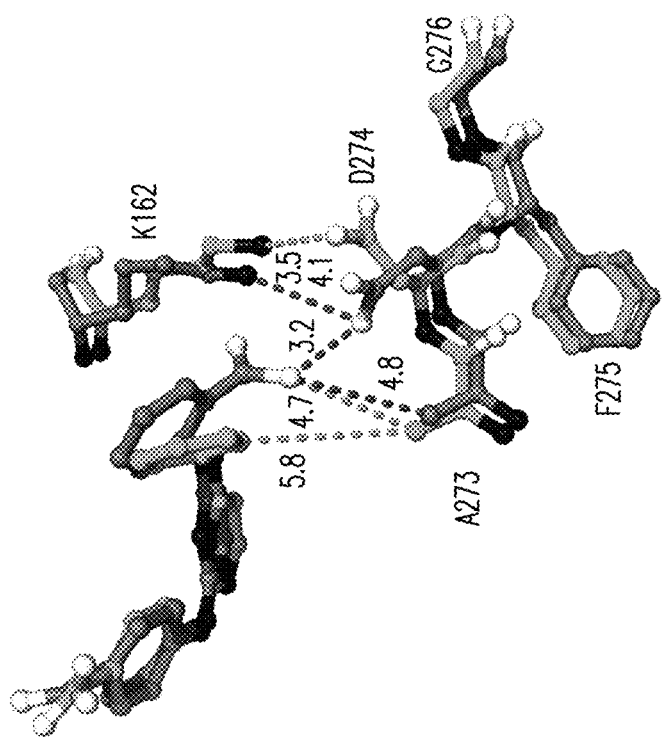
Figure 21B:
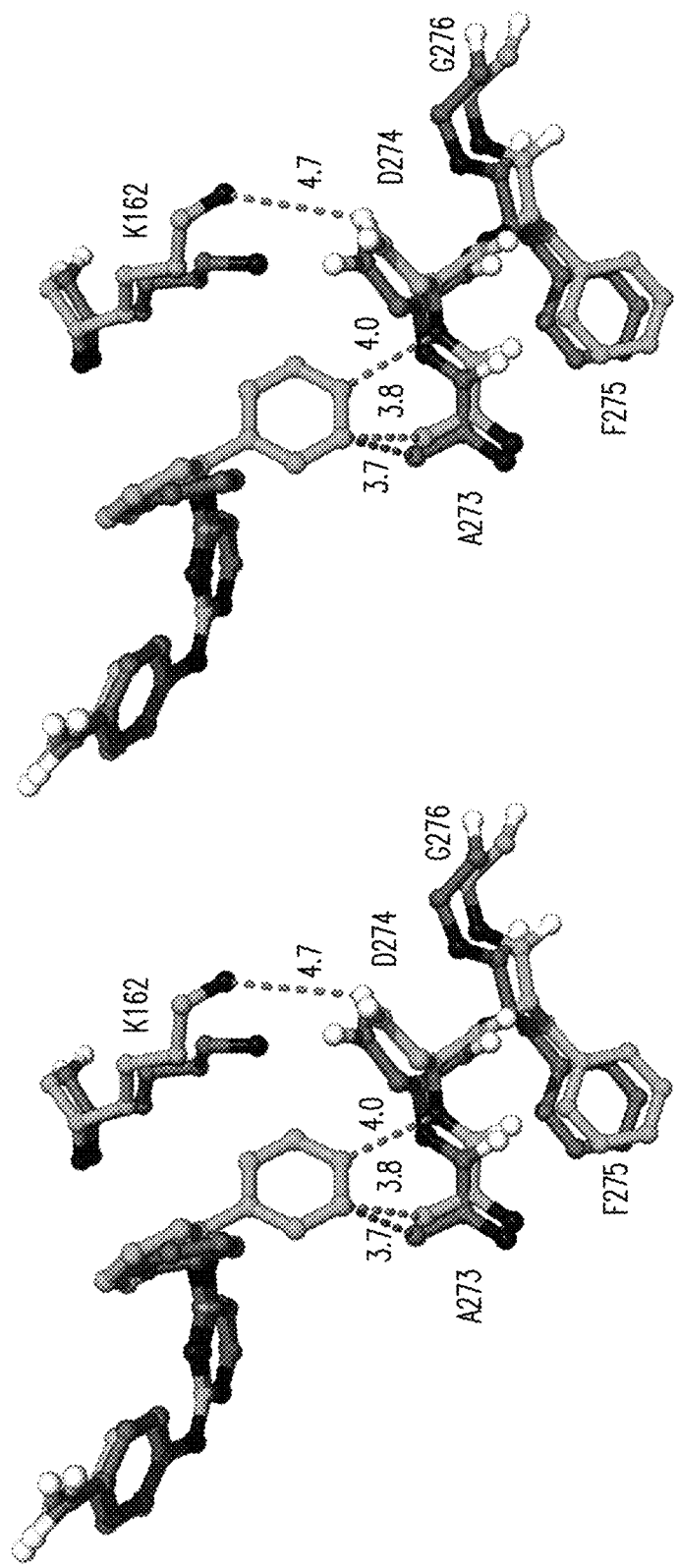
Figure 21C:
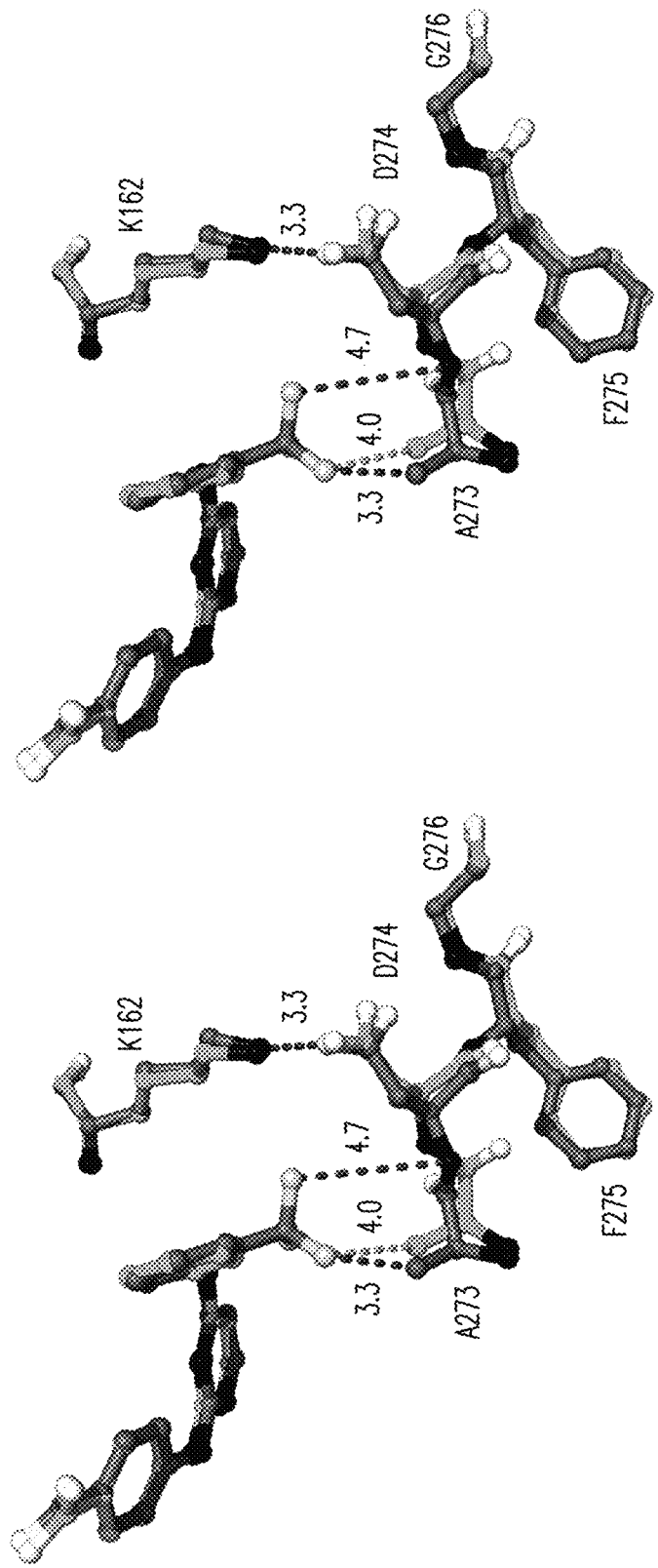
Figure 21D:
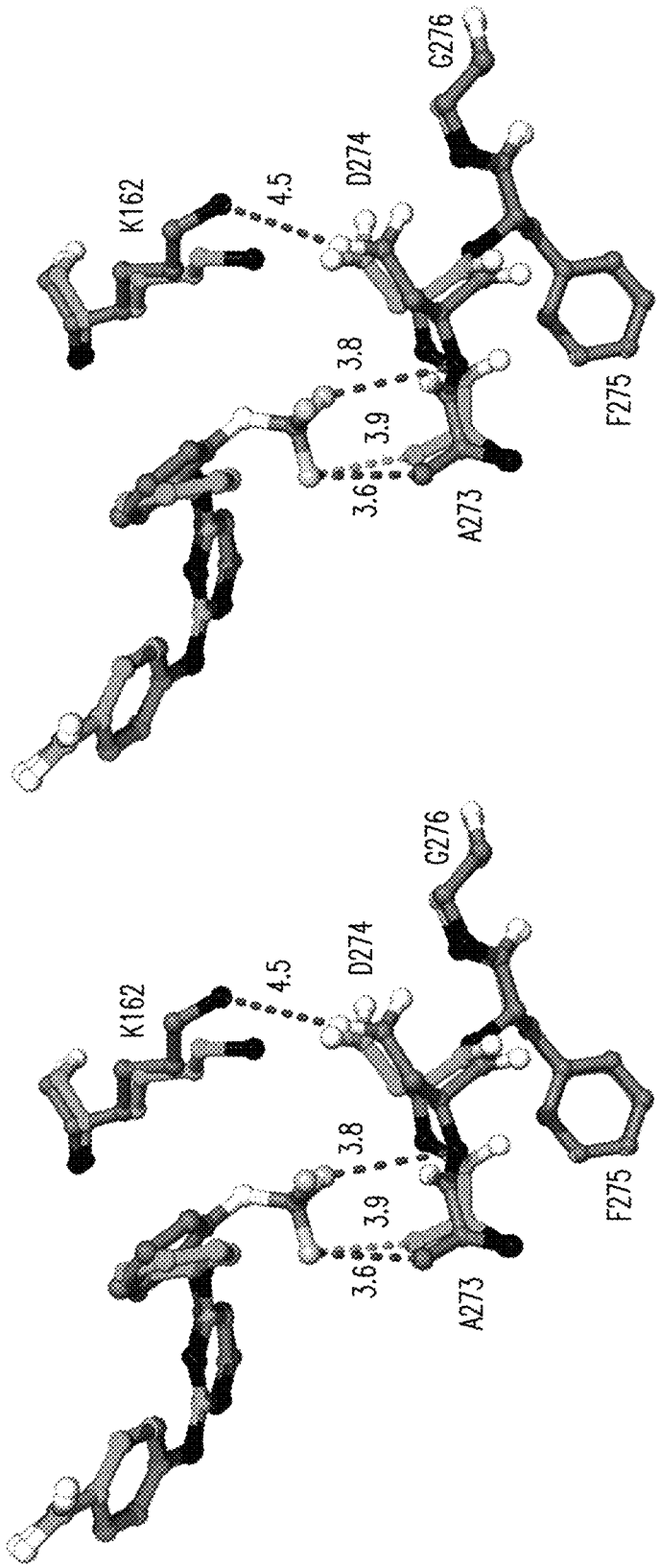

Experimental data are shown in FIG. 19 through FIG. 20E.

Example 4

Halogen Substituents Induce a DFG-Out State with Concomitant Closure of the ATP Site The major difference between the binding interactions of hit compound 1 and all other compounds tested is the establishment of a salt bridge between the carboxyl group on the A-ring and the side chain of Lys162 (FIG. 14A through FIG. 14I and FIG. 21A through FIG. 21D). Lys162 normally interacts with the carboxyl group of Asp274, and the loss of Lys162 as a binding partner allows the Asp274 side chain to swing towards the inhibitor. A similar interaction pattern is found upon binding of ADP, in which the diphospho moiety interacts with both Lys162 and Asp274. The unsubstituted parent compound 3h retains high activity and binding affinity as fewer spatial constraints and loss of the electrostatic interaction with Lys162 allow the A-ring to rotate by approximately 40° into a position that is presumably more energetically favorable. Introducing a phenyl group (compound 6q) resulted in significant reduction of activity due to steric hindrance with the DFG segment. Although the DFG segment shifts away from the inhibitor to accommodate the bulky phenyl ring, the DFG-in state is maintained. In addition, the A-ring rotates away from the favorable orientation of compound 3h. The trifluoromethyl (compound 6h) and trifluoromethoxy (compound 6d) substituents were approximately three-fold less active than parent compound 3h. These substituents caused steric hindrance with the DFG as indicated by rotation of the A-ring, particularly for compound 6d. Binding of compounds 6h and 6d induced a flip of the Ala-Asp peptide bond from a cis-like configuration to trans. This backbone structural change is localized and did not alter the DFG-in conformation, but it indicated that the N-terminal flank of the DFG may respond to halogen substituents.

Figure 15D:
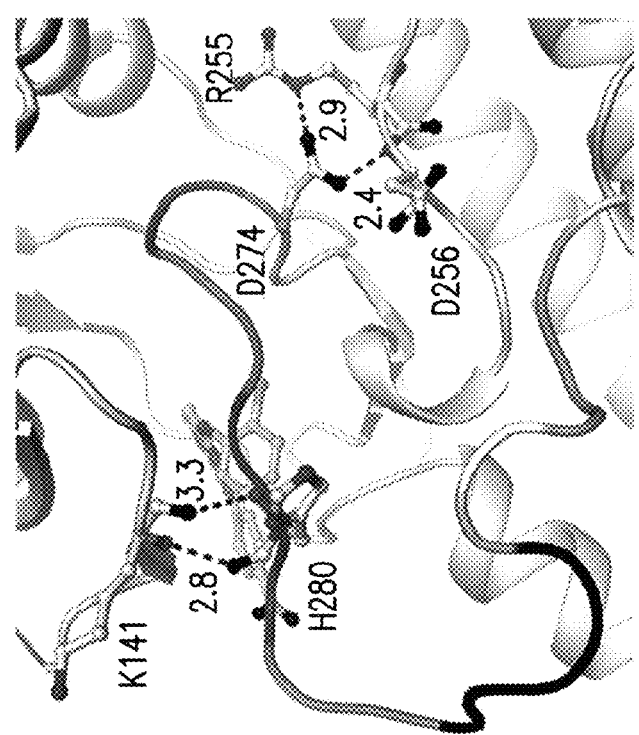
Figure 15C:
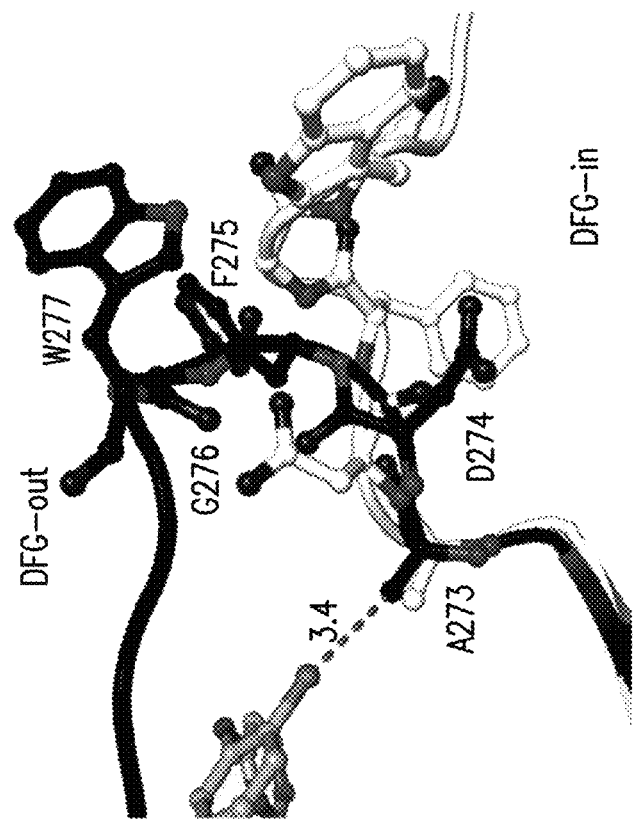
Figure 15E:
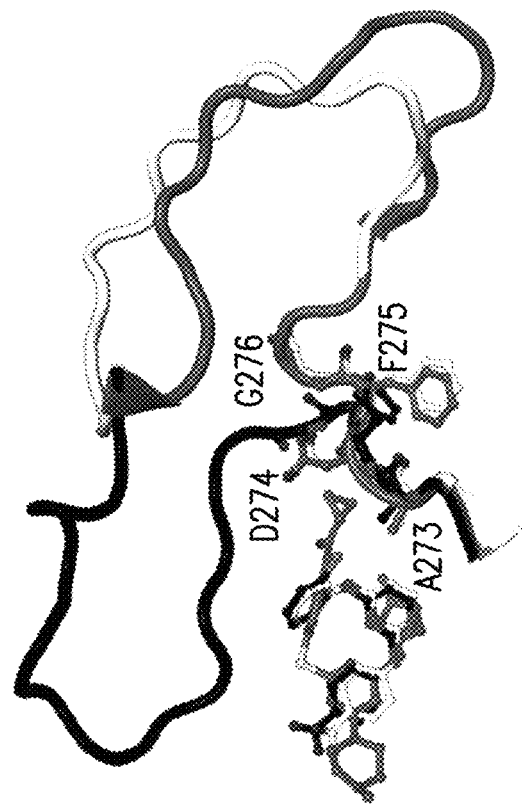
Figure 15E:
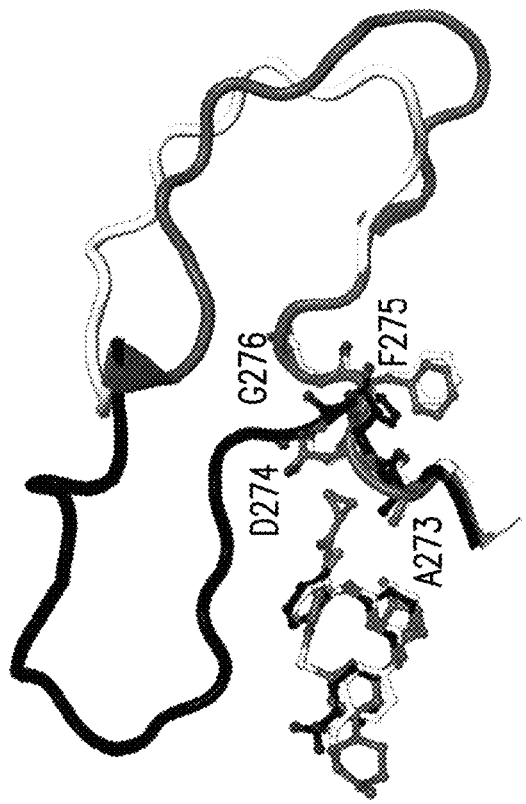

Remarkably, introduction of a fluorine (compound 6a), chlorine (compound 3l), or bromine (compound 6i) moiety resulted in a significant increase of inhibitory activity and binding affinity for progressively larger and less electronegative substituents (Table 5). Co-crystallization attempts using the established conditions for DFG-in compound 3h, 1, 6q, 6h, and 6d were unsuccessful and in-diffusion experiments using crystals of ligand-free Aurora A resulted in rapid deterioration of diffraction power. These observations suggested that compounds 6a, 3l, and 6i induce structural changes in the enzyme that are incompatible with the crystal lattice. New conditions suitable for the crystallization of Aurora A in the presence of these inhibitors were established. The resulting structures revealed a complete switch from the DFG-in to the DFG-out state (FIG. 14A through FIG. 15E). In the DFG-out state, Asp274 is rotated approximately 100° away from the ATP site and interacts with Arg255 and Asn256 (FIG. 15A through FIG. 15E). The main chain conformational change of Asp274 is perpetuated towards Phe275 and Gly276, resulting in a complete 180° flip of the DFG motif and the adjacent activation loop (residues 277-293), which moves inward atop the ATP cleft. The new loop conformation is stabilized by hydrogen bonding interactions between the main chain atoms of Lys141 and His280 and by multiple van-der-Waals interactions of Trp277, which shifts position from a largely polar environment to a strictly hydrophobic pocket (FIG. 15D). Another effect of the DFG flip is a ~4 Å shift in the C-helix to accommodate Phe275 and movement of the catalytic glutamate residue (Glut 81) away from the ATP active site. Notably, VX680 and compound 3h share the same DFG-in mode of action and exhibit similar conformations in the DFG segment and the activation loop (FIG. 15E). The closed loop conformation exhibits clearly defined electron density for the N-terminal strand (residues 277-282), which is anti-parallel to a β-strand of the upper N-terminal lobe of the kinase domain. In contrast, the tip of the loop (residues 283-289) is largely flexible (FIG. 15D).

Figure 16A:
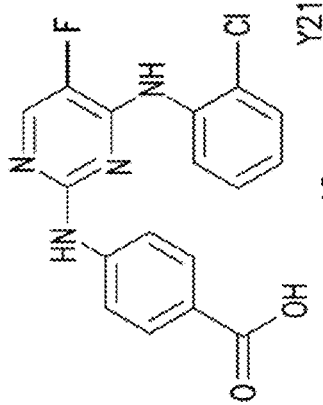
FIG. 16A through FIG. 16C show substitutions in other regions of the bisanilinopyrimidine scaffold do not affect the DFG-out mode of action (stereo presentations).
Figure 16A:
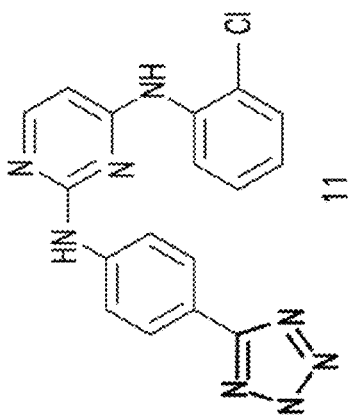
Figure 16B:
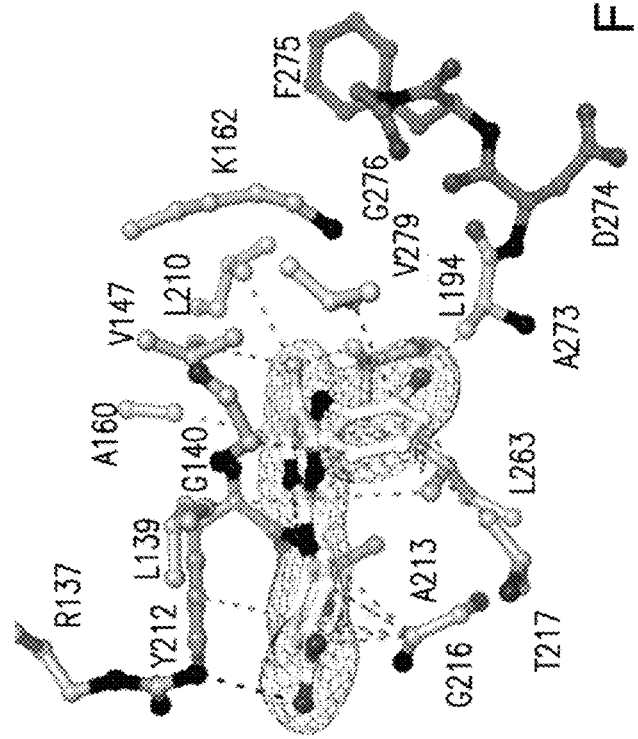
Figure 16B:
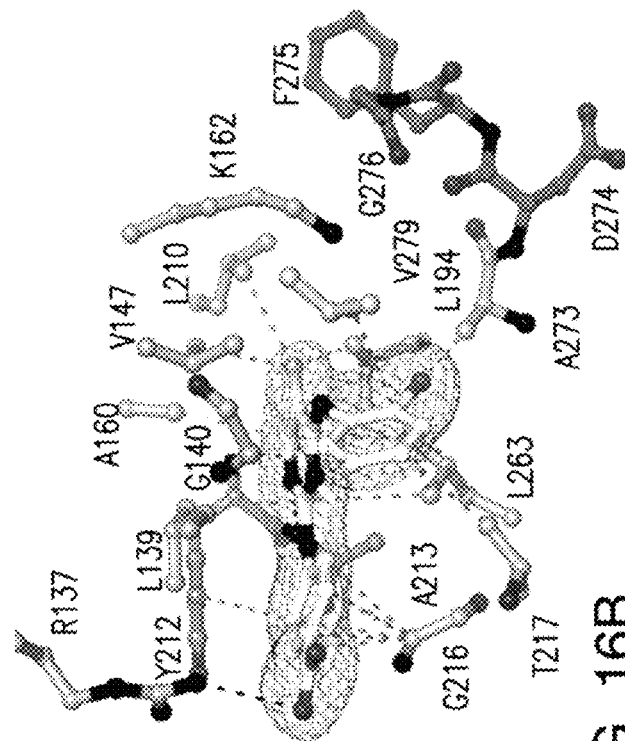
Figure 16C:
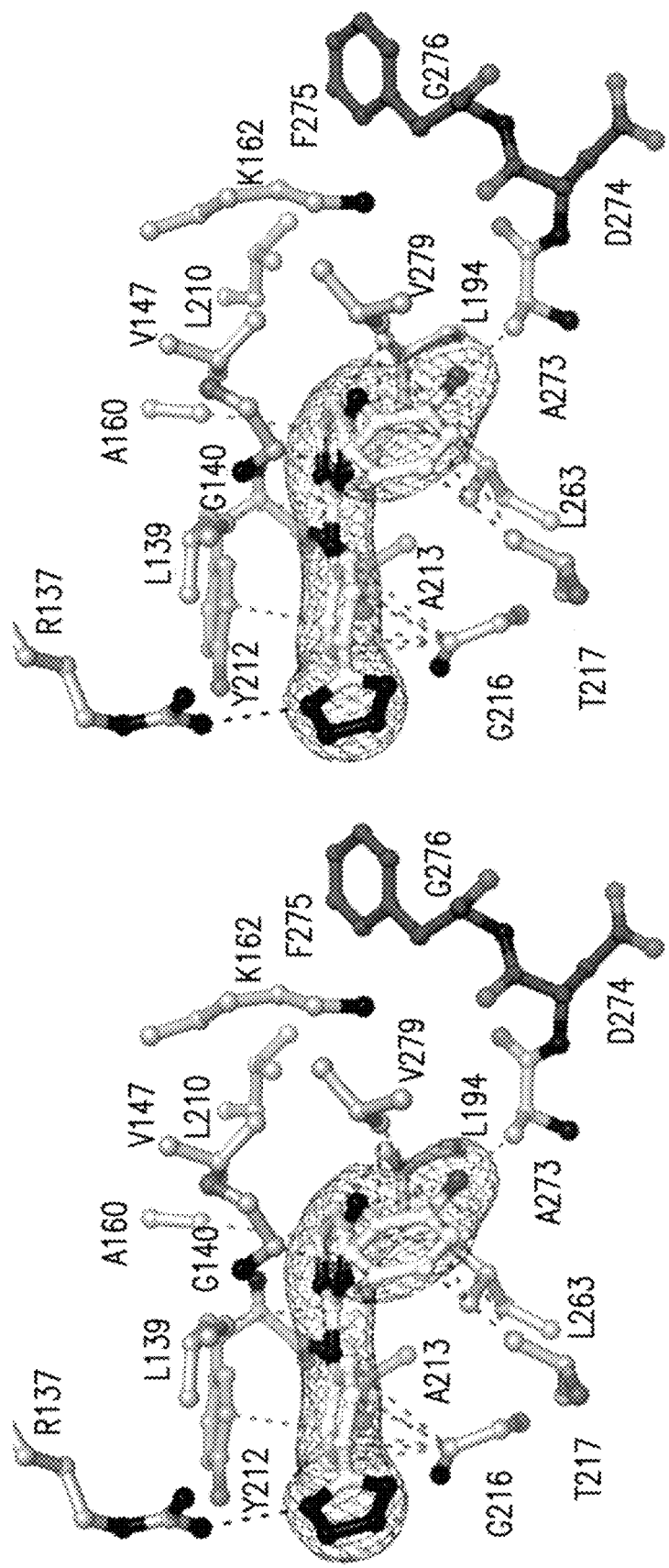

The high potency of the halogenated compounds 6a, 3l, and 6i appears to result from structural rearrangement of the activation loop, which effectively shields the inhibitor from solvent and ATP in the dead-end complex. The increase in enthalpy observed by ITC (Table 5) is likely due to the addition of hydrogen bonding interactions between the loop and the enzyme upon inhibitor binding. The chlorinated scaffold of compound 3l was analyzed by introducing a fluorine in the pyrimidine ring (compound 3o), which increased the inhibitory potency by greater than two-fold ($IC_{50}$=0.8 nM). The co-crystal structure confirmed the DFG-out mode of compound 3o, and the increased potency over compound 3l is attributable to additional van der Waals interactions of the fluorine substituent with the small hydrophobic pocket around the gatekeeper residue Leu210 (FIG. 16A through FIG. 16C). Substitution of the para-carboxyl group of the B-ring with a tetrazole moiety (compound 13a) rendered the DFG-out characteristics unchanged, but did not improve inhibitory activity ($IC_{50}$=3.1 nM). The tetrazole ring mimics the anionic character of the carboxyl group by establishing a salt bridge with Arg137. The data demonstrate that substitutions in other regions of the bisanilinopyrimidine scaffold do not affect the DFG-out mode of action of ortho substituents in the A-ring.

Example 5

The DFG-Out Inhibitors Target Ala273, the Residue N-Terminal to the DFG

Figure 17A:
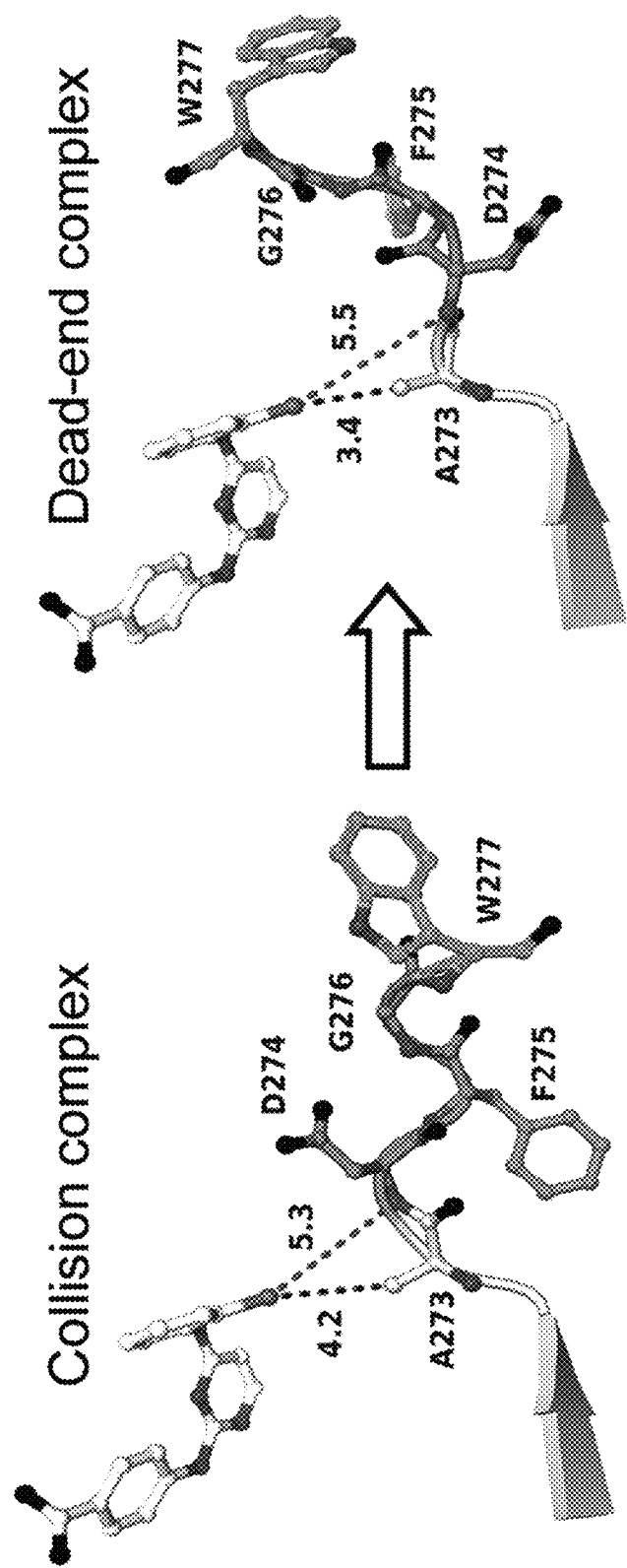
FIG. 17A through FIG. 17C show the dipole-induced mechanism of action for Aurora A DFG-out inhibitors.

The studies of the ortho position of the B-ring show that the observed conformational changes are attributed to the substituents in this position. Analysis of the binding interactions of mono-halogenated compounds 6a, 3l, and 6i in the respective dead-end complexes did not reveal a reason for the unique conformational changes of the DFG and the activation loop. The position of the A-ring remains unchanged with respect to parent compound 3h, and no additional interactions with enzyme residues are observed at first glance. The DFG flip cannot be attributed to steric forces, as the bulky phenyl and trifluoromethoxy substituents of compounds 6q and 6d did not invoke similar structural changes. Furthermore, proximity and net electronegativity alone do not explain these observations, as binding of the fluorinated substituents of compounds 6h and 6d renders the DFG-in state unchanged. Superimposition of compound 3l onto the DFG-in state simulates the collision complex of halogenated inhibitors with the active site prior to the DFG flip (FIG. 17A). Comparison with the dead-end complex indicates that the chlorine atom attracts the methyl group of Ala273, resulting in 0.8 Å shorter distance and almost collinear alignment of the Phe-Cl and $C_\alpha$-$C_\beta$ bonds. The positional shift of Ala273 towards the inhibitor is only observed for the halogenated compounds 6h, 6d, 6a, 3l, and 6i and nitrile derivative compound 6n (FIG. 21A through FIG. 22D).

Halogen substituents are known for their abilities to significantly enhance the activity of small molecule inhibitors (Muller et al., (2007) *Science* 317:1881-1886), but the mechanism for the attraction of halocarbons to active site residues is not fully understood. C—X groups (X=F, Cl, Br) frequently display lipophilic characteristics, such as fitting into a hydrophobic pocket as observed for the fluorine substituent of compound 3o (FIG. 16A through FIG. 16B). Recent analyses of the PDB revealed a large number of halogenated ligands that appear to establish polar "halogen bonding" interactions with their target proteins (Lu et al., (2009) *J Med Chem* 52:2854-2862; Lu et al., (2009) *J Phys Chem. B* 113:12615-12621; Parisini et al., (2011) Halogen bonding in halocarbon-protein complexes: a structural survey, *Chem Soc Rev* 40:2267-2278). Non-covalent halogen bonds are weaker than hydrogen bonding interactions, and they are typically established with polar acceptor groups in the form of perpendicular C—X . . . H or linear C—X . . . D bonds, in which D (electron donor) is a Lewis base. Halogen bonding is a potential mechanism for the DFG-out inhibitors, taking into account the concept of the 'sigma-hole' (Auffinger et al., (2004) *Proc Natl Acad Sci USA* 101:16789-16794), which describes the positive electrostatic potential at the tip of the C—X bond due to the unevenly distributed partial charges around the halogen atom (Cl, Br, and I). C—X bonds therefore assume either electrophilic or nucleophilic characteristics, depending on the geometry of the halogen bond (Politzer et al., (2007) *J Mol Model* 13:305-311; Murray et al., (2009) *J Mol Model* 15:723-729). Halogen bonding is highly directional, with the C—X . . . D bond typically existing in a linear alignment (angles between 140-180°) (Metrangolo et al., (2001) *Chemistry* 7:2511-2519; Metrangolo et al., (2008) *Angew Chem*

*Int Ed Engl* 47:6114-6127; Politzer et al., (2010) *Phys Chem Chem Physics: PCCP* 12:7748-7757). This implies that the strength of the sigma-hole halogen bond is directly related to the C—X . . . D alignment, with the strongest orbital overlap in the linear orientation and deviation from 180° resulting in a partial to total loss of effect. In the case of the DFG-out inhibitors, however, several experimental observations render halogen bonding interactions an unlikely cause for the DFG flip. First, the sigma-hole concept may be applicable to the chlorine and bromine substituents of compounds 31 and 6i, but not to the fluorine of compound 6a (Parisini et al., (2011) *Chem Soc Rev* 40:2267-2278). Second, the methyl group of Ala273 is a poor Lewis base/electron donor for an interaction of this nature. Third, halogen bonding interactions contribute to the binding potential of small molecules only moderately, and they have not been associated with conformational changes in proteins. The magnitude of the structural changes in Aurora A induced by compounds 6a, 31, and 6i therefore suggested a different mechanism of action involving electrostatic dipole-dipole interactions.

Example 6

Induced-Dipole Forces Likely Cause the DFG to Unwind

Figure 17B:
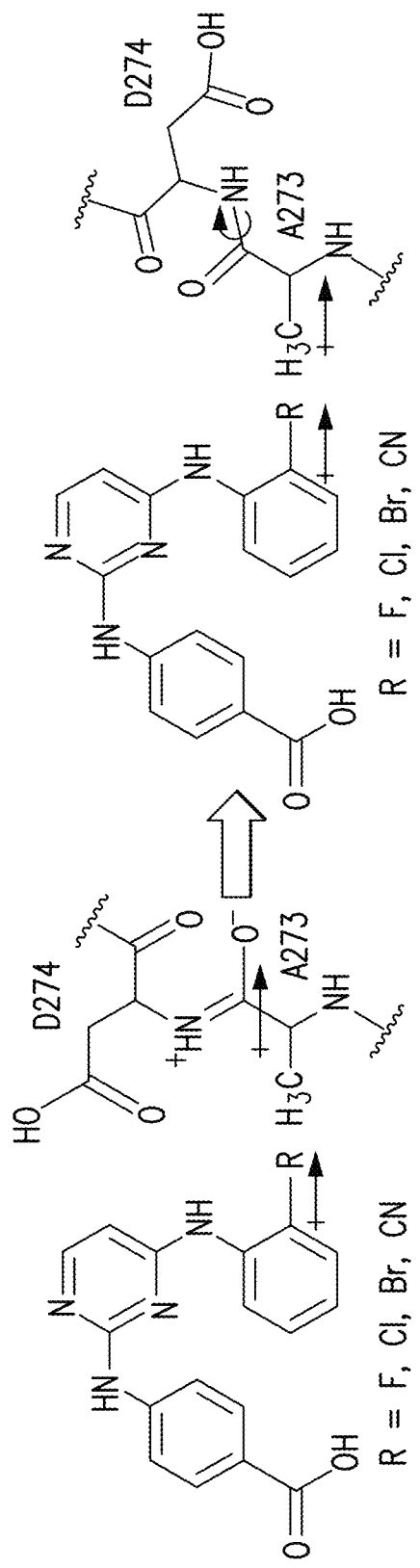

The fundamental concept that polar molecules have the ability to polarize a second, nonpolar molecule has been given much attention in molecular dynamics simulations to understand and predict the influence of electrostatic and van-der-Waals forces in proteins (Neves-Petersen et al., (2003) *Biotechnol Ann Rev* 9:315-395; Stork et al., (2007) *J Chem Phys* 126:165106; Nakamura (1996) *Q Rev Biophys* 29:1-90). The asymmetric packing of the main chain amide dipoles in folded proteins results in overall positive electrostatic potential of all side chains, particularly for alanine (Gunner et al., (2000) *Biophys J* 78: 1126-1144). The dipole moment and molecular orbital signature of L-alanine has been thoroughly analyzed (Falzon et al., (2006) *J Phys Chem B* 110:9713-9719), and the polarizability of Ala273 in Aurora A may therefore play an important role in the mode of action of the inhibitors. The Phe-X bonds of compound 6a, 31, and 6i align with the $C_\alpha$-$C_\beta$ bond of Ala273, reminiscent of the attraction exerted by a permanent magnet on an iron rod (FIG. 17B). In this mechanism, the electric dipole of the inhibitor induces a dipole in the polarizable $C_\alpha$-$C_\beta$ bond of Ala273. Establishment of this dipole-dipole interaction is relayed to the π-system of the amide bond, altering the charge distribution along the DFG backbone and allowing unrestrained rotation. As a consequence, the DFG unwinds and the activation loop adopts a potentially lower energy state. Such an unprecedented mechanism of action is difficult to prove, and computational drug design has not probed the effect of exogenous electric dipoles on protein structure (Lu et al., (2009) *J Phys Chem B* 113:12615-12621).

Figure 17C:
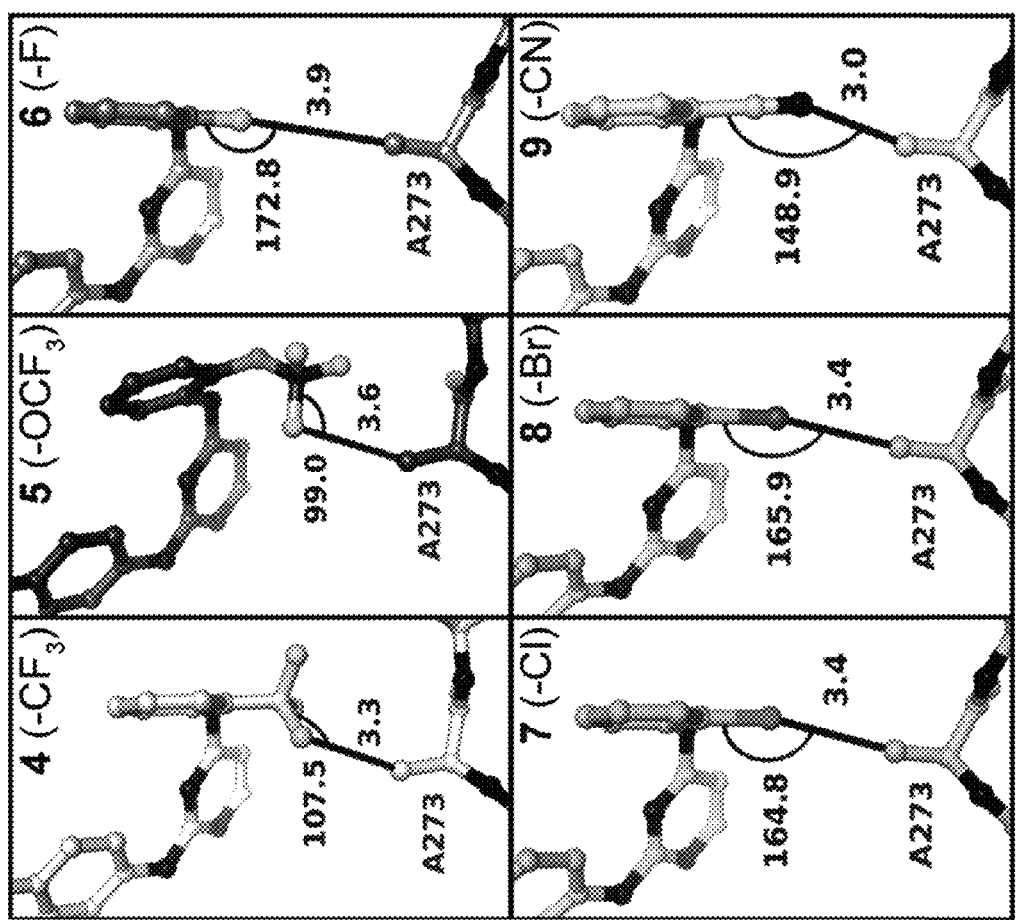

To test the hypothesis of induced-dipole forces being responsible for the DFG flip, and to rule out halogen bonding as a plausible mechanism, the strong dipolar and electron-withdrawing nitrile group was introduced (Jones et al., (2010) *Med Chem Comm* 1:309-318; Fleming et al., (2010) *J Med Chem* 53:7902-7917). Compound 6n induced the same structural changes as compounds 6a, 31, and 6i (FIG. 14A through FIG. 14I), demonstrating that the DFG-in state of Aurora A is readily perturbed by dipoles able to align with Ala273. The distances between the substituents and the $C_\beta$ atom of Ala273 range from 3.9 Å for the fluorine to as low as 3.0 Å for the nitrile substituent (FIG. 17C). While the respective halocarbon bonds are positioned almost collinearly with the $C_\alpha$-$C_\beta$ bond of Ala273, accommodation of the longer nitrile group necessitates rotation of the A-ring out of the energetically favored position by ~20°. Although slightly misaligned, the close proximity of the nitrile dipole to Ala273 induces the same conformational changes in the enzyme as the halogen substituents. However, steric repulsion exerted by Ala273 causes strain in the inhibitor molecule explaining the decrease of binding potential for compound 6n (Table 5). The inhibitory efficacy of DFG-out inhibitors harboring electric dipoles depends on a precise geometry between the substituents and the flanking alanine residue. Although Ala273 is in close distance to compounds 4 and 5, the dipoles introduced by the —$CF_3$ and —$OCF_3$ substituents lack the potential to induce the DFG flip. The C—F bonds are positioned almost orthogonal to the $C_\alpha$-$C_\beta$ bond, and steric repulsion prevents the proper alignment of the overall dipole along the Phe-$CF_3$ axis of compound 4 with Ala273 (~150° angle and 4 Å distance).

Example 7

Implications for the Design of DFG-Out Inhibitors of Other Kinases

Figure 18B:
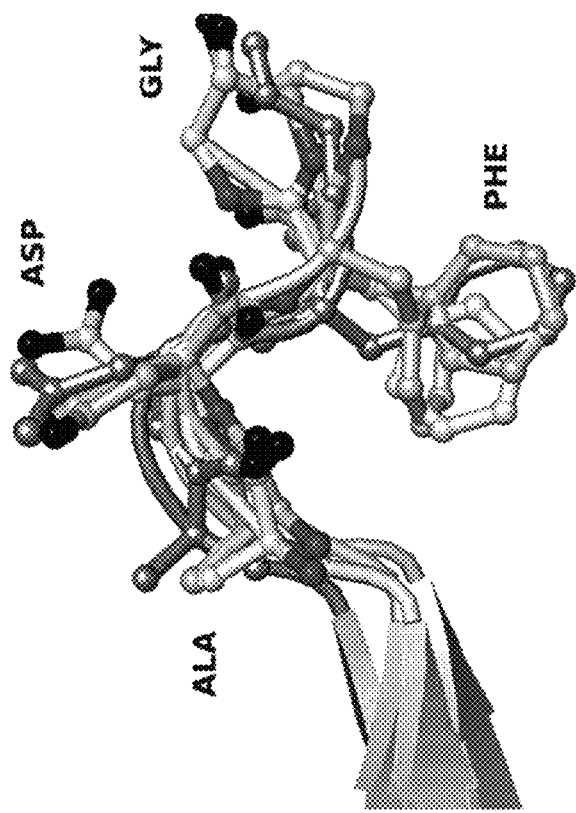
FIG. 18A through FIG. 18E show the implications for the design of DFG-out inhibitors of other kinases.
Figure 18A:
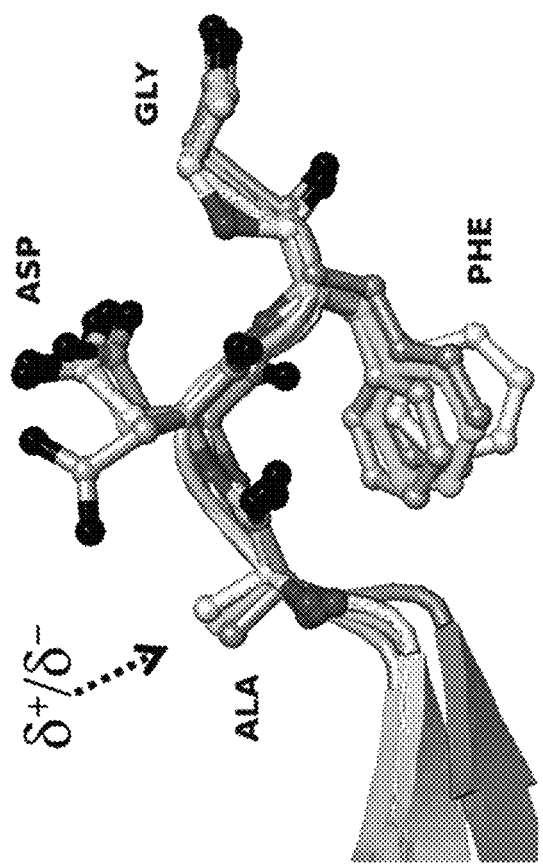
Figure 18D:
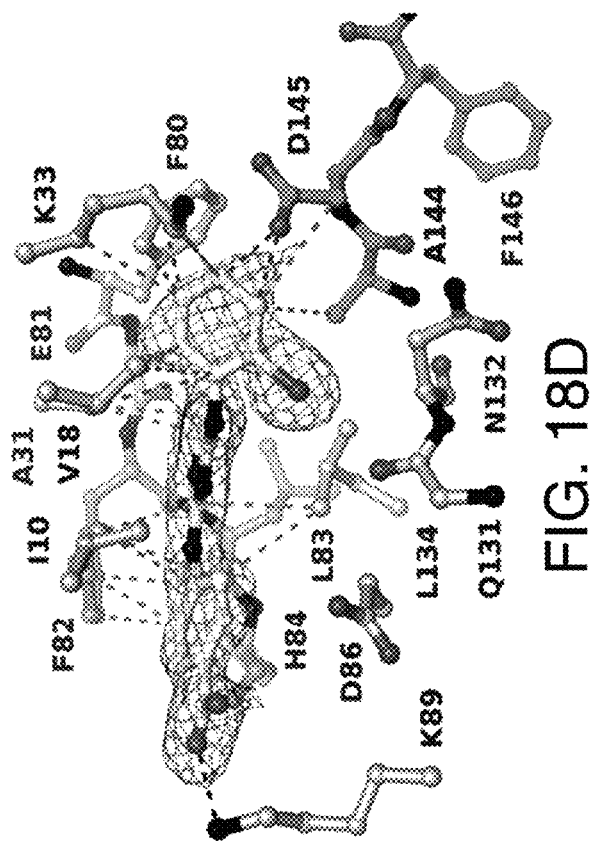
Figure 18C:
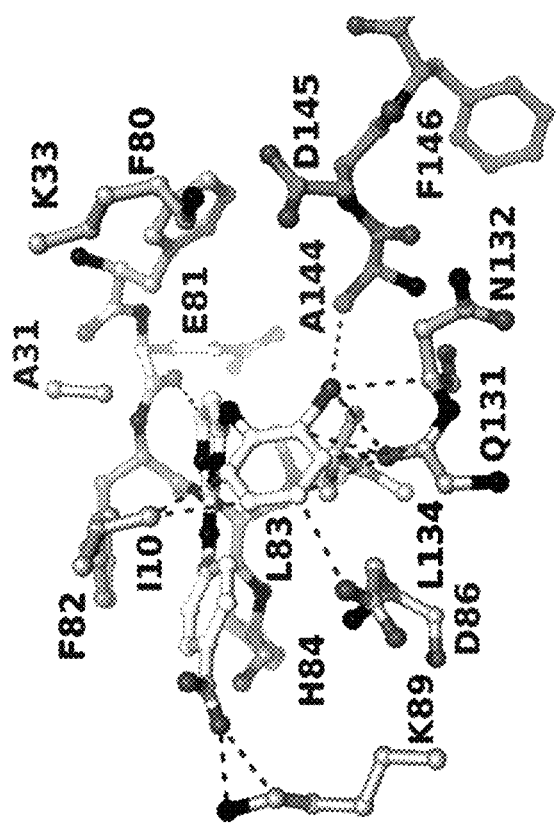
Figure 18E:
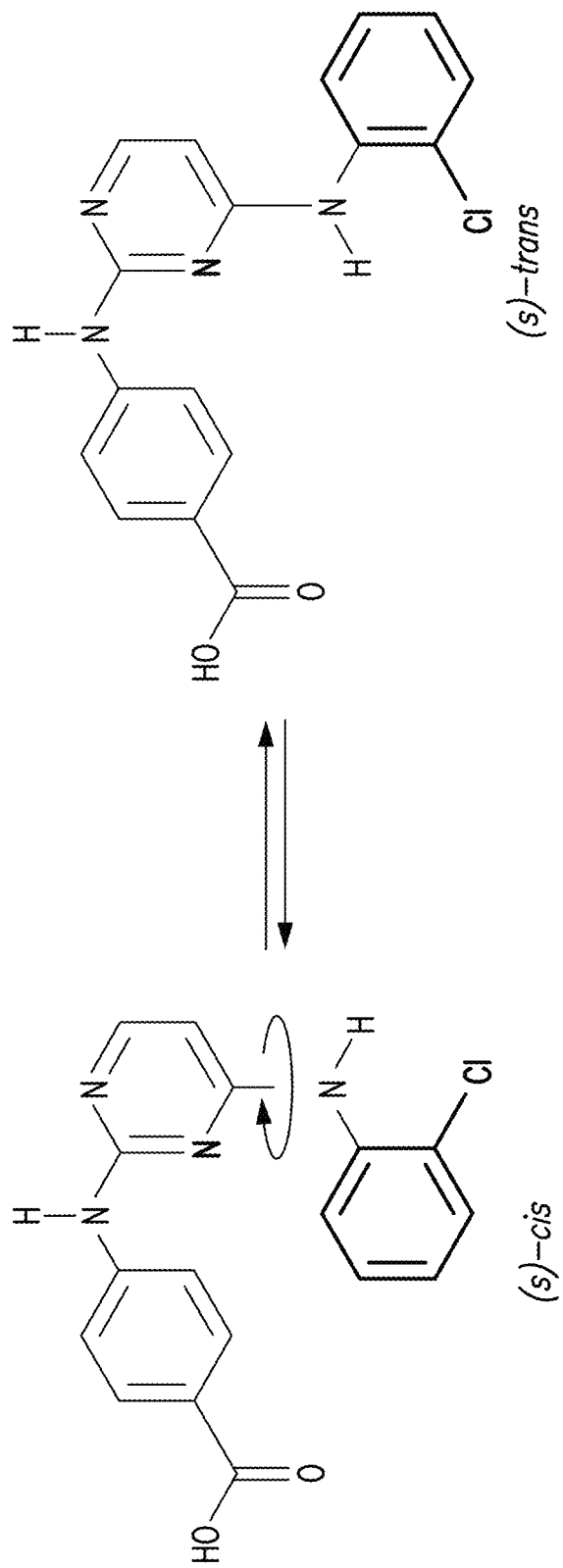

The DFG-out inhibitors designed herein are among the most potent described for Aurora A and protein kinases in general. The ADFG sequence and the three-dimensional architecture of the DFG-in state are well-conserved among kinases for which structural information is available (Table 6, FIG. 18A and FIG. 18B). It is conceivable that kinases with highest structural similarity to the DFG-in state of Aurora A respond similarly to the introduction of electric dipoles directed at the flanking alanine residue. The bisanilinopyrimidine scaffold of compound 1 proved to be advantageous for the design of DFG-out inhibitors of Aurora A, as it already binds with high affinity to the DFG-in state. However, slight variations in the ATP site may prevent proper positioning of this scaffold to other kinases. For example, compounds 1 and 7 are poor inhibitors of CDK2 with $IC_{50}$ values of 11 and 15 μM, respectively. With the exception of CDK8 (Schneider et al., (2011) *J Mol Biol* 412:251-266), CDKs are known only in the DFG-in state, despite the numerous inhibitor scaffolds that have been discovered. The conformation of the C-terminal DFG flank in CDK2 differs significantly from most kinases and can contribute to the stabilization of the DFG-in state. Modeling of the conformer of compound 7 (Aurora A) into the active site of CDK2 indicates substantial steric hindrance caused by the A-ring (FIG. 18C). Co-crystal structures revealed that these inhibitors bind to CDK2 in the (s)-trans conformation as opposed to the (s)-cis conformation adopted in Aurora A (FIG. 18D). As a result, the A-ring projects away from the DFG, preventing dipolar substituents from linear alignment with Ala273. Therefore, targeting the DFG of other kinases by induced-dipole forces initially requires the identification of candidate scaffolds that satisfy the geometric framework for efficient interaction with the N-terminal flank.

TABLE 6

Structural comparison of the DFG-in states of selected kinases harboring an ADFG sequence.

| PDB ID | Overall identity/similarity (%)[a] | Kinase | r.m.s.d. (Å)[b] |
|---|---|---|---|
| 2HK5 | 22.3/41.1 | HCK | 0.2 |
| 2DQ7 | 23.8/40.9 | Fyn | 0.2 |
| 1QPC | 23.7/39.0 | LCK | 0.2 |
| 2ZV7 | 23.8/40.2 | Lyn | 0.2 |
| 3KF4 | 24.8/42.6 | ABL1 | 0.3 |
| 2EU9 | 19.9/36.5 | CLK3 | 0.3 |
| 3COK | 35.1/56.2 | PLK4 | 0.3 |
| 2XIK | 30.3/49.0 | STK25 | 0.3 |
| 2J7T | 28.3/46.9 | STK10 | 0.3 |
| 3A7F | 28.6/48.1 | STK24 | 0.3 |
| 3COM | 26.8/49.7 | STK4 | 0.3 |
| 2QLU | 21.7/41.5 | ACTR-IIB | 0.3 |
| 2J51 | 28.5/49.3 | hSLK | 0.3 |
| 3S95 | 22.8/39.9 | LIMK1 | 0.3 |
| 3LXL | 24.6/42.4 | JAK3 | 0.3 |
| 2BDJ | 22.9/40.5 | Src | 0.3 |
| 1XJD | 30.8/49.3 | PKC theta | 0.4 |
| 2VD5 | 30.8/48.4 | DMPK | 0.4 |
| 2ETR | 30.2/48.2 | ROCK 1 | 0.5 |
| 2VZ6 | 31.3/48.1 | CaMK2A | 0.5 |
| 3DAK | 25.9/41.3 | OSR1 | 1.0 |
| 3PXR | 26.4/44.4 | CDK2 | 1.0 |
| 3FE3 | 31.2/51.5 | MAPK3 | 1.0 |
| 3LMG | 20.8/39.1 | erbB-3 | 1.0 |
| 3KY2 | 25.4/42.2 | FGFR1 | 1.1 |
| 3L8P | 25.2/40.2 | Tie-2 | 1.2 |
| 3PLS | 21.3/35.4 | RON | 1.2 |
| 3BRB | 22.9/36.7 | MER | 1.3 |
| 1BLX | 24.3/41.0 | CDK6 | 1.3 |
| 3F66 | 21.1/36.0 | c-Met | 1.4 |

[a]Computed with EMBOSS Needle against the kinase domain of human Aurora A.
[b]r.m.s.d. = root mean square deviation of the main chain atoms upon superposition with the ADFG of Aurora A in complex with compound 1 (computed with Superpose from the CCP4 program suite).

Example 8

Compounds

All reagents were purchased from commercial suppliers and used without further purification. Melting points were determined using a Barnstead international melting point apparatus and remain uncorrected. $^1$H NMR spectra were recorded on a Varian Mercury 400 MHz spectrometer with $CDCl_3$ or DMSO-$d_6$ as the solvent. $^{13}$C NMR spectra are recorded at 100 MHz. All coupling constants are measured in Hertz (Hz) and the chemical shifts ($\delta_H$ and $\delta_C$) are quoted in parts per million (ppm) relative to TMS ($\delta$ 0), which was used as the internal standard. High resolution mass spectroscopy was carried out on an Agilent 6210 LC/MS (ESI-TOF). Microwave reactions were performed in CEM 908005 model and Biotage initiator 8 machines. HPLC analysis was performed using a JASCO HPLC system equipped with a PU-2089 Plus quaternary gradient pump and a UV-2075 Plus UV-VIS detector, using an Alltech Kromasil C-18 column (150×4.6 mm, 5 µm) and Agilent Eclipse XDB-C18 (150×4.6 mm, 5 µm). Melting points were recorded on an Optimelt automated melting point system (Stanford Research Systems). Thin layer chromatography was performed using silica gel 60 F254 plates (Fisher), with observation under UV when necessary. Anhydrous solvents (acetonitrile, dimethylformamide, ethanol, isopropanol, methanol and tetrahydrofuran) were used as purchased from Aldrich. Burdick and Jackson HPLC grade solvents (methanol, acetonitrile and water) were purchased from VWR for HPLC and mass analysis. HPLC grade TFA was purchased from Fisher.

Synthetic Protocols for 2a to 2o

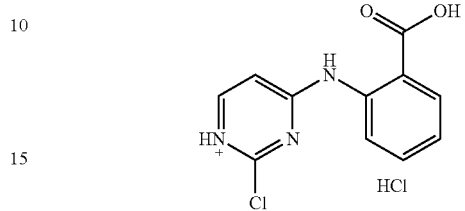

Figure 4A:
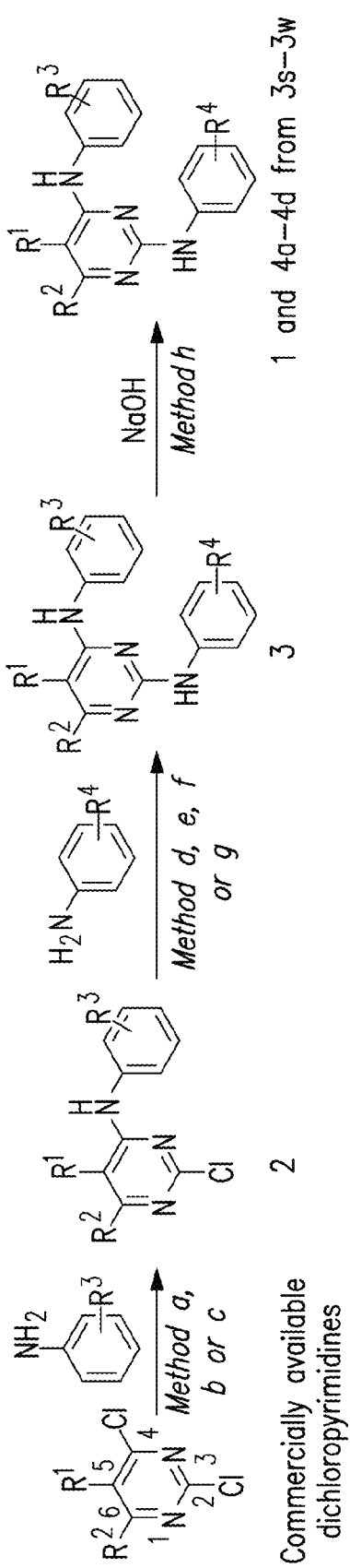
FIG. 4A is a synthetic route to a bisanilinopyrimidine carboxylic acid library, which is shown in FIG. 4B and in FIG. 4C. Reagents and conditions; method a: HCl (0.1 M, aq., 1-3 mL/mmol), microwave, 100° C., 30 min. method b: HCl (0.1 M, aq., 3 mL/mmol), r.t., 3-5 days. method c: HCl (0.1 M, aq., 1.5 mL/mmol), sealed tube, 100° C., 24 h. method d: HCl (0.1 M, aq., 3-6 mL/mmol), microwave, 160° C., 15 min. method e: EtOH: HCl (1 M, aq., 1:1, 4 mL/mmol), microwave, 160° C., 15 min.-1 h. method f: (i) HCl (4 M in dioxane, 0.5 mL/mmol), 2-butanol (3 mL/mmol), sealed tube, 120° C., overnight (24 h), 72% or (ii) EtOH, sealed tube, 120° C., overnight—4 days. method g: THF: HCl (1 M, aq.) (1:2, 6 mL/mmol), microwave, 160° C., 15 min. method h: THF:NaOH (2 M, aq.) (1:2, 4-7 mL/mmol), sealed tube, 85-100° C., 0.5-16 h.

$N^4$-(2-Carboxyphenyl)-2-chloropyrimidine-4-amine hydrochloride (2a, method a in FIG. 4A)

A mixture of 2,4-dichloropyrimidine (0.149 g, 1.00 mmol) and 2-aminobenzoic acid (0.137 g, 1.00 mmol) in HCl (3.0 mL, 0.1 M) was heated in a microwave reactor at 100° C. for 30 min. The precipitate obtained was filtered and the product washed with water (10 mL), hot MeOH (2×10 mL) and dried under vacuum to provide 2a (0.195 g, 68%) as a light yellow solid. m.p. 169° C. (dec.). $^1$H NMR (400 MHz, DMSO-$d_6$) δ 10.70 (s, 1H), 8.21 (d, J=6.0 Hz, 1H), 8.13 (d, J=8.0 Hz, 1H), 7.95 (dd, J=8.0, 1.6 Hz, 1H), 7.65-7.60 (m, 1H), 7.20 (appt, J=7.6 Hz, 1H), 6.90 (d, J=5.6 Hz, 1H); LRMS (ESI−) m/z 248.0 (M−H—HCl)$^-$; HRMS (ESI+) m/z calculated for $C_{11}H_9ClN_3O_7$ (M-Cl)$^+$ 250.0378. found 250.0380.

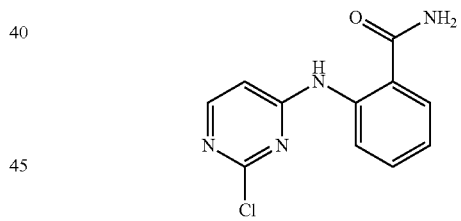

$N^4$-(2-Carbamoylphenyl)-2-chloropyrimidine-4-amine (2b, method a in FIG. 4A)

A mixture of 2,4-dichloropyrimidine (0.149 g, 1.00 mmol) and 2-aminobenzamide (0.136 g, 1.00 mmol) in HCl (3.0 mL, 0.1 M) was heated in a microwave reactor at 100° C. for 30 min. The precipitate obtained was filtered and the product was washed with water (10 mL) and recrystallized in methanol to obtain pure 2b (0.179 g, 63%) as a light yellow solid. m.p. 197° C. (dec.). $^1$H NMR (400 MHz, DMSO-$d_6$) δ 11.24 (s, 1H), 8.21 (brs, 1H partially overlapping), 8.19 (d, J=5.6 Hz, 1H partially overlapping), 8.15 (d, J=8.0 Hz, 1H partially overlapping), 7.75 (dd, J=8.4, 1.6 Hz, 1H), 7.71 (brs, 1H), 7.55-7.51 (m, 1H), 7.16 (td, J=7.6, 1.2 Hz, 1H), 6.85 (d, J=5.6 Hz, 1H); LRMS (ESI−) m/z 249.0 (M-Cl)$^+$; HRMS (ESI+) m/z calculated for $C_{11}H_{10}ClN_4O$ (M-Cl)$^+$ 249.0538. found 249.0545.

53

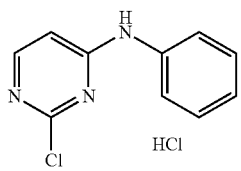

N⁴-Phenyl-2-chloropyrimidine-4-amine hydrochloride (2c, method a in FIG. 4A)

A mixture of 2,4-dichloropyrimidine (0.317 g, 2.12 mmol) and aniline (0.198 g, 2.12 mmol) in HCl (6.0 mL, 0.1 M) was heated in a microwave reactor at 100° C. for 30 min. The product obtained was purified using SiO₂ chromatography to afford the desired compound 2c (0.130 g, 26%) as a white solid. m.p. 159-161° C. ¹H NMR (400 MHz, CD₃OD) δ 8.03 (dd, J=6.0, 1.0 Hz, 1H), 7.57 (d, J=8.0 Hz, 2H), 7.37-7.33 (m, 2H), 7.12 (t, J=7.6 Hz, 1H), 6.67 (dd, J=6.0, 1.0 Hz, 1H); LRMS (ESI+) m/z 206.0 (M-Cl)⁺; HRMS (ESI) m/z calculated for C₁₀H₉ClN₃ (M-Cl)⁺ 206.0480. found 206.0477.

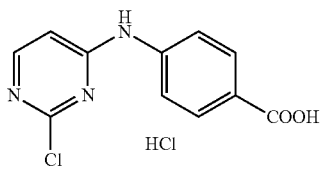 [SMILES: O=C(O)c1ccc(Nc2ccnc(Cl)n2)cc1 ; Cl]

N⁴-(4-Carboxyphenyl)-2-chloropyrimidine-4-amine hydrochloride (2d, method a in FIG. 4A)

A mixture of 2,4-dichloropyrimidine (0.596 g, 4.00 mmol) and 4-aminobenzoic acid (0.549 g, 4.00 mmol) in HCl (12.0 mL, 0.1 M) was heated in a microwave reactor at 100° C. for 30 min. The precipitate obtained was filtered and the product was washed with water (10 mL×2) and dried under high vacuum to give the desired compound 2d (0.895 g, 78%) as a white solid. m.p. 244° C. (dec.). ¹H NMR (400 MHz, DMSO-d₆) δ 10.38 (s, 1H), 8.24 (d, J=6.0 Hz, 1H), 7.92 (d, J=8.8 Hz, 2H), 7.73 (d, J=8.8 Hz, 2H), 6.85 (d, J=5.6 Hz, 1H); LC-MS (ESI+) m/z 250.03 (M-Cl)⁺; HRMS (ESI+) m/z calculated for C₁₁H₉ClN₃O₂ (M-Cl)⁺ 250.0378. found 250.0378.

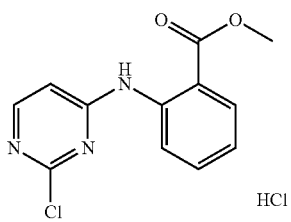 [SMILES: COC(=O)c1ccccc1Nc1ccnc(Cl)n1 ; Cl]

N⁴-(2-Carbomethoxyphenyl)-2-chloropyrimidine-4-amine hydrochloride (2e, method a in FIG. 4A)

A mixture of 2,4-dichloropyrimidine (0.149 g, 1.00 mmol) and methyl 2-aminobenzoate (0.151 g, 1.00 mmol) in

54

HCl (3.0 mL, 0.1 M) was heated using a microwave reactor at 100° C. for 30 min. The pale yellow solid which precipitated upon cooling was filtered and washed with water (10 mL). The solid was then dissolved in hot EtOH (20 mL) and filtered to remove the insoluble impurity. The filtrate was concentrated to obtain the desired product 2e (0.135 g, 45%) as a pale yellow solid. m.p.: 119° C. (dec). ¹H NMR (400 MHz, DMSO-d₆) δ 10.24 (s, 1H), 8.18 (d, J=6.0 Hz, 1H), 7.85 (dd, J=7.6, 1.6 Hz, 1H), 7.79 (d, J=8.4 Hz, 1H), 7.64-7.60 (m, 1H), 7.25 (appt, J=7.6 Hz, 1H), 6.82 (d, J=6.0 Hz, 1H), 3.74 (s, 3H); LRMS (ESI+) m/z 264.0 (M-Cl)⁺; HRMS (ESI+) m/z calculated for C₁₂H₁₂ClN₃O₂ (M-Cl)⁺ 264.0534. found 264.0542.

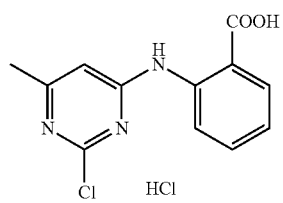 [SMILES: Cc1cc(Nc2ccccc2C(=O)O)nc(Cl)n1 ; Cl]

N⁴-(2-Carboxyphenyl)-2-chloro-6-methylpyrimidine-4-amine hydrochloride (2f, method a in FIG. 4A)

A mixture of 2,4-dichloro-6-methylpyrimidine (1.630 g, 0.010 mol) and 2-aminobenzoic acid (1.370 g, 0.010 mol) in HCl (15.0 mL, 0.1 M) was heated in a microwave reactor at 100° C. for 30 min. The precipitate obtained was filtered and washed with water (10 mL×2), MeOH (10 mL×2) and acetone (5 mL×2) sequentially. The product obtained was dissolved in hot EtOH (30 mL), filtered and the filtrate was concentrated and recrystallized in MeOH to afford the desired compound 2f (1.240 g, 41%) as a white solid. m.p. 169° C. (dec.). ¹H NMR (400 MHz, DMSO-d₆) δ 10.71 (s, 1H), 8.21 (d, J=8.4 Hz, 1H), 7.96 (dd, J=7.9, 1.5 Hz, 1H), 7.63 (appt, J=7.2 Hz, 1H), 7.16 (appt, J=7.6 Hz, 1H), 6.80 (s, 1H), 2.31 (s, 3H); LC-MS (ESI−) m/z 262.03 (M−H—HCl)⁻; HRMS (ESI−) m/z calculated for C₁₂H₉ClN₃O₂ (M−H—HCl)⁻ 262.0389. found 262.0393.

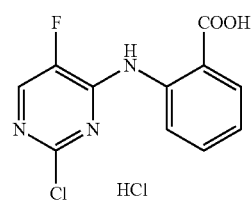 [SMILES: O=C(O)c1ccccc1Nc1nc(Cl)ncc1F ; Cl]

N⁴-(2-Carboxyphenyl)-2-chloro-5-fluoropyrimidine-4-amine hydrochloride (2g, method a in FIG. 4A)

A suspension of 2,4-dichloro-5-fluoropyrimidine (0.835 g, 5.00 mmol) and 2-aminobenzoic acid (0.685 g, 5.00 mmol) in HCl (15.0 mL, 0.1 M) was heated in a microwave reactor at 100° C. for 30 min. The precipitate obtained was filtered and washed with water (10 mL×2). The product obtained was slurried in hot MeOH (10 mL×2), filtered and dried under high vacuum to afford the desired compound 2g (0.836 g, 55%) as a light yellow solid. m.p. 194-197° C. ¹H NMR (400 MHz, DMSO-d₆) δ 11.67 (s, 1H), 8.57 (d, J=8.4

Hz, 1H), 8.44 (d, J=3.0 Hz, 1H), 8.03 (dd, J=8.0, 1.6 Hz, 1H), 7.71 (appt, J=7.8 Hz 1H), 7.21 (t, J=7.6 Hz, 1H); $^{19}$F NMR (376 MHz, DMSO-d$_6$) δ −155.07 (appt d, J=2.4 Hz); LC-MS (ESI−) m/z 266.01 (M−H—HCl)$^-$; HRMS (ESI−) m/z calculated for $C_{11}H_6ClFN_3O_2$ (M−H—HCl)$^-$ 266.0138. found 266.0143.

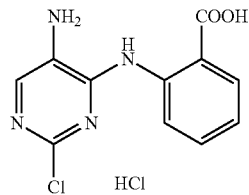 [SMILES: Nc1cnc(Cl)nc1Nc1ccccc1C(=O)O ; Cl]

$N^4$-(2-Carboxyphenyl)-2-chloropyrimidine-4,5-diamine hydrochloride (2h, method a in FIG. 4A)

A mixture of 2,4-dichloropyrimidin-5-amine (0.270 g, 1.646 mmol) and 2-aminobenzoic acid (0.225 g, 1.646 mmol) in HCl (4.0 mL 0.1 M) was heated in a microwave reactor at 100° C. for 30 min. The precipitate obtained was filtered and washed with water (5 mL), then with MeOH (3 mL, quick wash) and dried to afford the desired compound 2h (0.280 g, 57%) as a yellow solid. m.p. 172° C. (dec.). $^1$H NMR (400 MHz, DMSO-d$_6$) δ 13.45 (brs, 1H), 10.76 (s, 1H), 8.49 (d, J=8.5 Hz, 1H), 8.00 (dd, J=7.9, 1.4 Hz, 1H), 7.80 (s, 1H), 7.63 (appt, J=7.2 Hz, 1H), 7.11 (appt d, J=7.6 Hz, 1H), 5.04 (brs, 2H); LC-MS (ESI+) m/z 265.06 (M-Cl)+; HRMS (ESI+) m/z calculated for $C_{11}H_{10}ClN_4O_2$ (M-Cl)$^+$ 265.0487. found 265.0492.

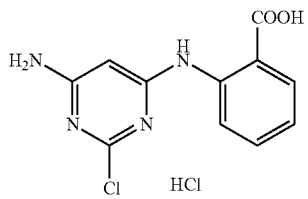 [SMILES: Nc1cc(Nc2ccccc2C(=O)O)nc(Cl)n1 ; Cl]

$N^4$-(2-Carboxyphenyl)-2-chloropyrimidine-4,6-diamine hydrochloride (2i, method c in FIG. 4A)

A mixture of 2,6-dichloropyrimidin-4-amine (2.006 g, 12.23 mmol) and 2-aminobenzoic acid (1.676 g, 12.23 mmol) in HCl (18.0 mL, 0.1 M) was heated at 100° C. in a sealed pressure tube for 24 h. The suspension was filtered after cooling to r.t. and washed with water (5 mL) and acetone (5 mL). The product obtained was slurried with acetone (10 mL), MeOH (10 mL), and again with acetone (10 mL) sequentially to afford pure compound 2i (1.562 g, 43%) as a light brown solid. m.p. 207-210° C. $^1$H NMR (400 MHz, DMSO-d$_6$) δ 10.89 (s, 1H), 8.83 (d, J=8.4 Hz, 1H), 7.97 (d, J=7.6 Hz, 1H), 7.54 (t, J=6.8 Hz, 1H), 7.18 (s, 2H), 6.99 (t, J=7.2 Hz, 1H), 6.02 (s, 1H); LC-MS (ESI+) m/z 265.06 (M-Cl)$^+$; HRMS (ESI+) m/z calculated for $C_{11}H_{10}ClN_4O_2$ (M-Cl)$^+$ 265.0487. found 265.0488.

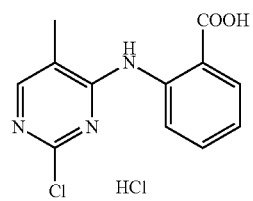 [SMILES: Cc1cnc(Cl)nc1Nc1ccccc1C(=O)O ; Cl]

$N^4$-(2-Carboxyphenyl)-2-chloro-5-methylpyrimidine-4-amine hydrochloride (2j, method a in FIG. 4A)

A mixture of 2,4-dichloro-5-methylpyrimidine (0.535 g, 3.28 mmol) and 2-aminobenzoic acid (0.450 g, 3.28 mmol) in HCl (6.0 mL of 0.1 M) was heated in a microwave reactor at 100° C. for 30 min. The product obtained was filtered and washed with water (10 mL), slurried using hot MeOH (10 mL). The product was filtered and dried to obtain the desired compound 2j (0.512 g, 52%) as a light yellow solid. m.p. 184° C. (dec.). $^1$H NMR (400 MHz, DMSO-d$_6$) δ 11.28 (s, 1H), 8.76 (d, J=8.5 Hz, 1H), 8.20 (s, 1H), 8.04 (dd, J=8.0, 1.5 Hz, 1H), 7.68 (t, J=7.2 Hz, 1H), 7.16 (t, J=7.6 Hz, 1H), 2.20 (s, 3H); LC-MS (ESI+) m/z 264.05 (M-Cl)$^+$; HRMS (ESI+) m/z calculated for $C_{12}H_{11}ClN_3O_2$(M-Cl)$^+$ 264.0534. found 264.0539.

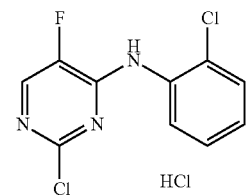

$N^4$-(2-Chlorophenyl)-2-chloro-5-fluoropyrimidine-4-amine hydrochloride (2k, method b in FIG. 4A)

A solution of 2,4-dichloro-5-fluoropyrimidine (2.00 g, 1.19 mmol) and 2-chloroaniline (1.53 g, 1.99 mmol) in HCl (0.1 M, 40.0 ml) were stirred at rt for 5 days. The precipitate obtained was filtered, washed with water and dried to obtain 2k.HCl (1.60 g, 47%) as a white solid. m.p. 128-129° C. $^1$H NMR (400 MHz, DMSO-d$_6$) δ 9.98 (s, 1H), 8.30 (d, J=3.4 Hz, 1H), 7.57 (dd, J=7.9, 1.5 Hz, 1H), 7.47 (dd, J=7.8, 1.7 Hz, 1H), 7.40 (td, J=7.6, 1.6 Hz, 1H), 7.34 (td, J=7.6, 1.8 Hz, 1H); $^{13}$C NMR (101 MHz, DMSO) δ 156.9 (d, J=3.1 Hz), 152.97 (d, J=12.3 Hz), 145.82 (d, J=257.5 Hz), 142.55 (d, J=20.5 Hz), 134.70, 131.40, 130.55, 129.86, 129.10, 128.49; $^{19}$F NMR (376 MHz, DMSO) δ −155.74 (s); LC-MS (ESI+) m/z 258.0001 (M-Cl)+, HRMS (ESI+) m/z calculated for $C_{10}H_7Cl_2FN_3$ (M-Cl)$^+$ 257.9996. found 258.0011.

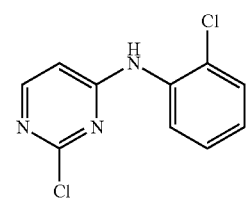

N⁴-(2-Chlorophenyl)-2-chloropyrimidine-4-amine (2l, method b in FIG. 4A)

A solution of 2,4-dichloropyrimidine (1.90 g, 1.3 mmol) and 2-chloroaniline (1.63 g, 1.3 mmol) in HCl (0.1 M, 40.0 mL) were stirred at RT for 3 days. The precipitate obtained was filtered and washed with sat. sodium bicarbonate solution and water. The product was purified by a quick wash with ether, dried to obtain 2l (2.70 g, 87%) as a white solid. Mp: 116-117° C.; ¹H NMR (400 MHz, DMSO-d₆) δ 9.75 (s, 1H), 8.13 (d, J=5.9 Hz, 1H), 7.59 (dd, J=8.0, 1.4 Hz, 1H), 7.55 (dd, J=8.0, 1.4 Hz, 1H), 7.38 (td, J=7.8, 1.6 Hz, 1H), 7.27 (td, J=7.8, 1.6 Hz, 1H), 6.65 (d, J=5.8 Hz, 1H). ¹³C NMR (100 MHz, DMSO) δ 163.19, 160.18, 158.34, 135.32, 130.64, 129.42, 128.53, 128.25, 128.11, 105.60. LC-MS (ESI+) m/z 240.01 (M–H)⁻; HRMS (ESI+) m/z calculated for $C_{10}H_7Cl_2N_3$(M+H)⁺ 240.0090. found 240.0090.

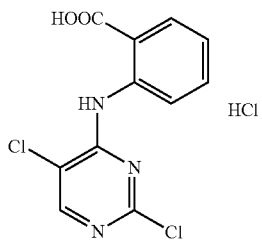 [SMILES: O=C(O)c1ccccc1Nc1nc(Cl)ncc1Cl ; Cl]

N⁴-(2-Carboxyphenyl)-2,5-dichloropyrimidine-4-amine hydrochloride (2m, method b in FIG. 4A)

A mixture of 2,4,5-trichloropyrimidine (0.156 g, 0.852 mmol) and 2-aminobenzoic acid (0.116 g, 0.852 mmol) in HCl (0.1 M aq., 3.0 mL), was heated in a microwave reactor at 100° C. for 30 min. The resulting precipitate was filtered and washed with water (3 mL×2), Et₂O (3 mL×2), DCM (5 mL×2) and EtOAc (5 mL) sequentially and dried under vacuum to afford the title compound 2m (0.114 g, 42%) as a white solid. m.p. 209.1-210.4° C. ¹H NMR (400 MHz, DMSO-d₆) δ 11.80 (s, 1H), 8.64 (d, J=8.4 Hz, 1H), 8.53 (s, 1H), 8.05 (dd, J=1.1, 7.9 Hz, 1H), 7.72-7.68 (m, 1H), 7.23 (t, J=7.8 Hz, 1H); LC-MS (ESI–) m/z 281.99 (M–H—HCl)⁻; HRMS (ESI–) m/z calculated for $C_{11}H_6Cl_2N_3O_2$ (M–H—HCl)⁻ 281.9843. found 281.9839.

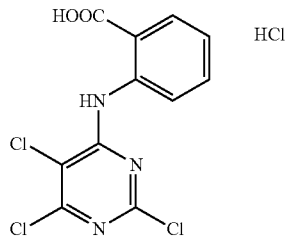 [SMILES: O=C(O)c1ccccc1Nc1nc(Cl)nc(Cl)c1Cl ; Cl]

N⁴-(2-Carboxyphenyl)-2,5,6-trichloropyrimidine-4-amine hydrochloride (2n, method b in FIG. 4A)

A mixture of 2,4,5,6-tetrachloropyrimidine (0.963 g, 4.45 mmol) and 2-aminobenzoic acid (0.610 g, 1.48 mmol) in HCl (0.1 M aq., 14.0 mL) was heated in a microwave reactor at 100° C. for 30 min. The resulting precipitate was filtered and washed with water (5 mL×2), dried and slurried in methanol (5 mL). The solid was filtered and dried under vacuum to afford the title compound 2n (0.513 g, 32%) as a white solid. m.p. 230° C. (dec.). ¹H NMR (400 MHz, DMSO-d₆) δ 11.88 (s, 1H), 8.53 (dd, J=0.8, 8.4 Hz, 1H), 8.05 (dd, J=1.6, 7.9 Hz, 1H), 7.73-7.79 (m, 1H), 7.70-7.23 (m, 1H); LC-MS (ESI–) m/z 315.94 (M–H—HCl)⁻; HRMS (ESI–) m/z calculated for $C_{11}H_5Cl_3N_3O_2$ (M–H—HCl)⁻ 315.9453. found 315.9454.

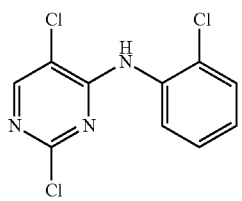

N⁴-(2-Chlorophenyl)-2,5-dichloropyrimidine-4-amine (2o, method b in FIG. 4A)

A solution of 2,4-dichloro-5-fluoropyrimidine (2.00 g, 10.9 mmol) and 2-chloroaniline (1.53 g, 12.0 mmol) in HCl (0.1 M, 40 ml) were stirred at RT for 5 days. The precipitate obtained was filtered, washed with water and sodium bicarbonate (2 M) and dried to obtain 2o (1.60 g, 47%) as a white solid. m.p. 128-129° C. ¹H NMR (400 MHz, CDCl₃) δ 8.58 (s, 1H), 8.50 (dd, J=8.4, 1.6 Hz, 1H), 7.98 (brs, 1H), 7.43 (dd, J=8.0, 1.2 Hz, 1H), 7.36 (apparent td J=7.6, 1.6 Hz, 1H), 7.10 (td, J=7.6, 1.2 Hz, 1H); LC-MS (ESI–) m/z 273.97 (M+H)⁺; HRMS (ESI+) m/z calculated for $C_{10}H_6Cl_3N_3$ (M+H)⁺ 273.9700. found 273.9700 9708.

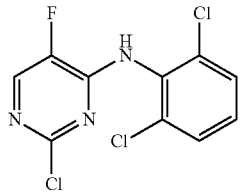

Figure 5A:
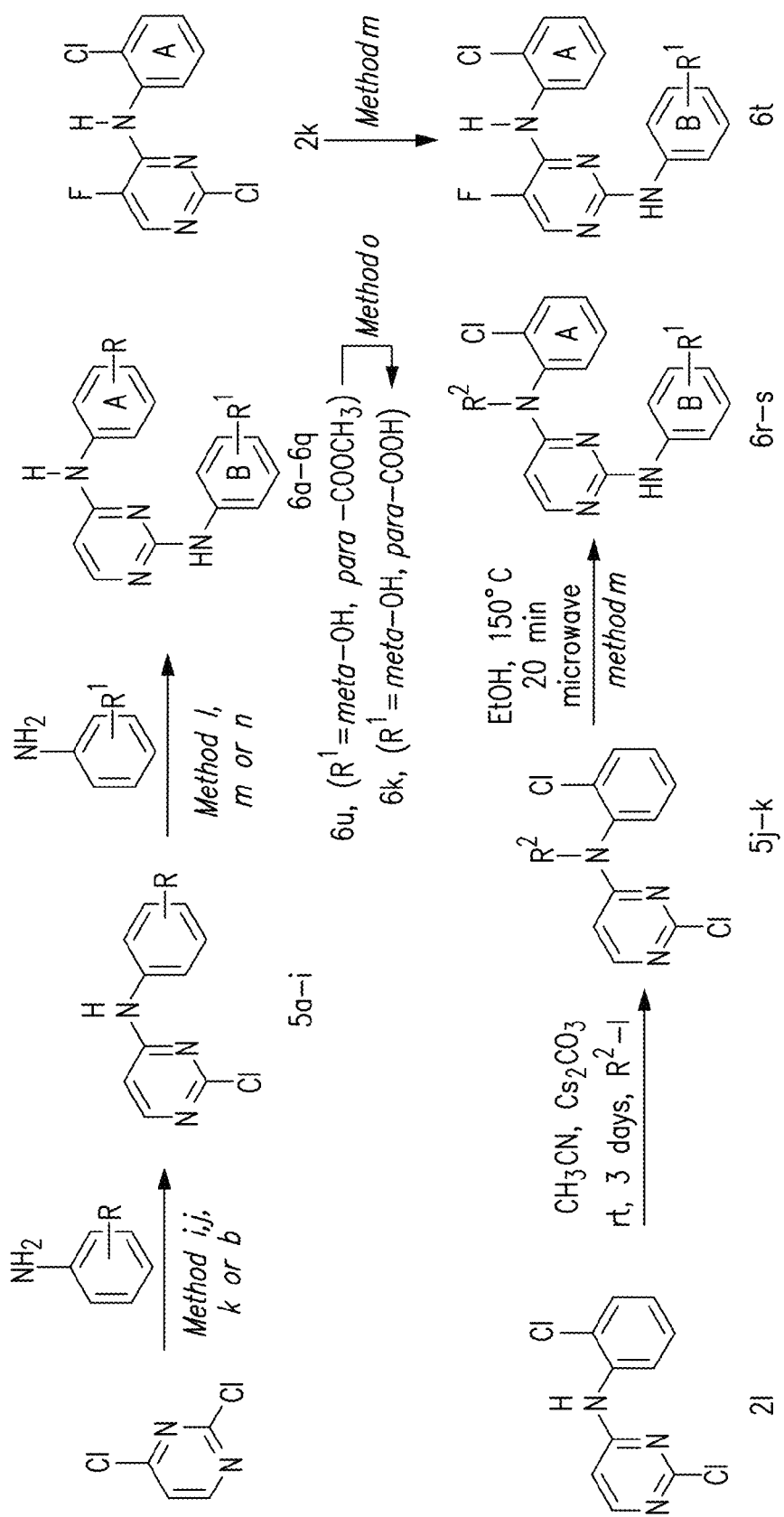
FIG. 5A is a synthetic route to bisanilinopyrimidine library 6 with halogens (F, Cl, Br, and I), CN, non-polar groups (H, Ph) and polar hydrophobic groups (OCF$_3$, CF$_3$ and OMe) on the A-ring, which library is shown in FIG. 5B and in FIG. 5C. Reagents and conditions: method i: n-BuOH, DIPEA, 125° C. method j: n-BuOH, Na$_2$CO$_3$, 100° C. method k: DMF, NaH, r.t., overnight (14-16 h). method l: EtOH (1 drop of 1M HCl), microwave, 160° C., 15 min., 56-75%. method m: EtOH or MeOH, 150° C., 20 min., microwave. method n: Cat. HCl, THF, reflux 14 h. method o: THF, NaOH (1.8 M aq., 5 equivalents), THF, reflux, 14 h., method b: HCl (0.1 M, aq., 3 mL/mmol), r.t., 3-5 days.

2-Chloro-N-(2,6-dichlorophenyl)-5-fluoropyrimidin-4-amine (2p, method k in FIG. 5A)

To a solution of 2,6-dichloroaniline (0.58 g, 3.89 mmol) in DMF (10 ml) under argon was added NaH (0.47 g, 19.45 mmol) and stirred for 30 min. To this mixture was added 2,4-dichloro-5-fluoropyrimidine (0.65g, 3.89 mmol) and stirred for 14 h. The reaction was quenched with water and extracted with DCM (2×15 ml). DCM extracts were washed with water (5×15 ml). Organic solvent was dried (MgSO₄), evaporated and the residue was purified by column chromatography (gradient elution with EtOAc: hexane) to provide 2p as a yellow solid. (421 mg, 37%); ¹H NMR (400 MHz, CDCl₃) δ 8.11 (d, J=2.6 Hz, 1H), 7.42 (d, J=8.1 Hz, 2H), 7.29-7.16 (m, 1H), 6.66 (s, 1H); LC-MS (ESI+) m/z 291.95 (M+H)⁺; HRMS (ESI+ve) m/z calculated for $C_{10}H_6Cl_3FN_3$ (M+H)⁺ 291.9606. found 291.9607.

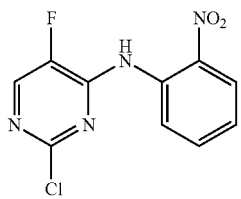 [SMILES: O=[N+]([O-])c1ccccc1Nc1nc(Cl)ncc1F]

2-Chloro-5-fluoro-N-(2-nitrophenyl)pyrimidin-4-amine (2q, method k in FIG. 5A)

This compound was synthesized using the same protocol for 2p except using 2-nitroaniline (0.35 g, 2.53 mmol), 2,4-dichloro-5-fluoropyrimidine (0.42 g, 2.53 mmol) and NaH (0.30g, 12.65 mmol). The compound 2q was obtained as a bright yellow solid. (217 mg, 32%). $^1$H NMR (400 MHz, CDCl$_3$) δ 10.79 (s, 1H), 8.98 (dd, J=8.6, 1.2 Hz, 1H), 8.31 (dd, J=8.5, 1.6 Hz, 1H), 8.24 (d, J=2.3 Hz, 1H), 7.76 (ddd, J=8.7, 7.4, 1.5 Hz, 1H), 7.29-7.18 (m, 1H); LC-MS (ESI+) m/z 269.02 (M+H)$^+$; HRMS (ESI+ve) m/z calculated for C$_{10}$H$_7$ClFN$_4$O$_2$ (M+H)$^+$ 269.0236. found 269.0241.

Synthetic Protocols for 5a to 5k

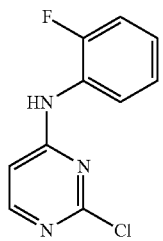

N$^4$-(2-Fluorophenyl)-2-chloropyrimidine-4-amine (5a, method i in FIG. 5A)

A mixture of 2,4-dichloropyrimidine (0.24 g, 1.61 mmol), 2-fluoroaniline (0.16 mL, 1.67 mmol) and DIPEA (0.308 mL, 1.77 mol) in n-butanol (1.0 mL) was stirred at 125° C. in sealed tube for 20 h. The solution was diluted with water (4 mL) and extracted with ethyl acetate (5 mL×2). The organic phase was dried over Na$_2$SO$_4$, filtered and washed with ethyl acetate. The filtrate was concentrated and the residue was purified with flash chromatography (10 g silica gel, hex/EtOAc) to afford 5a (0.213 g, 59%) as a white solid. m.p. 117.9-119.0° C. $^1$H NMR (400 MHz, DMSO-d$_6$) δ 9.83 (s, 1H), 8.17 (d, J=5.9 Hz, 1H), 7.74 (apparent t, 1H), 7.35-7.27 (m, 1H), 7.26-7.19 (m, 2H), 6.76 (d, J=5.6 Hz, 1H); LC-MS (ESI−) m/z 224.04 (M+H)$^+$; HRMS (ESI+) m/z calculated for C$_{10}$H$_8$ClFN$_3$ (M+H)$^+$ 224.0385. found 224.0385.

N$^4$-(2-Chloro-4-fluorophenyl)-2-chloropyrimidine-4-amine (5b, method i in FIG. 5A)

This was prepared using 2,4-dichloropyrimidine (0.239 g, 1.60 mmol), 2-chloro-4-fluoroaniline (0.2 mL, 1.67 mmol) and DIPEA (0.305 mL, 1.75 mmol) to afford 5b (0.192 g, 46%) as an off-white solid which was used without further purification. $^1$H NMR (400 MHz, DMSO-d$_6$) δ 9.75 (s, 1H), 8.14 (d, J=5.9 Hz, 1H), 7.68-7.47 (m, 2H), 7.33-7.25 (m, 1H), 6.62 (d, J=5.9 Hz, 1H); LC-MS (ESI+) m/z 258.01 (M+H)$^+$; HRMS (ESI+) m/z calculated for C$_{10}$H$_7$Cl$_2$FN$_3$ (M+H)$^+$ 258.9996. found 258.9990.

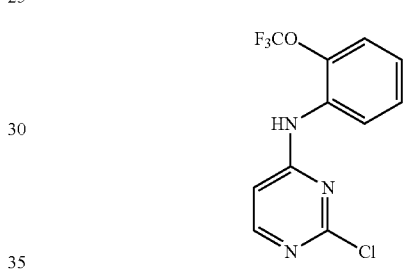

N$^4$-(2-(Trifluoromethoxy)phenyl)-2-chloropyrimidine-4-amine (5c, method i in FIG. 5A)

This was prepared using 2,4-dichloropyrimidine (0.246 g, 1.651 mmol), 2-(trifluoromethoxy)aniline (0.3 mL, 2.20 mmol) and DIPEA (0.315 mL, 1.81 mmol) to afford 5c (0.161 g, 50%) as an off-white solid. m.p. 92.0-94.8° C. $^1$H NMR (400 MHz, CDCl$_3$) δ 8.20 (d, J=5.9 Hz, 1H), 7.89 (d, J=7.9 Hz, 1H), 7.42-7.31 (m, 2H), 7.26-7.20 (m, 1H), 6.62 (d, J=5.9 Hz, 1H); LC-MS (ESI+) m/z 290.04 (M+H)$^+$; HRMS (ESI+) m/z calculated for C$_{11}$H$_8$F$_3$ClN$_3$O (M+H)$^+$ 290.0303. found 290.0300.

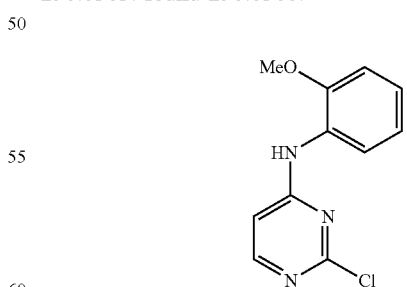

N$^4$-(2-Methoxyphenyl)-2-chloropyrimidine-4-amine (5d, method j, FIG. 5A)

A mixture of 2,4-dichloropyrimidine (2.569 g, 17.24 mmol), 2-methoxyaniline (1.9 mL, 16.19 mmol) and Na$_2$CO$_3$ (5.781 g, 54.54 mmol) in n-BuOH (36.0 ml) was heated at 100° C. under Argon for 24 h. The mixture was filtered and the resulting precipitate was washed with ethyl acetate (10 mL). The combined filtrates were concentrated to dryness to produce a brown solid. The solid was slurried with ethyl acetate (20 mL), filtered and washed with ethyl acetate (5 mL×2), then hexane (20 mL) to afford 5d (2.458 g, 60%) as a light brown solid. m.p. 126.3-129.2° C. $^1$H NMR (400 MHz, DMSO-d$_6$) δ 9.37 (s, 1H), 8.06 (d, J=5.9 Hz, 1H), 7.64 (d, J=7.3 Hz, 1H), 7.21-7.13 (m, 1H), 7.08 (dd, J=8.3, 1.3 Hz, 1H), 6.95 (td, J=7.7, 1.4 Hz, 1H), 6.66 (apparent s, 1H), 3.80 (s, 3H); LC-MS (ESI+) m/z 236.06 (M+H)$^+$; HRMS (ESI+) m/z calculated for C$_{11}$H$_{11}$ClN$_3$O (M+H)$^+$ 236.0585. found 236.0588.

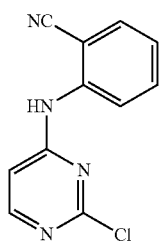

N$^4$-(2-Cyanophenyl)-2-chloropyrimidine-4-amine
(5e, method k in FIG. 5A)

To a solution of 2-cyanoaniline (0.543 g, 4.59 mmol) in anhydrous DMF (6.0 mL), NaH (60% dispersion in mineral oil, 0.384 g, 10.77 mmol) was added portion wise at 0° C., followed by the addition of 2,4-dichloropyrimidine (0.612 g, 4.10 mmol) under positive Argon pressure. The reaction mixture was slowly warmed to room temperature and stirred for a further for 24 h. Water (50 ml) was added and the resulting precipitate was filtered and washed with water (10 mL×2). The dried solid was dissolved in acetone (40 ml), activated charcoal (ca. 1 g) was added and the mixture was stirred for 10 min at room temperature. The activated charcoal was removed by filtration through a celite/silica bed. The filtrate was collected and the solvent removed under reduced pressure to provide the title compound 5e (0.218 g, 22%) as an off-white color solid. m.p. 160° C. (dec.). $^1$H NMR (400 MHz, DMSO-d$_6$) δ 10.23 (s, 1H), 8.21 (d, J=5.8 Hz, 1H), 7.86 (dd, J=1.3, 7.8 Hz, 1H), 7.74-7.70 (m, 1H), 7.62 (d, J=7.8 Hz, 1H), 7.38 (td, J=1.3, 7.8 Hz, 1H), 6.77 (d, J=5.8 Hz, 1H); LC-MS (ESI+) m/z 231.05 (M+H)$^+$; HRMS (ESI+) m/z calculated for C$_{11}$H$_8$ClN$_4$ (M+H)$^+$ 231.0432. found 231.0431.

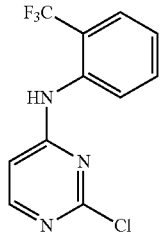

N$^4$-(2-(Trifluoromethyl)phenyl)-2-chloropyrimidine-4-amine (5f, method k in FIG. 5A)

To a solution of 2-(trifluoromethyl)aniline (0.570 g, 3.54 mmol) in anhydrous DMF (4 mL), NaH (60% dispersion in mineral oil, 0.384 g, 9.6 mmol) was added portion wise at 0° C. under Argon, followed by the addition of 2,4-dichloropyrimidine (0.528 g, 3.54 mmol). The reaction mixture was slowly warmed to room temperature and stirred for a further 24 h. The solvent was removed under reduced pressure to provide a red/orange solid. The residue was slurried with water (30 mL) and solid was filtered and washed with water (10 mL×2). The dried solid was suspended in diethyl ether (5 mL) and sonicated, then filtered and washed with diethyl ether (5 mL), hexane (10 mL) to afford the title compound as a yellow solid. The solid was re-dissolved in ethyl acetate, activated charcoal was added and the mixture was stirred for 20 min at room temperature. The activated charcoal was removed by filtration through a celite/silica bed. The filtrate was collected, the solvent removed under reduced pressure to provide 5f (0.261 g, 28%) as an off-white solid. m.p. 139° C. (dec.). $^1$H NMR (400 MHz, DMSO-d$_6$) δ 9.69 (s, 1H), 8.11 (d, J=5.9 Hz, 1H), 7.81 (d, J=8.2 Hz, 1H), 7.74 (t, J=7.7 Hz, 1H), 7.57-7.51 (m, 2H), 6.57 (d, J=5.9 Hz, 1H); LC-MS (ESI+) m/z 274.04 (M+H)$^+$; HRMS (ESI+) m/z calculated for C$_{11}$H$_8$F$_3$ClN$_3$ (M+H)$^+$ 274.0353. found 274.0354.

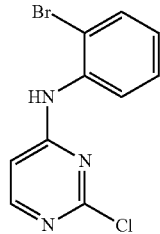 [SMILES: Clc1nccc(Nc2ccccc2Br)n1]

N$^4$-(2-Bromophenyl)-2-chloropyrimidine-4-amine
(5g, method b in FIG. 5A)

A solution of 2-bromoaniline (0.200 g, 1.16 mmol) and 2,4-dichloropyrimidine (0.175 g, 1.18 mmol) in aqueous HCl (0.1 M, 2.5 mL) was stirred at room temperature for 48 h. The precipitate was filtered, washed with water (5 mL×2). The dried solid was suspended in an aqueous solution of NaHCO$_3$ (sat., 20 mL) and extracted with ethyl acetate (20 ml×2). The organic extracts were combined, dried over Na$_2$CO$_3$, filtered, and the solvent removed under reduced pressure to provide the title compound 5g (0.207 g, 63%) as an off-white solid and was used in the next step without further purification. $^1$H NMR (400 MHz, DMSO-d$_6$) 9.70 (s, 1H), 8.11 (d, J=5.8 Hz, 1H), 7.71 (dd, J=1.5, 7.8 Hz, 1H), 7.51 (dd, J=1.5, 7.8 Hz, 1H), 7.41 (td, J=1.5, 7.8 Hz, 1H), 7.21 (td, J=1.5, 7.8 Hz, 1H), 6.57 (d, J=5.8 Hz, 1H); LC-MS (ESI+) m/z 285.95 (M+H)$^+$; HRMS (ESI+) m/z calculated for C$_{10}$H$_8$BrClN$_3$ (M+H)$^+$ 283.9585. found 283.9586.

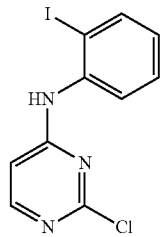 [SMILES: Clc1nccc(Nc2ccccc2I)n1]

N⁴-(2-Iodophenyl)-2-chloropyrimidine-4-amine (5h, method b in FIG. 5A)

A solution of 2-iodoaniline (0.375 g, 1.71 mmol) and 2,4-dichloropyrimidine (0.256 g, 1.72 mmol) in aqueous HCl (0.1 M, 3.0 mL) was stirred at room temperature for 5 days. The solid precipitate was filtered and washed with water (30 mL). The dried solid was suspended in an aqueous solution of NaHCO₃ (sat., 20 mL) and extracted with ethyl acetate (20 mL×2). The organic extracts were combined, dried over Na₂CO₃, filtered, and the solvent removed under reduced pressure to provide 5h (0.406 g, 79%) as an off-white solid and was used in the next step without further purification. $^1$H NMR (400 MHz, DMSO-d₆) 9.68 (s, 1H), 8.08 (d, J=5.9 Hz, 1H), 7.93 (dd, J=1.3, 7.9 Hz, 1H), 7.45-7.37 (m, 2H), 7.07-7.03 (m, 1H), 6.45 (d, J=5.9 Hz, 1H).

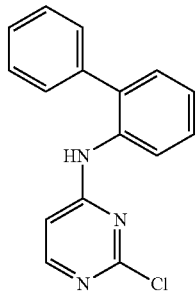 [SMILES: Clc1nccc(Nc2ccccc2-c2ccccc2)n1]

N⁴-(2-Biphenyl)-2-chloropyrimidine-4-amine (5i, method I in FIG. 5A)

This was prepared using 2,4-dichloropyrimidine (0.238 g, 1.597 mmol), biphenyl-2-amine (0.284 g, 1.678 mmol) and DIPEA (0.305 mL, 1.75 mmol) to afford the title compound 5i (0.252 g, 54%) as an off-white solid. m.p. 137.7-138.9° C. $^1$H NMR (400 MHz, DMSO-d₆) δ 9.57 (s, 1H), 7.93 (d, J=5.9 Hz, 1H), 7.49-7.19 (m, 9H), 6.32 (br s, 1H); LC-MS (ESI−) m/z 282.08 (M+H)⁺; HRMS (ESI+) m/z calculated for C₁₆H₁₃ClN₃ (M+H)⁺ 282.0793. found 282.0794.

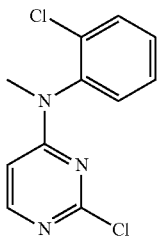

N⁴-(2-Chlorophenyl)-N⁴-methyl-2-chloropyrimidine-4-amine (5j, FIG. 5A)

Iodomethane (0.119 g, 0.837 mmol) was added to a mixture of 2l (0.201 g, 0.837 mmol) and cesium carbonate (0.540 g. 1.7 mmol) in anhydrous acetonitrile (1.4 mL) under argon at room temperature. The reaction mixture was then stirred at room temperature overnight. The resulting solution was diluted with ethyl acetate and the organic layer was washed with water, separated, dried (Na₂SO₄) and the solvent removed under reduced pressure to provide 5j (0.180 g, 84%) as a yellow oil. The compound was used in the next step without further purification. $^1$H NMR (400 MHz, CDCl₃) δ 7.90 (d, J=5.3 Hz, 1H), 7.57-7.54 (m, 1H), 7.42-7.35 (m, 2H), 7.29-7.27 (m, 1H), 5.83 (s, 1H), 3.43 (s, 3H); LC-MS (ESI+) m/z 254.02 (M+H)⁺; HRMS (ESI+) m/z calculated for C₁₁H₁₀Cl₂N₃ (M+H)⁺ 254.0246. found 254.0252.

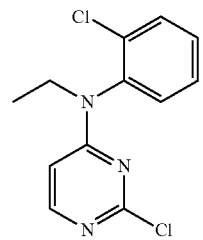 [SMILES: CCN(c1ccnc(Cl)n1)c1ccccc1Cl]

N⁴-(2-Chlorophenyl)-N⁴-ethyl-2-chloropyrimidine-4-amine (5k, FIG. 5A)

Iodoethane (0.203 g, 1.30 mmol) was added to a mixture of 2l (0.317 g, 1.32 mmol) and cesium carbonate (0.850 g, 2.61 mmol) in anhydrous acetonitrile (2.2 mL) at room temperature overnight under argon. The reaction mixture was stirred at room temperature overnight under argon overnight. The resulting solution was diluted with ethyl acetate (50 mL) and the organic layer was washed with water, separated, dried (Na₂SO₄) and the solvent removed under reduced pressure to provide a brown oil. Chromatography on silica gel [FlashMaster 3 purification station (hexane:ethyl acetate)] afforded 5k (0.207 g, 71%). as a yellow oil. $^1$H NMR (400 MHz, CDCl₃) $^1$H NMR (400 MHz, CDCl₃) δ 7.87 (d, J=5.7 Hz, 1H), 7.56-7.53 (m, 1H), 7.41-7.34 (m, 2H,), 7.26-7.23 (m, 1H), 5.75 (s, 1H), 4.20-4.15 (m, 1H), 3.75 (sextuplet, J=7.1 Hz, 1H), 1.20 (t, J=7.2 Hz, 3H); LC-MS (ESI+) m/z 268.03 (M+H)⁺; HRMS (ESI+) m/z calculated for C₁₂H₁₂Cl₂N₃ (M+H)⁺ 268.0403. found 268.0408.

Synthetic Protocols for 7a to 7c

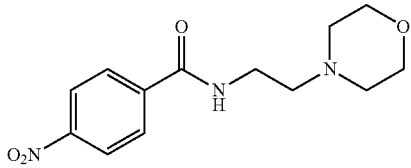 [SMILES: O=C(NCCN1CCOCC1)c1ccc([N+](=O)[O-])cc1]

Figure 6:
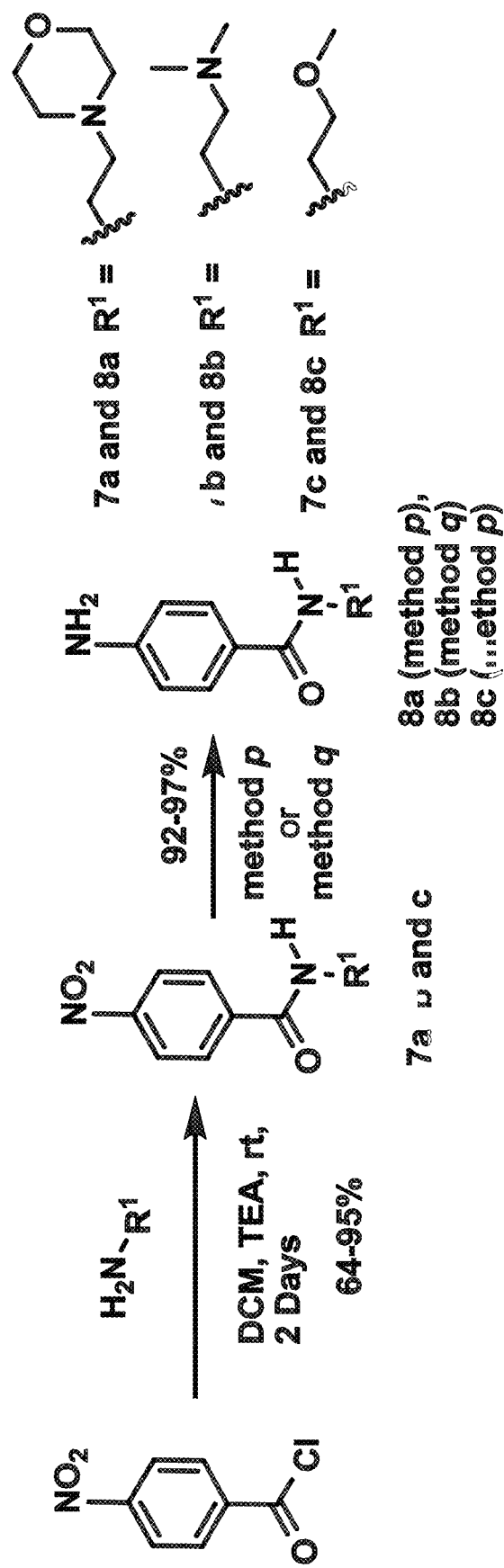
FIG. 6 is a synthetic route to building blocks with water solubilizing groups. Reagents and conditions: method p: 10% Pd/C, EtOH, H$_2$, r.t., overnight; method q: H-Cube, 10% Pd/C, MeOH, 30 bar, 4 Loops, rt.

N-(2-Morpholinoethyl)-4-nitrobenzamide (7a, FIG. 6)

2-Morpholinoethylamine (2.1 g, 16.13 mmol) was added to a solution of 4-nitrobenzoyl chloride (2.994 g, 16.13 mmol) and triethylamine (2.4 mL) in anhydrous dichloromethane (75 mL) under argon at room temperature. The reaction mixture was stirred under argon at room temperature for two days. Upon completion of the reaction, the organic phase was washed with a saturated solution of sodium bicarbonate, brine, separated, dried (Na₂SO₄), filtered and the solvent removed under reduced pressure to provide the title compound 7a (4.082 g, 95%) as a pale brown solid $^1$H NMR (400 MHz, DMSO-$d_6$) δ 8.76 (t, J=5.6 Hz, 1H), 8.29 (d, J=8.7 Hz, 2H), 8.03 (d, J=8.7 Hz, 2H), 3.57-3.51 (m, 4H), 3.43-3.36 (m, 2H), 2.50-2.43 (m, 2H), 2.42-2.35 (m, 4H); LC-MS (ESI+) m/z 238.2 (M+H)$^+$.

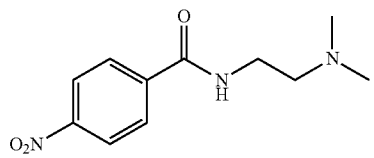 [SMILES: CN(C)CCNC(=O)c1ccc([N+](=O)[O-])cc1]

N-(2-(Dimethylamino)ethyl)-4-nitrobenzamide (7b, FIG. 6)

This was obtained as a yellow solid (3.770 g, 15.9 mmol, 64%) from 4-nitrobenzoyl chloride (3.953 g, 24.9 mmol), N$^1$,N$^1$-dimethylethane-1,2-diamine (2.197 g, 24.9 mmol), anhydrous triethylamine (3.75 mL) in the same manner as described for 7a. $^1$H NMR (400 MHz, DMSO-$d_6$) δ 8.80 (t, J=4.9 Hz, 1H), 8.29 (d, J=8.9 Hz, 2H), 8.04 (d, J=8.9 Hz, 2H), 3.40 (q, J=6.3 Hz, 2H), 2.49 (m, 2H), 2.23 (s, 6H); LC-MS (ESI+) m/z 238.2 (M+H)$^+$.

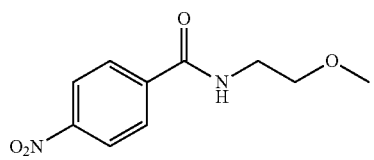 [SMILES: COCCNC(=O)c1ccc([N+](=O)[O-])cc1]

N-(2-Methoxyethyl)-4-nitrobenzamide (7c, FIG. 6)

This was obtained as an off-white solid (3.401 g, 81%) from 4-nitrobenzoyl chloride (3.173 g, 20 mmol), 2-methoxyethylamine (1.502 g, 20 mmol) and anhydrous triethylamine (3.00 mL) in the same manner as described for 7a. m.p. 108.0-110.5° C. $^1$H NMR (400 MHz, DMSO-$d_6$) δ 8.86 (t, J=5.0 Hz, 1H), 8.29 (d, J=8.9 Hz, 2H), 8.05 (d, J=8.9 Hz, 2H), 3.50-3.39 (m, 4H), 3.25 (s, 3H). LC-MS (ESI+) m/z 247.1 (M+Na)$^+$ Synthetic Protocols for 8a to 8c

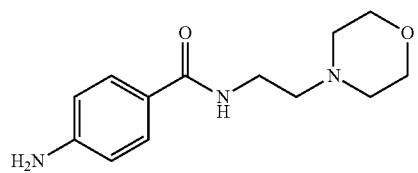

4-Amino-N-(2-morpholinoethyl)benzamide (8a, FIG. 6)

The nitrobenzenamide 7a (0.330 g, 1.32 mmol) was dissolved in methanol (15 mL) and hydrogenated using an H-Cube reactor (10% Pd/C, 30 bar, flow rate 1 mL/min, 2 loops, room temperature). The solution was collected and the solvent removed under reduced pressure to afford 8a (0.330 g, 100%) as a pale yellow solid. $^1$H NMR (400 MHz, DMSO-$d_6$) δ 7.91 (t, J=4.9 Hz, 1H), 7.52 (d, J=8.6 Hz, 2H), 6.50 (d, J=8.7 Hz, 2H), 5.58 (s, 2H), 3.54 (d, J=4.4 Hz, 4H), 3.38-3.23 (m, 2H), 2.50-2.47 (m, 2H), 2.42-2.33 (m, 4H); LC-MS (ESI+) m/z 250.2 (M+H)$^+$.

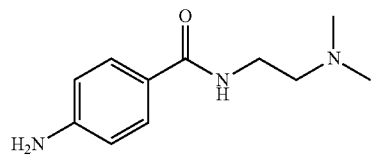

4-Amino-N-(2-(dimethylamino)ethyl)benzamide (8b, FIG. 6)

This was obtained as a brown oil (0.174 g, 0.84 mmol) from 7c (0.184 g, 0.77 mmol) in the same manner as described for 8a (H-Cube reactor, 10% Pd/C, 20 bar, 1 mL/min, 2 loops, room temperature). The compound was used in the next step without further purification. $^1$H NMR (400 MHz, DMSO-$d_6$) δ 7.87 (t, J=5.64, 1H), 7.52 (d, J=8.7 Hz, 2H), 6.50 (d, J=8.7 Hz, 2H), 5.57 (s, 2H), 3.26 (q, J=6.7 Hz, 2H), 2.34 (t, J=6.9 Hz, 2H), 2.14 (s, 6H). LC-MS (ESI+) m/z 208.2 (M+H)$^+$.

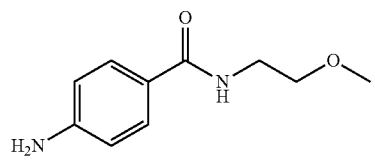

4-Amino-N-(2-methoxyethyl)benzamide (8c, FIG. 6)

A solution of 7c (0.884 g, 4.2 mmol) in ethanol (20 mL) was stirred in presence of 10% Pd/C (0.111 g) under hydrogen (balloon) at room temperature overnight. The solution was then filtered through celite. The celite was washed with methanol (60 mL). The filtrates were combined and the solvent removed under reduced pressure to provide 8c (0.730 g, 96%) as a yellow oil. $^1$H NMR (400 MHz, DMSO-$d_6$) δ 8.00 (t, J=5.4 Hz, 1H), 7.54 (d, J=8.6 Hz, 2H), 6.50 (d, J=8.6 Hz, 2H), 5.58 (s, 1H), 3.46-3.29 (m, 4H), 3.23 (s, 3H); LC-MS (ESI+) m/z 195.2 (M+H)$^+$ Synthetic Protocols for 10a, 10b, 11a and 11b

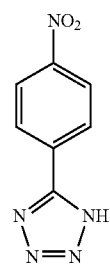

Figure 8:
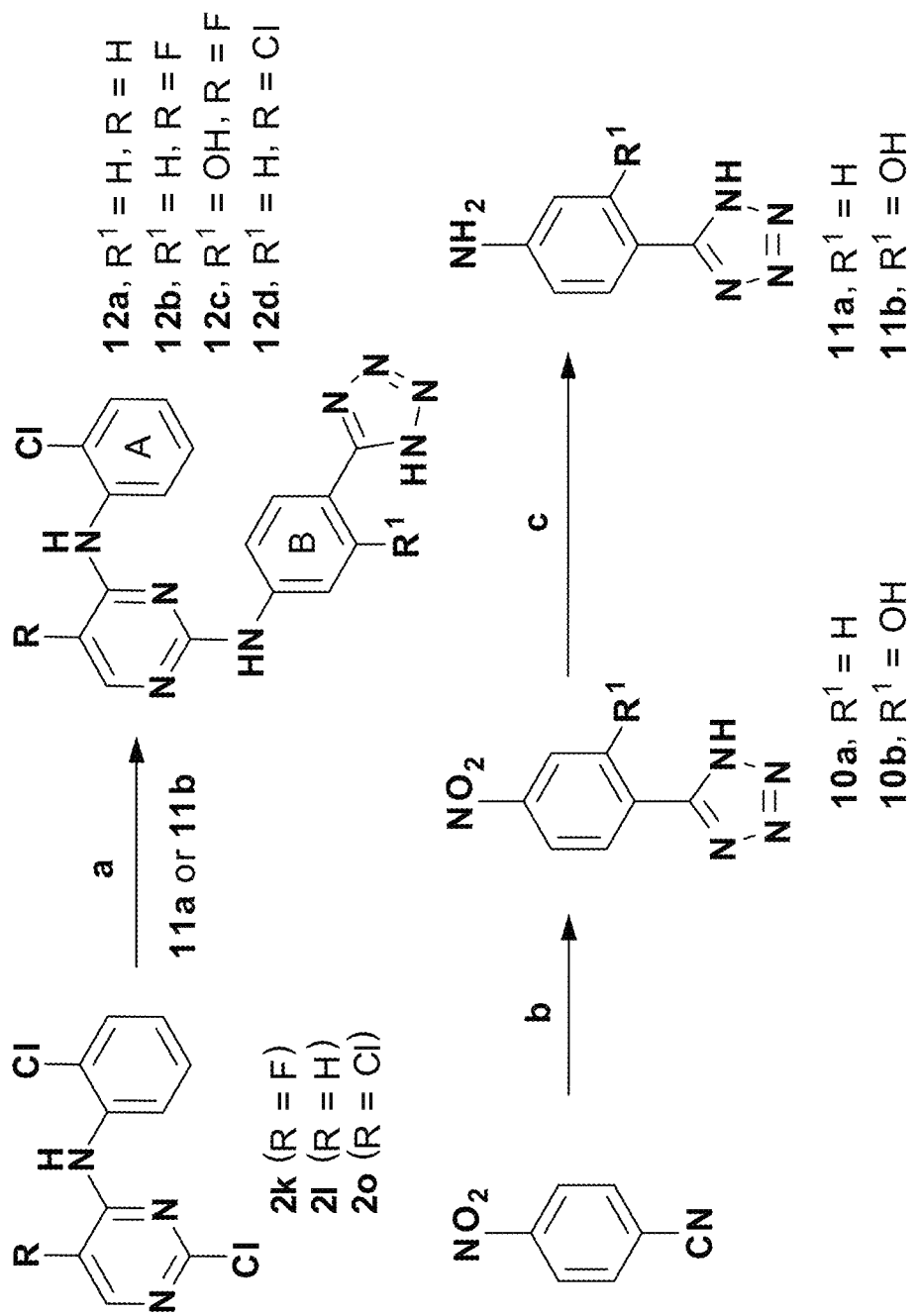
FIG. 8 is a synthetic route to bisanilinopyrimidine tetrazole derivatives. Reagents and conditions: method a: 12a: Ethanol, microwave, 150° C., 40 min., 37%; 12b: Ethanol, microwave, 170° C., 40 min., 33%; 12c: Ethanol, microwave, 160° C., 40 min., 36%; 12d: Ethanol, microwave, 150° C., 40 min., 25%; method b: 10a and 10b: NaN$_3$, Et$_3$N.HCl, toluene, 100° C., 15 h, 92% and 95%; method c: 11a and 11b: H$_2$, Pd/C, methanol, r.t., 20 h, 93% and 98%.
Figure 9:
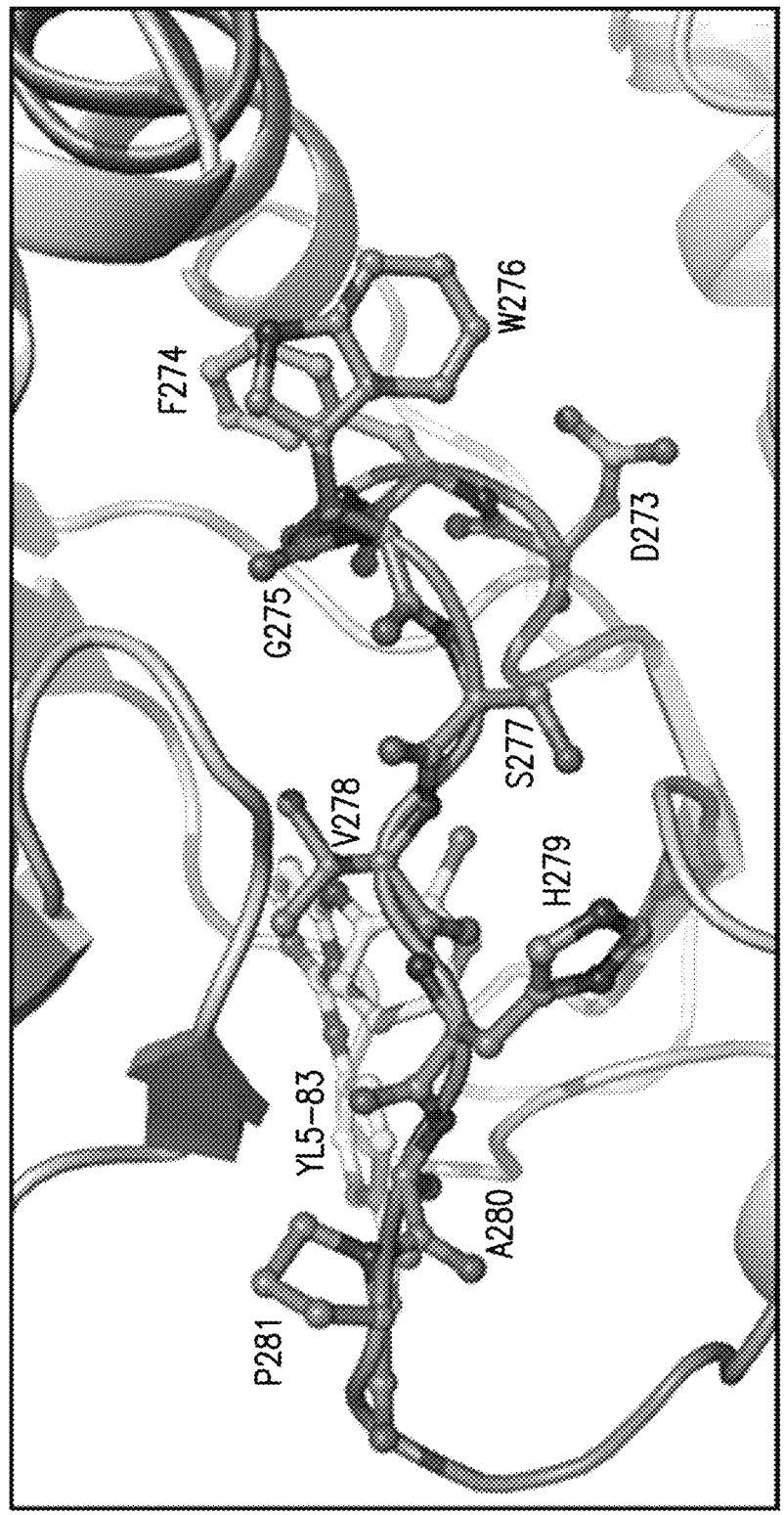
FIG. 9 illustrates compound 31 with DGF activation loop closed bound to Aurora A.
Figure 10A:
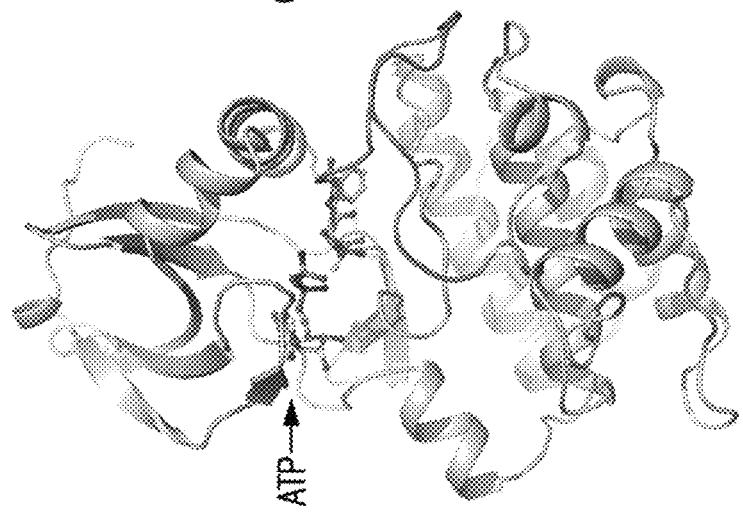
FIG. 10A, FIG. 10B and FIG. 10C illustrate a comparison of ATP, compounds 1 and 31 bound to Aurora A crystal structure.
Figure 10B:
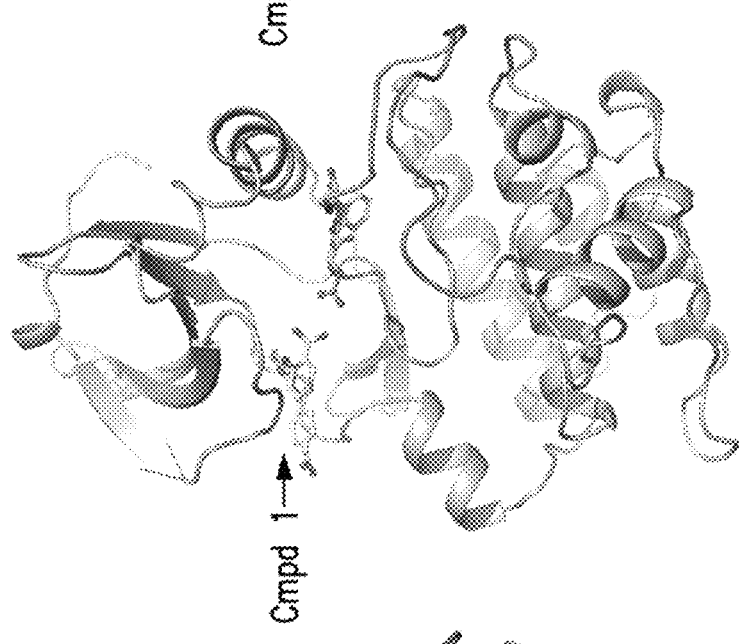
Figure 10C:
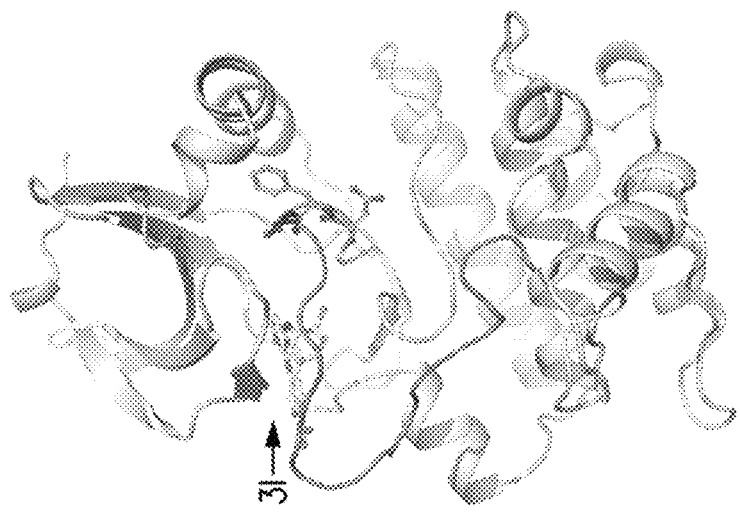
Figure 11A:
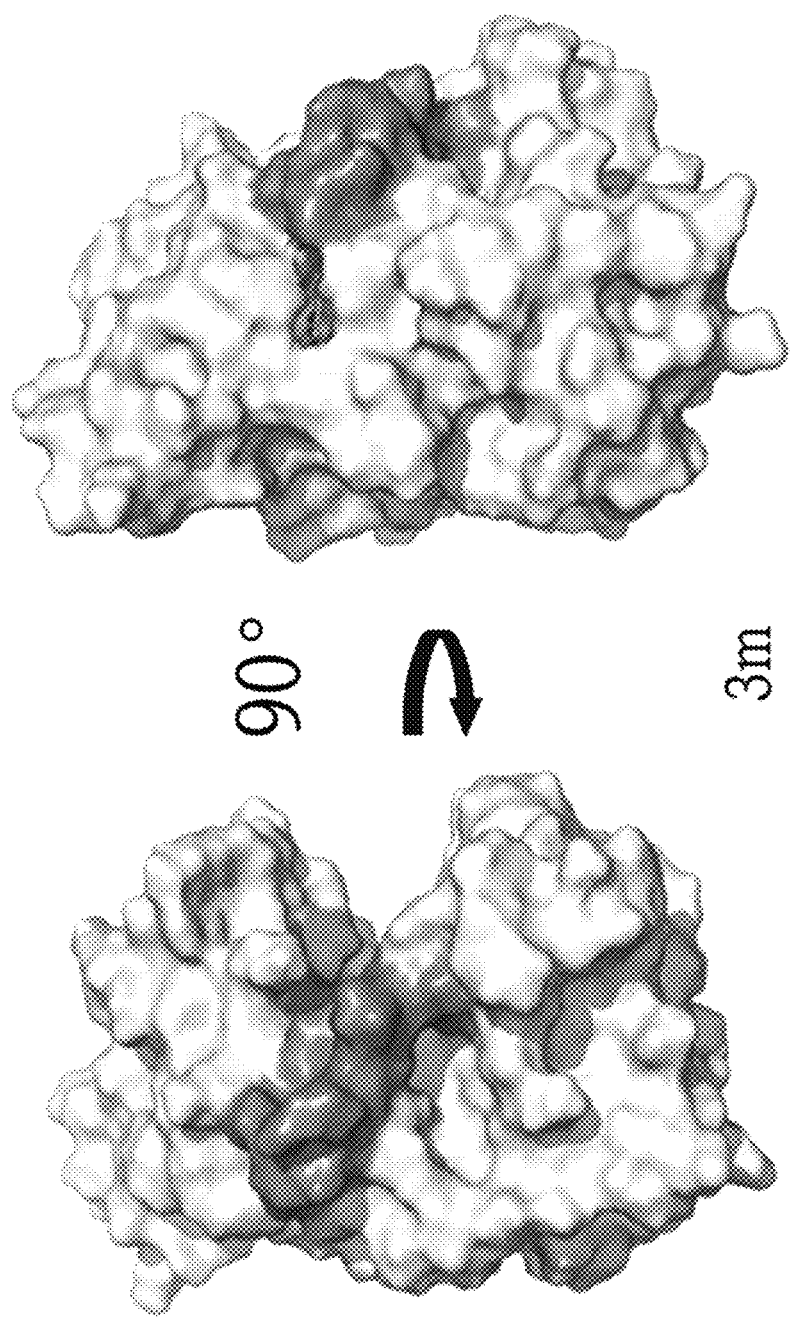
Figure 12A:
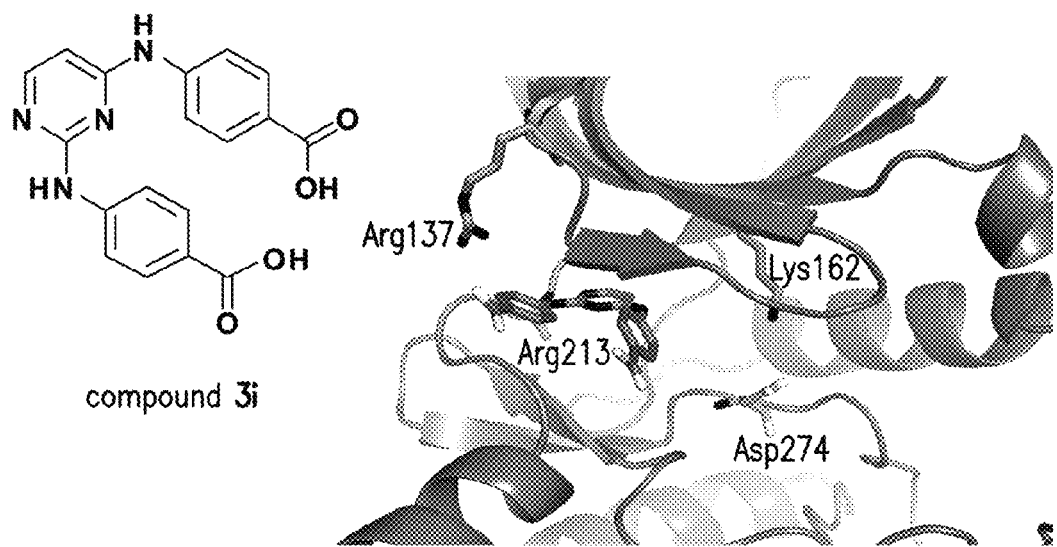
FIG. 12A through FIG. 12D illustrate the X-ray structures of compounds 3i (FIG. 12A), 3g (FIG. 12B) and compound 14 (FIG. 12C) bound to Aurora A active site.
Figure 12B:
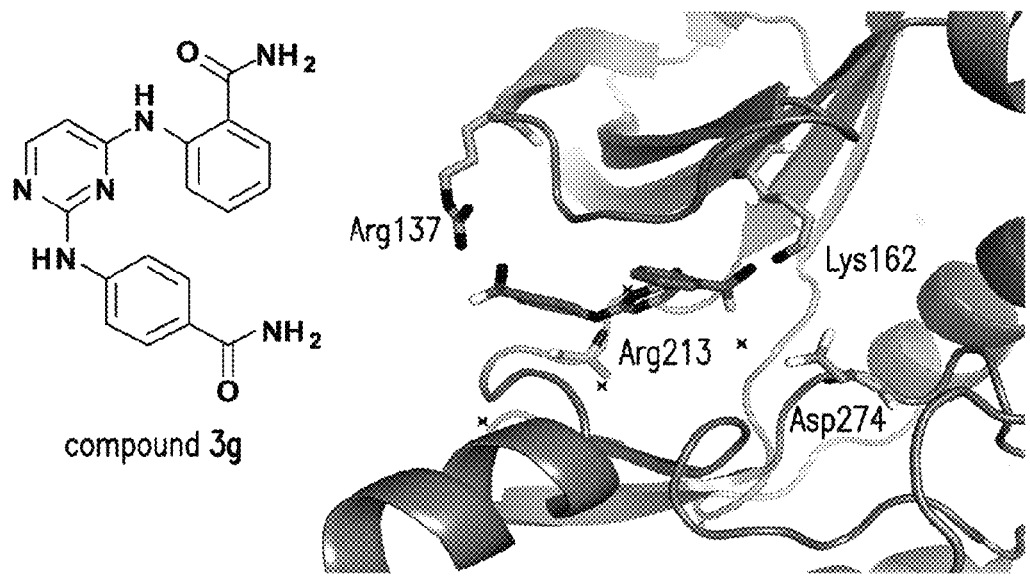
Figure 12C:
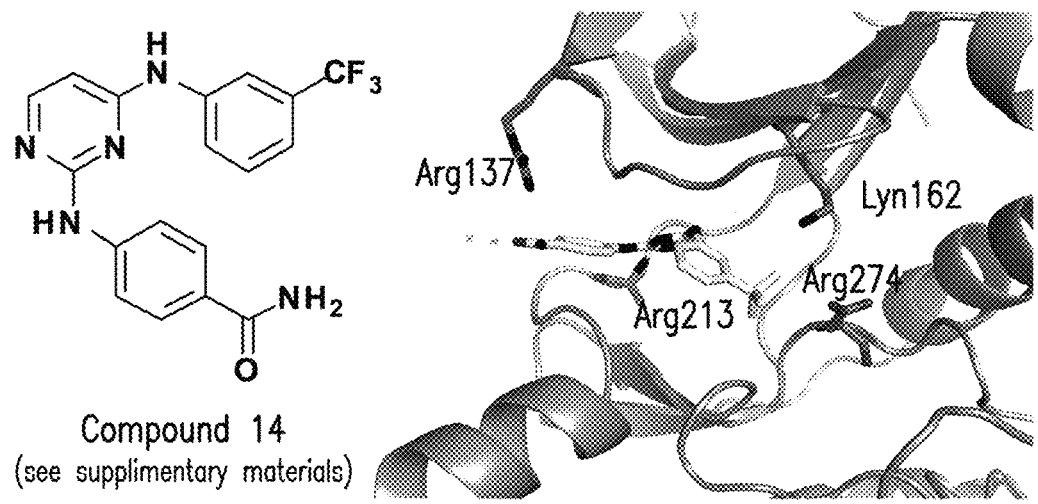
Figure 12D:
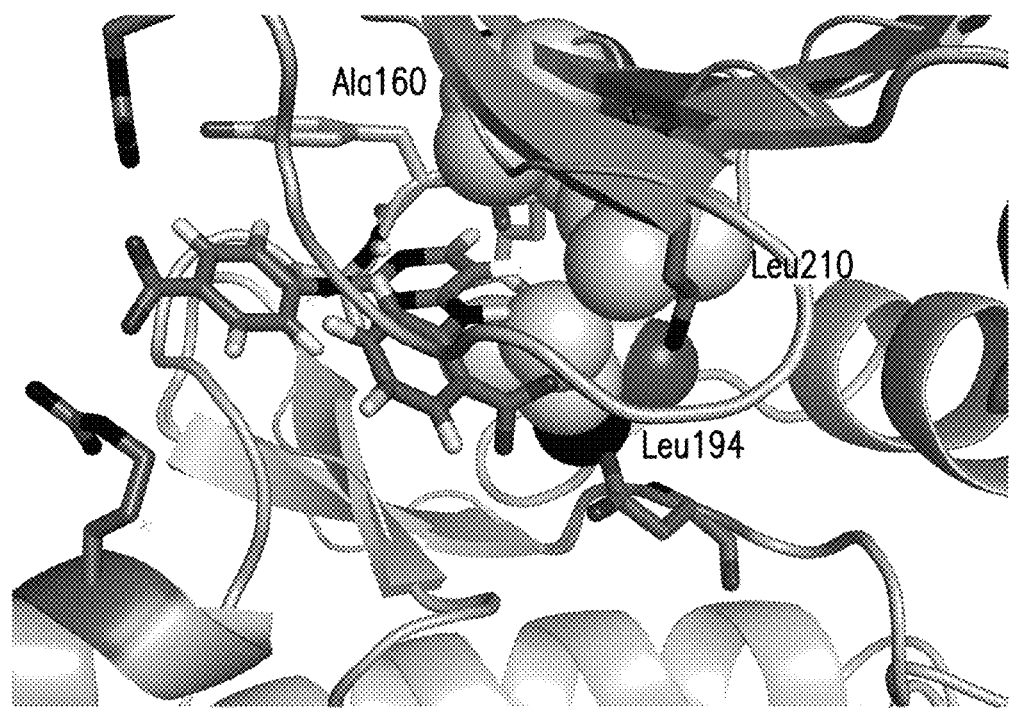
Figure 14A:
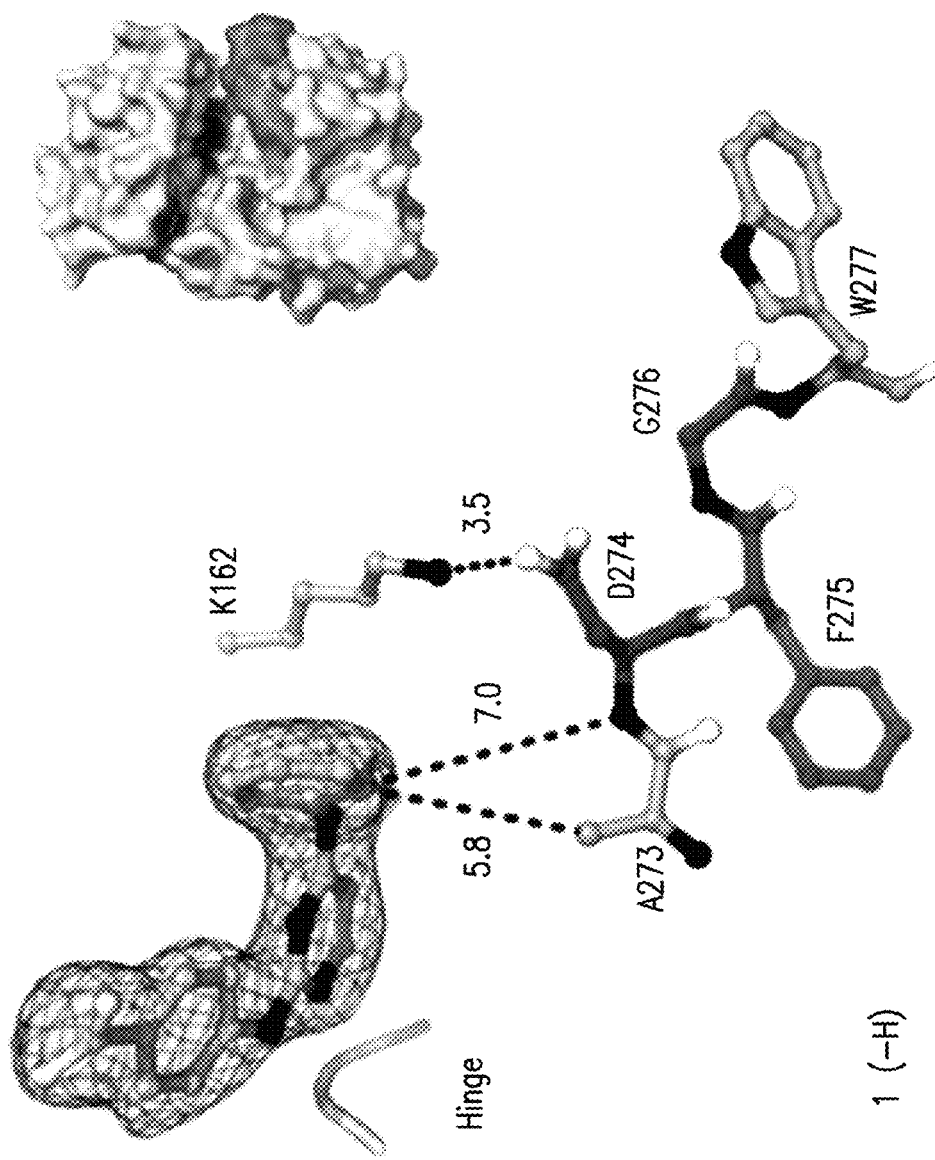
FIG. 14A through FIG. 14I show the binding modes of various bisanilinopyrimidine inhibitors (compounds 3h, 1, 6q, 6h, 6d, 6a, 3l, 6i, and 6n) with Aurora A. Crystal structures were determined for Aurora A liganded with different ortho-substituted bisanilinopyrimidine inhibitors (Table 6). The hinge region (residues 211-213) is indicated light grey, the DFG (residues 274-276) in darker grey, the activation loop (residues 277-293) in darkest grey. The dotted lines indicate the closest distances to the DFG. The $2F_o$-$F_c$ electron density, contoured at $1\sigma$, is shown as blue mesh around the inhibitor; the $F_o$-$F_c$ electron density maps from refinements omitting the inhibitor are shown in the supporting material (FIG. 23). The insets in the top right corners are surface representations of the overall structures. Compounds 3h, 1, 6q, 6h, and 6d are DFG-in inhibitors; compounds 6a, 3l, 6i, and 6n are DFG-out inhibitors.
Figure 14B:
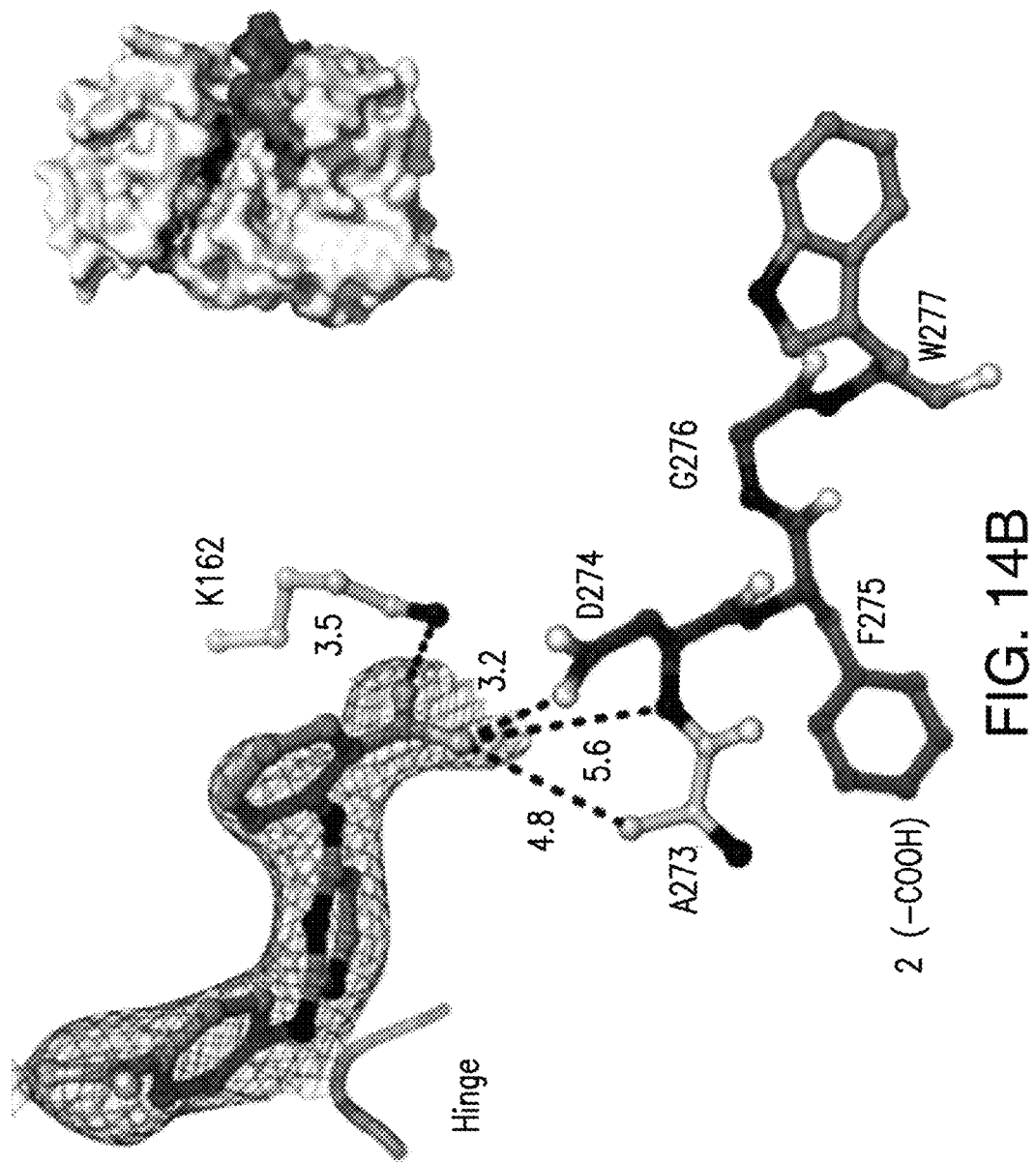
Figure 14C:
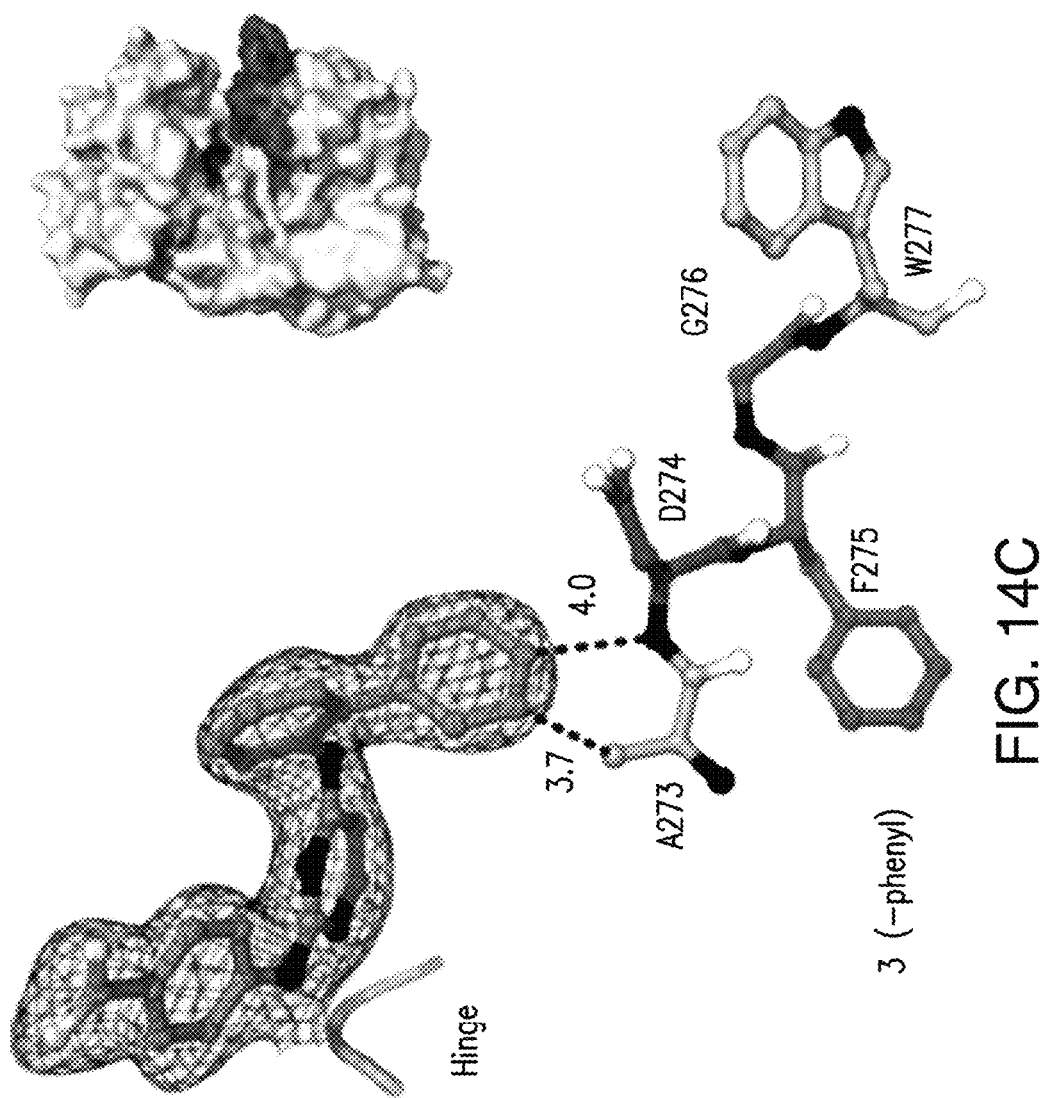
Figure 14D:
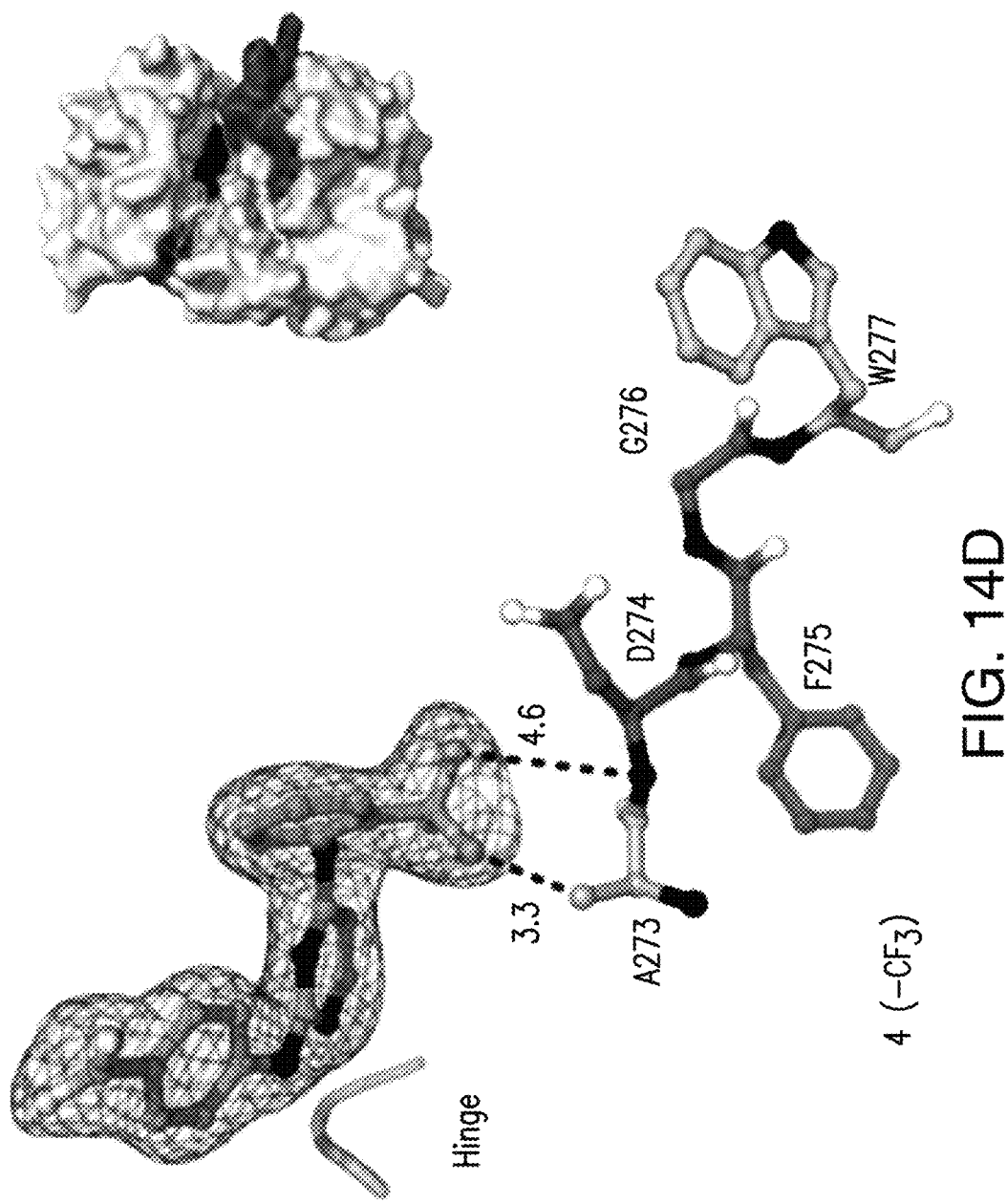
Figure 14E:
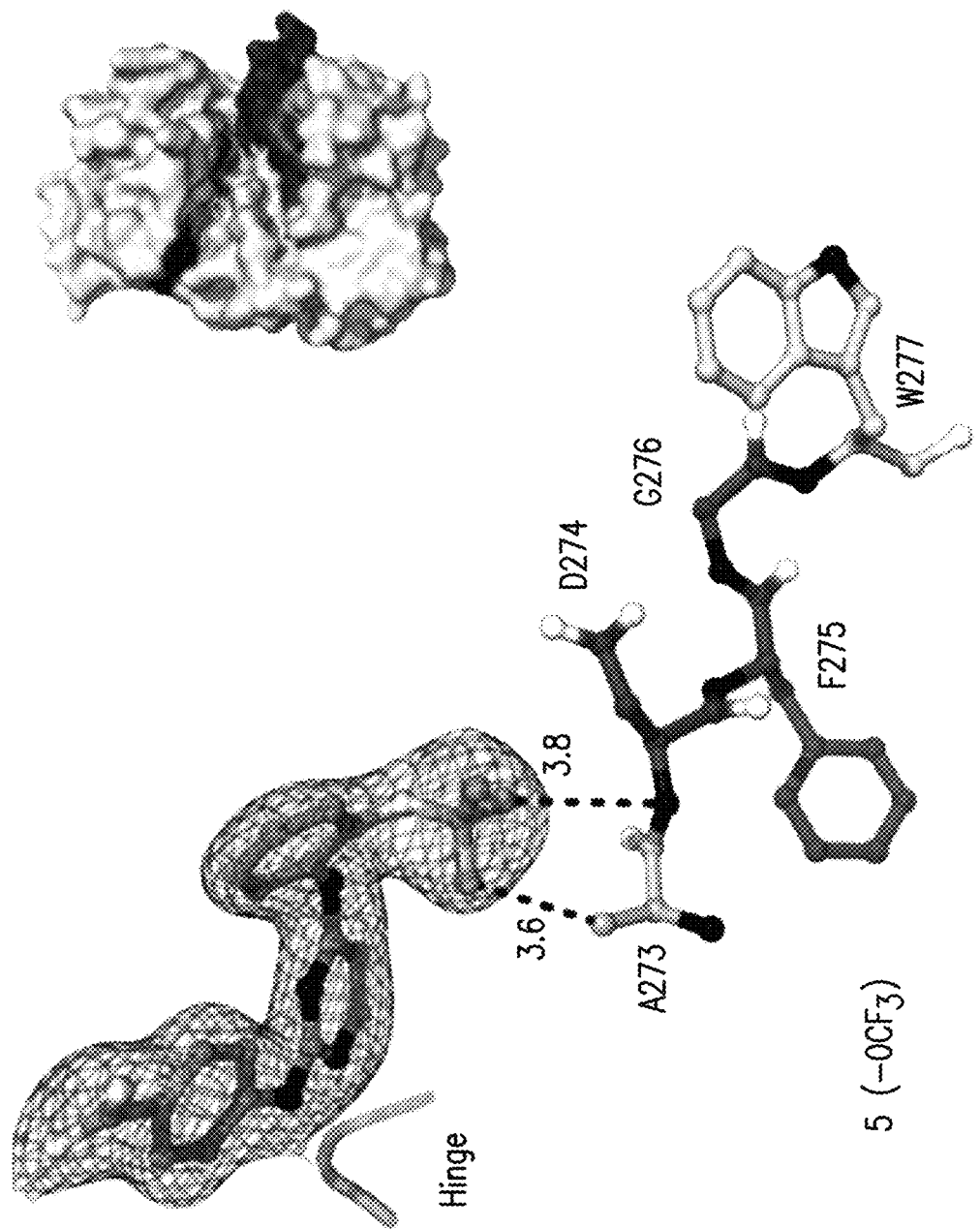
Figure 14F:
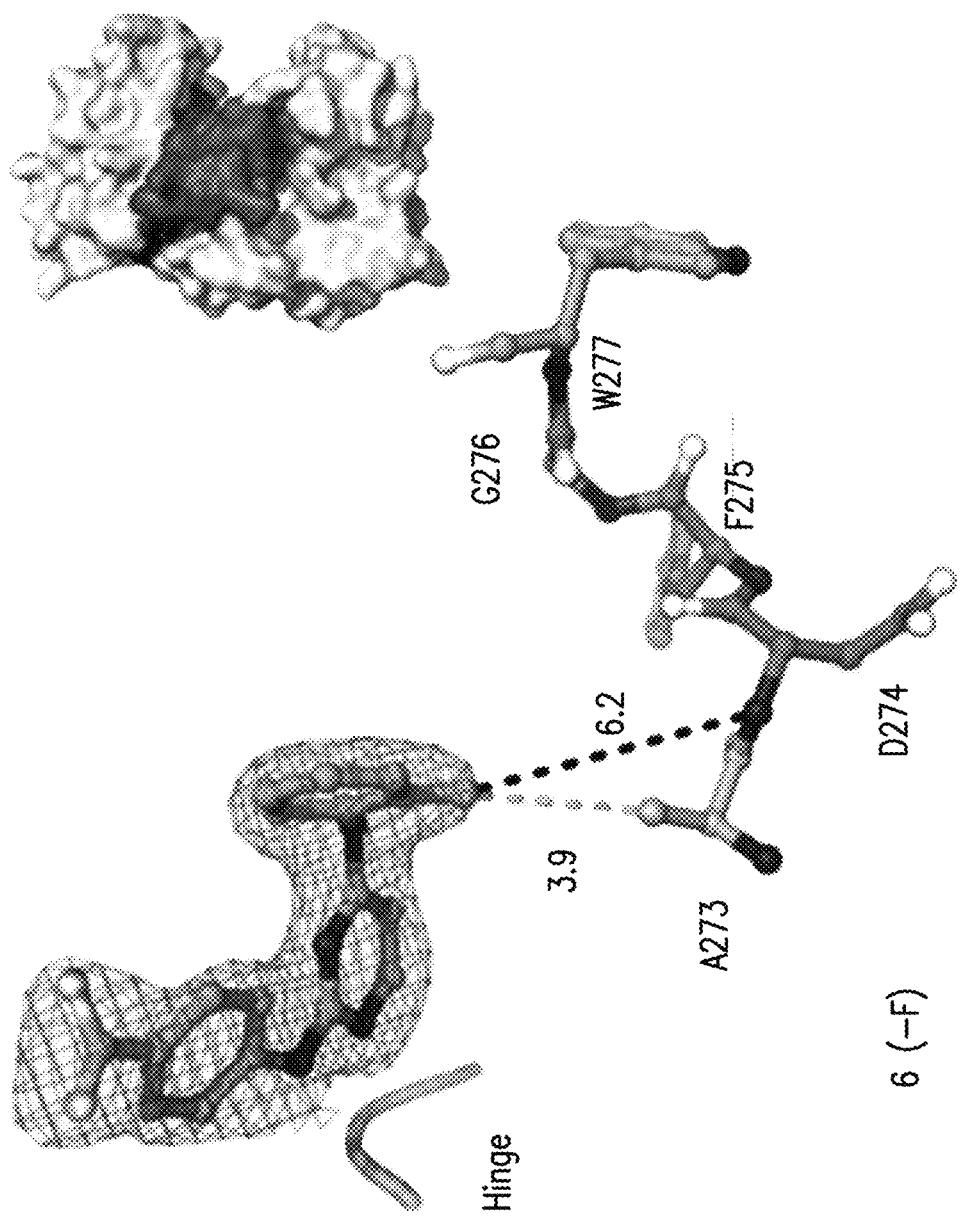
Figure 14G:
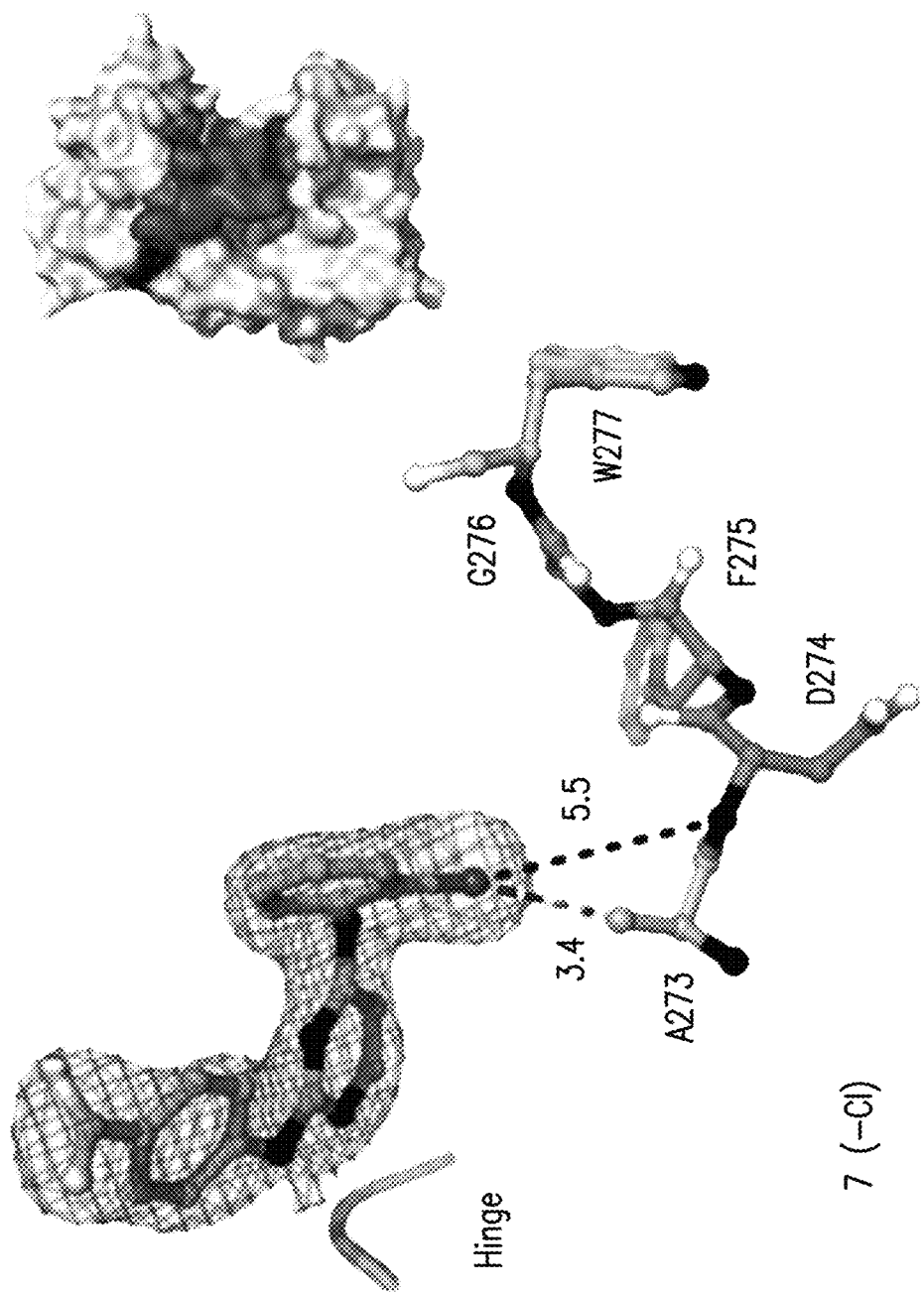
Figure 14H:
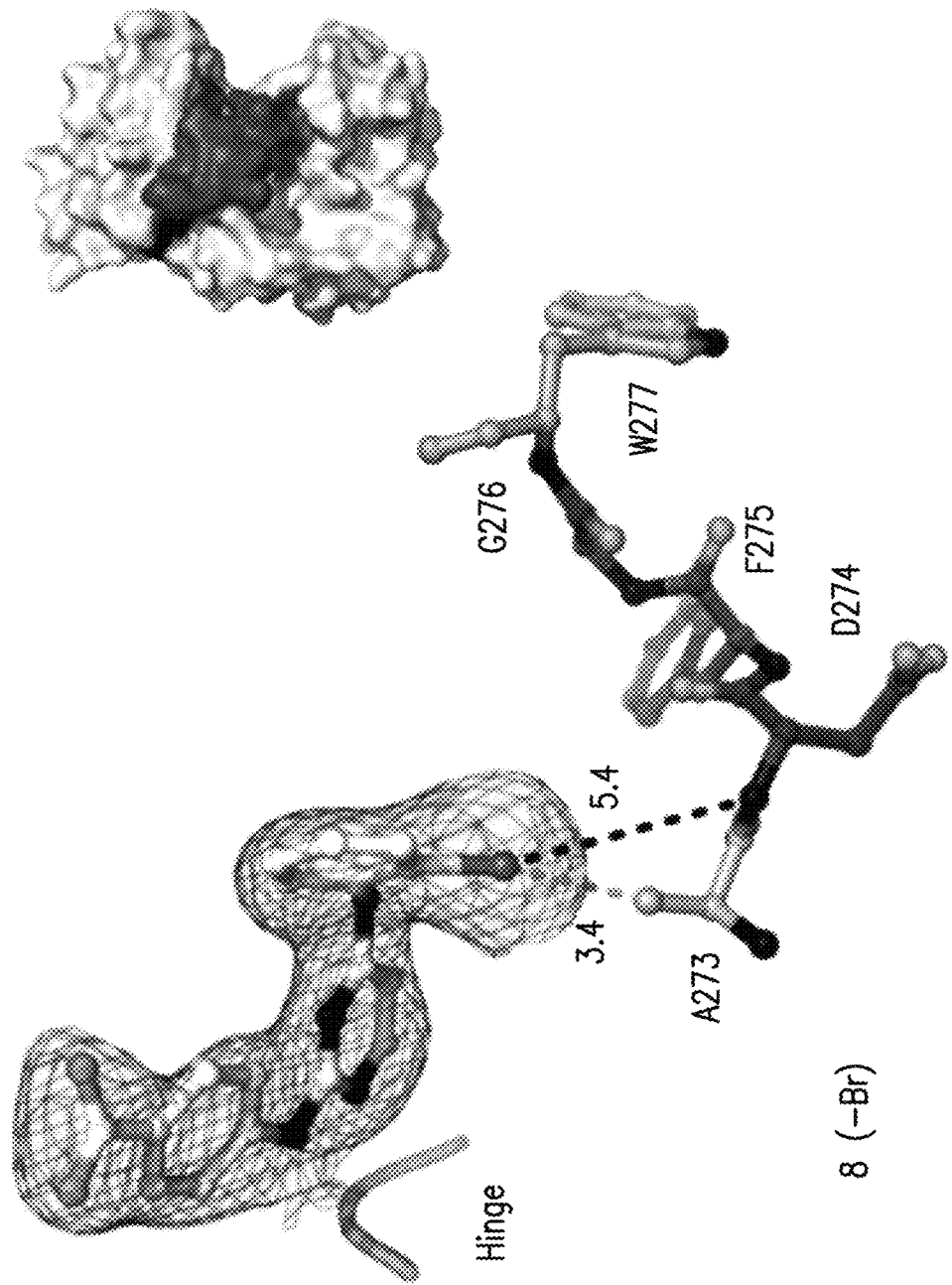
Figure 14I:
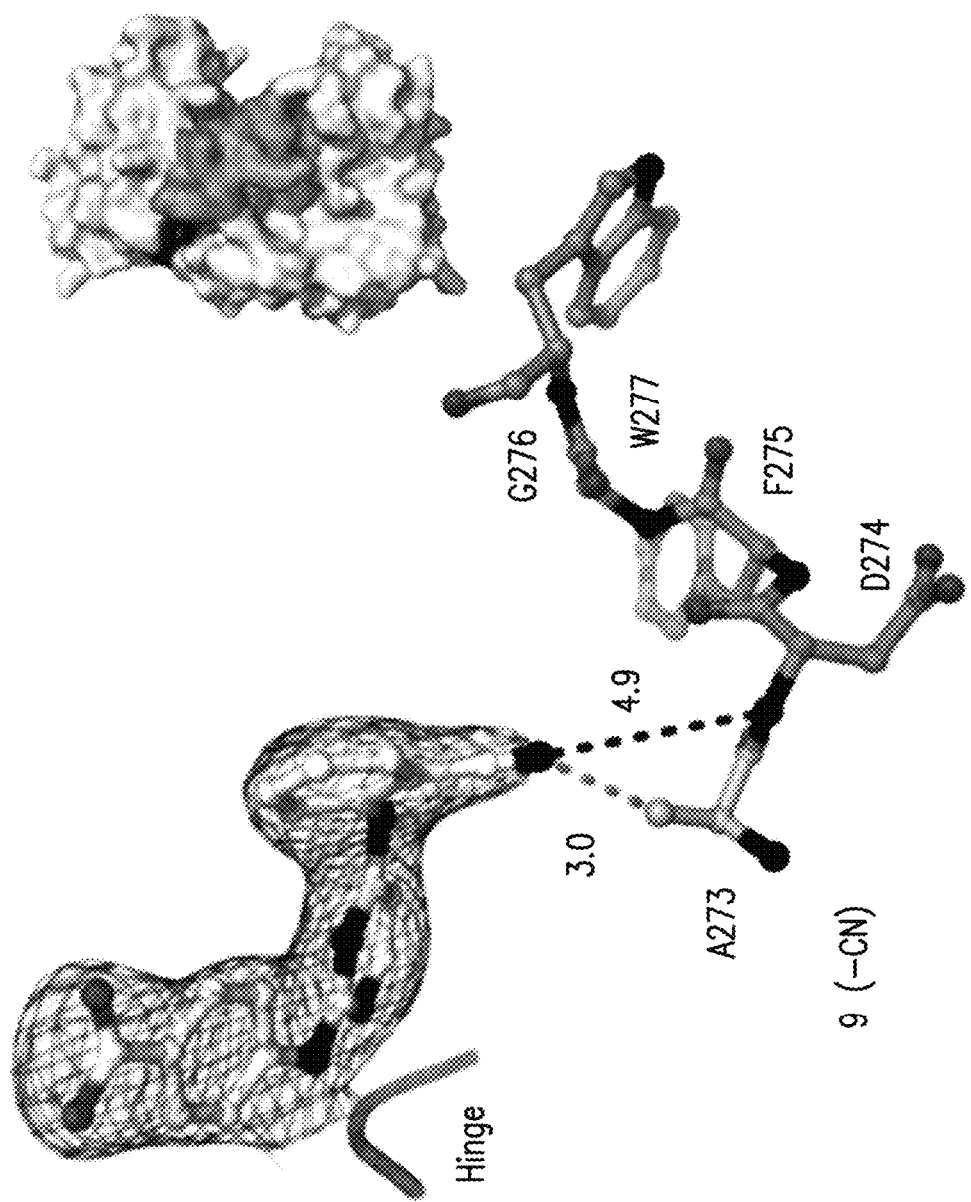

5-(4-Nitrophenyl)-1-tetrazole (10a, FIG. 8)

A solution of 4-nitrobenzonitrile (1.100 g, 7.4 mmol), NaN$_3$ (1.32 g, 20 mmol) and triethylamine hydrochloride (2.73 g, 20 mmol) in toluene (20 ml) were heated at 100° C. overnight. (formation of two phases was observed). Water (50 ml) was added and the phases were separated. The aqueous phase was acidified with concentrated HCl (pH=5-6) the solid that precipitated was filtered and washed with water. The product was dried under vacuum to give pure 10a (1.30 g, 92%) as a yellow-white compound. $^1$H NMR (400 MHz, DMSO-d$_6$) δ 8.40 (d, J=8.8 Hz, 2H), 8.26 (d, J=8.8 Hz, 2H). LC-MS (ESI–) m/z 190.04 (M–H)$^-$; HRMS (ESI–) m/z calculated for C$_7$H$_5$N$_5$O$_2$ (M–H)$^-$ 190.0371. found 190.0367.

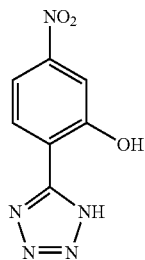

5-Nitro-2-(1H-tetrazol-5-yl)phenol (10b, FIG. 8)

A suspension of 2-hydroxy-4-nitrobenzonitrile (1.641 g, 10 mmol), sodium azide (1.951 g, 30 mmol) and triethylamine hydrochloride (4.130 g, 30 mmol) in toluene (20 mL) was stirred at 100° C. for 6 hours. Formation of a biphasic (the upper layer was pale yellow and the lower was wine red with the insoluble material) mixture was observed. The mixture was cooled to room temperature and the lower layer solidified. Water (40 ml) was added and the mixture was transferred to a separation funnel. The red aqueous phase was separated and the organic phase was washed with water (20 ml×2). The aqueous phase was combined and acidified (conc. HCl to pH 5-6) at 0° C. The precipitate was filtered, washed with water and dried affording the product 10b (1.971, 95%) as an off-white solid. $^1$H NMR (400 MHz, DMSO-d$_6$) δ 8.26-8.20 (m, 1H), 7.83-7.80 (m, 2H); LC-MS (ESI–) m/z 206.04 (M–H)$^-$; HRMS (ESI–) m/z calculated for C$_7$H$_4$N$_5$O$_3$ (M–H)$^-$ 206.0320. found 206.0309.

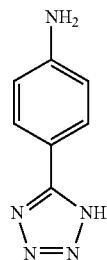

4-(1-Tetrazol-5-yl)aniline (11a, FIG. 8)

To a solution of 10a (1.1 g, 5.8 mmol) in methanol (70 ml) was added 10% Pd/C (0.25 g). The mixture was degassed and charged with hydrogen (repeated twice) and then stirred under hydrogen balloon overnight (approximately 14 h). The mixture was filtered through a celite pad, washed with methanol, and evaporated to obtain 10a (0.87 g, 93%) as a pink-white solid. $^1$H NMR (400 MHz, DMSO-d$_6$) δ 7.65 (d, J=8.7 Hz, 2H), 6.65 (d, J=8.7 Hz, 2H), 5.76 (s, 1H). LC-MS (ESI–) m/z 160.06 (M–H)$^-$; HRMS (ESI–) m/z calculated for C$_7$H$_7$N$_5$ (M–H)$^-$ 160.0629. found 160.0625.

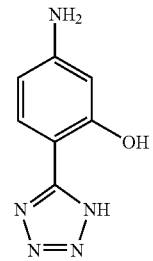 [SMILES: Nc1ccc(-c2nnn[nH]2)c(O)c1]

5-Amino-2-(1H-tetrazol-5-yl)phenol (11b, FIG. 8)

Nitrotetrazole 10b (0.622 g, 3 mmol) was suspended in methanol (60 ml) and hydrogenated under H2 atmosphere with Pd/C (10%, 0.1 g) at room temperature for 12 hours. The mixture was filtered using a pad of celite and washed with methanol and the filtrate was concentrated to dryness affording the product 11b (0.518 g, 98%). as pale yellow solid. $^1$H NMR (400 MHz, DMSO-d$_6$) δ 10.46 (brs, 1H, disappear at D$_2$O shake), 7.63-7.58 (m, 1H), 6.17-6.15 (m, 2H), 5.69 (brs, 2H, disappear at D$_2$O shake); LC-MS (ESI+) m/z 178.07 (M+H)$^+$; HRMS (ESI+) m/z calculated for C$_7$H$_8$N$_5$O (M+H)$^+$ 178.0723. found 178.0725.

N$^4$-(2-Carboxyphenyl)-N$^2$-(4-carboxyphenyl)pyrimidine-2,4-diamine hydrochloride (1, method h in FIG. 4A)

A suspension of 3w (0.040 mg, 0.100 mmol) in NaOH (0.2 mL, 4 M) and THF (0.5 mL) was refluxed in seal tube at 85° C. for 2 h. Upon cooling, THF was removed and water (2 mL) was added to the mixture, followed by adding HCl (1M) to acidify (pH=2) the mixture. The solid obtained was filtered and washed with water (3 mL×2) and MeOH (3 mL×2) and dried under high vacuum to afford 1 as a white solid (0.033 mg, 85%). m.p. 256-258° C. HPLC 98% (R$_t$=7.80 min., 45% MeOH in 0.1% TFA water, 20 min.); $^1$H NMR (400 MHz, DMSO-d$_6$) δ 12.57 (br s, 1H), 10.68 (s, 1H), 9.93 (s, 1H), 8.44 (appt, J=5.6 Hz, 1H), 8.15 (d, J=6.0 Hz, 1H), 7.98 (dd, J=8.0 Hz, 1H), 7.84-7.79 (m, 4H), 7.60 (t, J=7.6 Hz, 1H), 7.17 (t, J=7.6 Hz, 1H), 6.46 (d, J=5.6 Hz, 1H); $^{13}$C NMR (150 MHz, DMSO-d$_6$) δ 169.85, 167.77, 160.93, 158.28, 155.08, 144.94, 141.45, 134.18, 131.90, 130.81, 123.92, 123.22, 122.95, 119.22, 118.83, 101.18; LRMS (ESI–) m/z 351.11 (M-Cl)$^+$; HRMS (ESI+) m/z calculated for C$_{18}$H$_{15}$N$_4$O$_4$ (M-Cl)$^+$ 351.1088. found 351.1092.

N$^4$-(2-Carboxyphenyl)-N$^2$-(4-carbamoylphenyl)pyrimidine-2,4-diamine hydrochloride (3a, method d in FIG. 4A)

A mixture of 2a (0.050 g, 0.175 mmol) and 2-aminobenzamide (0.027 g, 0.199 mmol) in HCl (1.0 mL, 0.1 M) was heated in a microwave reactor at 160° C. for 15 min. The precipitate obtained upon cooling the mixture was filtered and washed with water (5 mL) and acetone (5 mL×2) to obtain pure compound 3a (0.036 g, 53%) as a light yellow solid. m.p. 226° C. (dec.). HPLC 96% ($R_t$=3.55 min., 55% MeOH in 0.1% TFA water, 20 min.); $^1$H NMR (400 MHz, DMSO-$d_6$) δ 8.82 (d, J=7.6 Hz, 1H), 8.63 (appd, J=7.6 Hz, 1H), 8.17 (d, J=8.0 Hz, 1H), 8.03 (dd, J=8.0, 1.4 Hz, 1H), 7.84 (td, J=7.6, 1.2 Hz, 1H), 7.72-7.69 (m, 1H), 7.59 (d, J=8.4 Hz, 1H), 7.40 (t, J=7.6 Hz, 1H), 7.30 (t, J=7.6 Hz, 1H), 6.83 (d, J=8.0 Hz, 1H); LRMS (ESI+) m/z 333.1 (M-NH$_2$—HCl)$^+$; HRMS (ESI+) m/z calculated for $C_{18}H_{15}N_5O_2$ (M-NH$_2$—HCl)$^+$ 333.0982. found 333.1002.

$N^4$-(2-Carboxyphenyl)-$N^2$-(phenyl)pyrimidine-2,4-diamine hydrochloride (3b, method d in FIG. 4A)

A mixture of 2a (0.100 g, 0.349 mmol) and aniline (0.038 g, 0.409 mmol) in HCl (1.0 mL, 0.1 M) was heated in a microwave reactor at 160° C. for 15 min. The precipitate formed upon cooling the mixture was filtered and washed with water (5 mL) and hot methanol (5 mL×2) to obtain 3b (0.065 g, 54%) as a white solid. m.p. 233° C. (dec.). HPLC 91% ($R_t$=17.27 min., 50% MeOH in 0.1% TFA water, 20 min.); $^1$H NMR (400 MHz, DMSO-$d_6$) δ 10.67 (s, 1H), 9.34 (s, 1H), 8.65 (d, J=8.0 Hz, 1H), 8.11 (d, J=5.6 Hz, 1H), 7.97 (d, J=7.6 Hz, 1H), 7.70 (d, J=8.4 Hz, 2H), 7.55 (t, J=6.8 Hz, 1H), 7.25 (t, J=8.0 Hz, 2H), 7.08 (t, J=7.6 Hz, 1H), 6.93 (t, J=6.8 Hz, 1H), 6.35 (d, J=5.6 Hz, 1H); LRMS (ESI−) m/z 305.1 (M-H—HCl)$^−$; HRMS (ESI+) m/z calculated for $C_{17}H_{15}N_4O_2$ (M-Cl)$^+$ 307.1189. found 307.1187.

$N^4$-(2-Carboxyphenyl)-$N^2$-(4-morpholinophenyl)pyrimidine-2,4-diamine hydrochloride (3c, method e in FIG. 4A)

A mixture of 2a (0.125 g, 0.437 mmol) and 4-morpholinoaniline (0.089 g, 0.500 mmol) in a solution of EtOH/1 M HCl (1:1, 2 mL) was heated in a microwave reactor at 160° C. for 20 min. Addition of EtOAc (0.5 mL) gave a precipitate. The precipitate was filtered and dried under vacuum to afford the desired compound 3c (0.060 g, 32%) as a light yellow solid. m.p. 162° C. (dec.). HPLC 97% ($R_t$=2.99 min., 50% MeOH in 0.1% DEA in water, 20 min.); $^1$H NMR (400 MHz, CD$_3$OD) δ 8.22 (brs, 1H), 8.14 (dd, J=8.0, 1.6 Hz, 1H), 7.88 (d, J=7.2 Hz, 1H), 7.64-7.54 (m, 5H), 7.35 (t, J=7.6 Hz, 1H), 6.56 (d, J=7.2 Hz, 1H), 4.06 (appt, J=4.6 Hz, 4H), 3.14 (appt, J=4.7 Hz, 4H); $^{13}$C NMR (100 MHz, DMSO-$d_6$) δ 168.36, 162.30, 152.53, 144.03, 137.78, 133.70, 131.71, 126.68, 126.62, 124.49, 123.42, 119.53, 100.29, 65.36, 52.16; LC-MS (ESI−) m/z 390.15 (M−HCl)$^−$; HRMS (ESI−) m/z calculated for $C_{21}H_{20}N_5O_3$ (M-H—Cl)$^−$ 390.1572. found 390.1577.

$N^4$-(2-Carboxyphenyl)-$N^2$-(2-carboxyphenyl)pyrimidine-2,4-diamine hydrochloride (3d, method d in FIG. 4A)

A suspension of 2,4-dichloropyrimidine (0.149 g, 1.00 mmol) and 2-aminobenzoic acid (0.274 g, 2.00 mmol) in HCl (3.0 ml, 0.1 M) was heated in a microwave reactor at 160° C. for 15 min. The precipitate obtained was filtered and washed with water (10 mL), followed by washing with acetone (5 mL×2) to obtain the desired compound 3d (0.232 g, 60%) as a white solid. m.p. 254° C. (dec.). HPLC 99% ($R_t$=3.53 min., 55% MeOH in 0.1% TFA water, 20 min.); $^1$H NMR (400 MHz, DMSO-$d_6$) δ 11.80 (s, 1H), 8.91 (d, J=8.0 Hz, 1H), 8.22 (dd, J=8.0, 1.2 Hz, 1H), 8.04 (dd, J=8.0, 1.2 Hz, 1H), 7.97-7.93 (m, 2H), 7.76 (td, J=7.6, 1.6 Hz, 1H), 7.60 (d, J=8.0 Hz, 1H), 7.54-7.47 (m, 2H), 7.11 (appd, J=8.0 Hz, 1H); LRMS (ESI−) m/z 331.0 (M-OH—HCl)$^−$; HRMS (ESI+) m/z calculated for $C_{18}H_{13}N_4O_3$ (M−HO—HCl)$^+$ 333.0982. found 333.0997.

$N^4$-(2-Carboxymethylphenyl)-$N^2$-(4-carboxymethylphenyl)pyrimidine-2,4-diamine hydrochloride (3e, method d in FIG. 4A)

To a mixture of methyl 4-aminobenzoate (0.166 g, 1.099 mmol) and 2e (0.263 g, 0.876 mmol) was added HCl (3.0 mL, 0.1 M). The reaction mixture was heated in a microwave reactor at 160° C. for 15 min. The crude product that was precipitated was filtered, dried under vacuum and purified using SiO$_2$ chromatography (gradient elution 0-20% EtOAc in hexane) to obtain the desired product 3e (0.116 g, 32%) as a white solid. m.p. 196-198° C. HPLC 99% ($R_t$=5.82 min., 60% MeOH in 0.1% TFA water, 20 min.); $^1$H NMR (400 MHz, DMSO-$d_6$) δ 10.08 (s, 1H), 9.73 (s, 1H), 8.37 (d, J=8.4 Hz, 1H), 8.16 (d, J=6.0 Hz, 1H), 7.94 (dd, J=8.0, 1.6 Hz, 1H), 7.84 (d, J=9.2 Hz, 2H), 7.80 (d, J=9.2 Hz, 2H), 7.64-7.60 (m, 1H), 7.18 (appt, J=7.2 Hz, 1H), 6.45 (d, J=6.0 Hz, 1H), 3.81 (s, 3H), 3.79 (s, 3H); $^{13}$C NMR (100 MHz, DMSO-$d_6$) δ 168.25, 166.69, 160.74, 159.58, 157.54, 146.04, 141.41, 134.30, 131.39, 130.62, 123.02, 122.94, 121.99, 118.58, 118.39, 101.12, 52.97, 52.35; LRMS (ESI+) m/z 379.1 (M-Cl)$^+$; HRMS (ESI+) m/z calculated for $C_{20}H_{19}N_4O_4$ (M-Cl)$^+$ 379.1401. found 379.1402.

$N^4$,$N^2$-Diphenylpyrimidine-2,4-diamine hydrochloride (3f, method d in FIG. 4A)

A mixture of 2,4-dichloropyrimidine (0.050 g, 0.336 mmol) and aniline (0.063 g, 0.677 mmol) in HCl (1.0 mL, 0.1 M) was heated in a microwave reactor at 160° C. for 15 min. The product obtained was purified using SiO$_2$ chromatography (gradient elution 0-20% EtOAc in hexane) to afford the desired product 3f (0.048 g, 49%) as a white solid. m.p. 144° C. (dec.). HPLC 96% ($R_t$=5.33 min., 60% MeOH in 0.1% TFA water, 40 min.); $^1$H NMR (400 MHz, CD$_3$OD) δ 7.85 (d, J=6.0 Hz, 1H), 7.59 (d, J=7.6 Hz, 2H), 7.55 (dd, J=7.6 Hz, 2H), 7.27 (d, J=7.6 Hz, 2H), 7.23 (d, J=7.6 Hz, 2H), 7.05-6.98 (m, 2H), 6.20 (d, J=6.0 Hz, 1H); LRMS (ESI+) m/z 263.1 (M-Cl)$^+$; HRMS (ESI+) m/z calculated for $C_{16}H_{15}N_4$ (M-Cl)$^+$ 263.1291. found 263.1293.

$N^4$-(2-Carbamoylphenyl)-$N^2$-(4-carbamoylphenyl)pyrimidine-2,4-diamine hydrochloride (3g, method d in FIG. 4A)

A mixture of 2b (0.248 g, 0.871 mmol) and 4-aminobenzamide (0.136 g, 1.00 mmol) in HCl (3.0 mL, 0.1 M) was heated in a microwave reactor at 160° C. for 15 min. The precipitate was filtered and washed with water (10 mL), hot MeOH (10 mL), hot THF (10 mL), dioxane (5 mL), DMF (5 mL) and MeOH (10 mL) sequentially to obtain pure 3g (0.160 g, 48%) as a light yellow solid. m.p. 257-260° C. HPLC 97% ($R_t$=3.32 min., 50% MeOH in 0.1% TFA water, 20 min.); $^1$H NMR (400 MHz, DMSO-$d_6$) δ 10.63 (s, 1H disappeared on D$_2$O shake), 9.65 (s, 1H disappeared on D$_2$O shake), 8.57 (d, J=8.4 Hz, 1H), 8.15 (d, J=5.2 Hz, 1H), 7.98 (dd, J=7.6, 1.6 Hz, 1H), 7.83-7.73 (m, 5H becomes 4H on D$_2$O shake), 7.63-7.58 (m, 1H), 7.17 (brs, 1H disappeared on D$_2$O shake), 7.12 (t, J=8.4 Hz, 1H), 6.42 (d, J=6.0 Hz, 1H); $^{13}$C NMR (100 MHz, DMSO-$d_6$) δ 170.31, 168.30, 160.55, 159.67, 157.36, 144.07, 142.41, 134.35, 131.96, 128.81, 127.22, 122.25, 121.83, 118.50, 117.57, 101.05;

LRMS (ESI+) m/z 349.1 (M-Cl)⁺; HRMS (ESI+) m/z calculated for $C_{18}H_{17}N_6O_2$ (M-Cl)⁺ 349.1408. found 349.1407.

$N^4$-(Phenyl)-$N^2$-(4-carboxyphenyl)pyrimidine-2,4-diamine hydrochloride (3h, method d in FIG. 4A)

A mixture of 2c (0.020 g, 0.082 mmol) and 4-aminobenzoic acid (0.013 g, 0.097 mmol) in HCl (1.5 mL, 0.1 M) was heated in a microwave reactor at 160° C. for 15 min. The solid obtained upon cooling the mixture was filtered, washed with water (5 mL) and dried under vacuum to obtain the desired compound 3h (0.020 g, 71%) as a white solid. m.p. 215° C. (dec.). HPLC 99% ($R_t$=7.28 min., 50% MeOH in 0.1% TFA water, 20 min.); ¹H NMR (400 MHz, CD₃OD) δ 8.00 (d, J=8.8 Hz, 2H), 7.86 (d, J=7.2 Hz, 1H), 7.63 (d, J=8.4 Hz, 2H), 7.57 (d, J=7.6 Hz, 2H), 7.41 (t, J=7.6 Hz, 2H), 7.28 (t, J=7.6 Hz, 1H), 6.46 (d, J=7.2 Hz, 1H); ¹³C NMR (100 MHz, DMSO-d₆) δ 167.44, 161.79, 152.70, 144.17, 141.82, 137.81, 130.87, 129.50, 126.80, 126.15, 123.30, 121.17, 100.58. LRMS (ESI-) m/z 305.0 (M-Cl)⁻; HRMS (ESI+) m/z calculated for $C_{17}H_{15}N_4O_2$ (M-Cl)⁺ 307.1190. found 307.1187.

$N^4,N^2$-Di(4-carboxyphenyl)pyrimidine-2,4-diamine hydrochloride (3i, method d in FIG. 4A)

A mixture of 2d (0.100 g, 0.350 mmol) and 4-aminobenzoic acid (0.055 g, 0.401 mmol) in HCl (1.5 mL, 0.1 M) was heated in a microwave reactor at 160° C. for 15 min. The precipitate obtained upon cooling the mixture was filtered and washed with water (10 mL), followed by quick wash with acetone (5 mL×2) to give pure 3i (0.136 g, 99%) as a white solid. m.p. 281-283° C. HPLC 98% ($R_t$=4.97 min., 50% MeOH in 0.1% TFA in water, 20 min.); ¹H NMR (400 MHz, DMSO-d₆) δ 10.71 (brs, 1H), 10.46 (brs, 1H), 8.09 (d, J=6.8 Hz), 7.90 (d, J=6.0 Hz, 2H partially overlapping) 7.88 (d, J=6.0 Hz, 2H partially overlapping), 7.79 (d, J=8.8 Hz, 2H), 7.71 (d, J=8.4 Hz, 2H), 6.50 (d, J=6.4 Hz, 1H); LRMS (ESI-) m/z 349.0 (M-H—HCl)⁻; HRMS (ESI+) m/z calculated for $C_{18}H_{15}N_4O_4$ (M-Cl)⁺ 351.1088. found 351.1082.

$N^4$-(2-Carboxyphenyl)-$N^2$-(4-carboxyphenyl)-5-methylpyrimidine-2,4-diamine hydrochloride (3j, method g in FIG. 4A)

A mixture of 2j (0.115 g, 0.383 mmol) and 4-aminobenzoic acid (0.179 g, 1.307 mmol) in HCl (1 M)/THF (2:1, 3.0 mL) was heated in a microwave reactor at 160° C. for 15 min. The precipitate obtained upon cooling the mixture was filtered and washed with water (5 mL) and MeOH (5 mL×2). The solid obtained was slurried in DMF (2 mL), filtered and washed with MeOH (5 mL), acetone (5 mL) and DCM (5 mL) sequentially to obtain the desired compound 3j (0.055 g, 36%) as a white solid. m.p. 213° C. (dec.). HPLC 97% ($R_t$=5.17 min., 55% MeOH in 0.1% TFA water, 20 min.); ¹H NMR (400 MHz, DMSO-d₆) δ 12.50 (brs, 1H, disappeared on D₂O shake), 11.00 (s, 1H disappear on D₂O shake), 9.68 (s, 1H disappeared on D₂O shake), 9.01 (d, J=8.4 Hz, 1H), 8.08 (s, 1H), 8.03 (d, J=7.9 Hz, 1H), 7.85-7.80 (m, 4H), 7.60 (t, J=7.9 Hz, 1H), 7.11 (t, J=7.6 Hz, 1H), 2.16 (s, 3H); LC-MS (ESI+) m/z 365.13 (M-Cl)⁺; HRMS (ESI+) m/z calculated for $C_{19}H_{17}N_4O_4$(M-Cl)⁺ 365.1244. found 365.1240.

$N^4$-(2-Carboxyphenyl)-$N^2$-(4-carboxyphenyl)-6-methylpyrimidine-2,4-diamine hydrochloride (3k, method d in FIG. 4A)

A mixture of 2f (0.263 g, 0.877 mmol) and 4-aminobenzoic acid (0.137 g, 1.00 mmol) in HCl (3.0 mL, 0.1 M) was heated in a microwave reactor at 160° C. for 15 min. The precipitate obtained was filtered and washed with water (10 mL), MeOH (10 mL×2), DMSO (1 mL, quick wash), and acetone (5 ml) to obtain the desired compound 3k (0.187 g, 53%) as a white solid. m.p. 243° C. (dec.). HPLC 90% ($R_t$=5.11 min., 55% MeOH in 0.1% TFA water, 20 min.); ¹H NMR (400 MHz, DMSO-d₆) δ 10.56 (s, 1H), 9.73 (s, 1H), 8.55 (d, J=8.4 Hz, 1H), 7.98 (d, J=6.8 Hz, 1H), 7.86 (d, J=8.8 Hz, 2H), 7.81 (d, J=8.8 Hz, 2H), 7.58 (t, J=7.2 Hz, 1H), 7.11 (t, J=7.2 Hz, 1H), 6.33 (s, 1H), 2.28 (s, 3H); LC-MS (ESI-) m/z 363.11 (M-H—HCl)⁻; HRMS (ESI-) m/z calculated for $C_{19}H_{15}N_4O_4$ (M-H—HCl)⁻ 363.1099. found 363.1107.

$N^4$-(2-Chlorophenyl)-$N^2$-(4-carboxyphenyl)pyrimidine-2,4-diamine hydrochloride (3l, method e in FIG. 4A)

A mixture of 2l (0.094 g, 0.340 mmol) and 4-aminobenzoic acid (0.107 g, 0.781 mmol) in EtOH/1M HCl (2.0 mL, 1:1) was heated in a microwave reactor at 160° C. for 15 min. The mixture was cooled to r.t. The precipitate obtained was filtered, washed with water (2 mL), and MeOH (2 mL) sequentially to afford the desired compound 3l (0.055 g, 43%) as a white solid. m.p. 234° C. (dec.). HPLC 99% ($R_t$=4.32 min., 55% MeOH in 0.1% TFA water, 20 min.); ¹H NMR (400 MHz, DMSO-d₆) δ 12.59 (s, 1H), 10.00 (s, 1H), 9.76 (s, 1H), 8.06 (d, J=6.0 Hz, 1H), 7.70-7.68 (m, 3H), 7.63-7.58 (m, 3H), 7.43 (t, J=7.8 Hz, 1H), 7.33 (t, J=7.4 Hz, 1H), 6.40 (d, J=6.1 Hz, 1H); ¹³C NMR (100 MHz, DMSO-d₆) δ 167.36, 163.18, 152.30, 145.07, 141.91, 134.61, 130.72, 130.64, 130.47, 129.67, 129.52, 128.56, 126.30, 120.01, 95.58; LC-MS (ESI+) m/z 341.09 (M-Cl)⁺; HRMS (ESI+) m/z calculated for $C_{17}H_{14}ClN_4O_2$ (M-Cl)⁺ 341.0800. found 341.0810.

$N^4$-(2-Carboxyphenyl)-$N^2$-phenyl-5-fluoropyrimidine-2,4-diamine hydrochloride (3m, method e in FIG. 4A)

A mixture of 2g (0.134 g, 0.441 mmol) and aniline (0.140 g, 1.50 mmol) in 1:1 ratio of EtOH/1M HCl (2.0 mL) was heated in a microwave reactor at 160° C. for 30 min. The precipitate formed upon cooling the mixture was filtered and washed with MeOH (5 mL), acetone (5 mL) and dried under vacuum to afford the desired compound 3m (0.150 g, 94%) as a white solid. m.p. 240° C. (dec.). HPLC 99% ($R_t$=4.21 min., 70% MeOH in 0.1% TFA water, 20 min.); ¹H NMR (400 MHz, DMSO-d₆) δ 11.50 (s, 1H), 9.41 (s, 1H), 8.96 (d, J=8.4 Hz, 1H), 8.21 (d, J=3.1 Hz, 1H), 8.04 (dd, J=7.9, 1.5 Hz, 1H), 7.67 (d, J=8.4 Hz, 2H), 7.60 (t, J=8.4 Hz, 1H), 7.27 (t, J=8.4 Hz, 2H), 7.12 (t, J=7.6 Hz, 1H), 6.94 (t, J=7.3 Hz, 1H); ¹⁹F NMR (376 MHz, DMSO-d₆) δ −166.03 (s); ¹³C NMR (100 MHz, DMSO-d₆) δ 170.83, 156.07 (d, J=3.0 Hz), 149.60 (d, J=10.0 Hz), 142.26, 141.68 (d, J=245 Hz), 141.52, 141.33, 141.25, 134.72, 132.02, 129.05, 122.15 (d, J=21.0 Hz), 120.74, 119.80, 116.24; LC-MS (ESI+) m/z 325.12 (M-Cl)⁺; HRMS (ESI+) m/z calculated for $C_{17}H_{14}FN_4O_2$ (M-Cl)⁺ 325.1095. found 325.1093.

$N^4$-(2-Carboxyphenyl)-$N^2$-(4-carboxyphenyl)-5-fluoropyrimidine-2,4-diamine acid (3n, method e in FIG. 4A)

A mixture of 2g (0.134 g, 0.44 mmol) and 4-aminobenzoic acid (0.206 g, 1.50 mmol) in 1:1 ratio of EtOH/HCl (2.0 mL, 1 M) was heated in a microwave reactor at 160° C. for 30 min. The precipitate formed upon cooling the mixture was filtered and washed with sat. NaHCO$_3$ (3 mL) and water (5 mL). The solid obtained was slurried in hot DMF (3 mL), filtered and washed with MeOH (5 mL) and dried under vacuum to afford the desired compound 3n (0.096 g, 59%) as a white solid. m.p. 287-290° C. HPLC 99% (R$_t$=14.73 min., 55% MeOH in 0.1% TFA, water 20 min.); $^1$H NMR (400 MHz, DMSO-d$_6$) δ 11.42 (s, 1H disappeared on D$_2$O shake), 9.83 (s, 1H disappeared on D$_2$O shake), 8.94 (d, J=8.6 Hz, 1H), 8.29 (appd, J=2.7 Hz, 1H), 8.05 (d, J=7.9 Hz, 1H), 7.83 (d, J=8.4 Hz, 2H), 7.83 (d, J=8.4 Hz, 2H), 7.63 (t, J=7.2 Hz, 1H), 7.16 (t, J=7.5 Hz, 1H); $^{19}$F NMR (376 MHz, DMSO-d$_6$) δ −164.42 (s); $^{13}$C NMR (100 MHz, DMSO-d$_6$) δ 170.76, 167.82, 155.42 (d, J=3.5 Hz), 149.76 (d, J=10 Hz), 145.58, 142.09 (d, J=247 Hz), 142.00, 141.25 (d, J=18 Hz), 134.70, 132.03, 130.87, 123.39, 122.57, 120.93, 118.13, 116.65; LC-MS (ESI+) m/z 369.10 (M+H)$^+$; HRMS (ESI+) m/z calculated for C$_{18}$H$_{14}$FN$_4$O$_4$(M+H)$^+$ 369.0994. found 369.0994.

N$^4$-(2-Chlorophenyl)-N$^2$-(4-carboxyphenyl)-5-fluoropyrimidine-2,4-diamine hydrochloride (3o, method d in FIG. 4A)

A mixture of 2k (0.300 g, 1.12 mmol) and 4-aminobenzoic acid (0.153 g, 1.12 mmol) in ethanol (1.5 mL) was heated in a microwave reactor at 150° C. for 20 min. The reaction mixture was cooled, and stirred at room temperature for 48 hours. The white precipitate was isolated by filtration and washed with ethyl acetate (5 mL). The product was suspended in ethyl acetate (5 mL) and sonicated for 5 min. and filtered to provide 3o (0.232 g, 52%) as a white powder. m.p. 308° C. (dec.). HPLC 99% (R$_t$=7.57 min., 55% MeOH in 0.1% TFA water, 20 min.); $^1$H NMR (400 MHz, DMSO-d$_6$) δ 12.44 (s, 1H), 9.59 (s, 1H), 9.38 (s, 1H), 8.15 (d, J=3.4 Hz, 1H), 7.62-7.52 (m, 6H), 7.45-7.36 (m, 2H); $^{19}$F NMR (376 MHz, DMSO-d$_6$) δ −164.92; $^{13}$C NMR (100 MHz, DMSO-d$_6$) δ 167.77, 155.67 (d, J=3.0 Hz), 151.48 (d, J=12.0 Hz), 145.80, 141.60 (d, J=20.0 Hz), 141.46 (d, J=245.0 Hz), 136.04, 131.63, 130.55, 130.40, 130.19, 128.44, 128.38, 122.66, 117.37; LC-MS (ESI+) m/z 359.07 (M-Cl)$^+$; HRMS (ESI+) m/z calculated for C$_{17}$H$_{13}$ClFN$_4$O$_2$ (M-Cl)$^+$ 359.0706. found 359.0709.

N$^4$-(2-Chlorophenyl)-N$^2$-phenyl-5-fluoropyrimidine-2,4-diamine hydrochloride (3p, method m in FIG. 4A)

A mixture of 2k (0.061 g, 0.207 mmol) and aniline (0.020 g, 0.207 mmol) in EtOH (2.0 mL) was heated in a microwave reactor at 150° C. for 20 min. The precipitate formed upon cooling the mixture was filtered and quickly washed with MeOH (1 mL) to afford the desired product 3p (0.037 g, 51%) as a white solid. m.p. 145-148° C. HPLC 99% (R$_t$=9.43 min., 55% MeOH in 0.1% TFA water, 20 min.); $^1$H NMR (400 MHz, DMSO-d$_6$) δ 9.18 (s, 1H disappeared on D$_2$O shake), 9.12 (s, 1H disappeared on D$_2$O shake), 8.08 (d, J=4.0 Hz, 1H), 7.59-7.56 (m, 2H), 7.44 (d, J=8.4 Hz, 2H), 7.39 (td, J=7.6, 1.6 Hz, 1H), 7.31 (td, J=7.6, 1.6 Hz, 1H), 7.02 (t, J=7.2 Hz, 2H), 6.77 (t, J=7.6 Hz, 1H); $^{19}$F NMR (376 MHz, DMSO-d$_6$) δ −166.49; $^{13}$C NMR (100 MHz, DMSO-d$_6$) δ 155.97, 151.42 (d, J=12 Hz), 141.40, 141.24 (d, J=20 Hz), 141.11 (d, J=244 Hz), 136.05, 131.18, 130.35, 129.80, 128.76, 128.29, 128.13, 121.33, 118.80; LC-MS (ESI+) m/z 315.08 (M-Cl)$^+$; HRMS (ESI+) m/z calculated for C$_{16}$H$_{13}$ClFN$_4$(M-Cl)$^+$ 315.0807. found 315.0812.

N$^4$-(2-Carboxyphenyl)-N$^2$-(3-carboxyphenyl)pyrimidine-2,4-diamine hydrochloride (3q method d in FIG. 4A)

A mixture of 2a (0.050 g, 0.175 mmol) and 3-aminobenzoic acid (0.024 g, 0.175 mmol) in HCl (0.1 mL, 0.1 M) was heated in a microwave reactor at 160° C. for 15 min. The solution was cooled and the precipitate obtained was filtered and washed quickly with hot methanol (3 ml) to obtain the desired product 3q (0.056 g, 72%) as a white solid. m.p. 275° C. (dec). HPLC 99% (R$_t$=6.31 min., 50% MeOH in 0.1% TFA water, 20 min.); $^1$H NMR (400 MHz, DMSO-d$_6$) δ 12.85 (brs, 1H), 10.73 (s, 1H), 9.52 (s, 1H), 8.67 (d, J=8.4 Hz, 1H), 8.27 (s, 1H), 8.12 (d, J=5.7 Hz, 1H), 7.96 (d, J=7.9 Hz, 2H), 7.54-7.47 (m, 2H), 7.51 (t, J=7.7 Hz, 2H), 7.05 (t, J=7.6 Hz, 1H), 6.36 (d, J=5.7 Hz, 1H); $^{13}$C NMR (100 MHz, DMSO-d$_6$) δ 170.49, 168.16, 160.41, 159.99, 157.52, 142.75, 141.52, 134.46, 131.93, 131.72, 129.22, 124.08, 122.79, 121.79, 121.25, 120.71, 116.79, 100.98. LC-MS (ESI−) m/z 349.10 (M−H—HCl)$^−$; HRMS (ESI−) m/z calculated for C$_{18}$H$_4$N$_4$O$_4$ (M−H—HCl)$^−$ 349.0942. found 397.0940.

N$^4$-(2-Carboxyphenyl)-N$^2$-(3-carboxyphenyl)-5-fluoropyrimidine-2,4-diamine hydrochloride (3r method m in FIG. 4A)

A mixture of 2g (0.100 g, 0.329 mmol) and 3-aminobenzoic acid (0.048 g, 0.350 mmol) in HCl (1.0 mL, 0.1 M) was heated in a microwave reactor at 150° C. for 20 min. The mixture was cooled to r.t. and the precipitate obtained was filtered and washed quickly with ethanol (3 ml) to obtain the desired product 3r (0.089 g, 66%) as a white solid. m.p. 272° C. (dec.). HPLC 99% (R$_t$=14.34 min., 50% MeOH in 0.1% TFA water, 20 min.); $^1$H NMR (400 MHz, DMSO-d$_6$) δ 13.07 (brs, 1H), 11.48 (s, 1H), 9.61 (s, 1H), 8.97 (d, J=8.4 Hz, 1H), 8.31-8.23 (m, 2H), 8.03 (d, J=7.9 Hz, 1H), 7.60-7.48 (m, 2H), 7.39 (t, J=7.9 Hz, 1H), 7.12 (t, J=7.6 Hz, 1H); $^{13}$C NMR (101 MHz, DMSO-d$_6$) δ 170.87, 168.29, 155.90, 149.69 (d, J=9.7 Hz), 151.37 (d, J=11.5 Hz), 141.91 (d, J=235.3 Hz), 142.22, 141.54, 134.89, 132.04, 131.77, 129.32, 123.78, 122.87, 122.29, 120.62, 120.37, 116.19; $^{19}$F NMR (376 MHz, DMSO) δ −165.34; Elemental analysis: calculated for C$_{18}$H$_{14}$ClFN$_4$O$_4$ C, 53.41; H, 3.49; N, 13.84. Found: C, 53.22; H, 3.37; N, 13.57.

N$^4$-(2-Carboxyphenyl)-N$^2$-(4-ethoxycarbonylphenyl)-5-chloropyrimidine-2,4-diamine hydrochloride (3s, method f (ii) in FIG. 4A)

A mixture of 2m (0.063 g, 0.193 mmol) and ethyl 4-aminobenzoate (0.043 g, 0.260 mmol) in ethanol (0.8 mL), was heated in a sealed tube at 120° C. (oil bath temperature) overnight. The resulting precipitate was filtered and washed with ethanol (1 mL×2), Et$_2$O (3 mL), hexane (2 mL) sequentially and dried under vacuum to afford the title compound 3s (0.079 g, 90%), as a white solid. m.p. 221° C. (dec.). $^1$H NMR (400 MHz, DMSO-d$_6$) δ 13.77 (s, 1H), 11.46 (s, 1H), 9.97 (s, 1H), 8.93 (d, J=8.3 Hz, 1H), 8.34 (s, 1H), 8.04 (dd, J=1.5, 7.9 Hz, 1H), 7.86 (d, J=9.1 Hz, 2H), 7.83 (d, J=9.1 Hz, 2H), 7.64-7.60 (m, 1H), 7.19-7.15 (m, 1H), 4.26 (q, J=7.1 Hz, 2H), 1.29 (t, J=7.1 Hz, 3H). LC-MS (ESI−) m/z 412.09 (M+H)$^+$; HRMS (ESI−) m/z calculated for C$_{20}$H$_{18}$ClN$_4$O$_4$ (M+H)$^+$ 413.1011. found 413.0989.

N$^4$-(2-Carboxyphenyl)-N$^2$-(4-ethoxycarbonylphenyl)-5,6-dichloropyrimidine-2,4-diamine hydrochloride (3t, method f (h) in FIG. 4A)

A mixture of 2n (0.091 g, 0.257 mmol) and ethyl 4-aminobenzoate (0.044 g, 0.266 mmol) in ethanol (1.0 mL), was heated in a sealed tube at 110° C. (oil bath temperature) for 4 days. The resulting precipitate was filtered and washed with ethanol (1 mL×2) and suspended in methanol (1 mL). The mixture was sonicated and the solid was filtered and dried under vacuum to afford the title compound 3t (0.022 g, 17%) as a white solid. m.p. 206° C. (dec.). $^1$H NMR (400 MHz, DMSO-$d_6$) δ 11.52 (s, 1H), 10.25 (s, 1H), 8.74 (s, 1H), 8.04 (dd, J=1.5, 7.9 Hz, 1H,), 7.86 (d, J=8.8 Hz, 2H), 7.75 (d, J=8.9 Hz, 2H), 7.64-7.60 (m, 1H,), 7.23-7.20 (m, 1H), 4.27 (q, J=7.1 Hz, 2H,), 1.29 (t, J=7.1 Hz, 3H). LC-MS (ESI−) m/z 447.07 (M-Cl)$^+$; HRMS (ESI−) m/z calculated for $C_{24}H_{17}Cl_2N_4O_4$ (M-Cl)$^+$ 447.0621. found 447.00598.

5-Amino-N$^4$-(2-carboxyphenyl)-N$^2$-(4-ethoxycarbonylphenyl)pyrimidine-2,4-diamine hydrochloride (3u, method f (i) in FIG. 4A)

This was prepared by using a method described Gray and co-workers.[47] A mixture of 2h (0.080 g, 0.266 mmol), ethyl 4-aminobenzoate (0.099 g, 0.600 mmol) and HCl (0.15 mL, 4M in dioxane) in 2-butanol (1.0 mL) was heated in a sealed tube at 120° C. (oil bath temperature) for 24 h. After cooling the mixture to r.t., the suspension obtained was filtered and washed with water (5 mL), MeOH (3 mL) to afford the desired compound 3u (0.082 g, 72%) as a yellow solid. m.p. 262° C. (dec.). HPLC 99% ($R_t$=15.48 min., 50% MeOH in 0.1% TFA water, 20 min.); $^1$H NMR (400 MHz, DMSO-$d_6$) δ 9.88 (s, 1H), 9.87 (s, 1H), 9.18 (s, 1H), 7.94-7.84 (m, 5H), 7.80 (d, J=8.0 Hz, 1H), 7.42 (t, J=8.4 Hz, 1H), 7.19 (d, J=8.0 Hz, 1H), 7.04 (t, J=7.5 Hz, 1H), 4.26 (q, J=7.0 Hz, 2H), 1.30 (t, J=7.0 Hz, 3H); LC-MS (ESI+) m/z 376.15 (M-OH—HCl)$^+$; HRMS (ESI+) m/z calculated for $C_{20}H_{18}N_5O_3$(M-OH—HCl)$^+$ 376.1404. found 376.1405.

6-Amino-N$^4$-(2-carboxyphenyl)-N$^2$-(4-ethoxycarbonylphenyl)pyrimidine-2,4-diamine hydrochloride (3v, method e in FIG. 4A)

A mixture of 2i (0.265 g, 0.880 mmol) and ethyl 4-aminobenzoate (1.65 g, 10.00 mmol) in EtOH/1 M HCl (1:1, 12 mL) was heated in a microwave reactor at 160° C. for 1 h. The mixture was cooled to r.t., and the solid obtained was filtered, washed with MeOH (5 mL) and slurried in acetone (10×5 mL) until no impurity was shown by NMR to afford the desired compound 3v (0.125 g, 33%) as a beige color solid. m.p. 280° C. (dec.). $^1$H NMR (400 MHz, DMSO-$d_6$) δ 10.65 (s, 1H disappeared on $D_2O$ shake), 9.36 (s, 1H disappeared on $D_2O$ shake), 8.85 (appd, J=7.6 Hz, 1H), 7.94 (d, J=8.4 Hz, 1H), 7.83 (d, J=8.0 Hz, 2H), 7.65 (d, J=8.4 Hz, 2H), 7.47 (t, J=8.4 Hz, 1H), 6.94 (t, J=8.0 Hz, 1H), 6.54 (brs, 2H disappeared on $D_2O$ shake), 5.54 (s, 1H), 4.26 (q, J=7.0 Hz, 2H), 1.29 (t, J=7.0 Hz, 3H); LC-MS (ESI+) m/z 394.15 (M-Cl)$^+$; HRMS (ESI+) m/z calculated for $C_{20}H_{20}N_5O_4$ (M-Cl)$^+$ 394.1510. found 394.1509.

N$^4$-(2-Carboxyphenyl)-N$^2$-(4-methoxycarbonylphenyl)pyrimidine-2,4-diamine hydrochloride (3w, method m in FIG. 4A)

A suspension of 2a (0.060 g, 0.210 mmol) and methyl 4-aminobenzoate (0.032 g, 0.210 mmol) in MeOH (1 mL) was heated in a microwave reactor at 150° C. for 20 min. Upon cooling, the resulting precipitate was filtered and washed with MeOH (2 mL) to afford 3w (0.064 mg, 76%) as a yellow solid which was used without further purification. $^1$H NMR (400 MHz, DMSO-$d_6$) δ 13.40 (br s, 1H), 10.74 (s, 1H), 10.11 (s, 1H), 8.33 (br d, J=5.6 Hz, 1H), 8.14 (d, J=6.0 Hz, 1H), 7.99 (d, J=8.0 Hz, 1H), 7.84-7.76 (m, 4H), 7.63 (t, J=7.6 Hz, 1H), 7.22 (t, J=7.6 Hz, 1H), 6.50 (d, J=6.4 Hz, 1H), 3.80 (s, 3H); LC-MS (ESI+) m/z 365.13 (M-Cl)$^+$; HRMS (ESI+) m/z calculated for $C_{19}H_{17}N_4O_4$ (M-Cl)$^+$ 365.1244. found 365.1243.

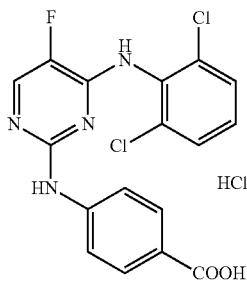 [SMILES: O=C(O)c1ccc(Nc2ncc(F)c(Nc3c(Cl)cccc3Cl)n2)cc1 ; Cl]

4-(4-(2,6-Dichlorophenylamino)-5-fluoropyrimidin-2-ylamino)benzoic acid hydrochloride (3x, method f (ii) in FIG. 4A)

A solution of 2-chloro-N-(2,6-dichlorophenyl)-5-fluoropyrimidin-4-amine (50 mg, 0.17 mmol) and 4-aminobenzoic acid (23 mg, 0.17 mmol) in ethanol (1 ml) were heated at 100° C. for 18 h. The compound precipitated was filtered and washed quickly with methanol to provide pure 3x as a white solid (36 mg, 49%). $^1$H NMR (400 MHz, DMSO) δ 9.92 (s, 1H), 9.85 (s, 1H), 8.23 (d, J=3.4 Hz, 1H), 7.67 (d, J=8.0 Hz, 2H), 7.56 (d, J=8.6 Hz, 2H), 7.49 (t, J=8.1 Hz, 1H), 7.41 (s, 2H). $^{19}$F NMR (376 MHz, DMSO) δ −164.28 (s); LC-MS (ESI−) m/z 391.03 (M-H—HCl)$^-$; HRMS (ESI-ve) m/z calculated for $C_{17}H_{10}Cl_2FN_4O_2$ (M-H—HCl)$^-$ 391.0170. found 391.0140.

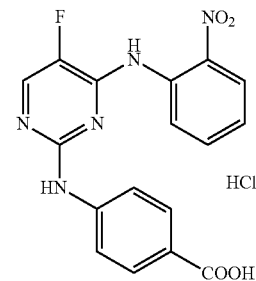 [SMILES: O=C(O)c1ccc(Nc2ncc(F)c(Nc3ccccc3[N+](=O)[O-])n2)cc1 ; Cl]

4-(5-Fluoro-4-(2-nitrophenylamino)pyrimidin-2-ylamino)benzoic acid hydrochloride (3y, method f (ii) in FIG. 4A)

A solution of 2-chloro-5-fluoro-N-(2-nitrophenyl)pyrimidin-4-amine (40 mg, 0.15 mmol) and 4-aminobenzoic acid (23 mg, 0.17 mmol) in ethanol (1 ml) were heated at 100° C. for 44 h. The compound precipitated was filtered and washed quickly with methanol to provide pure 3y as a white solid (33 mg, 53%); $^1$H NMR (400 MHz, DMSO) δ 10.03 (s, 1H), 9.70 (s, 1H), 8.28 (d, J=3.3 Hz, 1H), 8.12 (dd, J=8.3, 1.4 Hz, 1H), 8.05 (d, J=8.1 Hz, 1H), 7.86-7.76 (m, 1H), 7.70 (d, J=8.9 Hz, 2H), 7.63 (d, J=8.9 Hz, 2H), 7.54-7.35 (m, 1H); LC-MS (ESI−) m/z 368.09 (M-H—HCl)$^-$; HRMS (ESI-ve) m/z calculated for $C_{17}H_{11}FN_5O_4$ (M-H—HCl)$^-$ 368.0801. found 368.0768.

5-Amino-N$^4$-(2-carboxyphenyl)-N$^2$-(4-carboxyphenyl)pyrimidine-2,4-diamine (4a, method h in FIG. 4A)

A suspension of 3u (0.069 g, 0.161 mmol) in NaOH/THF (2 M, 0.44 mL/0.2 mL) was heated at 100° C. (oil bath temperature) in a sealed tube for 30 min. A solution of HCl (1 M) was added to acidify the solution to pH=1-2 after removing THF. The solid obtained was filtered and washed with water (5 mL), sat. NaHCO$_3$ (3 mL), water (5 mL), acetone (3 mL), and MeOH (3 mL) sequentially to afford the desired compound 4a (0.038 g, 65%) as a brown solid. m.p. 160° C. (dec.). HPLC 96% (R$_t$=4.19 min., 55% MeOH in 0.1% TFA water 20 min.); $^1$H NMR (400 MHz, DMSO-d$_6$) δ 9.33 (brs, 1H disappeared on D$_2$O shake), 8.86 (brs, 1H), 7.99 (brs, 1H), 7.88-7.78 (m, 5H), 7.50 (brs, 1H), 7.01 (brs, 1H); LC-MS (ESI+) m/z 366.12 (M+H)$^+$; HRMS (ESI+) m/z calculated for C$_{18}$H$_{16}$N$_5$O$_4$(M+H)$^+$ 366.1197. found 366.1198.

6-Amino-N$^4$-(2-carboxyphenyl)-N$^2$-(4-carboxyphenyl)pyrimidine-2,4-diamine (4b, method h in FIG. 4A)

A suspension of 3v (0.070 g, 0.163 mmol) in NaOH (0.45 mL, 2 M) and THF (0.25 mL) was heated at 100° C. (oil bath temperature) in a sealed tube for 16 h. The THF in the mixture was evaporated and HCl (1 M) was added to acidify (pH=1-2) the mixture. The solid obtained was filtered and washed with water (3 mL), sat. aq. NaHCO$_3$ (3 mL) and water (3 mL) sequentially, and dried to afford the desired compound 4b (0.047 g, 79%) as a yellow solid. m.p. 220° C. (dec.). HPLC 95% (R$_t$=5.20 min., 55% MeOH in 0.1% TFA water, 20 min.); $^1$H NMR (400 MHz, DMSO-d$_6$) δ 10.65 (s, 1H disappeared on D$_2$O shake), 9.78 (s, 1H disappeared on D$_2$O shake), 8.54 (brs, 1H), 7.96 (appd, J=5.2 Hz, 1H), 7.82-7.80 (m, 2H), 7.59-7.53 (m, 3H), 7.34-7.10 (m, 3H), 5.60 (s, 1H); LC-MS (ESI+) 366.13 m/z (M+H)$^+$; HRMS (ESI+) m/z calculated for C$_{18}$H$_{16}$N$_5$O$_4$(M+H)$^+$ 366.1197. found 366.1194.

N$^4$-(2-Carboxyphenyl)-N$^2$-(4-carboxyphenyl)-5,6-dichloropyrimidine-2,4-diamine hydrochloride (4c, method h in FIG. 4A)

A mixture of 3t (0.018 g, 0.034 mmol) in THF (0.3 mL) and NaOH (0.1 mL, 2 M) was heated in a sealed tube at 110° C. (oil bath temperature) overnight. The THF was then removed under reduced pressure and HCl (1 M aq., 0.5 mL) was added to the residue. The resulting precipitate was filtered and washed with water (2 mL) and dried under vacuum. The solid obtained was then slurried in methanol (1 mL), filtered and dried under vacuum to afford the title compound 4c (0.005 g, 32%) as a white solid. m.p. 230° C. (dec.). HPLC 84% [R$_t$=10.84 min., 20% MeOH, 80% water (with 0.1% DEA), 20 min.]; $^1$H NMR (400 MHz, DMSO-d$_6$) δ 12.62 (s, 1H), 11.47 (s, 1H), 10.21 (s, 1H), 8.72 (s, 1H), 8.04 (dd, J=7.9, 1.4 Hz, 1H), 7.84 (d, J=8.8 Hz, 2H), 7.72 (d, J=8.7 Hz, 2H), 7.65-7.54 (m, 1H), 7.23-7.20 (m, 1H); LC-MS (ESI-) m/z 417.02 (M-H—HCl)$^-$; HRMS (ESI-) m/z calculated for C$_{18}$H$_{13}$Cl$_2$N$_4$O$_4$ (M-H—HCl)$^-$ 417.0163. found 417.0160.

N$^4$-(2-Carboxyphenyl)-N$^2$-(4-carboxyphenyl)-5-chloropyrimidine-2,4-diamine hydrochloride (4d, method h in FIG. 4A)

A mixture of 3s (0.058 g, 0.119 mmol) in THF (0.4 mL) and NaOH (2 M aq. 0.2 mL) was heated in a sealed tube at 110° C. (oil bath temperature) overnight. The THF was then removed under reduced pressure and HCl (1 M aq., 0.6 mL) was added to the residue. The resulting precipitate was filtered, washed with water (2 mL×3) and dried under vacuum. The solid obtained was then slurried in DMF (2 mL), filtered, washed with DMF (5 mL), methanol (1 mL), Et$_2$O (3 mL) sequentially and dried under vacuum to afford the title compound 4d (0.036 g, 72%) as a white solid. m.p. 261° C. (dec.). $^1$H NMR (400 MHz, DMSO-d$_6$) δ 12.59 (s, 1H), 11.45 (s, 1H), 9.90 (s, 1H), 8.87 (s, 1H), 8.30 (s, 1H), 8.01-7.55 (m, 6H), 7.13 (s, 1H); $^{13}$C NMR (100 MHz, DMSO-d$_6$) δ 170.57 167.72, 157.79, 155.85, 155.36, 145.16, 141.90, 134.51, 131.90, 130.84, 123.84, 122.82, 121.54, 118.76, 117.26, 107.11; HPLC 97% [R$_t$=8.74 min., 15% MeOH, 85% water (with 0.1% DEA) 20 min.]; LC-MS (ESI-) m/z 383.04 (M-H—HCl)$^-$; HRMS (ESI-) m/z calculated for C$_{18}$H$_{14}$ClN$_4$O$_4$ (M-H—HCl)$^-$ 383.0553. found 383.0552.

N$^4$-(2-Fluorophenyl)-N$^2$-(4-carboxyphenyl)pyrimidine-2,4-diamine hydrochloride (6a, method m in FIG. 5A)

A mixture of 2-chloro-N-(2-fluorophenyl)pyrimidin-4-amine (5a) (0.096 g, 0.428 mmol) and 4-aminobenzoic acid (0.069 g, 0.503 mmol) in EtOH (0.5 mL) was heated in a microwave reactor at 150° C. for 20 min. The mixture was filtered and the resulting precipitate was washed with EtOH (0.5 mL×2) to provide the title compound 6a (0.107 g, 69%) as a white solid. m.p. 264° C. (dec). HPLC 98.7% (R$_t$=3.8 min., 55% MeOH in 0.1% TFA water 20 min.); $^1$H NMR (400 MHz, d$_6$-DMSO) δ 12.79 (s, 1H), 11.04 (s, 1H), 10.87 (s, 1H), 8.13 (d, J=7.0 Hz, 1H), 7.77 (d, J=8.7 Hz, 2H), 7.66 (t, J=7.9 Hz, 1H), 7.56 (d, J=8.5 Hz, 2H), 7.46-7.36 (m, 2H), 7.33-7.25 (m, 1H), 6.58 (d, J=6.7 Hz, 1H); $^{19}$F NMR (400 MHz, DMSO-d$_6$) δ 121.12; $^{13}$C NMR (100 MHz, DMSO-d$_6$) δ 167.40, 163.00, 156.59 (d, J=245 Hz), 152.55, 145.08, 141.92, 130.79, 129.14, (d, J=9.27 Hz), 128.30, 126.43, 125.39, 125.04 (d, J=12.15 Hz), 120.29, 116.88 (d, J=18.72 Hz), 99.84, LC-MS (ESI-) m/z 323.10 (M-H—HCl)$^-$; HRMS (ESI-) m/z calculated for C$_{17}$H$_{12}$FN$_4$O$_2$ (M-H—HCl)$^-$ 323.0950. found 323.0974.

N$^4$-[2-(Trifluoromethyl)phenyl]-N$^2$-phenylpyrimidine-2,4-diamine hydrochloride (6b, method m in FIG. 5A)

A mixture of chloropyrimidine 5f (0.076 g, 0.277 mmol) and aniline (0.03 mL, 0.328 mmol) in EtOH (0.4 mL) was heated in a microwave reactor at 150° C. for 20 min. The solvent was removed under reduced pressure to provide an off-white solid. Ethyl acetate (3 mL) was added to the reaction mixture. The mixture was left at r.t. for 30 min and sonicated occasionally. The resulting precipitate was isolated by filtration and washed with ethyl acetate (1 mL×5) and hexane (3 mL) to afford 6b (0.085 g, 84%) as a white solid. m.p. 207° C. (dec). HPLC 100% (R$_t$=9.1 min., 55% MeOH in 0.1% TFA water 20 min.); $^1$H NMR (400 MHz, DMSO-d$_6$) δ 10.62 (s, 1H), 10.43 (s, 1H), 8.01 (apparent s, 1H), 7.86-7.80 (m, 2H), 7.71-7.48 (m, 2H), 7.27 (d, J=7.2 Hz, 2H), 7.14 (t, J=7.5 Hz, 2H), 7.03 (t, J=7.3 Hz, 1H), 6.46 (s, 1H); LC-MS (ESI+) m/z 331.13 (M-Cl)$^+$; HRMS (ESI+) m/z calculated for C$_{17}$H$_{14}$F$_3$N$_4$ (M-Cl)$^+$ 331.1165. found 331.1170.

N$^4$-(2-Chloro-4-fluorophenyl)-N$^2$-(4-carboxyphenyl)pyrimidine-2,4-diamine hydrochloride (6c, method m in FIG. 5A)

A mixture of chloropyrimidine 5b (0.096 g, 0.372 mmol) and 4-aminobenzoic acid (0.058 g, 0.422 mmol) in EtOH (0.5 mL) was heated in a microwave reactor at 150° C. for 20 min. The resulting precipitate was isolated by filtration and washed with EtOH (0.5 mL×2), diethyl ether (2 mL) and hexane (2 mL) sequentially to provide the title compound 6c (0.102 g, 69%) as a white solid. m.p. 268° C. (dec). HPLC 97.7% ($R_t$=4.8 min., 55% MeOH in 0.1% TFA water 20 min.); $^1$H NMR (400 MHz, DMSO-$d_6$) δ 10.89 (s, 1H), 10.72 (s, 1H), 8.12 (d, J=7.0 Hz, 1H), 7.75 (d, J=8.7 Hz, 2H), 7.72-7.63 (m, 2H), 7.50 (d, J=8.6 Hz, 2H), 7.40 (td, J=8.5, 2.9 Hz, 1H), 6.53 (d, J=7.0 Hz, 1H); $^{19}$F NMR (400 MHz, DMSO-$d_6$) δ 112.66; $^{13}$C NMR (100 MHz, DMSO-$d_6$) δ 167.37 163.39, 161.22 (d, J=246.3 Hz), 152.39, 145.37, 141.91, 131.87 (d, J=11.12 Hz); LC-MS (ESI−) m/z 357.06 (M−H—HCl)$^-$; HRMS (ESI−) m/z calculated for $C_{17}H_{11}ClFN_4O_2$ (M−H—HCl)$^-$ 357.0560. found 357.0521.

$N^4$-[2-(Trifluoromethoxy)phenyl]-$N^2$-(4-carboxyphenyl)pyrimidine-2,4-diamine hydrochloride (6d, method m in FIG. 5A)

A mixture of chloropyrimidine 5c (0.074 g, 0.255 mmol) and 4-aminobenzoic acid (0.042 g, 0.306 mmol) in EtOH (0.5 mL) was heated with a microwave reactor at 150° C. for 20 min. The resulting precipitate was isolated by filtration and washed with EtOH (0.5 mL×2), diethyl ether (2 mL) and hexane (2 mL) sequentially to provide the title compound 6d (0.63 g, 58%) as a white solid. m.p. 228° C. (dec). HPLC 96.4% ($R_t$=5.8 min., 55% MeOH in 0.1% TFA water 20 min.); $^1$H NMR (400 MHz, DMSO-$d_6$) δ 10.93 (s, 1H), 10.75 (s, 1H), 8.12 (d, J=7.0 Hz, 1H), 7.77-7.73 (m, 3H), 7.63-7.39 (m, 5H), 6.58 (d, J=6.7 Hz, 1H); $^{19}$F NMR (400 MHz, $d_6$-DMSO) δ 57.09; $^{13}$C NMR (100 MHz, DMSO-$d_6$) δ 167.40, 163.23, 152.77, 145.96, 143.26, 142.04, 130.77, 130.16, 129.31, 129.10, 128.65, 126.30, 122.51, 120.22, 118.10 (q, J=256 Hz), 99.76. LC-MS (ESI−) m/z 389.07 (M−H—HCl)$^-$; HRMS (ESI−) m/z calculated for $C_{18}H_{12}F_3N_4O_3$ (M−H—HCl)$^-$ 389.0867. found 389.0818.

$N^4$-(2-Methoxyphenyl)-$N^2$-(4-carboxyphenyl)pyrimidine-2,4-diamine hydrochloride (6e, method m in FIG. 5A)

A mixture of chloropyrimidine 5d (0.075 g, 0.317 mmol) and 4-aminobenzoic acid (0.046 g, 0.328 mmol) in EtOH (0.5 mL) was heated in a microwave reactor at 150° C. for 20 min. Ethanol (0.5 mL) was added to the reaction mixture. The resulting precipitate was isolated by filtration and washed with EtOH (0.5 mL) and hexane (5 mL) to provide the title compound 6e (0.8 g, 68%) as a white solid. m.p. 247.5-249.3° C. HPLC 99.6% ($R_t$=6.0 min., 50% MeOH in 0.1% TFA water 20 min.); $^1$H NMR (400 MHz, DMSO-$d_6$) δ 12.75 (s, 1H), 10.85 (s, 1H), 10.41 (s, 1H), 8.03 (d, J=7.1 Hz, 1H), 7.77 (d, J=8.6 Hz, 2H), 7.59-7.56 (m, 3H), 7.33 (t, J=7.9 Hz, 1H), 7.18 (d, J=8.3 Hz, 1H), 7.02 (t, J=7.5 Hz, 1H), 6.50 (apparent s, 1H), 3.80 (s, 3H); $^{13}$C NMR (100 MHz, DMSO-$d_6$) δ 167.42, 162.78, 153.64, 152.19, 144.09, 142.02, 130.81, 128.73, 127.42, 126.30, 125.47, 120.89, 120.17, 112.66, 99.85, 56.32; LC-MS (ESI−) m/z 335.11 (M-H—HCl)$^-$; HRMS (ESI−) m/z calculated for $C_{18}H_{15}N_4O_3$ (M−H—HCl)$^-$ 335.1150. found 335.1153.

$N^4$-(2-Methoxyphenyl)-$N^2$-(phenyl)pyrimidine-2,4-diamine (6f, method m in FIG. 5A)

A mixture of chloropyrimidine 5d (0.105 g, 0.444 mmol) and aniline (0.05 mL, 0.548 mmol) in EtOH (0.5 mL) was heated in a microwave reactor at 150° C. for 20 min. The solvent was removed under reduced pressure. Aqueous saturated NaHCO$_3$ (10 mL) was added to the residue and extracted with ethyl acetate (10 mL×2). The combined organic phase was dried (Na$_2$SO$_4$), filtered and concentrated to dryness. The residue was purified by flash chromatography (10 g silica gel, Hex/EtOAc) to afford the title compound 6f (0.100 g, 76%) as an off-white solid. m.p. 142.3-144.5° C. HPLC 99.4% ($R_t$=4.90 min, 60% MeOH in 0.1% TFA water 20 min.); $^1$H NMR (400 MHz, DMSO-$d_6$) δ 9.06 (s, 1H), 8.54 (s, 1H), 7.99 (d, J=8.0 Hz, 1H), 7.96 (d, J=5.7 Hz, 1H), 7.69 (d, J=7.6 Hz, 2H), 7.18-7.14 (m, 2H), 7.11-7.02 (m, 2H), 6.97-6.89 (m, 1H), 6.85 (t, J=7.3 Hz, 1H), 6.32 (d, J=5.8 Hz, 1H), 3.82 (s, 3H); $^{13}$C NMR (100 MHz, CDCl$_3$) 161.00, 160.08, 156.52, 149.55, 140.01, 128.97, 128.31, 123.69, 122.60, 121.50, 120.91, 120.33, 110.62, 98.24; LC-MS (ESI+) m/z 293.15 (M+H)$^+$; HRMS (ESI+) m/z calculated for $C_{17}H_{17}N_4O$ (M+H)$^+$ 293.1397. found 293.1393.

$N^4$-(2-Cyanophenyl)-$N^2$-(phenyl)pyrimidine-2,4-diamine (6g, method m in FIG. 5A)

A mixture of chloropyrimidine 5e (0.092 g, 0.398 mmol) and aniline (0.037 ml, 0.398 mmol) in EtOH (0.5 mL) was heated in a microwave reactor at 150° C. for 20 min. The solvent was removed under reduced pressure. The solid obtained was slurried in ethyl acetate (3 mL), filtered, and washed with ethyl acetate (5 mL), and hexane (5 mL). The dried solid was dissolved in methanol (3 mL). Diisopropylethylamine (1 ml) was added and the solvent was removed under reduced pressure. The solid obtained was slurried with water (5 ml), filtered, washed with water (10 ml×2), ether (5 ml), slurried with methanol (1 ml), filtered and dried under vacuum to provide the title compound 6g (0.027 g, 24%) as an off-white solid. m.p. 170.0.2-172.7° C. HPLC 100% [$R_t$=5.1 min., 50% MeOH, 50% water (with 0.1% TFA) 20 min.]; $^1$H NMR (400 MHz, DMSO-$d_6$) δ 9.52 (s, 1H), 9.15 (s, 1H), 8.07 (d, J=5.7 Hz, 1H), 7.82 (d, J=8.8 Hz, 1H), 7.77-7.66 (m, 2H), 7.59 (d, J=8.8 Hz, 2H), 7.32 (t, J=8.0 Hz, 1H), 7.11 (t, J=7.9 Hz, 2H), 6.83 (t, J=7.3 Hz, 1H), 6.28 (d, J=5.7 Hz, 1H); LC-MS (ESI+) m/z 288.13 (M+H)$^+$; HRMS (ESI+) m/z calculated for $C_{17}H_{14}N_5$ (M+H)$^+$ 288.1244. found 288.1241.

$N^4$-[2-(Trifluoromethyl)phenyl]-$N^2$-(4-carboxyphenyl)pyrimidine-2,4-diamine hydrochloride (6h, method m in FIG. 5A)

A mixture of chloropyrimidine 5f (0.055 g, 0.2 mmol) and 4-aminobenzoic acid (0.03 g, 0.218 mmol) in EtOH (0.3 mL) was heated in a microwave reactor at 150° C. for 20 min. Ethanol (0.5 mL) was added to the reaction mixture and sonicated at room temperature for 5 min. The resulting precipitate was isolated by filtration and washed with EtOH (0.5 mL×2), and hexane (3 mL×2) to afford the title compound 6h (0.067 g, 82%) as a white solid. m.p. 240.0-242.6° C. HPLC 99.6% ($R_t$=7.7 min., 50% MeOH in 0.1% TFA water 30 min.); $^1$H NMR (400 MHz, DMSO-$d_6$) δ 10.91 (s, 1H), 10.76 (s, 1H), 8.11 (d, J=7.0 Hz, 1H), 7.90-7.85 (m, 2H), 7.69-7.64 (m, 4H), 7.38 (d, J=8.5 Hz, 2H), 6.53 (d, J=6.7 Hz, 1H); $^{19}$F NMR (400 MHz, DMSO-$d_6$) δ 59.99 (s); $^{13}$C NMR (100 MHz, $d_6$-DMSO) δ 167.35, 164.21, 152.47, 145.71, 142.05, 135.37, 134.40, 131.77, 130.65, 129.09, 127. (q, J=4.6 Hz), 126.62 (q, J=29.5 Hz), 126.10, 124.03 (q, J=271.5 Hz), 119.77; LC-MS (ESI−) m/z 373.08 (M+H)$^+$;

LC-MS (ESI+) m/z 375.11 (M+H)$^+$; HRMS (ESI+) m/z calculated for $C_{18}H_{14}F_3N_4O_2$ (M+H)$^+$ 375.1063. found 375.1068.

$N^4$-(2-Bromophenyl)-$N^2$-(4-carboxyphenyl)pyrimidine-2,4-diamine hydrochloride (6i, method m in FIG. 5A)

A mixture of chloropyrimidine 5g (0.100 g, 0.350 mmol) and 4-aminobenzoic acid (0.048 g, 0.350 mmol) in EtOH (0.5 mL) was heated in a microwave reactor at 150° C. for 20 min. The resulting precipitate was isolated by filtration and washed with EtOH (0.5 mL×2) and dried under vacuum to provide the title compound 6i (0.069 g, 47%) as a white solid. m.p. 240° C. (dec.). HPLC 98% [$R_t$=7.40 min., 50% MeOH, 50% water (with 0.1% TFA) 20 min.]; $^1$H NMR (400 MHz, DMSO-d$_6$) δ 10.46 (s, 2H), 8.06 (d, J=6.8 Hz, 1H), 7.78 (d, J=8.3 Hz, 1H), 7.68 (d, J=8.5 Hz, 2H), 7.59 (d, J=8.3 Hz, 1H), 7.51-7.47 (m, 3H), 7.32 (t, J=8.3 Hz, 1H), 6.45 (s, 1H); $^{13}$C NMR (100 MHz, d$_6$-DMSO) 167.43, 163.07, 153.17, 146.60, 142.37, 136.36, 133.80, 130.71, 129.95, 129.71, 129.19, 125.91, 121.27, 119.83, 99.45; LC-MS (ESI+) m/z 385.02 (M-Cl)$^+$; HRMS (ESI+) m/z calculated for $C_{17}H_{14}BrN_4O_2$ (M-Cl)$^+$ 385.0295. found 385.0292.

$N^4$-(2-Chlorophenyl)-$N^2$-(4-methylcarboxyphenyl)pyrimidine-2,4-diamine hydrochloride (6j, method/ in FIG. 5A)

A mixture of chloropyrimidine 2l (0.120 g, 0.500 mmol) and 4-aminophenylacetic acid (0.076 g, 0.5 mmol) in EtOH (2 mL with 1 drop of 1 M hydrochloric acid) was heated in a microwave reactor at 160° C. for 15 min. A clear solution was obtained. Ethanol was removed from the mixture under vacuum, and the analysis of the crude NMR showed formation of 25% ethyl ester of 6j. The crude material was stirred in THF (0.5 mL) and NaOH solution (1 mL, 2 M) at r.t. for 16 h. The THF was evaporated from the mixture and HCl (1 M) was added to acidify the mixture (pH=1-2). The precipitate obtained was filtered, washed with water (5 mL) and dried under high vacuum to afford 6j (0.137 g, 70%) as a beige solid. m.p. 132° C. (dec). HPLC 97% ($R_t$=3.77 min., 50% MeOH in 0.1% TFA water 20 min.); $^1$H NMR (400 MHz, DMSO-d$_6$) δ 12.19 (s, 1H disappeared on D$_2$O shake), 9.30 (s, 1H disappeared on D$_2$O shake), 9.21 (s, 1H disappeared on D$_2$O shake), 8.01 (d, J=6.0 Hz, 1H), 7.79 (d, J=8.0 Hz, 1H), 7.54 (dd, J=8.0, 1.4 Hz, 1H partially overlapping), 7.51 (d, J=8.4 Hz, 2H partially overlapping with dd), 7.38 (apptd, J=8.0, 1.4 Hz, 1H), 7.24 (apptd, J=8.0, 1.4 Hz, 1H), 7.03 (d, J=8.4 Hz, 2H), 6.30 (d, J=6.0 Hz, 1H), 3.45 (s, 2H); $^{13}$C NMR (100 MHz, DMSO-d$_6$) δ 173.65, 162.04, 158.90, 155.15, 139.43, 136.41, 130.31, 129.87, 129.85, 128.56, 128.44, 128.10, 126.90, 119.66, 119.63, 98.71; LC-MS (ESI+) m/z 355.11 (M-Cl)$^+$; HRMS (ESI+) m/z calculated for $C_{18}H_{16}ClN_4O_2$ (M-Cl)$^+$ 355.0956. found 355.0971.

$N^4$-(2-Chloromethyl)phenyl]-$N^2$-(4-carboxy-3-hydroxyphenyl)pyrimidine-2,4-diamine hydrochloride (6k, methods n and o in FIG. 5A)

A mixture of chloropyrimidine 2l (0.100 g, 0.416 mmol) and methyl 5-aminosalicylate (0.070 g, 0.416 mmol) in THF (10 mL) was stirred at room temperature for 10 min. Two drops of concentrated HCl were added and the mixture heated at reflux for 14 hours. The solvent was removed under reduced pressure to provide a gray solid which was suspended in sodium bicarbonate (sat. aq. 50 mL), sonicated for 10 min, filtered, and washed with water (10 mL) to provide a white powder. The crude material was washed with methanol (2×10 ml) and finally with ethyl acetate (20 ml) to give methyl 4-(4-(2-chlorophenylamino)pyrimidin-2-ylamino)-2-hydroxybenzoate (6u) (0.081 g, 56%). $^1$H NMR (400 MHz, d$_6$-DMSO) δ 10.61 (s, 1H), 9.63 (s, 1H), 9.15 (s, 1H), 8.07 (s, 1H), 7.76 (s, 1H), 7.59-7.33 (3×broad s, 3H), 7.25-7.10 (2× broad s, 2H), 6.35 (s, 1H), 3.83 (s, 3H). LC-MS (ESI+) 371.09, m/z calculated for $C_{18}H_{16}ClN_4O_3$ (M+H)$^+$ 371.0905. found 371.0914. To a stirred solution of ester 6u (200 mg, 0.540 mmol) in THF (15 ml), was added sodium hydroxide (108 mg, 2.70 mmol) in water (1.5 ml). The reaction was heated under reflux for 14 hours. The solvent was removed under reduced pressure to provide a white solid which was then dissolved in water (20 ml) and acidified to pH~6-7 by addition of HCl (1 M). The colorless precipitate was filtered, washed with water and dried under vacuum. The crude solid was suspended in methanol (20 ml), sonicated for 10 min., filtered, washed with methanol (5 ml) and dried under vacuum to provide the title compound 6k (118 mg, 62%) as an off-white powder. m.p. 202-204° C. HPLC 100% [$R_t$=8.3 min, 45% MeOH, 65% water (with 0.1% TFA) 20 min.]; $^1$H NMR (400 MHz, DMSO-d$_6$) δ 13.55 (brs, 1H), 11.29 (brs, 1H), 10.14 (brs, 1H), 9.93 (s, 1H), 8.07 (d, J=6.7 Hz, 1H), 7.70 (d, J=7.8 Hz, 1H), 7.57 (d, J=7.6 Hz, 1H), 7.53 (d, J=8.5 Hz, 1H), 7.41 (t, J=7.8 Hz, 1H), 7.30 (t, J=8.0 Hz, 1H), 7.25 (s, 1H), 7.02 (d, J=8.5 Hz, 1H), 6.43 (d, J=5.7 Hz, 1H); $^{13}$C NMR (100 MHz, d$_6$-DMSO), δ 172.34, 162.82, 162.58, 155.69, 146.06, 135.35, 131.18, 130.58, 129.32, 128.64, 128.53, 128.25, 111.11, 107.27, 106.54, 99.78; LC-MS (ESI+) m/z 357.08 (M-Cl)$^+$; HRMS (ESI+) m/z calculated for $C_{17}H_{14}ClN_4O_3$ (M-Cl)$^+$ 357.0749. found 357.0751.

$N^4$-(2-Fluorophenyl)-$N^2$-4-phenylpyrimidine-2,4-diamine (6l, method m in FIG. 5A)

A mixture of chloropyrimidine 5a (0.073 g, 0.325 mmol) and aniline (0.04 mL, 0.438 mmol) in EtOH (0.5 mL) was heated in a microwave reactor at 150° C. for 20 min. The solvent was removed under reduced pressure. Aqueous saturated NaHCO$_3$ (10 mL) was added to the residue and extracted with ethyl acetate (10 mL×2). The combined organic phase was dried (Na$_2$SO$_4$), filtered and concentrated to dryness. The residue was purified by flash chromatography (10 g silica gel, hex/EtOAc) to afford the title compound 6l (0.050 g, 55%) as an off-white solid. m.p. 133.2-134.6° C. HPLC 99.5% ($R_t$=4.4 min, 60% MeOH in 0.1% TFA water 20 min.); $^1$H NMR (400 MHz, DMSO-d$_6$) δ 9.11 (s, 1H), 9.07 (s, 1H), 8.02 (d, J=5.7 Hz, 1H), 7.97 (t, J=7.9 Hz, 1H), 7.65 (d, J=8.6 Hz, 2H), 7.32-7.23 (m, 1H), 7.22-7.07 (m, 4H), 6.86 (t, J=7.3 Hz, 1H), 6.30 (d, J=5.7 Hz, 1H); LC-MS (ESI+) m/z 281.11 (M-Cl)$^+$; HRMS (ESI+) m/z calculated for $C_{16}H_{14}FN_4$ (M-Cl)$^+$ 281.1197. found 281.1209.

$N^4$-(2-Iodophenyl)-$N^2$-(4-carboxyphenyl)pyrimidine-2,4-diamine hydrochloride (6m, method m in FIG. 5A)

A mixture of chloropyrimidine 5h (0.119 g, 0.358 mmol) and 4-aminobenzoic acid (0.048 g, 0.350 mmol) in EtOH (0.5 mL) was heated in a microwave reactor at 150° C. for 20 min. The solvent was then removed under reduced pressure to provide an off-white solid. The solid was slurried in methanol (2 mL), filtered, washed with methanol (2 mL), and dried under vacuum to provide the title compound 6m (0.053 g, 32%) as a white solid. m.p. 253° C. (dec). HPLC 99.7% [$R_t$=7.80 min., 50% MeOH, 50% water (with 0.1% TFA) 20 min.]; $^1$H NMR (400 MHz, DMSO-$d_6$) δ 12.76 (bs, 1H), 10.72 (s, 1H), 10.62 (s, 1H), 8.07 (d, J=7.0 Hz, 1H), 8.01 (dd, J=1.2, 7.9 Hz, 1H), 7.67 (d, J=8.5 Hz, 2H), 7.54-7.45 (m, 4H), 7.19-7.15 (m, 1H), 6.44 (s, 1H); $^{13}$C NMR (100 MHz, DMSO-$d_6$) δ 167.36, 163.09, 152.32, 145.44, 142.04, 139.99, 139.67, 130.68, 130.04, 129.94, 129.45, 126.12, 119.90, 99.24; LC-MS (ESI+) m/z 433.02 (M-Cl)$^+$; HRMS (ESI+) m/z calculated for $C_{17}H_{14}IN_4O_2$ (M-Cl)$^+$ 433.0156. found 433.0150.

$N^4$-(2-Cyanophenyl)-$N^2$-(4-carboxyphenyl)pyrimidine-2,4-diamine hydrochloride (6n, method m in FIG. 5A)

A mixture of chloropyrimidine 5e (0.094 g, 0.406 mmol) and 4-aminobenzoic acid (0.037 mg, 0.408 mmol) in EtOH (0.5 mL) was heated with in a microwave reactor at 150° C. for 20 min. The solvent was removed under reduced pressure. The compound was purified by reverse phase C-18 preparative HPLC [Eclipse XDB-C18 PrepHT 21.2×250 mm, 7 μm; 40% MeOH, 60% water (with 0.1% TFA) 20 min, 20 mL/min.] to provide the title compound as its TFA salt. The solid obtained was suspended in methanol (9 mL) followed by the addition of HCl (4 M in dioxane, 1 mL). The solvent was then removed in a Genevac evaporator. The dried solid was slurried with acetonitrile (1 mL), filtered, washed with acetonitrile (1 mL) and dried under vacuum to provide the title compound 6n (0.022 g, 15%) as an off-white solid. m.p. 222° C. (dec). HPLC 97.6% [$R_t$=5.5 min., 40% MeOH, 60% water (with 0.1% TFA) 20 min.]; $^1$H NMR (400 MHz, DMSO-$d_6$) δ 10.67 (s, 1H), 10.43 (s, 1H), 8.14 (d, J=6.8 Hz, 1H,), 7.93 (d, J=7.6 Hz, 1H), 7.80 (t, J=7.6 Hz, 1H), 7.72-7.68 (m, 3H), 7.55 (d, J=7.3 Hz, 2H), 7.50 (t, J=7.6 Hz, 1H), 6.50 (d, J=6.8 Hz, 1H), LC-MS (ESI+) m/z 332.11 (M-Cl)$^+$; HRMS (ESI+) m/z calculated for $C_{18}H_{14}N_5O_2$ (M-Cl)$^+$ 332.1142. found 332.1139.

$N^4$-(2-Chlorophenyl)-$N^2$-(3-carboxyphenyl)pyrimidine-2,4-diamine hydrochloride (6o, method m in FIG. 5A)

A mixture of 2l (0.100 g, 0.417 mmol) and 3-aminobenzoic acid (0.057 g, 0.417 mmol) in EtOH (0.5 mL) was heated in a microwave reactor at 150° C. for 20 min. The precipitate obtained upon cooling the reaction mixture was filtered and washed quickly with ethanol (3 ml) to obtain the 6o (0.097 g, 62%) as a white solid. m.p. 290-296° C. (dec). HPLC 100% ($R_t$=7.58 min., 50% MeOH in 0.1% TFA water, 20 min.); $^1$H NMR (400 MHz, DMSO-$d_6$) δ 13.03 (s, 1H), 10.49 (brs, 1H), 8.04 (d, J=6.4 Hz, 1H), 7.88 (brs, 1H), 7.73 (appd, J=7.6 Hz, 1H), 7.65 (d, J=8.0 Hz, 1H), 7.60 (d, J=7.6 Hz, 1H), 7.57 (dd, J=7.9, 1.5 Hz, 1H), 7.37 (td, J=7.6, 0.8 Hz, 1H), 7.32-7.27 (m, 2H), 6.49 (s, 1H); $^{13}$C NMR (101 MHz, DMSO) δ 167.5, 162.95, 153.3, 145.9, 138.08, 134.6, 132.1, 130.5, 129.6, 129.5, 129.1, 128.89, 128.36, 125.9, 125.5, 122.6, 99.5; elemental analysis calculated for $C_{17}H_{14}Cl_2N_4O_2$: C, 54.13; H, 3.74; N, 14.85. Found: C, 53.78; H, 3.64; N, 14.66.

$N^4$-(2-Chlorophenyl)-$N^2$-(4-carbamoyl)pyrimidine-2,4-diamine hydrochloride (6p, method 1 in FIG. 5A)

A mixture of chloropyrimidine 2l (0.100 g, 0.417 mmol) and 4-aminobenzamide (0.057 g, 0.417 mmol) in EtOH (2.0 mL with 1 drop of 1 M hydrochloric acid) was heated with a microwave reactor at 160° C. for 15 min. The mixture was filtered and the solid obtained was washed with MeOH (1 mL) and dried to afford the desired compound 6p (0.110 g, 70%) as a white solid. m.p. 227° C. (dec.). HPLC 99% ($R_t$=3.70 min., 50% MeOH in 0.1% TFA water 20 min.); $^1$H NMR (400 MHz, DMSO-$d_6$) δ 10.75 (brs, 2H disappeared on D$_2$O shake), 8.09 (dd, J=6.1, 3.5 Hz, 1H), 7.91 (brs, 1H disappeared on D$_2$O shake), 7.71-7.64 (m, 4H), 7.50-7.42 (m, 4H), 7.30 (brs, 1H disappeared on D$_2$O shake), 6.52 (brs, 1H); $^{13}$C NMR (100 MHz, DMSO-$d_6$) δ 167.76, 163.15, 152.33, 144.97, 140.39, 134.55, 130.62, 130.29, 130.02, 129.54, 129.49, 128.90, 128.55, 119.98, 99.43; LC-MS (ESI+) m/z 340.10 (M-Cl)$^+$; HRMS (ESI+) m/z calculated for $C_{17}H_{15}ClN_5O$ (M-Cl)$^+$ 340.0960. found 340.0971.

$N^4$-(2-Biphenyl)-$N^2$-(4-carboxyphenyl)pyrimidine-2,4-diamine hydrochloride (6q, method m in FIG. 5A)

A mixture of chloropyrimidine 5i (0.096 g, 0.34 mmol) and 4-aminobenzoic acid (0.054 g, 0.393 mmol) in EtOH (0.4 mL) was heated in a microwave reactor at 150° C. for 20 min. The resulting precipitate was filtered and washed with EtOH (0.5 mL×3) to provide the title compound 6q (0.098 g, 67%), as a white solid. m.p. 259° C. (dec). HPLC 100% ($R_t$=8.7 min., 55% MeOH in 0.1% TFA water 20 min.); $^1$H NMR (400 MHz, DMSO-$d_6$) δ 12.83 (s, 1H), 10.96 (s, 1H), 10.71 (s, 1H), 7.96 (d, J=7.2 Hz, 1H), 7.73 (d, J=8.3 Hz, 2H), 7.61-7.42 (m, 6H), 7.42-7.17 (m, 5H), 6.31 (apparent s, 1H); $^{13}$C NMR (100 MHz, DMSO-$d_6$) δ 167.41, 163.26, 152.00, 144.30, 142.07, 138.96, 134.37, 131.35, 130.75, 129.35, 129.09, 128.74, 128.17, 126.18, 119.89, 99.22; LC-MS (ESI−) m/z 381.13 (M−H—HCl)$^-$; HRMS (ESI−) m/z calculated for $C_{23}H_{17}N_4O_2$ (M−H—HCl)$^-$ 381.1357. found 381.11366.

$N^4$-(2-Chlorophenyl)-$N^2$-(4-carboxyphenyl)-$N^4$-methylpyrimidine-2,4-diamine hydrochloride (6r, method m in FIG. 5A)

This was obtained as a white solid (0.127 g, 0.36 mmol, 80%) from 5j (0.115 g, 0.452 mmol) and 4-aminobenzoic acid (0.062 g, 0.452 mmol) in the same manner as described for 6s. m.p. 288° C. (dec.). HPLC 98% [$R_t$=8.39 min., 50% MeOH, 50% water (with 0.1% TFA) 20 min.]. $^1$H NMR (400 MHz, CD$_3$OD) δ 8.17-8.04 (m, 2.57H), 7.77-7.74 (m, 3H), 7.70-7.67 (m, 2H), 7.58-7.54 (m, 4H), 7.49-7.41 (m, 0.42H), 7.17 (d, J=8.8 Hz, 1H, major), 6.83 (d, J=7.5 Hz, 0.41H, minor), 5.80 (d, J=7.4 Hz, 1H, major), 3.55 (s, 4H); LC-MS (ESI+) m/z 355.10 (M-Cl)$^+$; HRMS (ESI+) m/z calculated for $C_{18}H_{16}ClN_4O_2$ (M-Cl)$^+$ 355.0956. found 355.0962; Elemental Analysis: Found C, 54.98%; H, 4.12; N, 14.18. $C_{18}H_{16}Cl_2N_4O_2$ requires C, 55.26%; H, 4.12; N, 14.32.

$N^4$-(2-Chlorophenyl)-$N^2$-(4-carboxyphenyl)-$N^4$-ethylpyrimidine-2,4-diamine hydrochloride (6s, method m in FIG. 5A)

A solution of 5k (0.151 g, 0.673 mmol) and 4-aminobenzoic acid (0.092 g, 0.674 mmol) in anhydrous ethanol (0.673 mL) was heated in a microwave reactor at 150° C. for 20 min. The resulting precipitate was isolated by filtration and washed with EtOH (1 mL×2) and dried under vacuum to provide the title compound 6s (0.172 g, 71%), as a white solid. m.p. 284° C. (dec). HPLC 100% [$R_t$=13.96 min., 50%

MeOH, 50% water (with 0.1% TFA) 20 min.]. Two rotamers are present: $^1$H NMR (400 MHz, CD$_3$OD) δ 8.11 (d, J=8.8 Hz, 2H, major), 8.07 (d, J=7.6 Hz, 0.4H, minor), 7.75-7.66 (m, 5H), 7.63-7.54 (m, 5H), 7.15 (d, J=8.8 Hz, 1H, major), 6.87 (d, J=7.5 Hz, 0.5H, minor), 5.74 (d, J=7.4 Hz, 1H, major), 4.30-4.21 (m, 1H), 4.09-4.02 (m, 0.6H, minor), 3.93-3.83 (m, 2H), 1.35 (t, J=7.2 Hz, 1.5H, minor), 1.29 (t, J=7.2 Hz, 3H, major); LC-MS (ESI+) m/z 369.12 (M-Cl)$^+$; HRMS (ESI+) m/z calculated for C$_{19}$H$_{18}$ClN$_4$O$_2$ (M-Cl)$^+$ 369.1113. found 369.1123; Elemental Analysis: Found C, 56.30%; H, 4.45; N, 13.76. C$_{19}$H$_{18}$Cl$_2$N$_4$O$_2$ requires C, 56.31%; H, 4.48; N, 13.82.

N$^4$-(2-Chlorophenyl)-N$^2$-(3-carboxyphenyl)-5-fluoropyrimidine-2,4-diamine hydrochloride (6t, method m in FIG. 5A)

A mixture of 2k (0.100 g, 0.350 mmol) and 3-aminobenzoic acid (0.048 g, 0.350 mmol) in EtOH (0.5 mL) was heated in a microwave reactor at 150° C. for 20 min. The reaction mixture was cooled and the precipitate obtained was filtered and washed quickly with ethanol (3 ml) to provide 6t (0.080 g, 57%) as a white solid. m.p. 257° C. (dec.). HPLC 98% (R$_t$=9.45 min., 50% MeOH in 0.1% TFA water, 20 min.); $^1$H NMR (400 MHz, DMSO-d$_6$) δ 12.74 (brs, 1H), 9.32 (s, 1H), 9.18 (s, 1H), 8.12 (d, J=3.5 Hz, 1H), 8.02 (s, 1H), 7.80 (d, J=8.2 Hz, 1H), 7.61 (d, J=7.8 Hz, 1H), 7.56 (d, J=7.9 Hz, 1H), 7.40-7.36 (m, 2H), 7.29 (t, J=7.6 Hz, 1H), 7.11 (t, J=7.9 Hz, 1H); $^{13}$C NMR (100 MHz, DMSO-d$_6$) δ 168.14, 156.0 (d, J=2.9 Hz), 151.37 (d, J=11.5 Hz), 141.75, 141.43 (d, J=246.44 Hz), 141.39 (d, J=18.4 Hz), 135.92, 131.54, 130.88, 130.38, 129.55, 128.90, 128.32, 128.03, 122.84, 122.18, 119.87; $^{19}$F NMR (376 MHz, DMSO) δ -165.76; LC-MS (ESI-) m/z 357.06 (M-H-HCl)$^-$; HRMS (ESI-) m/z calculated for C$_{17}$H$_{12}$ClFN$_4$O$_2$ (M-H-HCl)$^-$ 357.0560. found 357.0554.

Figure 7A:
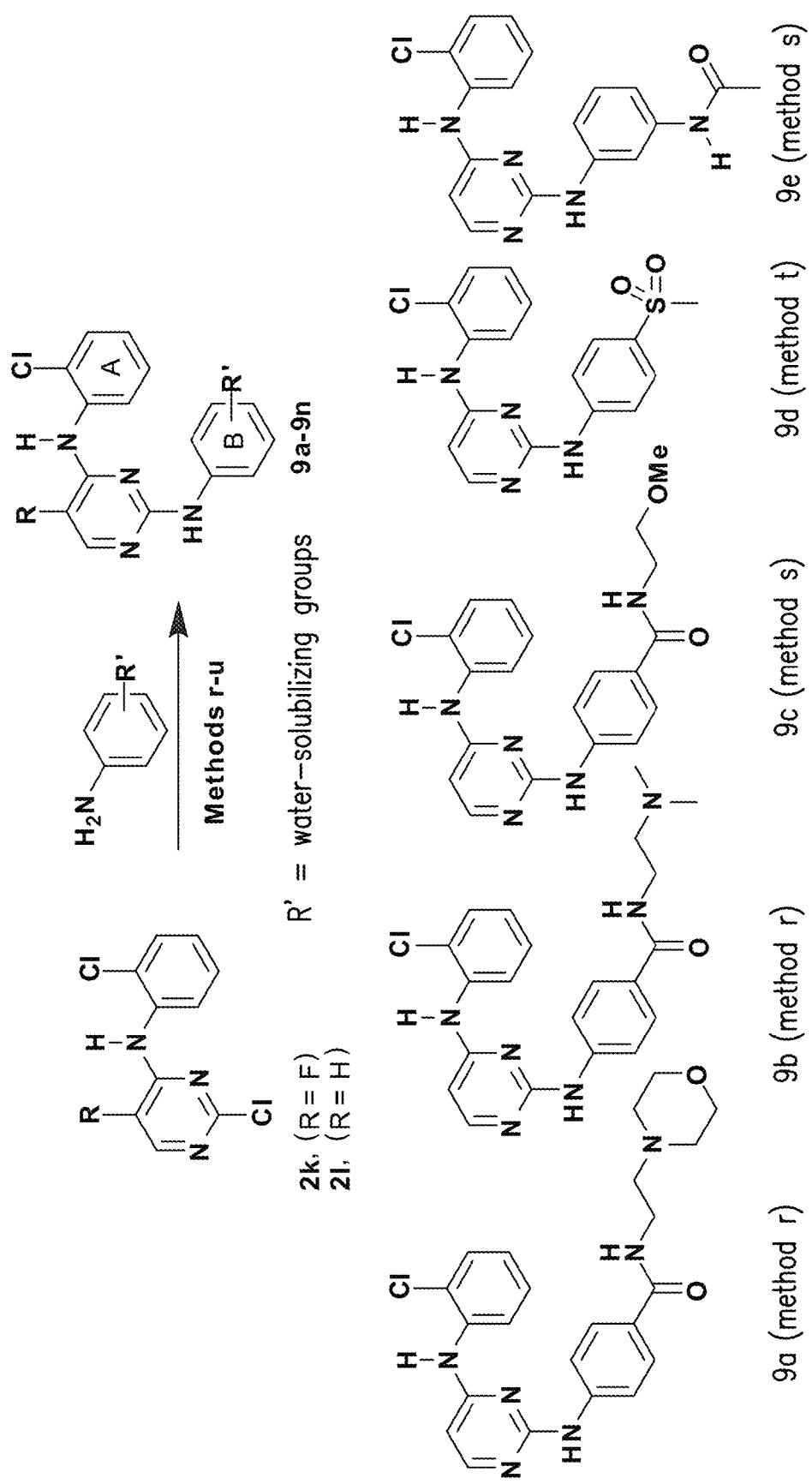
FIG. 7A is a synthetic route to bisanilinopyrimidines with water-solubilizing groups in the B-ring. Various derivatives are also shown in FIG. 7B. Reagents and conditions; method r: Conc. HCl, iso-PrOH, 170° C., microwave, 20 min., methods: EtOH, 150° C., microwave, 20 min., method t: EtOH, cat. HCl, 180° C. or 160° C. or 140° C. microwave, 15 min., method u: X-Phos (10 mmol %), bis(dibenzylideneacetone) palladium(0) (10 mmol %), K$_2$CO$_3$, tert-BuOH, reflux, 18 h., method v: MeOH, 100° C., seal tube, 6 h.
Figure 7B:
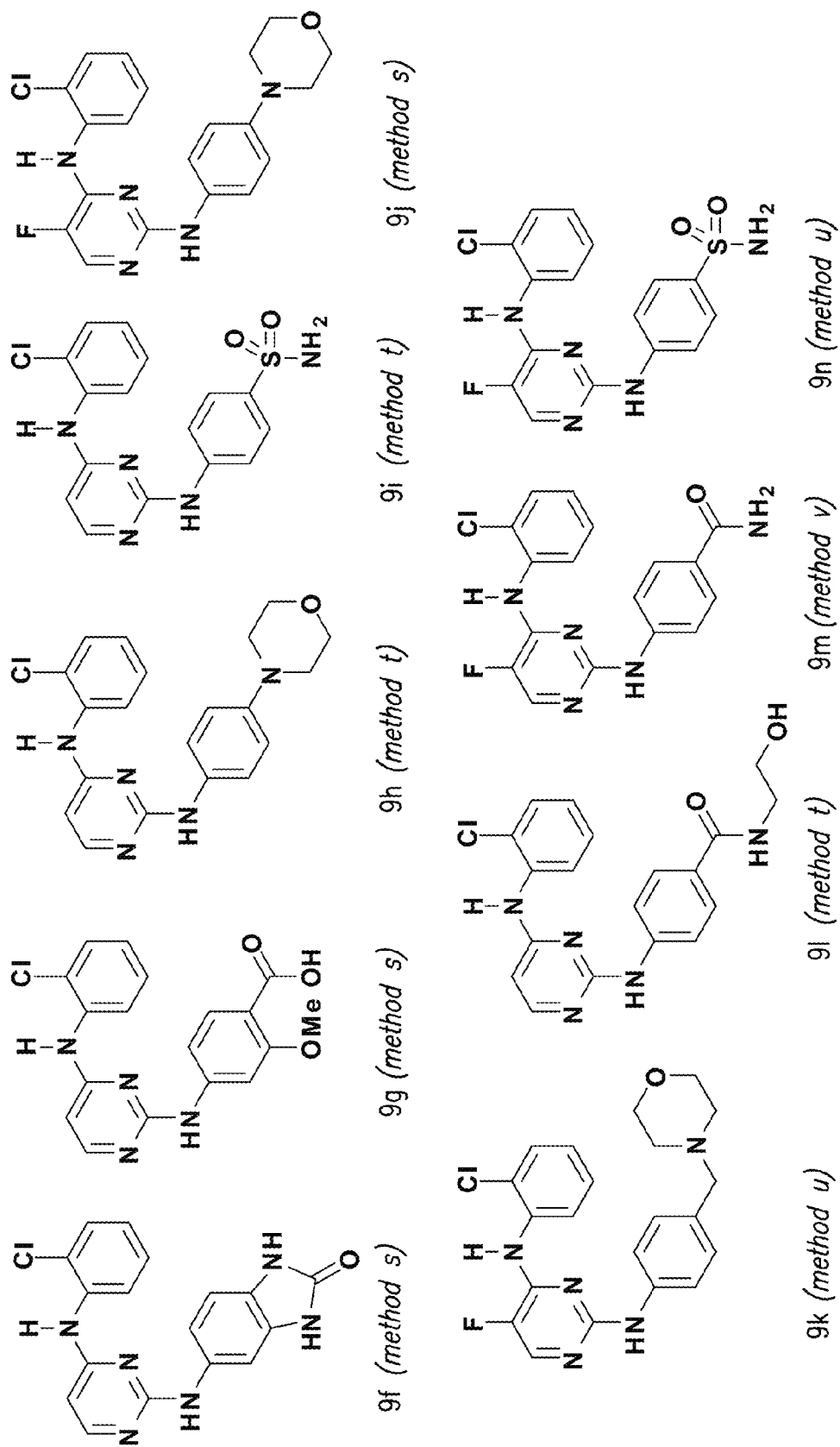

N$^4$-(2-Chlorophenyl)-N$^2$-[4-N-(2-morpholinoethyl)carbamoylphenyl]-pyrimidine-2,4-diamine dihydrochloride (9a, method r in FIG. 7A)

A solution of 2l (0.100 g, 0.42 mmol) and 8a (0.105 g, 0.42 mmol) in isopropyl alcohol (8 mL) and concentrated HCl (0.315 mL) was heated in a microwave reactor at 170° C. for 20 min. The solvent was removed under reduced pressure. The resulting solid was dissolved in methanol (2 mL) followed by the addition of diethyl ether (10 mL). The precipitate was filtered and dried under vacuum to afford the title compound 9a (0.054 g, 29%) as white crystals. m.p. 173.0-174.6° C. HPLC 99.0% [R$_t$=5.53 min., 50% MeOH, 40% water (with 0.1% TFA) 20 min.]; $^1$H NMR (400 MHz, DMSO-d$_6$) δ 11.37-10.62 (m, 1H), 8.88 (s, 1H), 8.59-8.43 (m, 1H), 8.12 (s, 1H), 7.78 (s, 2H), 7.69-7.61 (m, 2H), 7.50 (s, 2H), 7.43 (s, 1H), 6.76-6.41 (m, 2H), 4.03-2.95 (m, 12H); $^{13}$C NMR (100 MHz, DMSO-d$_6$) δ 166.39, 163.08, 152.86, 145.97, 140.91, 134.67, 130.67, 130.15, 129.42, 129.24, 128.82, 128.60, 119.81, 99.46, 63.80, 56.32, 51.87, 34.28. LC-MS (ESI+) m/z 453.17 (M-HCl-Cl)$^+$; HRMS (ESI+) m/z calculated for C$_{23}$H$_{25}$ClN$_6$O$_2$ (M-HCl-Cl)$^+$ 453.1800. found 453.1797.

N$^4$-(2-Chlorophenyl)-N$^2$-[4-N-(2-dimethylaminoethyl)carbamoylphenyl]-pyrimidine-2,4-diamine dihydro-chloride (9b, method r in FIG. 7A)

This was obtained as a white solid (0.02 g, 0.04 mmol, 8%) from 2l (0.100 g, 0.48 mmol) and 8b (0.116 g, 0.48 mmol) in a similar manner as described for 9a. m.p. 143.1-145.8° C. HPLC 98% [R$_t$=5.10 min., 60% MeOH, 40% water (with 0.1% TFA) 20 min.]; $^1$H NMR (400 MHz, DMSO-d$_6$) 10.65 (s, 1H), 9.96 (s, 1H), 8.75 (s, 1H), 8.09 (s, 1H), 7.73 (s, 2H), 7.71-7.61 (m, 2H), 7.58-7.45 (m, 3H), 7.45-7.35 (m, 1H), 6.50 (s, 1H), 3.62-3.55 (m, 2H), 3.23 (d, J=5.7 Hz, 2H), 2.80 (d, J=4.0 Hz, 6H); $^{13}$C NMR (100 MHz, DMSO-d$_6$) δ 166.50, 163.10, 152.72, 145.80, 140.87, 134.73, 130.67, 130.19, 129.45, 129.31, 128.61, 119.80, 99.50, 56.76, 43.01, 35.16; LC-MS (ESI+) m/z 411.18 (M-HCl-Cl)$^+$; HRMS (ESI+) m/z calculated for C$_{21}$H$_{24}$ClN$_6$O (M-HCl-Cl)$^+$ 411.1695. found 411.1693.

N$^4$-(2-Chlorophenyl)-N$^2$-[4-N-(2-methoxyethyl)carbamoylphenyl]-pyrimidine-2,4-diamine hydrochloride (9c, method s in FIG. 7A)

This was obtained as a white solid (0.047 g, 0.12 mmol) from 2l (0.092 g, 0.47 mmol) and 8c (0.060 g, 0.47 mmol) in a similar manner as described for compound 6s m.p. 210.4-213.0° C. HPLC 97% [R$_t$=5.61 min., 50% MeOH, 50% water (with 0.1% TFA) 20 min.]; $^1$H NMR (400 MHz, DMSO-d$_6$) δ 10.71 (s, 2H), 8.44 (t, J=5.6 Hz, 1H), 8.08 (d, J=7.3 Hz, 1H), 7.68-7.62 (m, 4H), 7.49-7.38 (m, 3H), 6.52 (s, 1H), 3.41-3.37 (m, 4H), 3.24 (s, 3H); $^{13}$C NMR (100 MHz, DMSO-d$_6$) δ 166.06, 163.12, 152.41, 145.17, 140.32, 134.55, 130.60, 130.23, 130.08, 129.50, 129.42, 128.56, 119.98, 99.48, 71.50, 58.58, 58.55 LC-MS (ESI+) m/z 398.14 (M-Cl)$^+$. HRMS (ESI+) m/z calculated for C$_{20}$H$_{21}$ClN$_5$O$_2$ (M-Cl)$^+$ 398.1378. found 398.1370.

N$^4$-(2-Chlorophenyl)-N$^2$-[4-(methylsulfonyl)phenyl]pyrimidine-2,4-diamine (9d, method t in FIG. 7A)

A solution of 2l (0.098 g, 0.41 mmol) and 4-(methylsulfonyl)aniline (0.070 g, 0.41 mmol) in ethanol (1 mL) and 1M HCl (aq., 1.0 mL) was heated in a microwave reactor at 180° C. for 15 min. The solvent was removed under reduced pressure. The solid obtained was slurried in a saturated solution of sodium bicarbonate filtered, slurried with methanol (1 mL), then filtered to yield the title compound 9d (0.077 g, 44%) as a white solid. m.p. 169.3-171.3° C. HPLC 99% [R$_t$=4.15 min., 50% MeOH, 50% water (with 0.1% TFA) 20 min.]; $^1$H NMR (400 MHz, DMSO-d$_6$) δ 9.72 (s, 1H), 9.17 (s, 1H), 8.08 (d, J=5.7 Hz, 1H), 7.84 (d, J=8.7 Hz, 2H), 7.74 (d, J=7.8, 1H), 7.65-7.51 (m, 3H), 7.41 (t, J=7.6, 1H), 7.26 (t, J=7.6 Hz, 1H), 6.35 (d, J=5.7 Hz, 1H), 3.09 (s, 3H); $^{13}$C NMR (100 MHz, DMSO-d$_6$) δ 162.03, 159.47, 156.92, 146.25, 136.52, 132.20, 130.40, 129.03, 128.38, 128.34, 128.21, 127.12, 118.38, 99.77, 44.70; LC-MS (ESI+) m/z 375.06 (M+H)$^+$; HRMS (ESI+) m/z calculated for C$_{17}$H$_{16}$ClN$_4$O$_2$S (M+H)$^+$ 375.0677. found 375.0670.

N$^4$-(2-Chlorophenyl)-N$^2$-(3-acetamidophenyl)pyrimidine-2,4-diamine hydrochloride (9e, method s in FIG. 7A)

This compound was prepared from 2l (0.105 g, 0.44 mmol) and N-(3-aminophenyl)acetamide (0.066 g, 0.44 mmol) in a similar manner as described for 6s. The solvent was then removed under reduced pressure. The resulting solid was dissolved in methanol (2 ml), followed by the addition of ethyl acetate (10 ml). A precipitate formed and the mixture was sonicated for 30 min at room temperature. The precipitate was filtered and washed with ethyl acetate (10 mL) and hexane (20 mL), affording the pure product 9e (0.166 g, 95%), as an off-white solid. m.p. 150° C. (dec.).

HPLC 100% [$R_t$=5.30 min., 50% MeOH, 50% water (with 0.1% TFA) 20 min.]; $^1$H NMR (400 MHz, DMSO-$d_6$) δ 10.63 (s, 1H), 10.45 (s, 1H), 10.00 (s, 1H), 8.00 (d, J=5.0 Hz, 1H), 7.70-7.52 (m, 3H), 7.4-7.28 (m, 2H), 7.24-7.13 (m, 2H), 7.13-7.07 (m, 1H), 2.02 (s, 3H); LC-MS (ESI+) m/z 354.11 (M-Cl)$^+$; HRMS (ESI+) m/z calculated for $C_{18}H_{17}ClN_5O$ (M-Cl)$^+$ 354.1116. found 354.1119.

$N^4$-(2-Chlorophenyl)-$N^2$-[6-(1H-benzo[d]imidazol-2(3H)-one)]pyrimidine-2,4-diamine hydrochloride (9f, method s in FIG. 7A)

A solution of 2l (0.105g, 0.437 mmol) and 5-amino-1H-benzo[d]imidazol-2(3H)-one (0.065 g, 0.437 mmol) and ethanol (0.437 mL) was heated in a microwave reactor at 150° C. for 40 min. The resulting precipitate was filtered, dried under vacuum and suspended in ethanol. The suspension was sonicated for thirty minutes, filtered and dried under vacuum to provide the title compound 9f (0.112 g, 66%) as an off-white solid. m.p. 263° C. (dec). HPLC 98% [$R_t$=3.21 min., 50% MeOH, 50% water (with 0.1% TFA) 20 min.]; $^1$H NMR (400 MHz, CD$_3$OD) δ 7.74 (s, 2H), 7.65-7.63 (m, 1H), 7.54-7.52 (m, 1H), 7.35-7.28 (m, 2H), 7.04 (d, J=7.4 Hz, 3H), 6.42 (s, 1H); LC-MS (ESI+) m/z 353.10 (M-Cl)$^+$; HRMS (ESI+) m/z calculated for $C_{17}H_{14}ClN_6O$ (M-Cl)$^+$ 353.0912. found 353.0913.

$N^4$-(2-Chlorophenyl)-$N^2$-(4-carboxyl-3-methoxyphenyl)pyrimidine-2,4-diamine hydrochloride (9g, method s in FIG. 7A)

A mixture of chloropyrimidine 2l (0.100 g, 0.416 mmol) and 4-amino-2-methoxybenzoic acid (0.070 g, 0.418 mmol) in EtOH (0.5 mL) was heated with a microwave reactor at 150° C. for 20 min. The solvent was evaporated from the resulting thick mass under reduced pressure. The residue was suspended in ethyl acetate (8 mL) and sonicated for 10 min. The mixture was filtered and the solid was washed with ethyl acetate (8 mL) and ethyl acetate:methanol (1:1, 1 mL) to provide the title compound 9g (0.068 g, 57%) as a gray solid. m.p. 160-162° C. HPLC 95% [$R_t$=4.5 min, 50% MeOH, 50% water (with 0.1% TFA) 20 min.]; $^1$H NMR (400 MHz, DMSO-$d_6$), δ 12.69 (s, 1H), 10.42 (s, 1H), 10.24 (s, 1H), 7.95 (d, J=6.2 Hz, 1H), 7.64-7.51 (m, 3H), 7.48 (d, J=8.4 Hz, 1H), 7.36 (t, J=7.7 Hz, 1H), 7.29 (t, J=7.4 Hz, 1H), 6.98 (d, J=8.8 Hz, 1H), 6.45 (s, 1H), 3.76 (s, 3H); $^{13}$C NMR (100 MHz, DMSO-$d_6$), δ 167.37, 162.97, 155.67, 152.95, 144.61, 134.39, 130.51, 129.61, 129.00, 128.35, 127.11, 124.90, 122.22, 113.36, 99.26, 56.70; LC-MS (ESI+) m/z 371.09 (M-Cl)$^+$; HRMS (ESI+) m/z calculated for $C_{18}H_{16}ClN_4O_3$ (M-Cl)$^+$ 371.0905. found 371.0909.

$N^4$-(2-Chlorophenyl)-$N^2$-[4-(N-morpholino)phenyl]pyrimidine-2,4-diamine hydrochloride (9h, method t in FIG. 7A)

A mixture of chloropyrimidine 2l (0.120 g, 0.500 mmol) and 4-morpholinoaniline (0.089 g, 0.500 mmol) in EtOH (2 mL with 1 drop of 1 M of hydrochloric acid) was heated in a microwave reactor at 160° C. for 15 min. The reaction mixture was cooled to r.t. and the product precipitated. The mixture was filtered, and the product obtained was quickly washed with MeOH (1 mL), DCM (1 mL) and dried to afford 9h (0.14 g, 67%) as a green solid. m.p. 136-138° C. HPLC 99% ($R_t$=7.43 min., 50% MeOH in 0.1% TFA water 20 min.); $^1$H NMR (400 MHz, DMSO-$d_6$) δ 12.11 (s, 1H disappeared on D$_2$O shake), 10.63 (s, 1H disappeared on D$_2$O shake), 10.37 (s, 1H disappeared on D$_2$O shake), 7.94 (brs, 1H), 7.65-0.60 (m, 2H), 7.43 (appt, J=7.6 Hz, 1H), 7.36 (appt, J=7.6 Hz, 1H), 7.22 (d, J=8.1 Hz, 2H), 6.84 (brs, 2H), 6.45 (brs, 1H), 3.73 (appt, J=4.4 Hz, 4H), 3.05 (brt, 4H); $^{13}$C NMR (100 MHz, DMSO-$d_6$) δ 163.03, 152.56, 148.63, 144.36, 134.58, 130.53, 129.99, 129.37, 129.12, 128.43, 122.90, 116.05, 98.78, 66.65, 49.38; LC-MS (ESI+) m/z 382.15 (M-Cl)$^+$; HRMS (ESI+) m/z calculated for $C_{20}H_{21}ClN_5O$ (M-Cl)$^+$ 382.1429. found 382.1434.

$N^4$-(2-Chlorophenyl)-$N^2$-[4-(aminosulfonyl)phenyl]pyrimidine-2,4-diamine hydrochloride (9i, method t in FIG. 7A)

A mixture of chloropyrimidine 2l (0.120 g, 0.500 mmol) and 4-aminobenzenesulfonamide (0.086 g, 0.500 mmol) in EtOH (2 mL with 1 drop of 1 M HCl) was heated in a microwave reactor at 160° C. for 15 min. The precipitate formed upon cooling filtered and washed with MeOH (2 mL), then slurried and sonicated in DCM (5 mL) and filtered. The product obtained was dried to afford 9i (0.155 g, 75%) as a white solid. m.p. 215° C. (dec.). HPLC 96% ($R_t$=3.23 min., 50% MeOH in 0.1% TFA water 20 min.); $^1$H NMR (400 MHz, DMSO-$d_6$) δ 10.81 (s, 1H), 10.67 (s, 1H), 8.10 (d, J=6.9 Hz, 1H), 7.67-7.63 (m, 2H), 7.61-7.56 (m, 4H), 7.47 (td, J=7.7, 1.6 Hz, 1H), 7.41 (td, J=7.7, 1.6 Hz, 1H), 7.28 (s, 2H), 6.53 (appd, J=5.2 Hz, 1H); $^{13}$C NMR (100 MHz, DMSO-$d_6$) δ 163.15, 152.43, 145.28, 140.86, 139.52, 134.61, 130.64, 130.38, 129.60, 129.50, 128.57, 127.10, 120.32, 99.66; LC-MS (ESI+) m/z 376.06 (M-Cl)$^+$; HRMS (ESI+) m/z calculated for $C_{16}H_{15}ClN_5O_2S$ (M-Cl)$^+$ 376.0629. found 376.0634.

$N^4$-(2-Chlorophenyl)-$N^2$-[4-(N-morpholino)phenyl]-5-fluoropyrimidine-2,4-diamine (9j, method s in FIG. 7A)

A mixture of chloropyrimidine 2k (0.100 g, 0.387 mmol) and 4-morpholinoaniline (0.069 g, 0.387 mmol) in ethanol (1 mL) was heated in a microwave reactor at 150° C. for 20 min. The reaction mixture was cooled, and stirred at room temperature for 30 min. The solvent was removed in vacuo. The residual solid was suspended in ethyl acetate (10 mL) and sonicated for 10 min, filtered and washed with ethyl acetate (5 mL). The solid was suspended in sodium bicarbonate (sat. aq. 50 mL), filtered, and washed with water (10 mL) to provide the title compound 9k (0.92 g, 60%) as an off-white solid. m.p. 209-211° C. HPLC 99% [$R_t$=7.2 min., 50% MeOH, 50% water (with 0.1% TFA) 20 min.]; $^1$H NMR (400 MHz, DMSO-$d_6$) δ 9.63 (s, 1H), 9.36 (s, 1H), 8.11 (d, $J_{H-F}$=4.2 Hz, 1H), 7.61-7.54 (m, 2H), 7.44-7.37 (m, 1H), 7.36-7.25 (m, 3H), 6.79 (s, 2H), 3.73 (s, 4H), 3.03 (s, 4H). $^1$H NMR (400 MHz, DMSO-$d_6$+D$_2$O) δ 8.06 (d, J=4.1 Hz, 1H), 7.59-7.51 (m, 2H), 7.39 (td, J=7.6, 1.5 Hz, 1H), 7.32 (td, J=7.7, 1.7 Hz, 1H), 7.27 (d, J=9.0 Hz, 2H), 6.79 (d, J=8.9 Hz, 2H), 3.71 (t, J=4.0 Hz, 4H), 3.03 (t, J=4.4 Hz, 4H); $^{19}$F NMR (376 MHz, DMSO-$d_6$), δ −165.59; $^{13}$C NMR (100 MHz, DMSO-$d_6$) δ 154.38, 152.31 (d, J=12.0 Hz), 141.63, 139.04, 139.19, 135.42, 134.20, 130.43, 129.76, 120.74, 117.11, 66.31, 50.71; LC-MS (ESI+) m/z 400.13 (M-Cl)$^+$; HRMS (ESI+) m/z calculated for $C_{20}H_{20}ClFN_5O$ (M-Cl)$^+$ 400.1335. found 400.1344.

4-(2-Chlorophenylamino)-2-(4-(morpholinomethyl)phenyl)-5-fluoropyrimidine (9k, method u in FIG. 7A)

A mixture of chloropyrimidine 2k (0.100 g, 0.387 mmol), 4-(morpholinomethyl)aniline (0.087 g, 0.452 mmol), X-Phos (2-dicyclohexylphosphino-2',4',6'-triisopropylbiphenyl) (0.019 g, 0.0387 mmol), bis(dibenzylideneacetone) palladium(0) (0.022 g, 0.0387 mmol), potassium carbonate (0.117 g, 0.851 mmol) in tert-BuOH (3.0 mL) was heated under reflux for 18 hours. The solvent was evaporated from the resulting dark solution. The dark residue was purified by chromatography ($SiO_2$, ethyl acetate and hexanes) to provide the title compound 9k (0.062 g, 39%) as an off-white solid. m.p. 142-144° C. HPLC 98% [$R_t$=23.4 min., 50% MeOH, 50% water (with 0.1% TFA) 36 min.]; $^1$H NMR (400 MHz, DMSO-$d_6$), δ 9.16 (s, 1H), 9.10 (s, 1H), 8.07 (d, $J_{H-F}$=2.6 Hz, 1H), 7.58 (t, J=6.8 Hz, 2H), 7.42-7.34 (m, 3H), 7.31 (t, J=8.2 Hz, 1H), 6.94 (d, J=7.7 Hz, 2H), 3.52 (s, 4H), 2.26 (s, 4H); $^{13}$C NMR (100 MHz, DMSO-$d_6$), δ 156.22 (d, $J_{CF}$=2.8 Hz), 151.27 (d, $J_{CF}$=11.4 Hz), 141.15 (d, $J_{CF}$=245 Hz), 141.62 (d, $J_{CF}$=18.9 Hz), 140.44, 136.11, 131.08, 130.33, 130.26, 129.73, 129.52, 128.26, 128.01, 118.57, 66.84, 62.79, 53.74; $^{19}$F NMR (376 MHz, DMSO-$d_6$), δ −166.63 (s); LC-MS (ESI+) m/z 327.08 (M-morpholine); HRMS (ESI+) m/z calculated for $C_{21}H_{22}ClFN_5O$ (M+H)$^+$ 414.1491. found 414.1497 (M+H)$^+$, 327.0819 (M—morpholine).

N$^4$-(2-Chlorophenyl)-N$^2$-[4-N-(2-hydroxyethyl)carbamoylphenyl]pyrimidine-2,4-diamine (9l, method t in FIG. 7A)

A mixture of chloropyrimidine 2l (0.100 g, 0.416 mmol) and 4-amino-N-(2-hydroxyethyl)benzamide (0.075 g, 0.416 mmol) in HCl (1 mL of 0.1 N aq.) was heated in a microwave reactor at 140° C. for 30 min. The contents were then stirred in the microwave vial at room temperature for 30 min. The mixture was filtered and the obtained solid was washed with water (20 mL) and sodium bicarbonate (sat. aq. 50 mL). The crude product was purified by chromatography (silica gel, hexane: ethyl acetate) to provide 9l as an off-white solid (0.087 g, 54%). m.p. 171-173° C., HPLC 100% [$R_t$=8.8 min, 40% MeOH, 60% water (with 0.1% TFA) 20 min.]; $^1$H NMR (400 MHz, MeOH-$d_4$), δ 8.28 (t, J=6.2 Hz, 1H, peak disappeared upon D$_2$O shake), 8.00 (d, J=5.9 Hz, 1H), 7.84 (dd, J=8.0, 1.5 Hz, 1H), 7.71-7.64 (m, 4H), 7.50 (dd, J=8.0, 1.5 Hz, 1H), 7.37 (td, J=8.0, 1.5 Hz, 1H), 7.22 (td, J=8.0, 1.5 Hz, 1H), 6.30 (d, J=5.9 Hz, 1H), 3.70 (t, J=5.5 Hz, 2H), 3.49 (q, J=5.5 Hz, 2H); $^{13}$C NMR (100 MHz, DMSO-$d_6$), δ 172.68, 166.63, 161.90, 159.62, 156.84, 144.10, 136.56, 130.31, 128.61, 128.27, 128.07, 126.92, 126.82, 117.93, 99.18, 60.56, 42.68; LC-MS (ESI+) m/z 384.12 (M+H)$^+$; HRMS (ESI+) m/z calculated for $C_{19}H_{19}ClN_5O_2$ (M+H)$^+$ 384.1222. found 384.1219.

N$^4$-(2-Chlorophenyl)-N$^2$-(4-carbamoyl)-5-fluoropyrimidine-2,4-diamine (9m, method v in FIG. 7A)

A mixture of chloropyrimidine 2k (0.500 g, 1.935 mmol), 4-aminobenzamide (0.265 g, 1.935 mmol) in methanol (3 mL), was heated in 5 ml sealed pressure tube at 100° C. for 6 hrs. The white precipitate was isolated by filtration and washed with methanol (2 mL). The white solid was sonicated for 5 min. in sodium bicarbonate (aq. sat., 10 mL). The mixture was filtered and the solid washed with water (10 mL) and finally with methanol (2 mL) to provide 9m (0.439 g, 63%) as an off-white powder. m.p. 250-252° C. HPLC 100% [$R_t$=7.8 min, 50% MeOH, 50% water (with 0.1% formic acid) 20 min.]; $^1$H NMR (400 MHz, DMSO-$d_6$), δ 9.42 (s, 1H), 9.31 (s, 2H), 8.12 (d, $J_{H-F}$=3.6 Hz, 1H), 7.70 (s, 1H), 7.59 (dd, J=8.6, 1.3 Hz, 1H), 7.56 (dd, J=8.6, 1.3 Hz) overlapping 7.54 (d, J=8.7 Hz, 2H), 7.48 (d, J=8.7 Hz, 2H), 7.42 (td, J=7.7, 1.5 Hz, 1H), 7.35 (td, J=7.6, 1.6 Hz, 1H), 7.08 (s, 1H); $^{13}$C NMR (100 MHz, DMSO-$d_6$) δ 168.57, 155.66 (d, $J_{C-F}$=3.0 Hz), 151.35 (d, $J_{C-F}$=11.7 Hz), 144.27, 142.54, 141.66 (d, $J_{C-F}$=19.0 Hz), 140.09, 135.77, 131.27, 130.41, 129.79, 128.67, 128.41, 126.18, 117.31; $^{19}$F NMR (376 MHz, DMSO-$d_6$), δ −165.45 (bd, $J_{H-F}$=3.4 Hz) LC-MS (ESI+) m/z 358.09 (M+H)$^+$; HRMS (ESI+) m/z calculated for $C_{17}H_{14}ClFN_5O$ (M+H)$^+$ 358.0865. found 358.0868.

N$^4$-(2-Chlorophenyl)-N$^2$-(4-aminosulfonyl)-5-fluoropyrimidine-2,4-diamine (9n, method u in FIG. 7A)

A mixture of chloropyrimidine 2k (free base) (0.100 g, 0.387 mmol), 4-aminobenzenesulfonamide (0.066 g, 0.0.387 mmol), X-Phos (2-dicyclohexylphosphino-2',4',6'-triisopropylbiphenyl) (0.019 g, 0.0387 mmol), bis(dibenzylideneacetone) palladium(0) (0.022 g, 0.0387 mmol), potassium carbonate (0117 g, 0.851 mmol) in tert-BuOH (2.0 mL) was heated in 5 ml sealed pressure tube at 100° C. for 64 hours under argon. The solid was isolated by filtration and suspended in ethyl acetate (5 mL) and sonicated for 5 minutes. The mixture was filtered and the solid washed with ethyl acetate (5 mL). The crude product was dissolved in DMSO (2 mL) and filtered to remove undissolved material. The DMSO was removed in vacuo at 50° C. to provide the title sulfonamide 9n (0.080 g, 53%) as a brown solid. m.p. 253-255° C. HPLC 99% [$R_t$=11.2 min, 40% MeOH, 60% water (with 0.1% TFA) 66 min.]; $^1$H NMR (400 MHz, DMSO-$d_6$), δ 9.57 (s, 1H), 9.39 (s, 1H), 8.13 (d, $J_{H-F}$=3.7 Hz, 1H), 7.61-7.52 (m, 4H), 7.46-7.38 (m, 3H), 7.35 (t, J=8.0 Hz, 1H), 7.07 (s, 1H). $^1$H NMR (400 MHz, DMSO-$d_6$+D$_2$O), δ 8.09 (d, $J_{H-F}$=3.5 Hz, 1H), 7.58 (dd, J=7.9, 1.5 Hz, 1H), 7.54-7.48 (m, 3H), 7.44-7.39 (m, 3H), 7.35 (dt, J=7.4, 1.7 Hz, 1H); $^{19}$F NMR (376 MHz, DMSO$d_6$-+D$_2$O), δ −164.56 (d, J=3.1 Hz); $^{13}$C NMR (100 MHz, DMSO-$d_6$) 155.67 (d, $J_{C-F}$=2.8 Hz), 151.57, 151.46, 144.66, 142.73, 141.79, 141.60, 140.27, 136.06, 135.87, 131.65, 130.42, 130.19, 128.42, 126.85, 117.46. LC-MS (ESI+) m/z 394.05 (M+H)$^+$; HRMS (ESI+) m/z calculated for $C_{16}H_{14}ClFN_5O_2S$ (M+H)$^+$ 394.0535. found 394.0537.

N$^4$-(2-Chlorophenyl)-N$^2$-[4-(2H-tetrazol-5-yl)phenyl]pyrimidine-2,4-diamine hydrochloride (12a, method a in FIG. 8)

A mixture of 2l (0.072 g, 0.299 mmol) and 4-(2H-tetrazol-5-yl)phenylamine (11a) (0.050 g, 0.310 mmol) in EtOH (2.0 mL) was heated in a microwave reactor at 150° C. for 40 min. The precipitate obtained upon cooling the reaction mixture was filtered and washed with EtOH (5 mL) to provide 12a (0.095 g, 79%) as a yellow solid ($^1$H NMR analysis indicated the presence of trace impurities). The product was further purified by washing with methanol (5 mL) to give pure 12a (0.045 g, 37%) as a yellow solid. m.p. 250° C. (dec.). HPLC 100% ($R_t$=6.21 min., 50% MeOH in 0.1% TFA water, 20 min.); $^1$H NMR (400 MHz, DMSO-$d_6$) δ 10.76 (s, 1H), 10.64 (s, 1H), 8.09 (d, J=6.9 Hz, 1H), 7.86 (d, J=8.4 Hz, 2H), 7.69-7.59 (m, 4H), 7.48 (t, J=7.4 Hz, 1H), 7.41 (t, J=7.5 Hz, 1H), 6.52 (s, 1H); $^{13}$C NMR (100 MHz, DMSO-$d_6$) δ 163.07, 153.08, 146.47, 140.76, 134.74, 130.64, 130.17, 129.48, 129.32, 129.31, 128.57, 128.21, 121.13, 119.58; elemental analysis calculated for $C_{17}H_{11}Cl_2N_8$: C, 50.89; H, 3.52; N, 27.93. Found: C, 51.22; H, 3.50; N, 27.54; LC-MS (ESI−) m/z 363.08 (M−H—

HCl)⁻; HRMS (ESI–) m/z calculated for C₁₇H₁₂ClN₈(M–H–HCl)⁻ 363.0879. found 363.0871.

N⁴-(2-Chlorophenyl)-N²-[4-(2H-tetrazol-5-yl)phenyl]-5-fluoropyrimidine-2,4-diamine hydrochloride (12b, method a in FIG. 8)

A mixture of 2k (free base) (0.076 g, 0.298 mmol) and 4-(2H-tetrazol-5-yl)phenylamine (11a) (0.050 g, 0.310 mmol) in EtOH (2.0 mL) was heated in a microwave reactor at 170° C. for 40 min. The precipitate obtained upon cooling the reaction mixture was filtered and washed with EtOH (5.0 mL) to get 12b (0.090 g, 72%) as a brown-yellow solid. The ¹H NMR spectrum showed the presence of a baseline impurity and the product was further purified by washing with methanol (5 mL) to provide pure 12b (0.041 g, 33%) as a brown-yellow solid. m.p.: 223° C. (dec.). HPLC 99% ($R_t$=10.37 min., 50% MeOH in 0.1% TFA water, 20 min.); ¹H NMR (400 MHz, DMSO-d₆) δ 9.98 (s, 1H), 9.91 (s, 1H), 8.25 (d, J=4.0 Hz, 1H), 7.74 (d, J=8.7 Hz, 2H), 7.64 (d, J=7.8 Hz, 1H), 7.62-7.56 (m, 3H), 7.50-7.38 (m, 2H); ¹³C NMR (100 MHz, DMSO-d₆) δ 155.74 (d, J=3.0 Hz), 151.50 (d, J=11.7 Hz), 144.37, 141.45 (d, J=247.45 Hz), 141.68 (d, J=17.6 Hz), 136.06, 131.58, 130.43, 130.15, 128.41, 127.85, 118.47. ¹⁹F NMR (376 MHz, DMSO) δ –165.12 (s); elemental analysis calculated for C₁₇H₁₃Cl₂FN₈: C, 48.70; H, 3.13; N, 26.73. Found: C, 49.09; H, 3.13; N, 26.48. LC-MS (ESI–) m/z 381.1 (M–H)⁻; HRMS (ESI–) m/z calculated for C₁₇H₁₁ClFN₈ (M–H)⁻ 381.0785. found 381.0784.

N⁴-(2-Chlorophenyl)-N²-[3-hydroxy-4-(2H-tetrazol-5-yl)phenyl]-5-fluoropyrimidine-2,4-diamine hydrochloride (12c, method a FIG. 8)

A mixture of 2k (freebase) (0.072 g, 0.279 mmol) and tetrazole 11b (0.050 g, 0.282 mmol) in EtOH:HCl (1:1, 2.0 mL, 0.1 M HCl) was heated in a microwave reactor at 160° C. for 40 min. The precipitate obtained upon cooling was filtered and rinsed with EtOH (5 mL) to obtain the product with base-line impurity (0.096 g, 77%) as a yellow solid. This solid was further purified by washing with methanol (5 mL) to provide pure 12c (0.044 g, 36%) as a yellow solid. m.p. 214° C. (dec.). HPLC 93% ($R_t$=12.99 min., 50% MeOH in 0.1% TFA water, 20 min.); ¹H NMR (400 MHz, DMSO-d₆) δ 10.66 (s, 1H), 9.44 (s, 1H), 9.24 (s, 1H), 8.13 (d, J=3.3 Hz, 1H), 7.66-7.54 (m, 4H), 7.41 (t, J=7.5 Hz, 1H), 7.33 (t, J=7.4 Hz, 1H), 7.29-7.23 (m, 2H); ¹³C NMR (100 MHz, DMSO-d₆) 156.34, 155.80 (d, J=3.1 Hz), 151.46 (d, J=11.5 Hz), 145.58, 141.61 (d, J=247.2 Hz), 141.23 (d, J=19.1 Hz), 135.90, 131.04, 130.42, 129.71, 129.25, 128.38, 128.20, 110.49, 105.32, 103.39; ¹⁹F NMR (376 MHz, DMSO-d₆) δ –165.94 (s); LC-MS (ESI–) m/z 397.07 (M–H)⁻; HRMS (ESI–) m/z calculated for C₁₇H₁₁ClFN₈O (M–H)⁻ 397.0734. found 397.0730.

N⁴-(2-Chlorophenyl)-N²-[4-(2H-tetrazol-5-yl)phenyl]-5-chloropyrimidine-2,4-diamine hydrochloride (12d, method a FIG. 8)

A mixture of chloropyrimidine 2o (0.093 g, 0.3 mmol) and 4-(2H-tetrazol-5-yl)phenylamine (11a) (50 mg, 0.3 mmol) in EtOH (2 mL) was heated in a microwave reactor at 150° C. for 40 min. The precipitate obtained upon cooling was filtered and washed with EtOH (5 mL) to provide impure 12d (105 mg, 81%) as a yellow color solid. Analysis of the ¹H NMR spectrum indicated the presence of trace impurities. The product was further purified by washing with hot ethyl acetate (5 mL) and hot methanol (5 mL) to provide pure 12d (0.032 g, 25%) as a yellow solid. m.p. 238° C. (dec.). HPLC 91% ($R_t$=5.71 min., 70% MeOH in 0.1% TFA water, 20 min.); ¹H NMR (400 MHz, DMSO-d₆) δ 9.72 (s, 1H), 9.05 (s, 1H), 8.19 (s, 1H), 7.71-7.56 (m, 6H), 7.52-7.38 (m, 2H); ¹³C NMR (100 MHz, DMSO-d₆) δ 157.73, 157.53, 154.65, 143.69, 136.39, 131.71, 130.38, 130.32, 128.69, 128.49, 127.87, 119.04, 104.93; LC-MS (ESI–) m/z 397.05 (M–H)⁻; HRMS (ESI–) m/z calculated for C₁₇H₁₁Cl₂N₈ (M–H)⁻ 397.0489. found 397.0472.

What is claimed is:

1. A method of treating cancer, comprising the step of administering to a patient in need thereof a compound of the following formula:

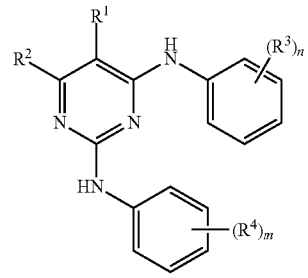

wherein $R^1$ is selected from the group consisting of H, Cl, F, Br, I, $C_1$-$C_6$ alkyl, CN, NO₂, and NH₂; $R^2$ is H, F, or Cl; each $R^3$ is 2-Cl; and each $R^4$ is selected, independently, from the group consisting of H, COOH, CONH₂, CONHR⁵, SO₂NH₂, CONHSO₂R⁵, tetrazole, 4-morpholine, or COR⁵, wherein $R^5$ is $C_1$-$C_6$ alkyl, cycloalkyl, heteroaryl, or heteroalkyl, n is 1, and m is 1-5, or a pharmaceutically acceptable salt thereof.

2. The method of claim 1, wherein the cancer is characterized by Aurora kinase up-regulation.

3. The method of claim 1, wherein the compound is a selective inhibitor of Aurora A kinase over Aurora B kinase.

4. The method of claim 1, wherein the compound is a DFG-out inhibitor.

5. The method of claim 1, wherein the cancer is selected from the group consisting of breast cancer and colorectal cancer.

6. The method of claim 1, wherein the compound has the following formula:

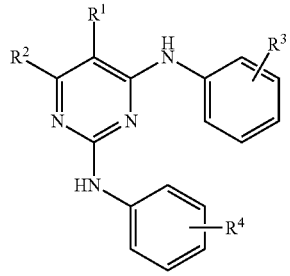

wherein $R^1$ is selected from the group consisting of H, Cl, F, Br, I, CH₃ and N₂; $R^2$ is H, F, or Cl; and $R^4$ is selected from the group consisting of H, COOH, 2-CONH₂, 4-CONH₂, SO₂NH₂, tetrazole, and 4-morpholine.

7. The method of claim 1, wherein $R^4$ is 4-COOH, and m is 1.

8. The method of claim 1, wherein m is 1, and $R^4$ is COOH, $COR^5$, $CONH_2$, $CONHR^5$, or $CONHSO_2R^5$, wherein $R^5$ is $C_1$-$C_6$ alkyl, cycloalkyl, heteroaryl, or heteroalkyl.

9. A method of treating cancer, comprising the step of administering to a patient in need thereof a compound of the following formula:

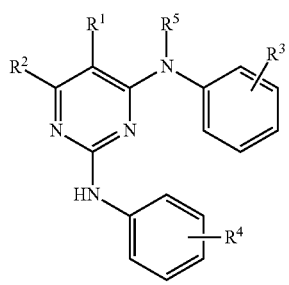

wherein $R^1$ is H, $R^3$ is ortho-Cl, $R^4$ is para-$CH_2$—COOH, and $R^5$ is H;

$R^1$ is H, $R^3$ is ortho-Cl, $R^4$ is para-COOH and meta-OH, and $R^5$ is H;

$R^1$ is H, $R^3$ is ortho-Cl, $R^4$ is meta-COOH, and $R^5$ is H;

$R^1$ is H, $R^3$ is ortho-Cl, $R^4$ is para-$CONH_2$, and $R^5$ is H;

$R^1$ is H, $R^3$ is ortho-Cl, $R^4$ is para-COOH, and $R^5$ is $CH_3$;

$R^1$ is H, $R^3$ is ortho-Cl, $R^4$ is para-COOH, and $R^5$ is $CH_3$—$CH_2$;

$R^1$ is F, $R^3$ is ortho-Cl, $R^4$ is meta-COOH, and $R^5$ is H;

$R^1$ is H, $R^3$ is ortho-Cl, $R^4$ is para-COOH and meta OH;

$R^1$ is H, $R^3$ is ortho-Cl, $R^4$ is para-COOH, and $R^5$ is H;

$R^1$ is F, $R^3$ is ortho-Cl, $R^4$ is para-COOH, and $R^5$ is H;

$R^1$ is F, $R^3$ is ortho-Cl, $R^4$ is H, and $R^5$ is H; or $R^1$ is H, $R^3$ is ortho-Cl, $R^4$ is para-$OCH_3$, and $R^5$ is H.

10. The method of claim 9, wherein the cancer is selected from the group consisting of breast cancer and colorectal cancer.

11. A method of treating cancer, comprising the step of administering to a patient in need thereof a compound chosen from the follow group:

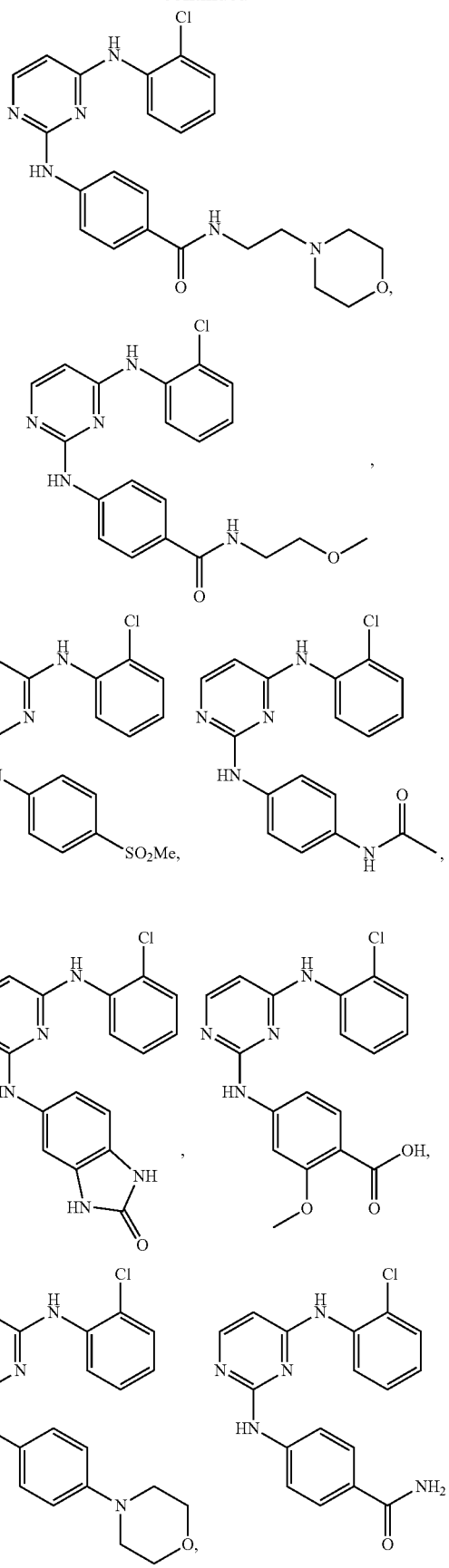

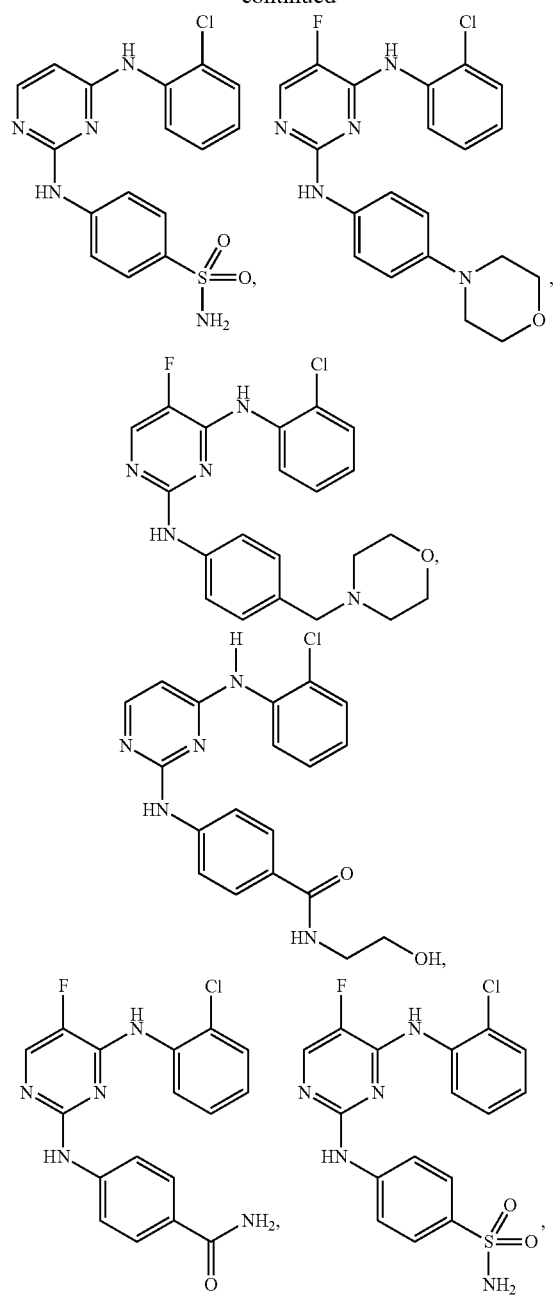
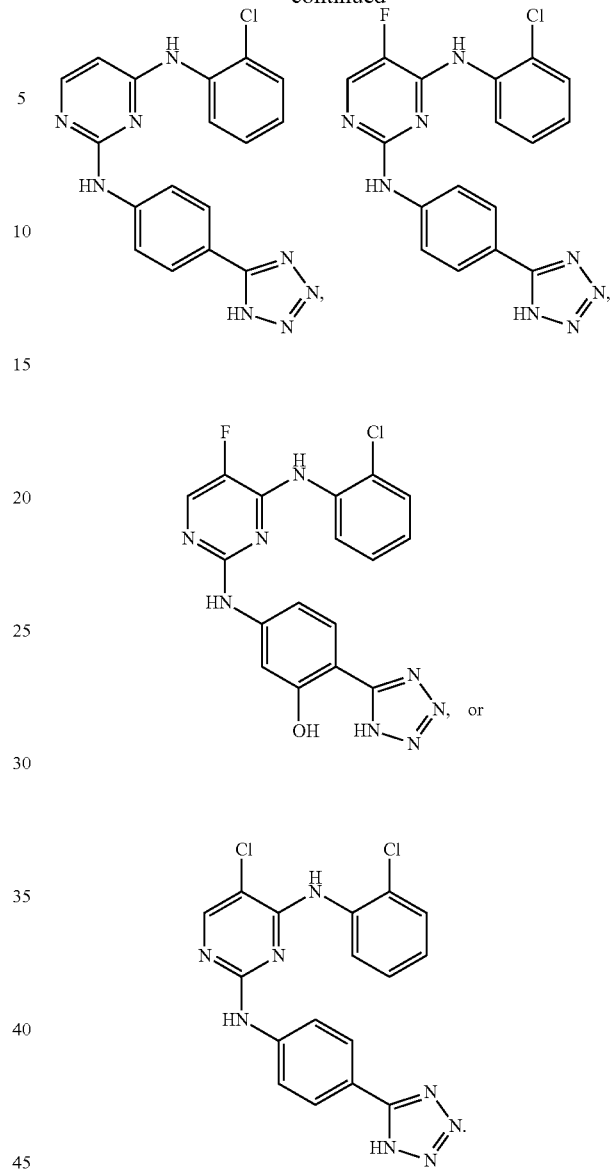
12. The method of claim 11, wherein the cancer is selected from the group consisting of breast cancer and colorectal cancer.
* * * * *